United States Patent
Chen et al.

(10) Patent No.: US 9,855,269 B2
(45) Date of Patent: *Jan. 2, 2018

(54) AMINOQUINAZOLINE AND PYRIDOPYRIMIDINE DERIVATIVES

(71) Applicant: Genentech, Inc., South San Francisco, CA (US)

(72) Inventors: Huifen Chen, Burlingame, CA (US); Terry Crawford, San Mateo, CA (US); Seth F. Harris, El Granada, CA (US); Steven R. Magnuson, Dublin, CA (US); Chudi Nbdubaku, San Francisco, CA (US); Lan Wang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/454,793

(22) Filed: Mar. 9, 2017

(65) Prior Publication Data

US 2017/0173026 A1     Jun. 22, 2017

Related U.S. Application Data

(62) Division of application No. 15/184,310, filed on Jun. 16, 2016, now Pat. No. 9,592,235, which is a division of application No. 13/906,626, filed on May 31, 2013, now Pat. No. 9,382,241.

(60) Provisional application No. 61/653,812, filed on May 31, 2012.

(51) Int. Cl.
| | |
|---|---|
| *A61K 31/519* | (2006.01) |
| *A61K 31/5377* | (2006.01) |
| *A61K 31/551* | (2006.01) |
| *A61K 31/553* | (2006.01) |

(52) U.S. Cl.
CPC ........ *A61K 31/519* (2013.01); *A61K 31/5377* (2013.01); *A61K 31/551* (2013.01); *A61K 31/553* (2013.01)

(58) Field of Classification Search
CPC .. C07D 239/94; C07D 471/04; A61K 31/517; A61K 31/519
See application file for complete search history.

(56) References Cited

U.S. PATENT DOCUMENTS

| | | | |
|---|---|---|---|
| 4,377,530 A | 3/1983 | Trenbeath et al. | |
| 9,595,235 B2 * | 3/2017 | Xiao | .................... G09G 3/3677 |

FOREIGN PATENT DOCUMENTS

| | | |
|---|---|---|
| EP | 030156 | 6/1981 |
| WO | 01/85760 | 11/2001 |

OTHER PUBLICATIONS

CAS Registry Database, 1347564-78-6.
CAS Registry Database, 1348936-14-0.
CAS Registry Database, 1349984-47-9.
CAS Registry Database, 79689-56-8.
CAS Registry Database, 950644-91-4.
PubChem CID 20718876.

* cited by examiner

*Primary Examiner* — Alexander R Pagano
(74) *Attorney, Agent, or Firm* — Brian L. Buckwalter

(57) ABSTRACT

The invention provides a method of inhibiting angiogenesis in a patient by administering a compound of formula (I):

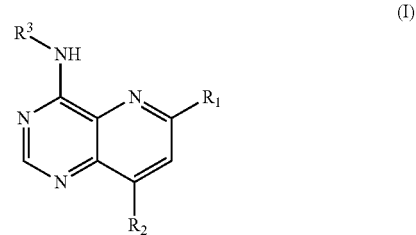

wherein $R^1$, $R^2$ and $R^3$ are as defined herein, compositions including the compounds and methods of using the compounds.

2 Claims, No Drawings

AMINOQUINAZOLINE AND PYRIDOPYRIMIDINE DERIVATIVES

CROSS REFERENCE TO RELATED APPLICATIONS

This application is a divisional application claiming priority to U.S. Ser. No. 15/184,310 filed Jun. 16, 2016 which claims priority to U.S. Pat. No. 9,382,241, filed May 31, 2013, which claims the benefit of priority to U.S. Provisional Application No. 61/653,812, filed May 31, 2012, all of which are incorporated herein by reference in their entirety

FIELD OF THE INVENTION

The present invention relates to organic compounds useful for therapy and/or prophylaxis in a mammal, and in particular to the inhibition of MAP4K4 useful for treating cancer.

BACKGROUND OF THE INVENTION

Angiogenesis, the process by which new blood vessels develop from existing vasculature, is a critical step in the progression of solid tumors. In response to growth factors, a subset of endothelial cells is activated and migrate away from their parent vessels. Though many factors such as VEGF and FGF have been implicated in promoting the migration of endothelial cells, little is known about what molecules regulate and coordinate the migratory machinery in this cohort of highly motile cells.

Development of a vascular system is a fundamental requirement for many physiological and pathological processes. Active growth of embryos and tumors requires an adequate blood supply. Pro-angiogenic factors promote new blood vessel formation and maintenance via a process generally referred to as angiogenesis. Vascular formation is a complex but orderly biological event involving all or many of the following steps: a) Endothelial cells (ECs) within existing vessels proliferate, or new ECs form via differentiation from progenitor cells; b) Newly formed ECs migrate to target sites and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. Science 277:48-50 (1997); Hogan, B. L. & Kolodziej, P. A. Nature Reviews Genetics. 3:513-23 (2002); Lubarsky, B. & Krasnow, M. A. Cell. 112:19-28 (2003).

Angiogenesis is implicated in the pathogenesis of a variety of disorders. These include malignant tumor growth, atherosclerosis, retrolental fibroplasia, hemangiomas, chronic inflammation, intraocular neovascular diseases such as proliferative retinopathies, e.g., diabetic retinopathy, age-related neovascular macular degeneration (nvAMD), neovascular glaucoma, immune rejection of transplanted corneal tissue and other tissues, rheumatoid arthritis, and psoriasis. Folkman et al., J. Biol. Chem., 267:10931-10934 (1992); Klagsbrun et al., Annu. Rev. Physiol. 53:217-239 (1991); and Garner A., "Vascular diseases", in: Pathobiology of Ocular Disease. A Dynamic Approach, Garner A., Klintworth G K, eds., 2nd Edition (Marcel Dekker, N Y, 1994), pp 1625-1710.

In the case of tumor growth, angiogenesis appears to be crucial for the transition from hyperplasia to neoplasia, and for providing nourishment for the growth and metastasis of the tumor. Folkman et al., Nature 339:58 (1989). The neovascularization allows the tumor cells to acquire a growth advantage and proliferative autonomy compared to the normal cells. A tumor usually begins as a single aberrant cell, which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., N. Engl. J. Med 324:1-6 (1991); Horak et al., Lancet 340:1120-1124 (1992); Macchiarini et al., Lancet 340:145-146 (1992). The precise mechanisms that control the angiogenic switch is not well understood, but it is believed that neovascularization of tumor mass results from the net balance of a multitude of angiogenesis stimulators and inhibitors (Folkman, 1995, Nat Med 1(1):27-31). MAP4K4 may play a role in promoting tumor cell migration/invasion. MAP4K4 RNAi inhibited both migration and invasion of SKOV3 human ovarian cancer cells in vitro (Collins et al, 2006, PNAS 103:3775-3780). Analysis of human tumors, including pancreatic, hepatocellular and colorectal cancer, shows a link between high MAP4K4 expression and worse prognosis, with increased tumor size and increased metastasis (Liang et al, 2008, Clin Cancer Res 14:7043-7049, Liu et al, 2011, Clin Cancer Res 17:710-720, Hao et al, 2010, J Pathol 220:475-489).

SUMMARY OF THE INVENTION

The present invention provides a method for inhibiting angiogenesis in an animal, e.g., a mammal by inhibition of MAP4K4.

In one aspect the invention relates to compounds of Formula (I):

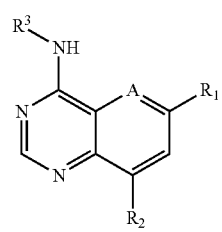

and stereoisomers, geometric isomers, tautomers, and pharmaceutically acceptable salts thereof, wherein A is N and $R^1$, $R^2$ and $R^3$ are as defined herein. Compounds of Formula (I) can be useful as MAP4K4 inhibitors.

Another aspect of the invention provides a pharmaceutical composition comprising a Formula (I) compound and a pharmaceutically acceptable carrier, glidant, diluent, or excipient.

Another aspect of the invention provides the use of a Formula (I) compound in the manufacture of a medicament for treating cancer.

The invention also relates to methods of using the Formula (I) compounds for in vitro, in situ, and in vivo diagnosis or treatment of mammalian cells, organisms, or associated pathological conditions, such as cancer.

The invention also relates to the use of compounds of Formula (I) and compounds described herein according to the invention in the inhibition of angiogenesis, cell migration, cell proliferation, cell survival or treatment of cancer.

Another aspect of the invention provides a method of treating a disease or disorder which method comprises administering a Formula (I) compound to a patient with cancer.

The methods of treating cancer include where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

Another aspect of the invention provides a kit for treating a condition modulated by the inhibition MAP4K4, comprising a first pharmaceutical composition comprising a Formula (I) compound; and instructions for use.

Other aspects of the invention include: (i) method for preventing or treating conditions, disorders or diseases mediated by the activation of the MAP4K4 enzyme, in a subject in need of such treatment, which method comprises administering to said subject an effective amount of a compound of Formula (I) or a pharmaceutically acceptable salt thereof, in free form or in a pharmaceutically acceptable salt form as a pharmaceutical, in any of the methods as indicated herein; (ii) a compound of the Formula (I) in free form or in pharmaceutically acceptable salt form for use as a pharmaceutical in any of the methods described herein, in particular for the use in one or more MAP4K4 mediated diseases; (iii) the use of a compound of Formula (I) in free form or in pharmaceutically acceptable salt form in any of the methods as indicated herein, in particular for the treatment of one or more MAP4K4 mediated diseases; (iv) the use of a compound of Formula (I) in free form or in pharmaceutically acceptable salt form in any of the methods as indicated herein, in particular for the manufacture of a medicament for the treatment of one or more MAP4K4 mediated diseases.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "$C_1$-$C_{12}$-alkoxy" means a $C_1$-$C_{12}$-alkyl group, wherein alkyl is as defined herein, that is linked to the rest of a molecule or to another group through an oxygen atom. Illustrative, non limiting examples of alkoxy include methoxy, ethoxy, n-propoxy, isopropoxy and the different butoxy isomers and $R^1$ groups as exemplified therein.

The expression "($C_1$-$C_{12}$-alkylenyl)$_n$-$C_1$-$C_{12}$-alkoxy" means either a ($C_1$-$C_{12}$-alkylenyl)-$C_1$-$C_{12}$-alkoxy or a $C_1$-$C_{12}$-alkoxy group, wherein alkylenyl and alkoxy are as defined herein.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituent(s) described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and $R^2$ groups as exemplified therein.

The term "alkylene" or "alkylenyl" as used herein refers to a saturated linear or branched-chain divalent hydrocarbon radical of one to twelve carbon atoms ($C_1$-$C_{12}$), wherein the alkylene radical may be optionally substituted independently with one or more substituent(s) described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and $R^1$ groups as exemplified therein.

"Aryl" means a monovalent aromatic hydrocarbon radical of 6-20 carbon atoms ($C_6$-$C_{20}$) or $C_6$-$C_{20}$-aryl, derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituent(s) described herein. Further non limiting examples of aryl groups can be found in the definition of $R^1$ herein.

"aryloxy" as used herein denotes an —O-aryl group, wherein aryl is as defined herein. Non-limiting examples of —O-aryl groups are —O-phenyl and —O-naphthyl groups.

The term "cyanoalkyl" as used herein refers to an alky group as defined herein that is substituted by one or more cyano group, for example one cyano group. In certain embodiments "cyanoalkyl" are $C_1$-$C_{12}$-cyanoalkyl groups. In other embodiments "cyanoalkyl" are $C_1$-$C_6$-cyanoalkyl groups, for example cyanomethyl and cyanoethyl.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantanyl, and $R^2$ groups as exemplified therein.

The term "halo" denotes chloro, iodo, fluoro and bromo, in one embodiment halo are fluoro, chloro and bromo, and yet in another embodiment fluoro and chloro.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include $C_1$-$C_{12}$-haloalkyl groups, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl. The term "$C_1$-$C_{12}$-haloalkyl" means a haloalkyl group having 1 to 12 carbon atoms, wherein the haloalkyl is as defined herein.

The term "haloalkoxy" denotes a alkoxy group as defined herein wherein at least one of the hydrogen atoms of the alkoxy group is replaced by a halogen atom, preferably fluoro or chloro, most preferably fluoro. Examples of haloalkoxy include $C_1$-$C_{12}$-haloalkoxy groups, but are not limited to, methoxy, ethoxy, propyloxy, isopropyloxy, isobutyloyx, sec-butyloxy, tert-butyloxy, pentyloxy or n-hexyloxy wherein one or more hydrogen atoms are replaced by Cl, F, Br or I atom(s), as well as those haloalkoxy groups specifically illustrated by the examples herein below. Among the preferred haloalkoxy groups are monofluoro-, difluoro- or trifluoro-methoxy, -ethoxy or -propyloxy, for example 3,3,3-trifluoropropyloxy, 2-fluoroethoxy, 2,2,2-trifluoroethoxy, fluoromethoxy, trifluoromethoxy. In a certain embodiment $C_1$-$C_{12}$-haloalkoxy groups are $C_1$-$C_6$-haloalkoxy groups.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituent(s) described below. Examples of heterocycly groups are $C_2$-$C_{12}$-heterocyclyl, i.e. heterocyclyl groups comprising 2 to 12 carbon atoms and 1 to 4 (1, 2, 3 or 4) heteroatoms selected from N, O, P, and S. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituent(s) described herein.

The term "heteroaryl" refers to a monovalent aromatic radical of 5-, 6-, or 7-membered rings, and includes fused ring systems (at least one of which is aromatic) of 5-20 atoms containing one or more heteroatoms independently selected from nitrogen, oxygen, and sulfur. Examples of heteroaryl groups include $C_2$-$C_{12}$-heteroaryls which denotes monocyclic of bicyclic heteroaryl having 2 to 12 carbon atoms and one or more heteroatoms independently selected from nitrogen, oxygen, and sulfur, for example, 1, 2, 3 or 4 heteroatoms independently selected from nitrogen, oxygen, and sulfur. Non limiting examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituent(s) described herein, for example alkyl, alkoxy, cyano, halo, oxo, $NH_2$, OH, hydroxyalkyl, amido groups. Further examples of heteroaryl groups and of possible substituents can be found in the definition of $R^2$.

The term "heteroaryloxy" as used herein means an —O-heteroaryl, wherein heteroaryl is as defined herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Ring nitrogen atoms of the heterocycle or heteroaryl groups may be bonded with oxygen to form N-oxides.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or O-carboline.

The term "hydroxy" denotes a group of formula —OH.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below. The term "$C_1$-$C_{12}$-hydroxyalkyl" means a hydroxyalkyl group having 1 to 12 carbon atoms, wherein hydroxyalkyl is as defined herein.

Oxo denotes a group of formula =O.

The expression "one or more substituent" denotes a substitution by 1, 2, 3, 4, 5, 6, 7, 8, 9, 10, 11 or 12 substituent(s) that can be independently selected from the list following this expression. In one embodiment, one or more substituent(s) denotes 1, 2, 3, 4 or 5 substituents. In one embodiment, one or more substituent(s) denotes 1, 2 or 3 substituents.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include enantiomers and diastereomers.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Diastereomers include geometric isomers, cis/trans and E/Z isomers, and atropisomers.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula (I)" include compounds of Formulas (I), (I-a), (I-b), (I-c), (I-d), specific compounds described herein and stereoisomers, tautomers, solvates, metabolites, and pharmaceutically acceptable salts and prodrugs thereof.

Any formula or structure given herein, including Formula (I) compounds, is also intended to represent hydrates, solvates, and polymorphs of such compounds, and mixtures thereof.

Any formula or structure given herein, including Formula (I) compounds, is also intended to represent isotopically labeled forms of the compounds as well as unlabeled forms. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT)

including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Inhibitors of MAP4K4

In one aspect, the invention relates to compounds of Formula (I):

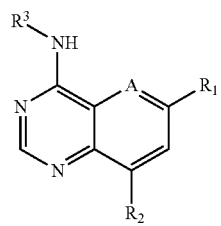

I and stereoisomers, geometric isomers, tautomers, and pharmaceutically acceptable salts thereof, wherein:

A is N;

$R^1$ is —NR—$C_1$-$C_{12}$-hydroxyalkyl, —NR—($C_1$-$C_{12}$-alkylenyl)$_n$-$C_3$-$C_6$-cycloalkyl, —NR—($C_1$-$C_{12}$-alkylenyl)$_n$-heterocyclyl, —NR—($C_1$-$C_{12}$-alkylenyl)$_n$-$C_6$-$C_{20}$-aryl, —NR—($C_1$-$C_{12}$-alkylenyl)$_n$-heteroaryl, —NR—($C_1$-$C_{12}$-alkylenyl)$_n$-$C_6$-$C_{20}$-aryloxy, $C_6$-$C_{20}$-aryl, pyridine, N-linked piperidine, N-linked pyrrolidine, N-linked piperazine, N-linked morpholine, 1H-pyrazol-4-yl, $C_6$-$C_{20}$-aryloxy or heteroaryloxy, each of which can be unsubstituted or substituted by one or more substituent(s) selected from the group consisting of:

CN;
oxo;
OH;
$NH_2$;
halo;
$C_1$-$C_{12}$-alkyl;

($C_1$-$C_{12}$-alkylenyl)$_n$-$C_1$-$C_{12}$-alkoxy, unsubstituted or substituted by one or more substituent(s) selected from the group consisting of $C_3$-$C_6$-cycloalkyl, heterocyclyl, aryl and heteroaryl;

$C_1$-$C_{12}$-hydroxyalkyl;
$C_1$-$C_{12}$-haloalkyl;
$C_1$-$C_{12}$-haloalkoxy;
($C_1$-$C_{12}$-alkylenyl)$_n$-C(O)O—$C_1$-$C_{12}$-alkyl;
—C(O)—$C_1$-$C_{12}$-alkyl;
O—R', wherein R' is $C_3$-$C_6$-cycloalkyl, heterocycloalkyl, aryl or heteroaryl, each of which are unsubstituted or substituted by one or more $R^g$;

($C_1$-$C_{12}$-alkylenyl)$_n$-cycloalkyl or ($C_1$-$C_{12}$-alkylenyl)$_n$-heterocyclyl unsubstituted or substituted by one or more substituent(s) selected from the group consisting of:

halo, oxo, OH, $NH_2$, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —NH($C_1$-$C_{12}$-alkyl), —N($C_1$-$C_{12}$-alkyl)$_2$, —N($C_1$-$C_{12}$-alkyl)-C(O)—$C_1$-$C_{12}$-alkyl, —C(O)—$C_1$-$C_{12}$-alkyl, —C(O)O—$C_1$-$C_{12}$-alkyl, ($C_1$-$C_{12}$-alkylenyl)$_n$-C(O)—$NH_2$, ($C_1$-$C_{12}$-alkylenyl)$_n$-C(O)—NH($C_1$-$C_{12}$-alkyl), —C(O)—NH($C_1$-$C_{12}$-hydroxyalkyl), ($C_1$-$C_{12}$-alkylenyl)$_n$-C(O)—N($C_1$-$C_{12}$-alkyl)$_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl)$_2$, —C(O)OH, —C(O)-heterocyclyl, ($C_1$-$C_{12}$-alkylenyl)$_n$-heterocyclyl and ($C_1$-$C_{12}$-alkylenyl)$_n$-heteroaryl, which heterocyclyl and heteroaryl group(s) can be unsubstituted or substituted by one or more substituent(s) selected from the group consisting of:

—OH, $NH_2$, halo, $C_1$-$C_{12}$-alkyl, $C_1$-$C_{12}$-alkoxy, $C_1$-$C_{12}$-haloalkyl and $C_1$-$C_{12}$-hydroxyalkyl;

($C_1$-$C_{12}$-alkylenyl)$_n$-aryl or ($C_1$-$C_{12}$-alkylenyl)$_n$-heteroaryl, wherein the aryl or heteroaryl is unsubstituted or substituted by one or more substituent(s) selected from the group consisting of:

halo, OH, $NH_2$, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —NH($C_1$-$C_{12}$-alkyl), —N($C_1$-$C_{12}$-alkyl)$_2$, —N($C_1$-$C_{12}$-alkyl)C(O)—$C_1$-$C_{12}$-alkyl, —C(O)—$NH_2$, —C(O)—NH($C_1$-$C_{12}$-alkyl), —C(O)—NH($C_1$-$C_{12}$-hydroxyalkyl), —C(O)—N($C_1$-$C_{12}$-alkyl)$_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl)$_2$, $C_1$-$C_{12}$-alkylenyl-C(O)N($C_1$-$C_{12}$-alkyl)$_2$, —C(O)OH, —C(O)-heterocyclyl and heterocyclyl, which heterocyclyl group(s) can be unsubstituted or substituted by one or more substituent(s) selected from the group consisting of:

OH, $NH_2$, halo, $C_1$-$C_{12}$-alkyl, $C_1$-$C_{12}$-alkoxy, $C_1$-$C_{12}$-haloalkyl, and $C_1$-$C_{12}$-hydroxyalkyl;

($C_1$-$C_{12}$-alkylenyl)$_n$-$NR^aR^b$, wherein $R^a$ and $R^b$ are independently selected from:

H,
$C_1$-$C_{12}$-alkyl,
$C_1$-$C_{12}$-hydroxyalkyl,
$C_1$-$C_{12}$-haloalkyl,
($C_1$-$C_{12}$-alkylenyl)$_n$-$C_1$-$C_{12}$-alkoxy,
—S(O)$_2$—($C_1$-$C_{12}$-alkylenyl)$_n$-heterocyclyl unsubstituted or substituted by one or more $R^g$,
($C_1$-$C_{12}$-alkylenyl)$_n$-$C_6$-$C_{20}$-aryl, which aryl is unsubstituted or substituted by one or more $R^g$,
($C_1$-$C_{12}$-alkylenyl)$_n$-$C_3$-$C_6$-cycloalkyl unsubstituted or substituted by one or more $R^g$, (C$_1$-C$_{12}$-alkylenyl)$_n$-heterocyclyl unsubstituted or substituted by one or more oxo, —C(O)O—C$_1$-C$_{12}$-alkyl or R$^g$, C$_1$-C$_{12}$-alkylenyl-C(O)-heteroaryl unsubstituted or substituted by one or more R$^g$, C$_1$-C$_{12}$-alkylenyl-NH$_2$, C$_1$-C$_{12}$-alkylenyl-NH(C$_1$-C$_{12}$-alkyl), C$_1$-C$_{12}$-alkylenyl-N(C$_1$-C$_{12}$-alkyl)$_2$, C$_1$-C$_{12}$-alkylenyl-C(O)NH$_2$, C$_1$-C$_{12}$-alkylenyl-C(O)NH(C$_1$-C$_{12}$-alkyl), C$_1$-C$_{12}$-alkylenyl-C(O)N(C$_1$-C$_{12}$-alkyl)$_2$, (C$_1$-C$_{12}$-alkylenyl)$_n$-C(O)NR$^c$R$^d$, wherein R$^c$ and R$^d$ are independently selected from:

H,

C$_1$-C$_{12}$-alkyl,

C$_1$-C$_{12}$-hydroxyalkyl,

C$_1$-C$_{12}$-haloalkyl, (C$_1$-C$_{12}$-alkylenyl)$_n$-C$_1$-C$_{12}$-alkoxy,

C$_1$-C$_{12}$-alkylenyl-NH(C$_1$-C$_{12}$-alkyl),

C$_1$-C$_{12}$-alkylenyl-N(C$_1$-C$_{12}$-alkyl)$_2$, (C$_1$-C$_{12}$-alkylenyl)$_n$-heterocyclyl, unsubstituted or substituted by one or more substituent(s) selected from the group consisting of oxo, —C(O)—C$_1$-C$_{12}$-alkyl and R$^g$, (C$_1$-C$_{12}$-alkylenyl)$_n$-C$_3$-C$_6$-cycloalkyl unsubstituted or substituted by one or more R$^g$, (C$_1$-C$_{12}$-alkylenyl)$_n$-C$_6$-C$_{20}$-aryl unsubstituted or substituted by one or more R$^g$, —NH—C$_3$-C$_6$-cycloalkyl;

or R$^c$ and R$^d$ together with the nitrogen atom to which they are attached, form a 5 or 6 membered heterocyclyl which can or cannot comprise 1 or 2 additional heteroatom selected from N, O or S;

(C$_1$-C$_{12}$-alkylenyl)$_n$-NR$^e$C(O)R$^f$, wherein R$^e$ is H or C$_1$-C$_{12}$-alkyl, R$^f$ is halo, CN, OH, C$_1$-C$_{12}$-alkyl, C$_1$-C$_{12}$-haloalkyl, (C$_1$-C$_{12}$-alkylenyl)$_n$-C$_1$-C$_{12}$-alkoxy, C$_1$-C$_{12}$-hydroxyalkyl, C$_1$-C$_{12}$-cyanoalkyl, (C$_1$-C$_{12}$-alkylenyl)$_n$-NH$_2$, (C$_1$-C$_{12}$-alkylenyl)$_n$-NH(C$_1$-C$_{12}$-alkyl), (C$_1$-C$_{12}$-alkylenyl)$_n$-N(C$_1$-C$_{12}$-alkyl)$_2$, (C$_1$-C$_{12}$-alkylenyl)$_n$-C$_3$-C$_6$-cycloalkyl, (C$_1$-C$_{12}$-alkylenyl)$_n$-heterocyclyl, (C$_1$-C$_{12}$-alkylenyl)$_n$-NH—C$_3$-C$_6$-cycloalkyl, wherein said cycloalkyl, heterocyclyl, aryl or heteroaryl are unsubstituted or substituted by oxo, —C(O)—C$_1$-C$_{12}$-alkyl or one or more R$^g$;

R$^2$ is H, CN, —C(O)—NH(C$_1$-C$_{12}$-alkyl)-NH—C(O)—C$_1$-C$_{12}$-alkyl, —C(O)—N(C$_1$-C$_{12}$-alkyl)(C$_1$-C$_{12}$-alkoxy), —C(O)—N(C$_1$-C$_{12}$-alkyl)(C$_1$-C$_{12}$-alkylalkoxy), —C(O)—NH(heterocyclyl), —C(O)—NH(C$_1$-C$_{12}$-alkyl-heterocyclyl), —C(O)—N(C$_1$-C$_{12}$-alkyl)(heterocyclyl), —C(O)-heterocyclyl, which heterocyclyl groups are unsubstituted or substituted by one or more R$^g$ or —N(C$_1$-C$_{12}$-alkyl)-C(O)—C$_1$-C$_{12}$-alkyl, and —N(C$_1$-C$_{12}$-alkyl)$_2$;

R$^3$ is H, i-butyl, C$_1$-C$_{12}$-haloalkyl, cyclobutyl, —C(O)—C$_1$-C$_{12}$-alkyl-C$_3$-C$_6$-cycloalkyl, —C(O)—C$_1$-C$_{12}$-alkyl-heterocyclyl —C(O)—C$_1$-C$_{12}$-alkyl-C$_6$-C$_{20}$-aryl, —C(O)—C$_1$-C$_{12}$-alkyl-heteroaryl and pyridinyl;

R is H or C$_1$-C$_{12}$-alkyl;

R$^g$ is H, OH, halo, NH$_2$, C$_1$-C$_{12}$-alkyl, (C$_1$-C$_{12}$-alkylenyl)$_n$-C$_1$-C$_{12}$-alkoxy, C$_1$-C$_{12}$-haloalkyl, C$_1$-C$_{12}$-haloalkoxy, C$_1$-C$_{12}$-hydroxyalkyl, and C$_1$-C$_{12}$-cyanoalkyl;

n is 0 or 1;

wherein in the preceeding heteroaryl groups are 5 or 6 membered heteroaryls comprising 1, 2 or 3 heteroatom(s) selected from N, O or S and heterocyclyl groups are 5 to 10 membered heterocyclyls comprising 1, 2 or 3 heteroatom(s) selected from N, O or S;

with the proviso that the compounds of Formula I is not:

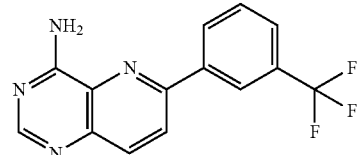

6-(3-(trifluoromethyl)phenyl)pyrido[3,2-d]pyrimidin-4-amine

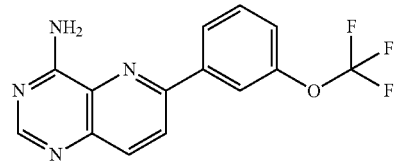

6-(3-(trifluoromethoxy)phenyl)pyrido[3,2-d]pyrimidin-4-amine

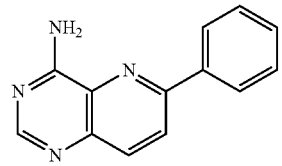

6-phenylpyrido[3,2-d]pyrimidin-4-amine

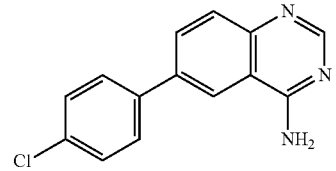

6-(4-chlorophenyl)quinazolin-4-amine

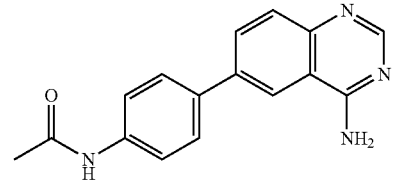

N-(4-(4-aminoquinazolin-6-yl)phenyl)acetamide

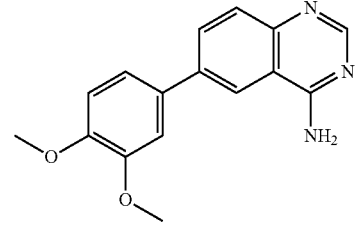

6-(3,4-dimethoxyphenyl)quinazolin-4-amine

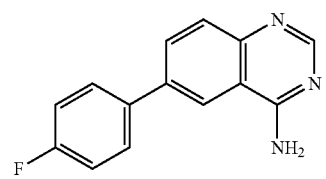

6-(4-fluorophenyl)quinazolin-4-amine

-continued

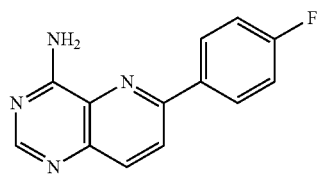

6-(4-fluorophenyl)pyrido[3,2-d]
pyrimidin-4-amine

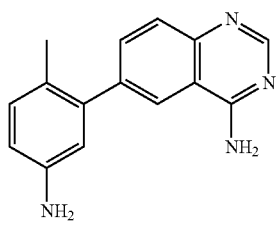

6-(5-amino-2-methylphenyl)
quinazolin-4-amine

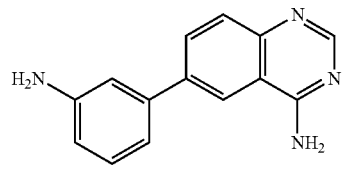

6-(3-aminophenyl)
quinazolin-4-amine

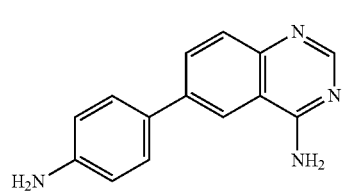

6-(4-aminophenyl)
quinazolin-4-amine

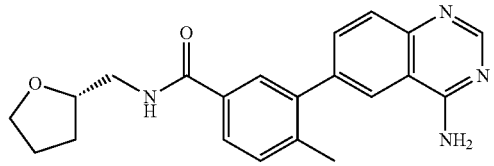

(S)-3-(4-aminoquinazolin-6-yl)-4-methyl-N-
((tetrahydrofuran-2-yl)methyl)benzamide

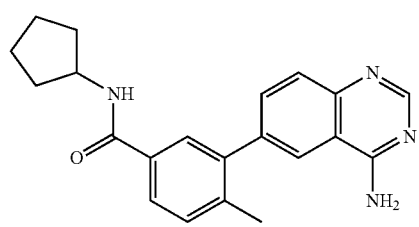

3-(4-aminoquinazolin-6-yl)-N-cyclopentyl-4-
methylbenzamide

-continued

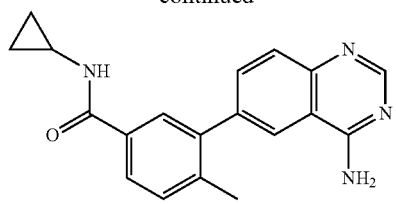

3-(4-aminoquinazolin-6-yl)-N-cyclopropyl-4-
methylbenzamide

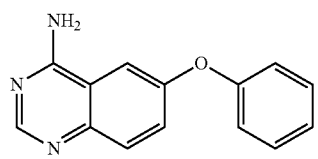

6-phenoxyquinazolin-4-amine

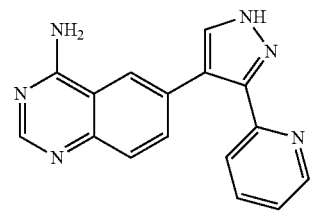

6-(3-(pyridin-2-yl)-1H-pyrazol-4-yl)
quinazolin-4-amine

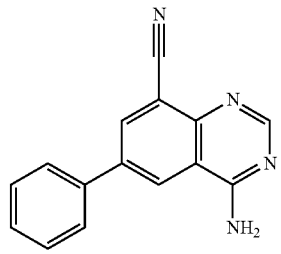

4-amino-6-phenyl-8-Quinazolinecarbonitrile

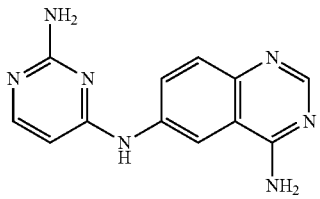

N6-(2-amino-4-pyrimidinyl)-4,6-Quinazolinediamine

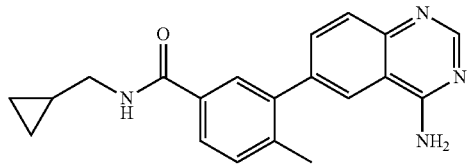

3-(4-amino-6-quinazolinyl)-N-(cyclopropylmethyl)-4-methyl-benzamide

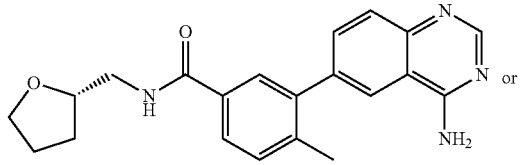

3-(4-amino-6-quinazolinyl)-4-methyl-N-[[(2S)-tetrahydro-2-
furanyl]methyl]-benzamide

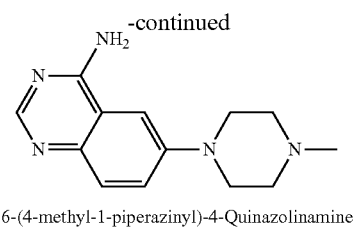

6-(4-methyl-1-piperazinyl)-4-Quinazolinamine 6-(3-(trifluoromethyl)phenyl)pyrido[3,2-d]pyrimidin-4-amine and 6-(3-(trifluoromethoxy)phenyl)pyrido[3,2-d]pyrimidin-4-amine are described in WO2009134973 as sirtuin modulators. WO2009134973 does not describe that these compounds can be useful to as MAP4K4 inhibitors or to treat angiogenesis. 6-phenylpyrido[3,2-d]pyrimidin-4-amine CAS 1025987-15-0 is commercially available and no pharmaceutical use thereof is described. 6-(4-chlorophenyl)quinazolin-4-amine, N-(4-(4-aminoquinazolin-6-yl)phenyl)acetamide, 6-(3,4-dimethoxyphenyl)quinazolin-4-amine and 6-(4-fluorophenyl)quinazolin-4-amine are described in WO2008009078 as useful for the treatment of viral infections. WO2008009078 does not describe these compounds as being useful as MAP4K4 inhibitors or to treat angiogenesis.

6-(4-fluorophenyl)pyrido[3,2-d]pyrimidin-4-amine is described in WO2006135993 as useful for the treatment of hepatitis. WO2006135993 does not describe this compound as being useful as MAP4K4 inhibitors or to treat angiogenesis. 6-(5-amino-2-methylphenyl)quinazolin-4-amine, 6-(3-aminophenyl)quinazolin-4-amine, 6-(4-aminophenyl)quinazolin-4-amine, (S)-3-(4-aminoquinazolin-6-yl)-4-methyl-N-((tetrahydrofuran-2-yl)methyl)benzamide, 3-(4-aminoquinazolin-6-yl)-N-cyclopentyl-4-methylbenzamide, 3-(4-aminoquinazolin-6-yl)-N-cyclopropyl-4-methylbenzamide, 3-(4-amino-6-quinazolinyl)-N-(cyclopropylmethyl)-4-methyl-benzamide, and 3-(4-amino-6-quinazolinyl)-4-methyl-N-[[(2S)-tetrahydro-2-furanyl]methyl]-benzamide are described in WO2006039718 as Tie-2 inhibitors, not as MAP4K4 inhibitors. 6-phenoxyquinazolin-4-amine and 6-(4-methyl-1-piperazinyl)-4-Quinazolinamine are described in EP30156 as intermediate compounds. No pharmaceutical use thereof is described. 6-(3-(pyridin-2-yl)-1H-pyrazol-4-yl)quinazolin-4-amine is described in WO2006044509 (ex. 420) as Alk4 and TGFβRI inhibitors. WO2006044509 does not describe this compound as being useful as MAP4K4 inhibitors or to treat angiogenesis. 4-amino-6-phenyl-8-Quinazolinecarbonitrile is described in Heterocycles, Volume 36, Issue 10 (Oct. 1, 1993), Pages 2273-2280 (compound 6dA). No pharmaceutical use is associated thereto. N6-(2-amino-4-pyrimidinyl)-4,6-Quinazolinediamine is described in U.S. Pat. No. 2,643,253.

In one embodiment, the invention relates to compounds of Formula (I-a):

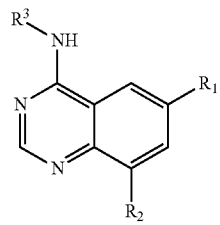

and stereoisomers, geometric isomers, tautomers, and pharmaceutically acceptable salts thereof, wherein $R^1$, $R^2$ and $R^3$ are as described herein.

In one embodiment, the invention relates to compounds of Formula (I-a-1):

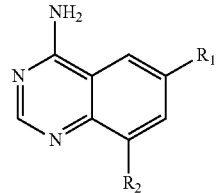

I-a-1 and stereoisomers, geometric isomers, tautomers, and pharmaceutically acceptable salts thereof, wherein $R^1$ and $R^2$ are as described herein.

In one embodiment, the invention relates to compounds of Formula (I-a-2):

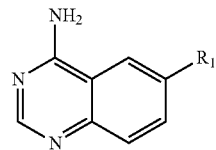

I-a-2 and stereoisomers, geometric isomers, tautomers, and pharmaceutically acceptable salts thereof, wherein $R^1$ is as described herein.

In one embodiment, the invention relates to compounds of Formula (I-b):

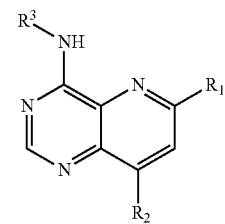

I-b and stereoisomers, geometric isomers, tautomers, and pharmaceutically acceptable salts thereof, wherein $R^1$, $R^2$ and $R^3$ are as described herein.

In one embodiment, the invention relates to compounds of Formula (I-b-1):

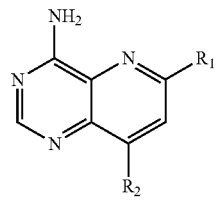

I-b-1 and stereoisomers, geometric isomers, tautomers, and pharmaceutically acceptable salts thereof, wherein $R^1$ and $R^2$ are as described herein.

In one embodiment, the invention relates to compounds of Formula (I-b-2):

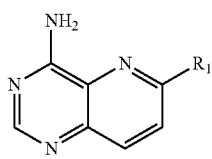

I-b-2 and stereoisomers, geometric isomers, tautomers, and pharmaceutically acceptable salts thereof, wherein $R^1$ is as described herein.

In one embodiment of the present invention, $R^2$ is H.

In one embodiment, $R^2$ is —C(O)—NH-heterocyclyl unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment, $R^2$ is —C(O)—NH-heterocyclyl, which heterocyclyl is selected from 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydrofurane, and is unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment, $R^2$ is CN.

In one embodiment, $R^2$ is —C(O)—NH($C_1$-$C_{12}$-alkyl)-NH—C(O)—$C_1$-$C_{12}$-alkyl.

In one embodiment, $R^2$ is C(O)—N($C_1$-$C_{12}$-alkyl)($C_1$-$C_{12}$-alkoxyl).

In one embodiment, $R^2$ is —C(O)—N($C_1$-$C_{12}$-alkyl)($C_1$-$C_{12}$-alkylalkoxy).

In one embodiment, $R^2$ is —C(O)—NH(heterocyclyl) unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment, $R^2$ is —C(O)—NH($C_1$-$C_{12}$-alkyl-heterocyclyl) unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment, $R^2$ is —C(O)—N($C_1$-$C_{12}$-alkyl)(heterocyclyl) unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$. In one embodiment this heterocyclyl is selected from 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydrofurane, and is unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment, $R^2$ is —C(O)-heterocyclyl unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$. In one embodiment, this heterocyclyl is selected from 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydrofurane, and is unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$.

In one embodiment n is 0. In one embodiment n is 1.

In one embodiment, $R^3$ is H.

In one embodiment, $R^3$ is i-butyl. In one embodiment, $R^3$ is $C_1$-$C_{12}$-haloalkyl. In one embodiment, $R^3$ is cyclobutyl. In one embodiment, $R^3$ is —C(O)—$C_1$-$C_{12}$-alkyl-$C_3$-$C_6$-cycloalkyl. In one embodiment, $R^3$ is —C(O)—$C_1$-$C_{12}$-alkyl-heterocyclyl. In one embodiment, this heterocyclyl is selected from 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydrofurane, and is unsubstituted or substituted by one or more $R^g$. In one embodiment, $R^3$ is —C(O)—$C_1$-$C_{12}$-alkyl-$C_6$-$C_{20}$-aryl, for example methylphenyl. In one embodiment, $R^3$ is —C(O)—$C_1$-$C_{12}$-alkyl-heteroaryl, for example 5 or 6 membered heteroaryls comprising 1, 2 or 3 heteroatom(s) selected from N, O or S. In one embodiment, $R^3$ is pyridinyl.

In one embodiment $R^1$ is $C_6$-$C_{20}$-aryl. In one embodiment $R^1$ is phenyl.

In one embodiment $R^1$ is $C_6$-$C_{20}$-aryl (for example phenyl) unsubstituted or substituted by one or more substituent(s) selected from the group consisting of CN, OH, $NH_2$, halo, $C_1$-$C_{12}$-alkyl, $C_1$-$C_{12}$-alkoxy unsubstituted or substituted by one or more substituent(s) selected from the group consisting: of $C_3$-$C_6$-cycloalkyl, heterocyclyl, aryl and heteroaryl; and $C_1$-$C_{12}$-hydroxyalkyl, for example the following groups:

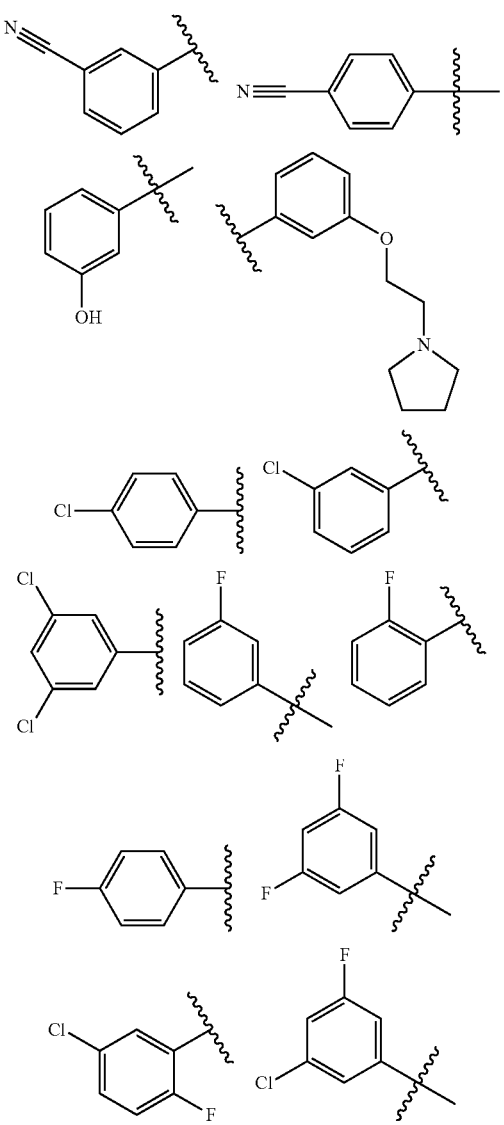

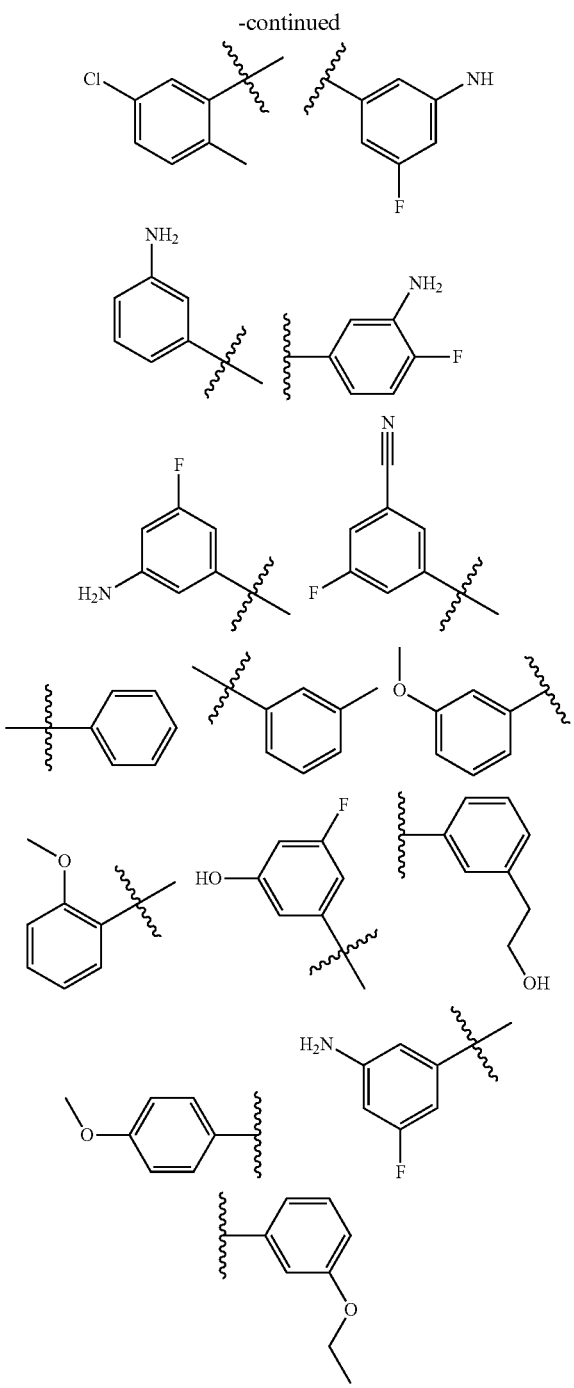

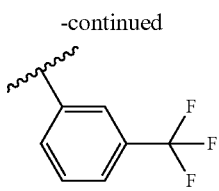

In one embodiment R[1] is $C_6$-$C_{20}$-aryl unsubstituted or substituted by one or more $(C_1$-$C_{12}$-alkylenyl$)_n$-C(O)OH, wherein n is 0 or 1.

In one embodiment R[1] is $C_6$-$C_{20}$-aryl unsubstituted or substituted by one or more substituent(s) selected from the group consisting of $C_6$-$C_{20}$-aryl and $C_3$-$C_6$-cycloalkyl, each of which is unsubstituted or substituted by one or more R[g], and R[g] is as defined herein.

In one embodiment R[1] is $C_6$-$C_{20}$-aryl unsubstituted or substituted by $(C_1$-$C_{12}$-alkylenyl$)_n$-heterocyclyl selected from the group consisting of 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydrofurane, each of which is unsubstituted or substituted by one or more substituent(s) selected from the group consisting of: halo, oxo, OH, $NH_2$, $C_1$-$C_{12}$-alkyl, $C_1$-$C_{12}$-hydroxyalkyl, $C_1$-$C_{12}$-haloalkyl, $(C_1$-$C_{12}$-alkylenyl$)_n$-$C_1$-$C_{12}$-alkoxy, —NH($C_1$-$C_{12}$-alkyl), —N($C_1$-$C_{12}$-alkyl$)_2$, —C(O)—$C_1$-$C_{12}$-alkyl, —C(O)O—$C_1$-$C_{12}$-alkyl, $(C_1$-$C_{12}$-alkylenyl$)_n$-C(O)—NH($C_1$-$C_{12}$-alkyl), —C(O)—NH($C_1$-$C_{12}$-hydroxyalkyl), $(C_1$-$C_{12}$-alkylenyl$)_n$-C(O)—N($C_1$-$C_{12}$-alkyl$)_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl$)_2$, $C_1$-$C_{12}$-alkylenyl-C(O)N($C_1$-$C_{12}$-alkyl$)_2$, —C(O)OH, —C(O)-heterocyclyl, heterocyclyl and $(C_1$-$C_{12}$-alkylenyl$)_n$-heteroaryl, which heterocyclyl and heteroaryl group(s) can be unsubstituted or substituted by one or more substituent(s) selected from the group consisting of: OH, $NH_2$, halo, $C_1$-$C_{12}$-alkyl, $C_1$-$C_{12}$-alkoxy, $C_1$-$C_{12}$-haloalkyl and $C_1$-$C_{12}$-hydroxyalkyl; and n is 0 or 1, for example the following groups:

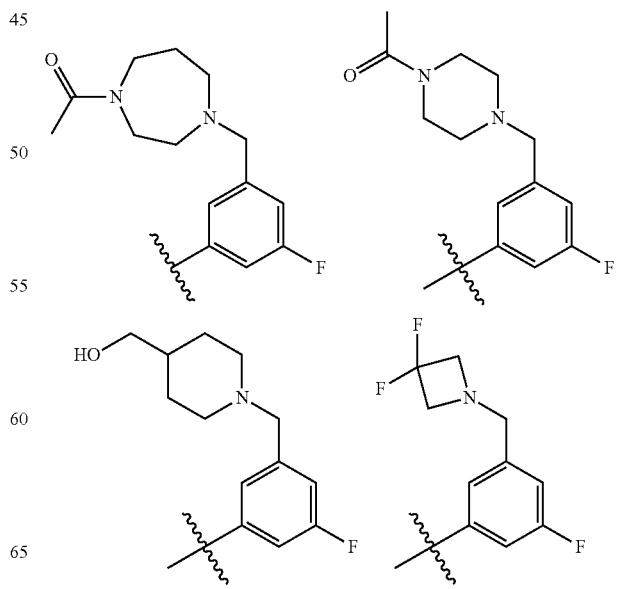

In one embodiment R[1] is $C_6$-$C_{20}$-aryl unsubstituted or substituted by one or more substituent(s) selected from the group consisting of $C_1$-$C_{12}$-haloalkyl and $C_1$-$C_{12}$-haloalkoxy, for example the following groups:

-continued
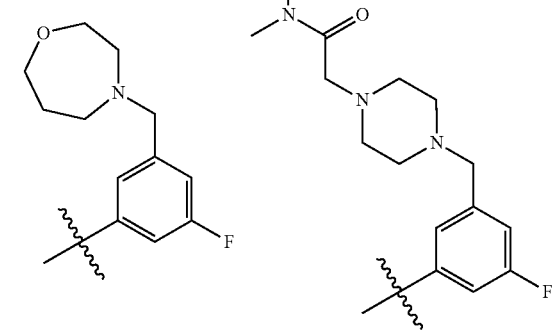
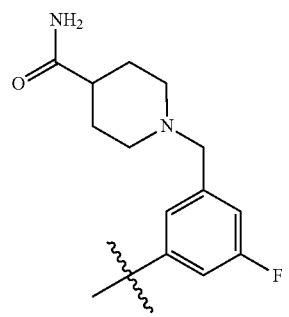
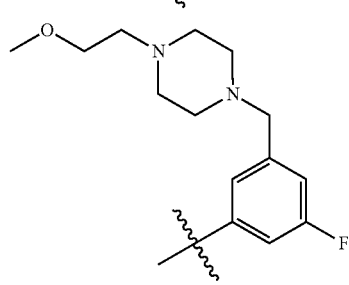
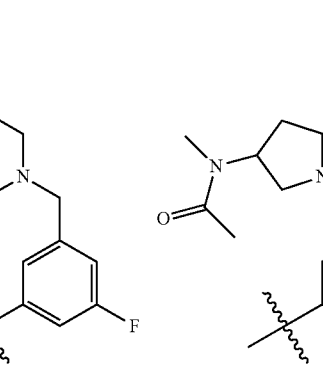
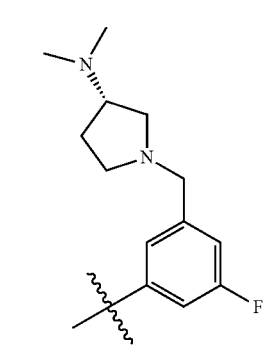
-continued
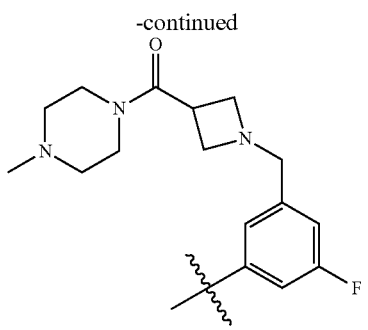
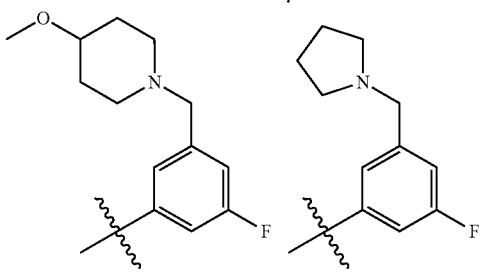
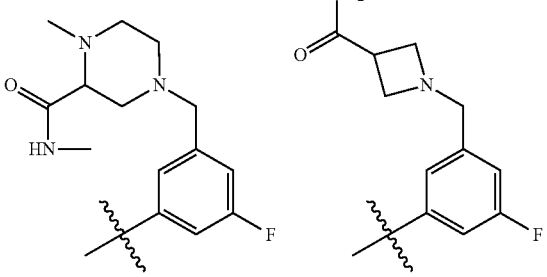
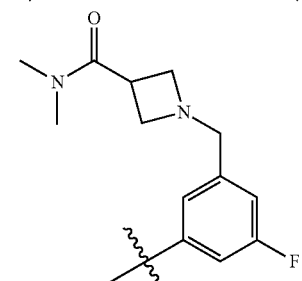
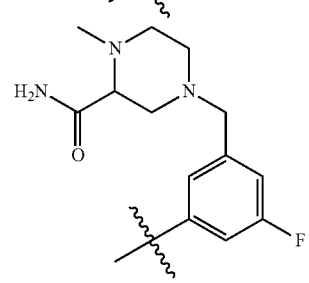
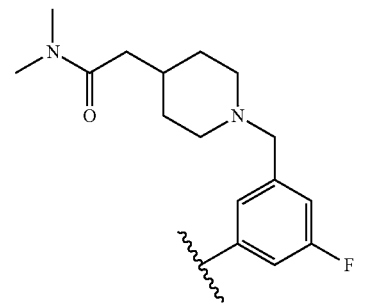

-continued

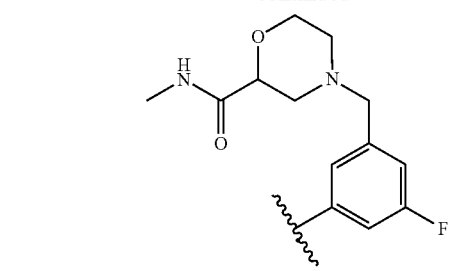
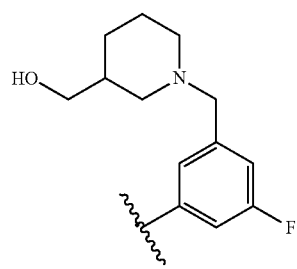
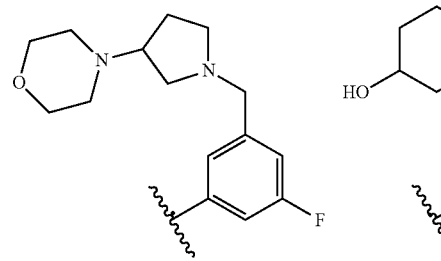
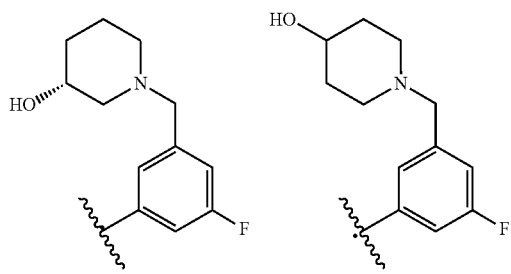
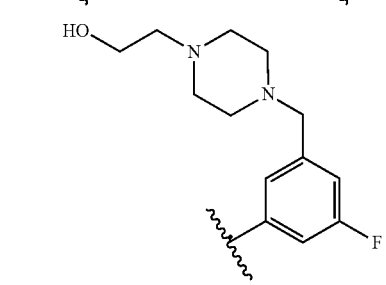
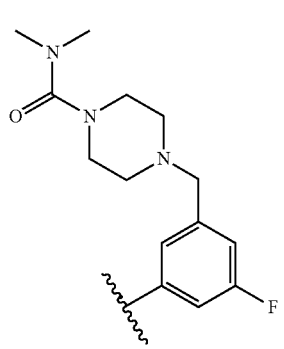

-continued

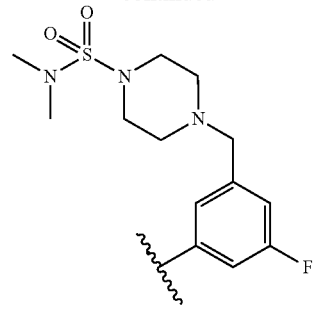
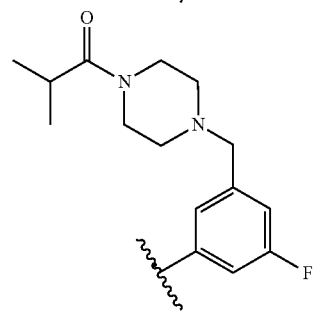
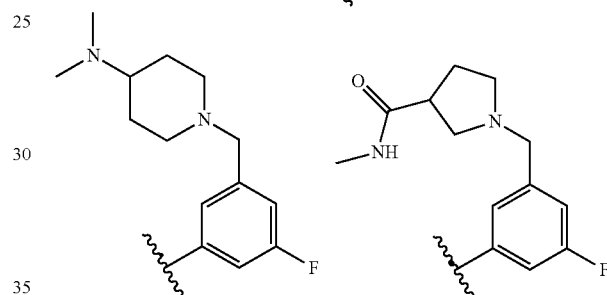
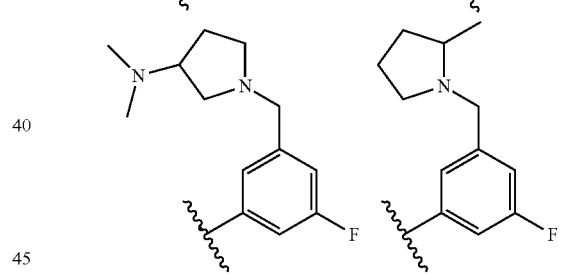
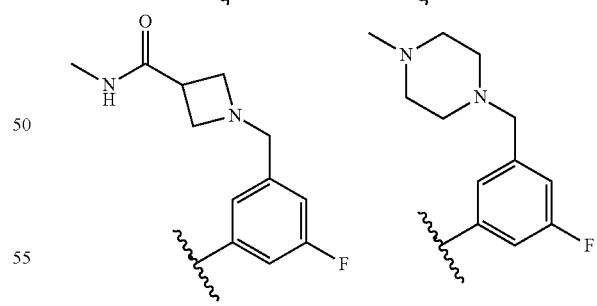

In one embodiment $R^1$ is $C_6$-$C_{20}$-aryl unsubstituted or substituted by one or more $(C_1$-$C_{12}$-alkylenyl$)_n$-heteroaryl unsubstituted or substituted by one or more substituent(s) selected from the group consisting of: halo, OH, $NH_2$, $C_1$-$C_{12}$-alkyl, $C_1$-$C_{12}$-hydroxyalkyl, $C_1$-$C_{12}$-haloalkyl, $(C_1$-$C_{12}$-alkylenyl$)_n$-$C_1$-$C_{12}$-alkoxy, —NH($C_1$-$C_{12}$-alkyl), —N($C_1$-$C_{12}$-alkyl)$_2$, —N($C_1$-$C_{12}$-alkyl)C(O)—$C_1$-$C_{12}$-alkyl, —C(O)—$C_1$-$C_{12}$-alkyl, —C(O)—$NH_2$, —C(O)—NH($C_1$-$C_{12}$-alkyl), —C(O)—NH($C_1$-$C_{12}$-hydroxyalkyl), —C(O)—N(C$_1$-C$_{12}$-alkyl)$_2$, —C(O)—NH(C$_1$-C$_{12}$-haloalkyl), —C(O)—NH-heterocyclyl, —S(O)$_2$—C$_1$-C$_{12}$-alkyl, —S(O)$_2$—N(C$_1$-C$_{12}$-alkyl)$_2$, C$_1$-C$_{12}$-alkylenyl-C(O)N(C$_1$-C$_{12}$-alkyl)$_2$, —C(O)OH, —C(O)-heterocyclyl and heterocyclyl, which heterocyclyl group(s) can be unsubstituted or substituted by one or more substituent(s) selected from the group consisting of: OH, NH$_2$, halo, C$_1$-C$_{12}$-alkyl, C$_1$-C$_{12}$-alkoxy, C$_1$-C$_{12}$-haloalkyl, and C$_1$-C$_{12}$-hydroxyalkyl and n is 0 or 1.

In one embodiment R$^1$ is C$_6$-C$_{20}$-aryl unsubstituted or substituted by one or more (C$_1$-C$_{12}$-alkylenyl)$_n$-NR$^a$R$^b$; wherein R$^a$ and R$^b$ are independently selected from: H, C$_1$-C$_{12}$-alkyl, C$_1$-C$_{12}$-hydroxyalkyl, C$_1$-C$_{12}$-haloalkyl, (C$_1$-C$_{12}$-alkylenyl)$_n$-C$_1$-C$_{12}$-alkoxy, —S(O)$_2$—(C$_1$-C$_{12}$-alkylenyl)$_n$-heterocyclyl unsubstituted or substituted by one or more R$^g$, C$_1$-C$_{12}$-alkylenyl-C$_6$-C$_{20}$-aryl, which aryl is unsubstituted or substituted by one or more R$^g$, (C$_1$-C$_{12}$-alkylenyl)$_n$-C$_3$-C$_6$-cycloalkyl unsubstituted or substituted by one or more R$^g$, (C$_1$-C$_{12}$-alkylenyl)$_n$-heterocyclyl unsubstituted or substituted by one or more oxo, —C(O)—C$_1$-C$_{12}$-alkyl, —C(O)O—C$_1$-C$_{12}$-alkyl and R$^g$, C$_1$-C$_{12}$-alkylenyl-C(O)-heteroaryl unsubstituted or substituted by one or more R$^g$, C$_1$-C$_{12}$-alkylenyl-NH$_2$, C$_1$-C$_{12}$-alkylenyl-NH(C$_1$-C$_{12}$-alkyl), C$_1$-C$_{12}$-alkylenyl-N(C$_1$-C$_{12}$-alkyl)$_2$, C$_1$-C$_{12}$-alkylenyl-C(O)NH$_2$, C$_1$-C$_{12}$-alkylenyl-C(O)NH(C$_1$-C$_{12}$-alkyl), C$_1$-C$_{12}$-alkylenyl-C(O)N(C$_1$-C$_{12}$-alkyl)$_2$, R$^g$ is as defined herein and n is 0 or 1, for example the following groups:

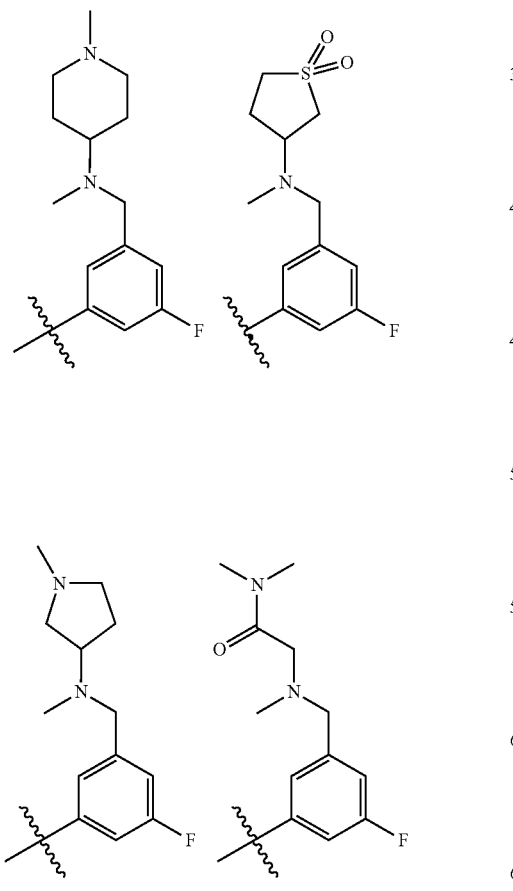

-continued

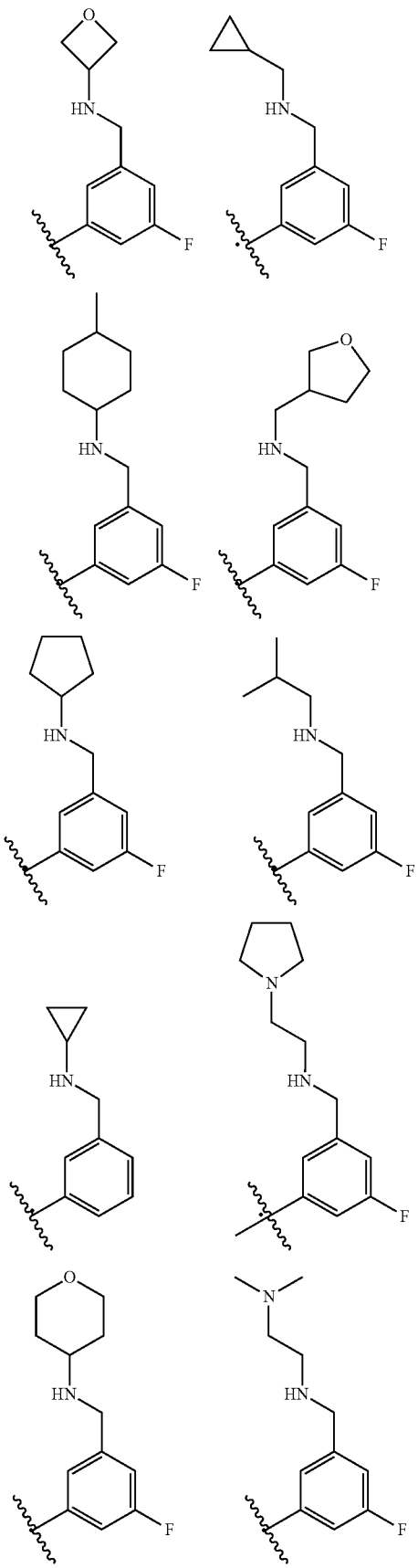

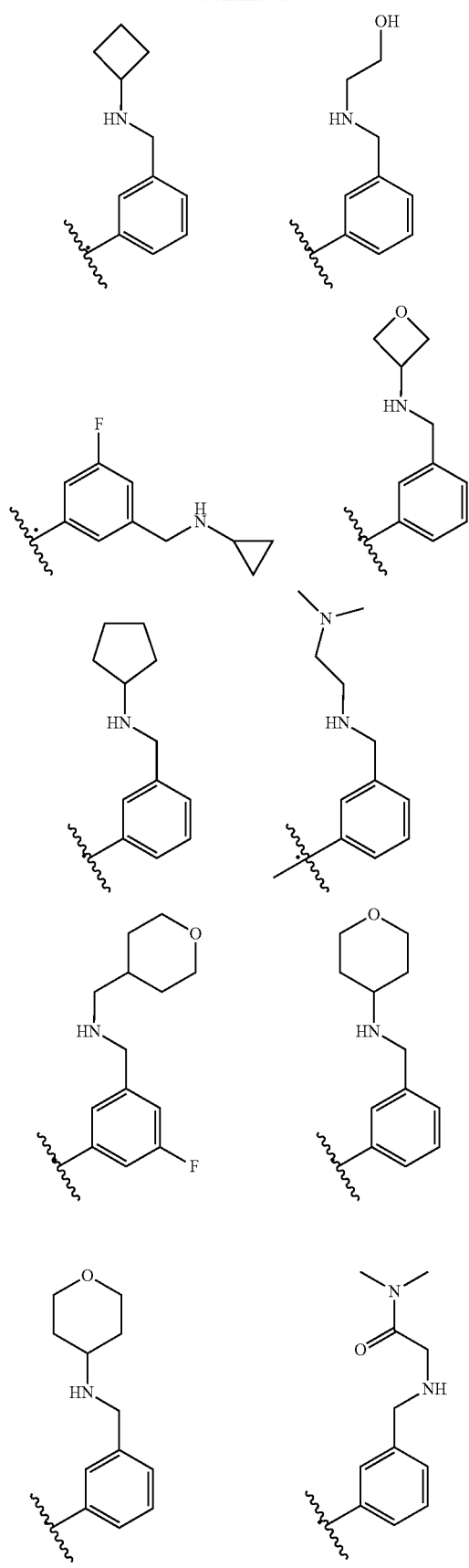
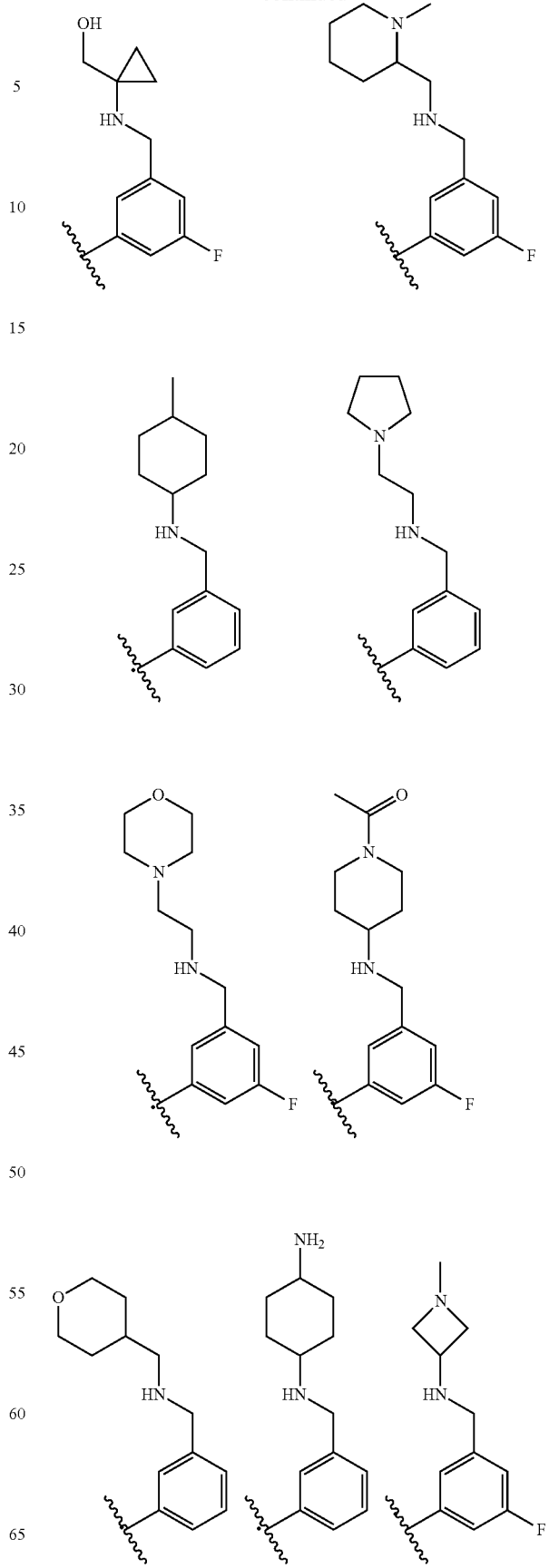

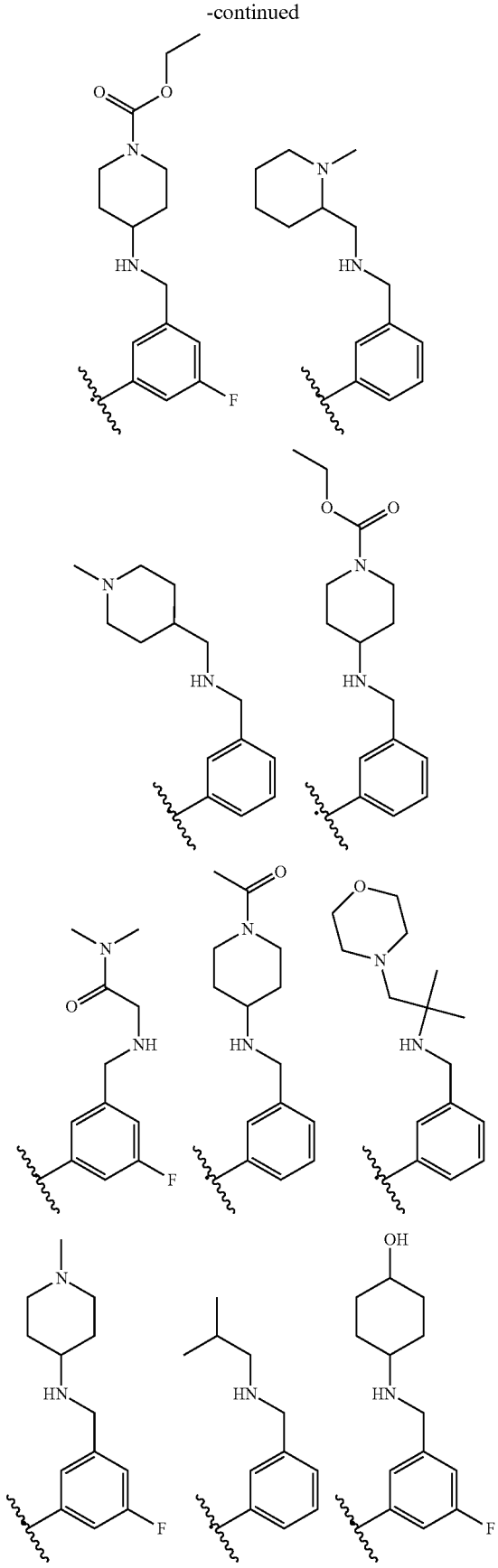
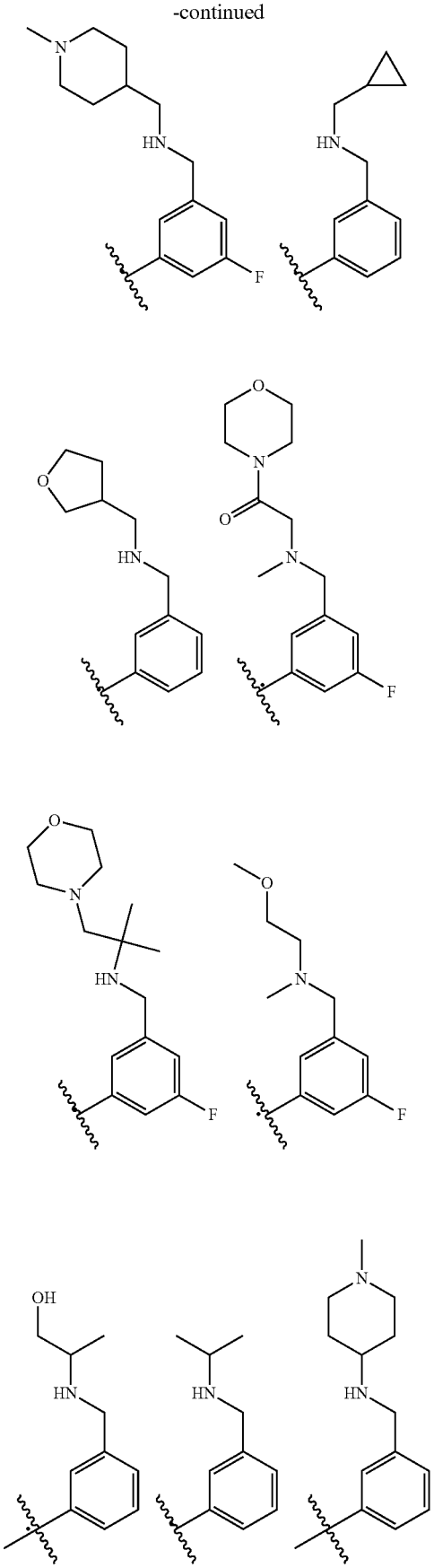

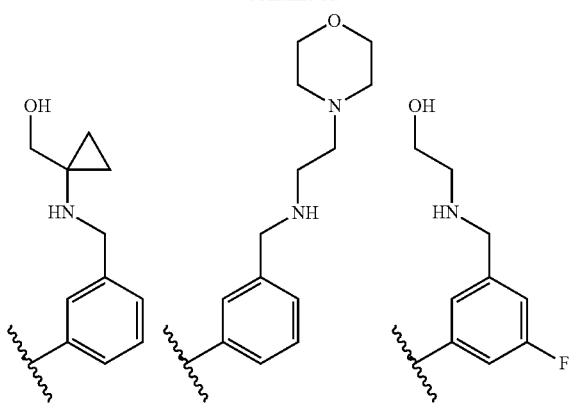

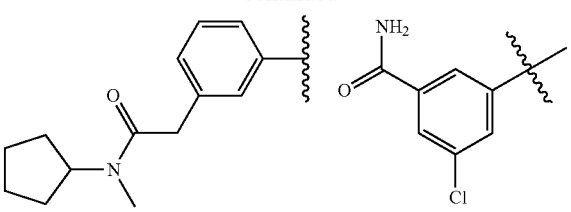

In one embodiment R¹ is $C_6$-$C_{20}$-aryl unsubstituted or substituted by one or more $(C_1$-$C_{12}$-alkylenyl$)_n$-NR$^e$C(O)R$^f$, wherein R$^e$ is H and R$^f$ is $C_1$-$C_{12}$-alkyl, $C_1$-$C_{12}$-haloalkyl, $(C_1$-$C_{12}$-alkylenyl$)_n$-$C_1$-$C_{12}$-alkoxy, $C_1$-$C_{12}$-hydroxyalkyl, $(C_1$-$C_{12}$-alkylenyl$)_n$-NH($C_1$-$C_{12}$-alkyl), $(C_1$-$C_{12}$-alkylenyl)-N($C_1$-$C_{12}$-alkyl$)_2$, $(C_1$-$C_{12}$-alkylenyl$)_n$-heterocyclyl unsubstituted or substituted by one or more R$^g$, $(C_1$-$C_{12}$-alkylenyl$)_n$-$C_3$-$C_6$-cycloalkyl, unsubstituted or substituted by one or more R$^g$ and R$^g$ is as defined herein and n is 0 or 1, for example the following groups:

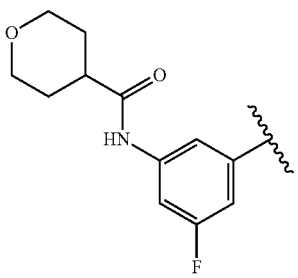

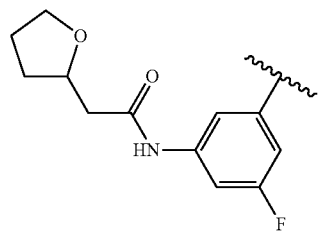

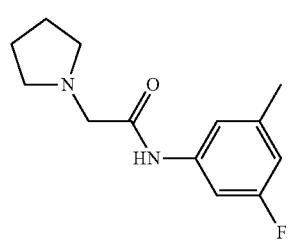

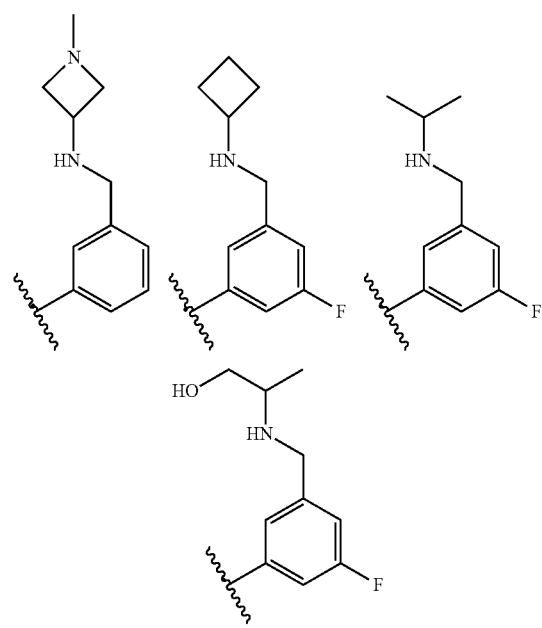

In one embodiment R¹ is $C_6$-$C_{20}$-aryl unsubstituted or substituted by one or more $(C_1$-$C_{12}$-alkylenyl$)_n$-C(O)NR$^c$R$^d$, wherein R$^c$ and R$^d$ are independently selected from H, $C_1$-$C_{12}$-alkyl, $C_1$-$C_{12}$-haloalkyl, $(C_1$-$C_{12}$-alkylenyl$)_n$-$C_1$-$C_{12}$-alkoxy, $C_1$-$C_{12}$-alkylenyl-NH($C_1$-$C_{12}$-alkyl), $C_1$-$C_{12}$-alkylenyl-N($C_1$-$C_{12}$-alkyl$)_2$, $(C_1$-$C_{12}$-alkylenyl$)_n$-heterocyclyl, unsubstituted or substituted by one or more substituent(s) selected from the group consisting of: oxo, —C(O)—$C_1$-$C_{12}$-alkyl and R$^g$, $(C_1$-$C_{12}$-alkylenyl$)_n$-$C_3$-$C_6$-cycloalkyl unsubstituted or substituted by one or more R$^g$, —NH—$C_3$-$C_6$-cycloalkyl; wherein R$^g$ is as defined herein and n is 0 or 1, for example the following groups:

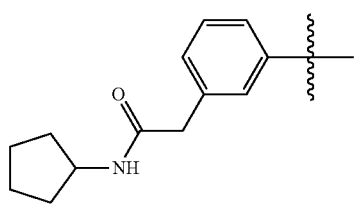

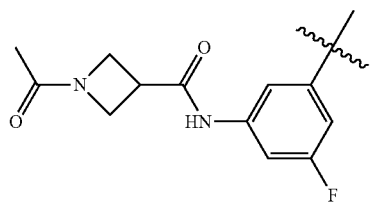

35
-continued
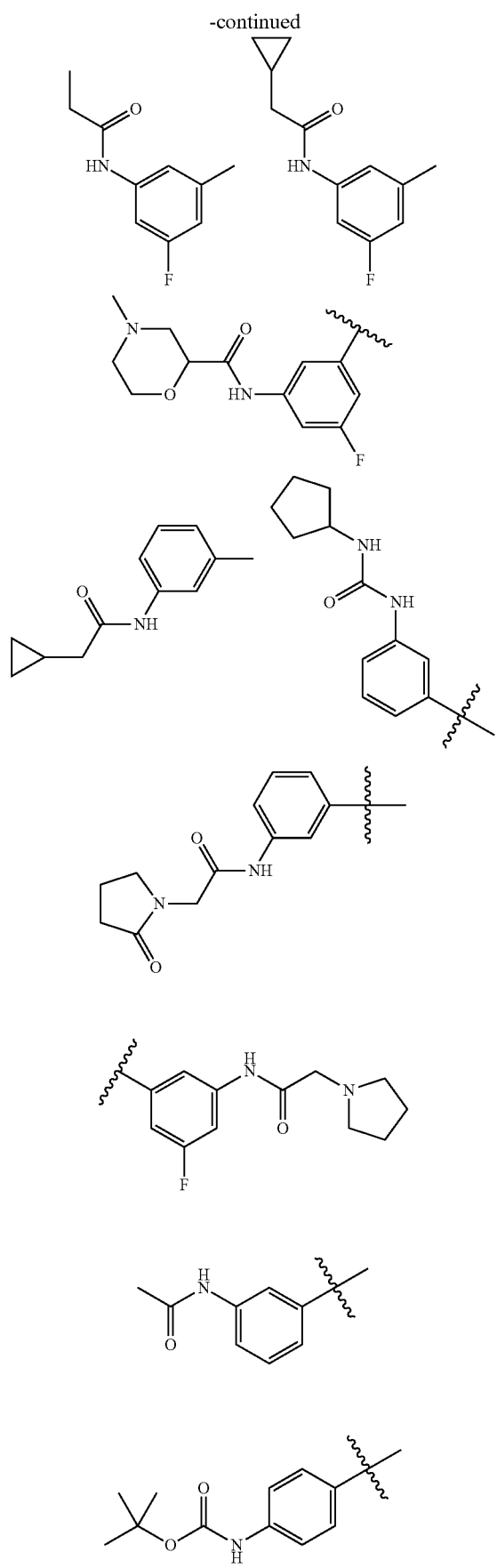
36
-continued
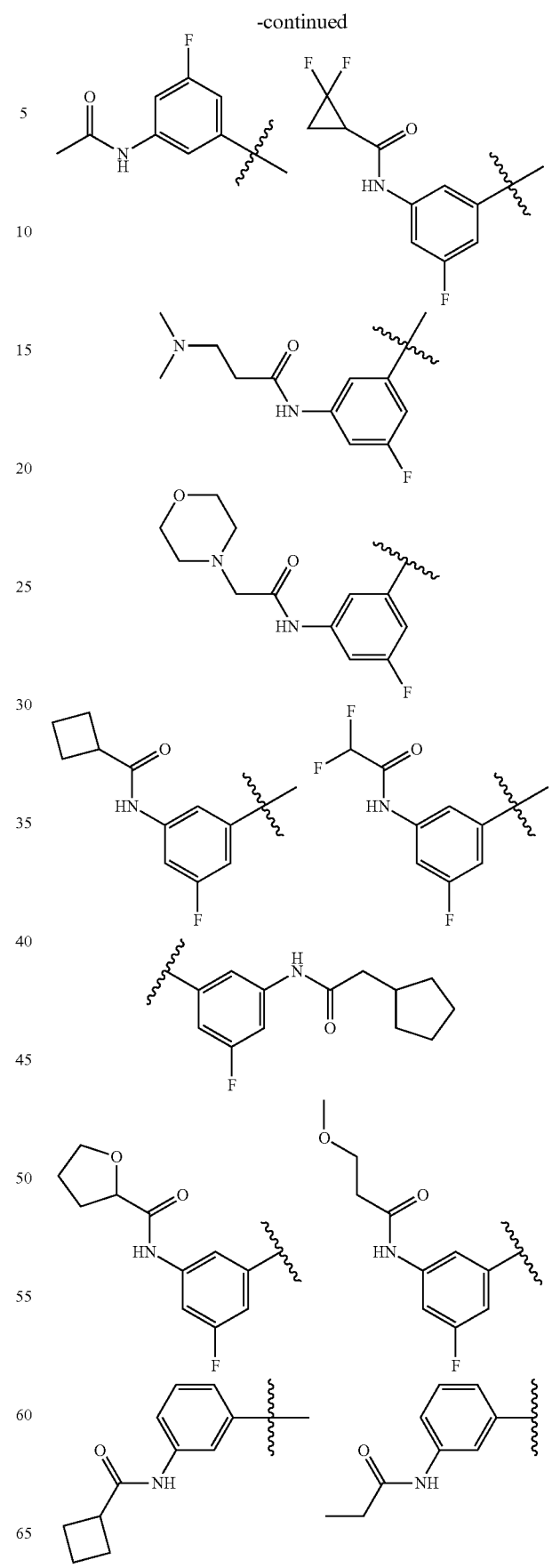

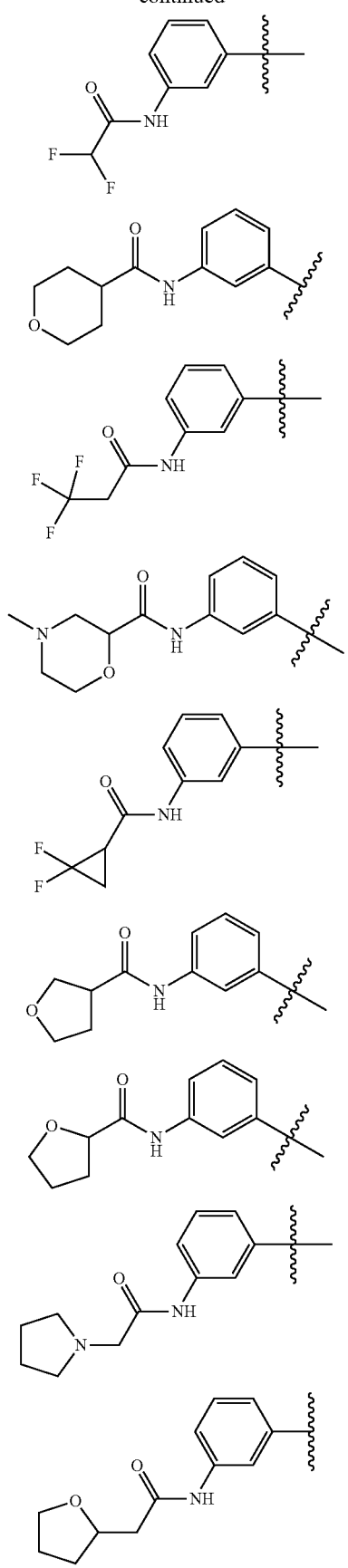
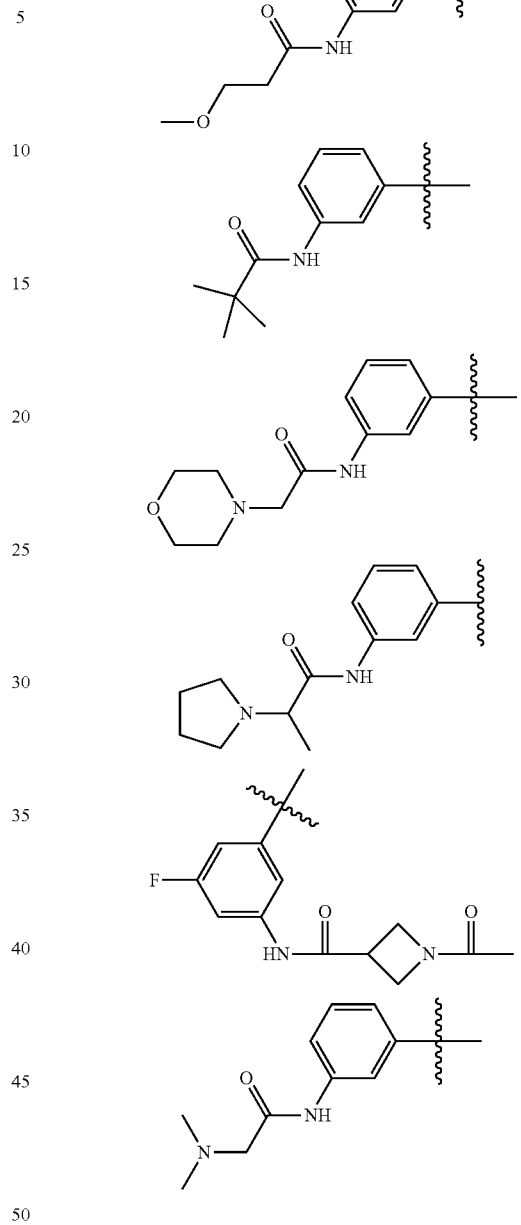

In all embodiments wherein $R^1$ is $C_6$-$C_{20}$-aryl it can for example be phenyl.

In one embodiment, $R^1$ is pyridine. In one embodiment, $R^1$ is pyridine unsubstituted or substituted by one or more substituent(s) selected from the group consisting of: CN; $NH_2$; Halo; $C_1$-$C_{12}$-alkyl; $C_1$-$C_{12}$-haloalkyl; ($C_1$-$C_{12}$-alkylenyl)$_n$-$NR^aR^b$; wherein $R^a$ and $R^b$ are independently selected from: H, $C_1$-$C_{12}$-alkylenyl-N($C_1$-$C_{12}$-alkyl)$_2$ and ($C_1$-$C_{12}$-alkylenyl)$_n$-heterocyclyl unsubstituted or substituted by one or more oxo, C(O)—$C_1$-$C_{12}$-alkyl, —C(O)O—$C_1$-$C_{12}$-alkyl and $R^g$, wherein $R^g$ is as defined herein and n is 0 or 1, for example the following groups:

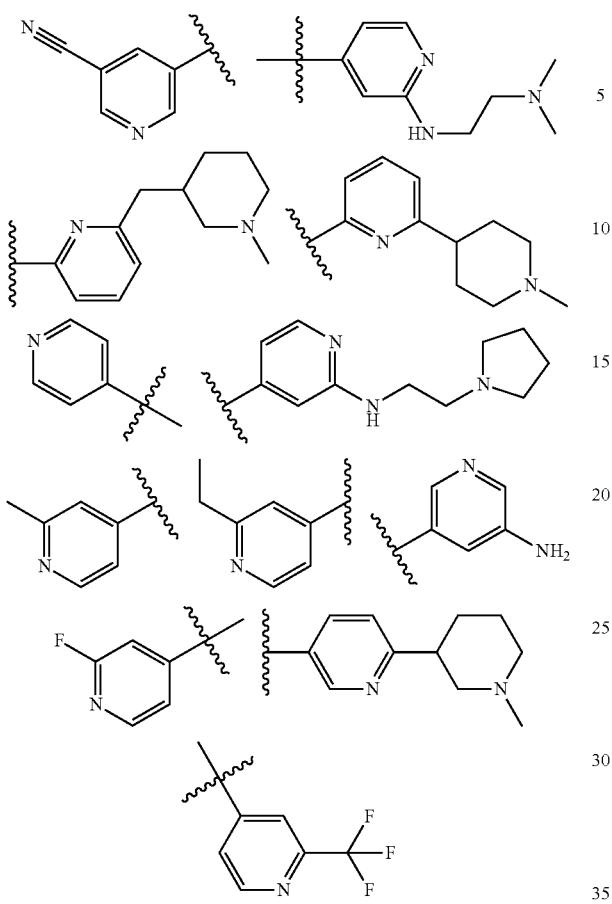
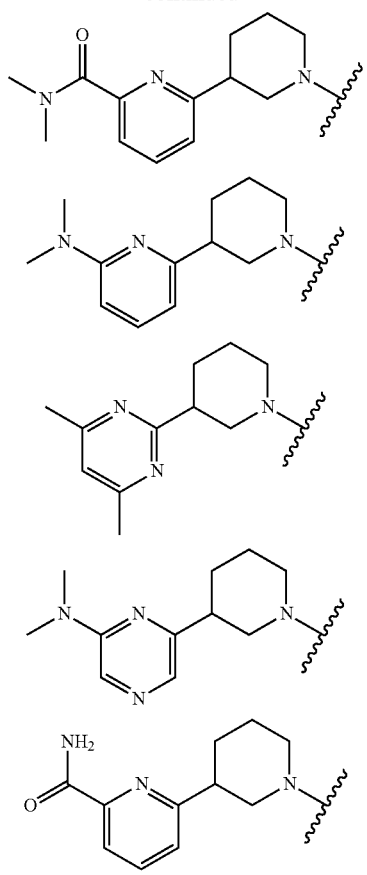

In one embodiment, R¹ is N-linked piperidine unsubstituted or substituted by $C_1$-$C_{12}$-alkyl, $(C_1$-$C_{12}$-alkylenyl)$_n$-$C_1$-$C_{12}$-alkoxy, $C_1$-$C_{12}$-hydroxyalkyl, $C_1$-$C_{12}$-haloalkyl, $(C_1$-$C_{12}$-alkylenyl)$_n$-heteroaryl unsubstituted or substituted by one or more substituent(s) selected from the group consisting of: OH, $C_1$-$C_{12}$-alkyl, $C_1$-$C_{12}$-haloalkyl, $(C_1$-$C_{12}$-alkylenyl)$_n$-$C_1$-$C_{12}$-alkoxy, —N($C_1$-$C_{12}$-alkyl)$_2$, —C(O)—NH$_2$, —C(O)—NH($C_1$-$C_{12}$-alkyl), —C(O)—N($C_1$-$C_{12}$-alkyl)$_2$, and —S(O)$_2$—$C_1$-$C_{12}$-alkyl, $(C_1$-$C_{12}$-alkylenyl)$_n$-C(O)NR$^c$R$^d$, wherein R$^c$ and R$^d$ are independently selected from: H, $C_1$-$C_{12}$-alkyl, $(C_1$-$C_{12}$-alkylenyl)$_n$-$C_1$-$C_{12}$-alkoxy, and $(C_1$-$C_{12}$-alkylenyl)$_n$-heterocyclyl, unsubstituted or substituted by one or more R$^g$, or R$^c$ and R$^d$ together with the nitrogen atom to which they are attached, form a 5 or 6 membered heterocyclyl comprising 1 or 2 additional heteroatom selected from N, O or S, or is $(C_1$-$C_{12}$-alkylenyl)$_n$-NR$^e$C(O)R$^f$, wherein R$^e$ is H and R$^f$ is $(C_1$-$C_{12}$-alkylenyl)$_n$-$C_1$-$C_{12}$-alkoxy, $(C_1$-$C_{12}$-alkylenyl)$_n$-heterocyclyl, and n and R$^g$ are as defined herein, for example the following groups:

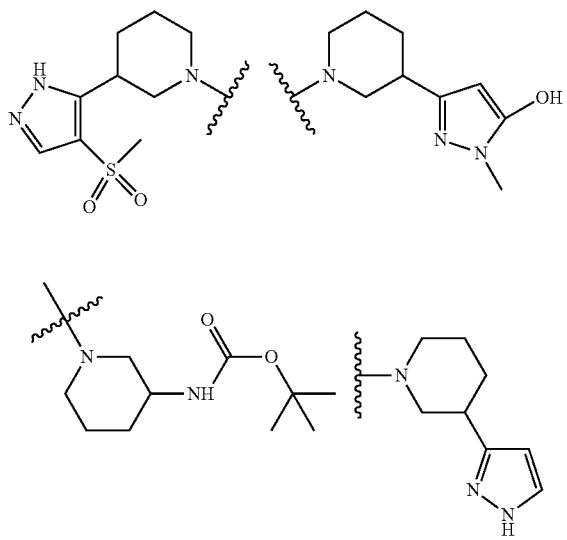
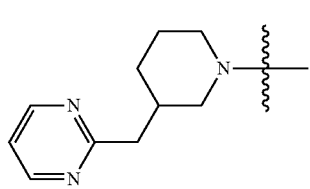
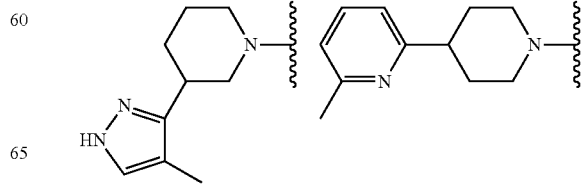

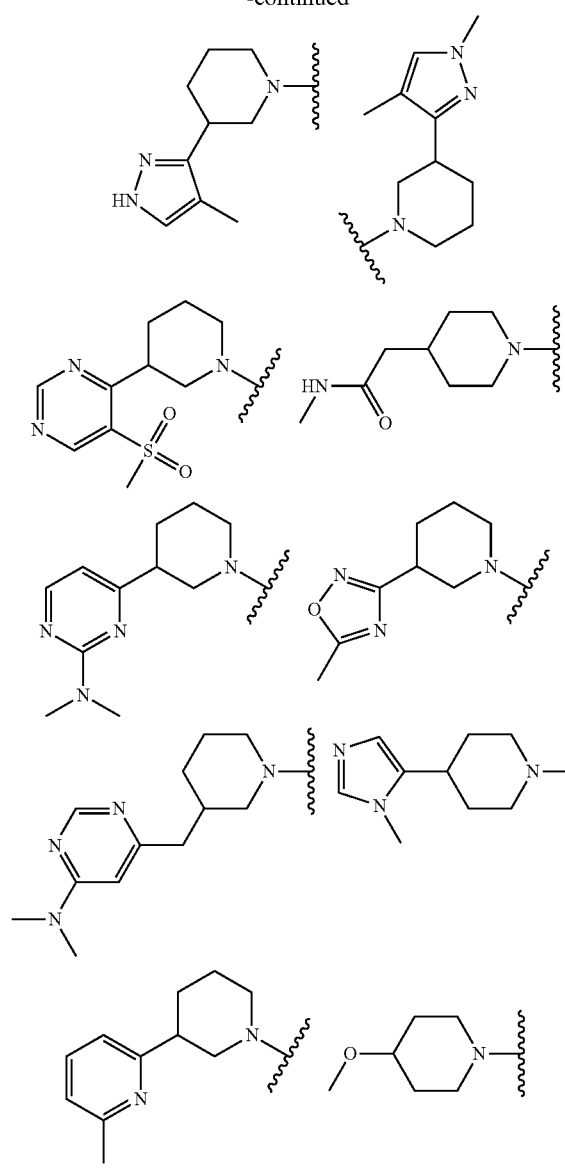
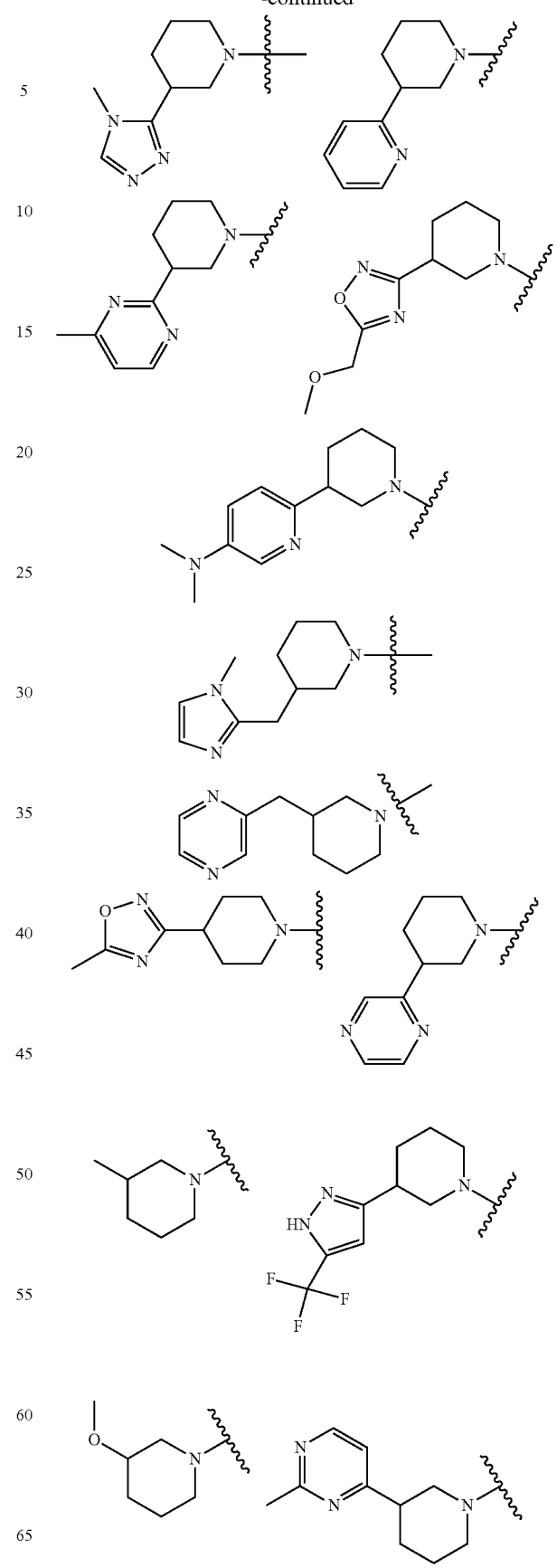

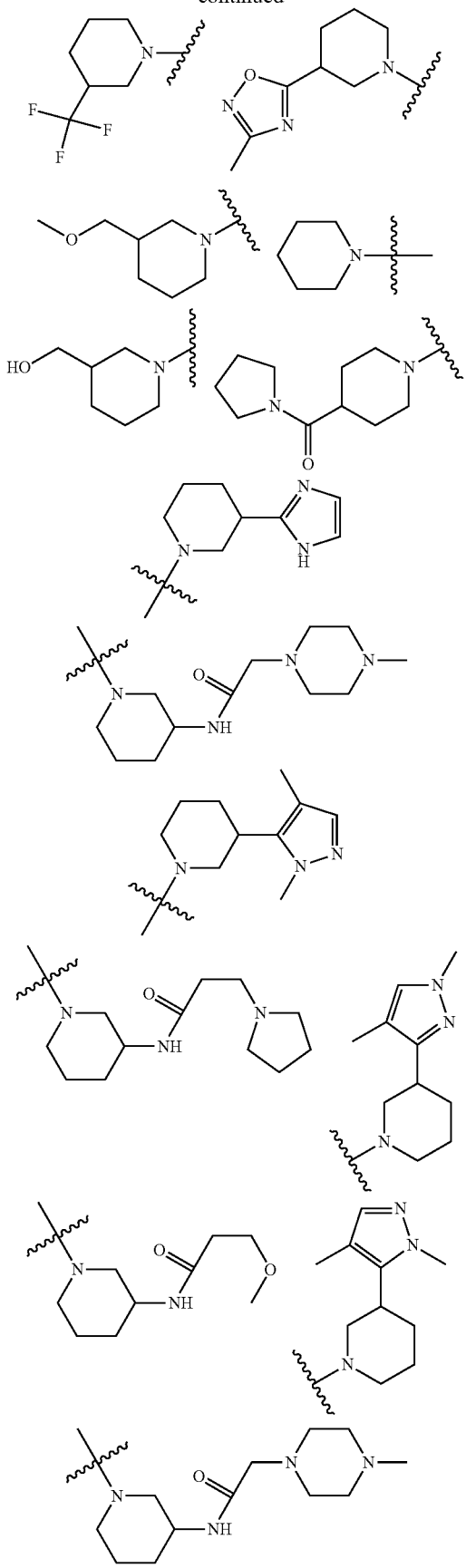
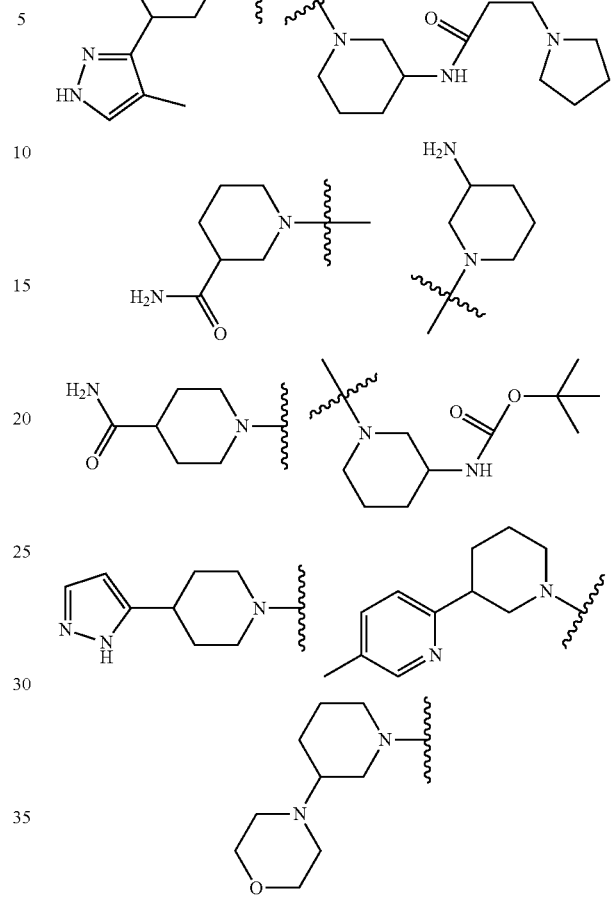
In one embodiment, R¹ is N-linked piperazine. In one embodiment, R¹ is N-linked piperazine unsubstituted or substituted by one or more substituent(s) selected from the group consisting of: $C_1$-$C_{12}$-alkyl, —C(O)—$C_1$-$C_{12}$-alkyl, ($C_1$-$C_{12}$-alkylenyl)$_n$-C(O)OH, and ($C_1$-$C_{12}$-alkylenyl)$_n$-C(O)O—$C_1$-$C_{12}$-alkyl, and n is as defined herein, for example the following groups:
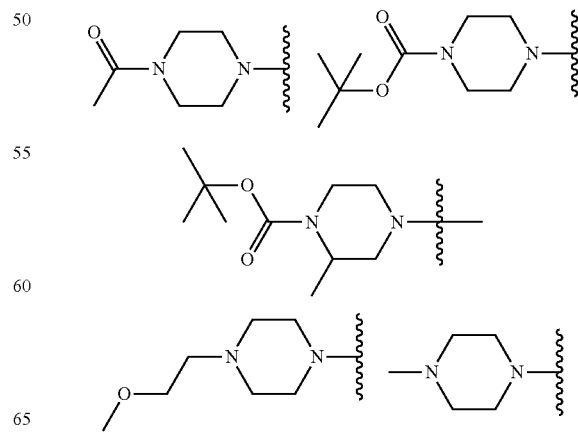

-continued

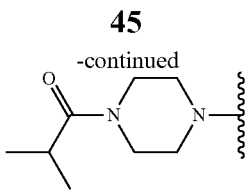

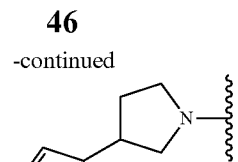

In one embodiment, $R^1$ is N-linked pyrrolidine. In one embodiment, $R^1$ is N-linked pyrrolidine unsubstituted or substituted by one or more substituent(s) selected from the group consisting of: $C_1$-$C_{12}$-haloalkyl, ($C_1$-$C_{12}$-alkylenyl)$_n$-heterocyclyl, ($C_1$-$C_{12}$-alkylenyl)$_n$-NR$^e$C(O)R$^f$, wherein R$^e$ is H or $C_1$-$C_{12}$-alkyl, R$^f$ is $C_1$-$C_{12}$-alkyl, ($C_1$-$C_{12}$-alkylenyl)$_n$-heteroaryl unsubstituted or substituted by one or more substituent(s) selected from the group consisting of: $C_1$-$C_{12}$-alkyl, $C_1$-$C_{12}$-hydroxyalkyl, —NH($C_1$-$C_{12}$-alkyl), and N($C_1$-$C_{12}$-alkyl)$_2$, ($C_1$-$C_{12}$-alkylenyl)$_n$-NR$^a$R$^b$, wherein R$^a$ and R$^b$ are independently selected from H and $C_1$-$C_{12}$-alkyl; ($C_1$-$C_{12}$-alkylenyl)$_n$-C(O)NR$^c$R$^d$, wherein R$^c$ and R$^d$ are independently selected from H and $C_1$-$C_{12}$-alkyl, for example the following groups:

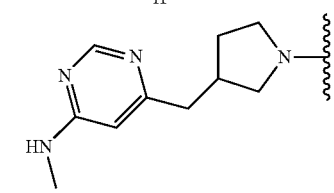

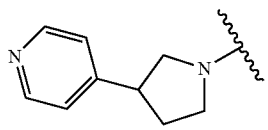

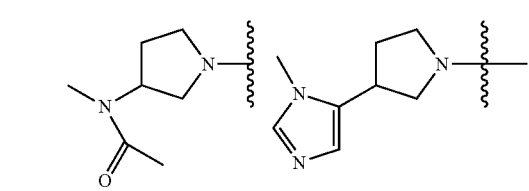
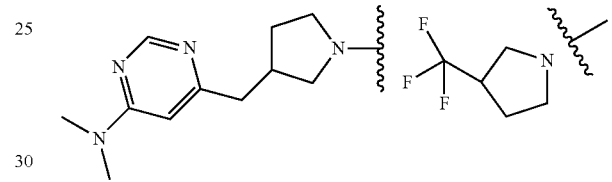

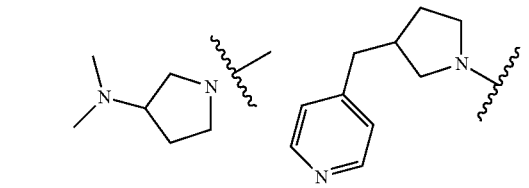
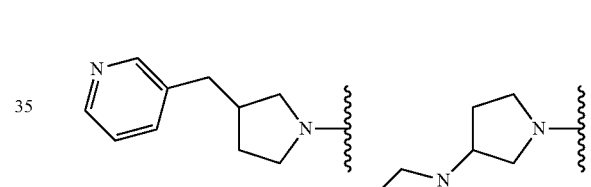

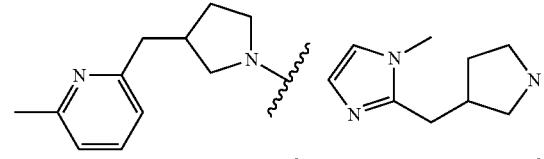

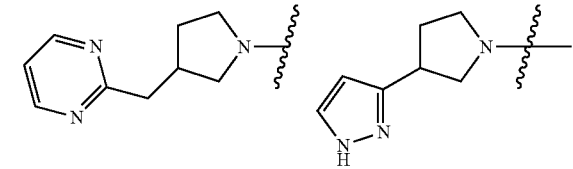
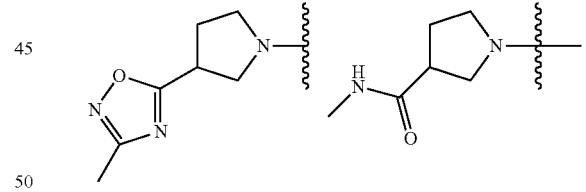

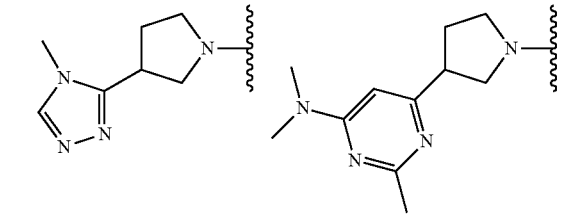
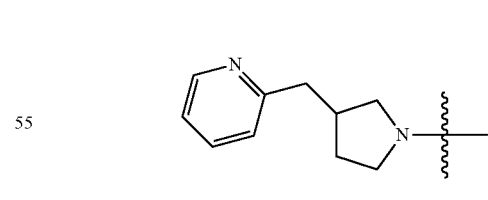

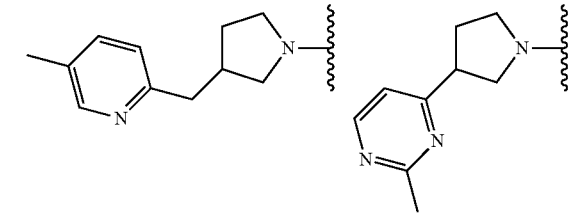

In one embodiment, $R^1$ is N-linked morpholine. In one embodiment, $R^1$ is N-linked morpholine unsubstituted or substituted by heteroaryl or ($C_1$-$C_{12}$-alkylenyl)$_n$-C(O)NR$^c$R$^d$, wherein R$^c$ and R$^d$ are independently selected from H, $C_1$-$C_{12}$-alkyl, and ($C_1$-$C_{12}$-alkylenyl)$_n$-$C_3$-$C_6$-cycloalkyl unsubstituted or substituted by one or more R$^g$, wherein n and R$^g$ are as defined herein, for example the following groups:

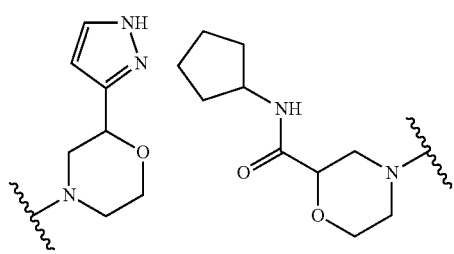

In one embodiment R¹ is octahydropyrrolo[1,2-a]pyrazine:

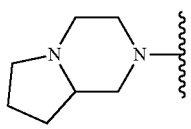

In one embodiment R¹ is 1H-pyrazol-4-yl, unsubstituted or substituted by $C_1$-$C_{12}$-alkyl, for example the following group:

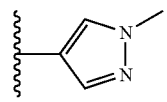 [SMILES: *c1cnn(C)c1]

In one embodiment, R¹ is $C_6$-$C_{20}$-aryloxy. In one embodiment, R¹ is —O-phenyl unsubstituted or substituted by one or more substituent(s) selected from the group consisting of: halo, CN, $C_1$-$C_{12}$-alkyl and —C(O)—NH₂, for example the following groups:

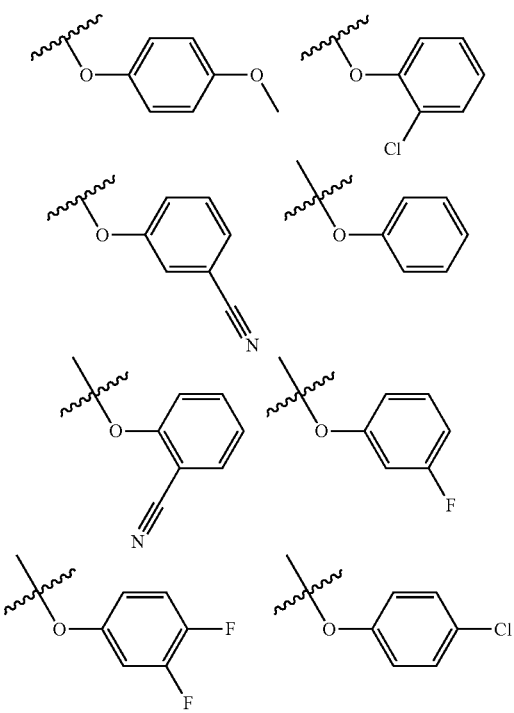

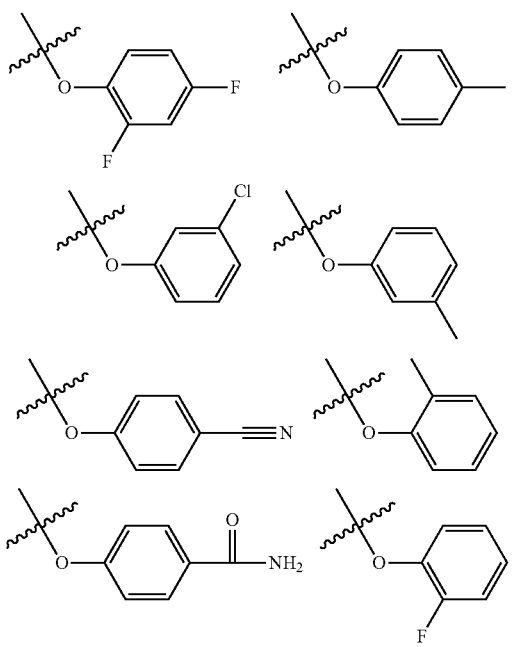

In one embodiment, R¹ is heteroaryloxy. In one embodiment, R¹ is —O-pyridine. In one embodiment, R¹ is —O-pyridine unsubstituted or substituted by one or more halo or $C_1$-$C_{12}$-alkyl, for example the following groups.

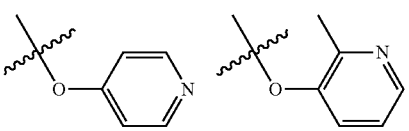

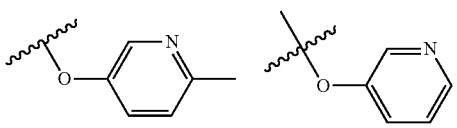

In one embodiment R¹ is —NR—($C_1$-$C_{12}$-alkylenyl)$_n$-$C_3$-$C_6$-cycloalkyl. In one embodiment R¹ is —NH-cyclopentyl, or —NH-cyclohexyl unsubstituted or substituted by $C_1$-$C_{12}$-alkyl for example the following groups, wherein R is as defined herein:

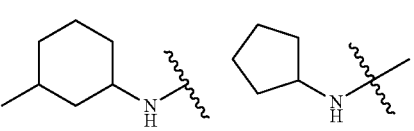

In one embodiment R¹ is —NR—($C_1$-$C_{12}$-alkylenyl)$_n$-heterocyclyl. In one embodiment R¹ is —NR—($C_1$-$C_{12}$-alkylenyl)$_n$-piperidine unsubstituted or substituted by —C(O)—$C_1$-$C_{12}$-alkyl or —C(O)O—$C_1$-$C_{12}$-alkyl, wherein R is as defined herein, for example the following groups:

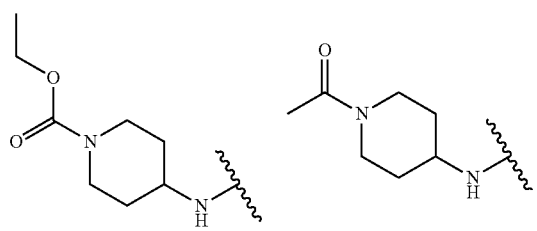 [SMILES: *NC1CCN(C(=O)OCC)CC1 ; *NC1CCN(C(C)=O)CC1]

In one embodiment $R^1$ is —NR—$(C_1$-$C_{12}$-alkylenyl)$_n$-$C_6$-$C_{20}$-aryl. In one embodiment $R^1$ is —NR—$(C_1$-$C_{12}$-alkylenyl)$_n$-phenyl unsubstituted or substituted by halo, $C_1$-$C_{12}$-alkyl, 5 or 6 membered heterocyclyl comprising 1, 2 or 3 heteroatom(s) selected from N, O and S, for example the following groups, wherein R is as defined herein:

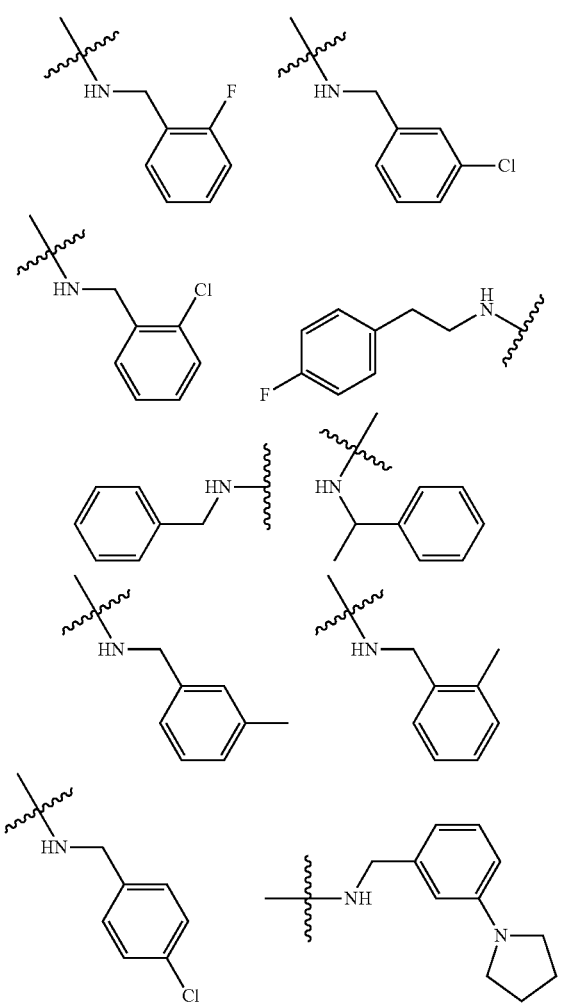

In one embodiment $R^1$ is —NR—$(C_1$-$C_{12}$-alkylenyl)$_n$-heteroaryl. In one embodiment $R^1$ is —NR—$(C_1$-$C_{12}$-alkylenyl)$_n$-pyridine or —NR—$(C_1$-$C_{12}$-alkylenyl)$_n$-pyrimidine, each of which can be unsubstituted or substituted by $C_1$-$C_{12}$-alkyl, wherein R is as defined herein, for example the following groups:

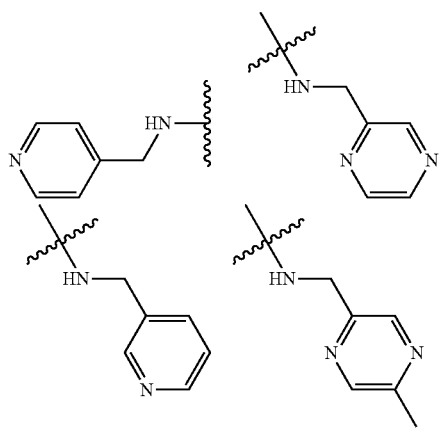

In one embodiment $R^1$ is —NR—$(C_1$-$C_{12}$-alkylenyl)$_n$-$C_6$-$C_{20}$-aryloxy. In one embodiment $R^1$ is —NR—$(C_1$-$C_{12}$-alkylenyl)$_n$-O-phenyl unsubstituted or substituted by halo, for example the following group, wherein R is as defined herein:

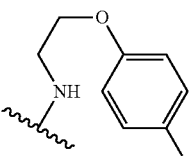

In one embodiment $R^1$ is —NR—$C_1$-$C_{12}$-hydroxyalkyl, for example the following group:

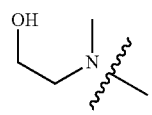

In one embodiment the compounds of Formula (I) are those compounds wherein:
$R^1$ is $C_6$-$C_{20}$-aryl unsubstituted;
$C_6$-$C_{20}$-aryl substituted by one or more substituent(s) selected from the group consisting of CN, OH, NH$_2$, halo, $C_1$-$C_{12}$-alkyl, $C_1$-$C_{12}$-alkoxy unsubstituted or substituted by one or more substituent(s) selected from the group consisting of $C_3$-$C_6$-cycloalkyl, heterocyclyl, aryl and heteroaryl or $C_1$-$C_{12}$-hydroxyalkyl;
$C_6$-$C_{20}$-aryl substituted by one or more substituent(s) selected from the group consisting of $C_1$-$C_{12}$-haloalkyl and $C_1$-$C_{12}$-haloalkoxy;
$C_6$-$C_{20}$-aryl substituted by $(C_1$-$C_{12}$-alkylenyl)$_n$-heterocyclyl selected from the group consisting of 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydropyrane, each of which is unsubstituted or substituted by one or more substituent(s) selected from the group consisting of: halo, oxo, OH, $NH_2$, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —NH($C_1$-$C_{12}$-alkyl), —N($C_1$-$C_{12}$-alkyl)$_2$, —C(O)—$C_1$-$C_{12}$-alkyl, —C(O)O—$C_1$-$C_{12}$-alkyl, ($C_1$-$C_{12}$-alkylenyl)$_n$-C(O)—NH($C_1$-$C_{12}$-alkyl), —C(O)—NH($C_1$-$C_{12}$-hydroxyalkyl), ($C_1$-$C_{12}$-alkylenyl)$_n$-C(O)—N($C_1$-$C_{12}$-alkyl)$_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl)$_2$, $C_1$-$C_{12}$-alkylenyl-C(O)N($C_1$-$C_{12}$-alkyl)$_2$, —C(O)OH, —C(O)-heterocyclyl, heterocyclyl and ($C_1$-$C_{12}$-alkylenyl)$_n$-heteroaryl, which heterocyclyl and heteroaryl group(s) can be unsubstituted or substituted by one or more substituent(s) selected from the group consisting of: OH, $NH_2$, halo, $C_1$-$C_{12}$-alkyl, $C_1$-$C_{12}$-alkoxy, $C_1$-$C_{12}$-haloalkyl and $C_1$-$C_{12}$-hydroxyalkyl;

$C_6$-$C_{20}$-aryl substituted by one or more ($C_1$-$C_{12}$-alkylenyl)$_n$-NR$^a$R$^b$; wherein R$^a$ and R$^b$ are independently selected from: H, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —S(O)$_2$—($C_1$-$C_{12}$-alkylenyl)$_n$-heterocyclyl unsubstituted or substituted by one or more R$^g$, $C_1$-$C_{12}$-alkylenyl-$C_6$-$C_{20}$-aryl, which aryl is unsubstituted or substituted by one or more R$^g$, ($C_1$-$C_{12}$-alkylenyl)$_n$-$C_3$-$C_6$-cycloalkyl unsubstituted or substituted by one or more R$^g$, ($C_1$-$C_{12}$-alkylenyl)$_n$-heterocyclyl unsubstituted or substituted by one or more oxo, —C(O)—$C_1$-$C_{12}$-alkyl, —C(O)O—$C_1$-$C_{12}$-alkyl and R$^g$, $C_1$-$C_{12}$-alkylenyl-C(O)-heteroaryl unsubstituted or substituted by one or more R$^g$, $C_1$-$C_{12}$-alkylenyl-$NH_2$, $C_1$-$C_{12}$-alkylenyl-NH($C_1$-$C_{12}$-alkyl), $C_1$-$C_{12}$-alkylenyl-N($C_1$-$C_{12}$-alkyl)$_2$, $C_1$-$C_{12}$-alkylenyl-C(O)$NH_2$, $C_1$-$C_{12}$-alkylenyl-C(O)NH($C_1$-$C_{12}$-alkyl), $C_1$-$C_{12}$-alkylenyl-C(O)N($C_1$-$C_{12}$-alkyl)$_2$;

$C_6$-$C_{20}$-aryl substituted by one or more ($C_1$-$C_{12}$-alkylenyl)$_n$-C(O)NR$^c$R$^d$, wherein R$^c$ and R$^d$ are independently selected from $C_1$-$C_{12}$-alkyl, $C_1$-$C_{12}$-haloalkyl, ($C_1$-$C_{12}$-alkylenyl)$_n$-$C_1$-$C_{12}$-alkoxy, $C_1$-$C_{12}$-alkylenyl-NH($C_1$-$C_{12}$-alkyl), $C_1$-$C_{12}$-alkylenyl-N($C_1$-$C_{12}$-alkyl)$_2$, ($C_1$-$C_{12}$-alkylenyl)$_n$-heterocyclyl, unsubstituted or substituted by one or more substituent(s) selected from the group consisting of: oxo, —C(O)—$C_1$-$C_{12}$-alkyl and R$^g$, ($C_1$-$C_{12}$-alkylenyl)$_n$-$C_3$-$C_6$-cycloalkyl unsubstituted or substituted by one or more R$^g$, and —NH—$C_3$-$C_6$-cycloalkyl;

$C_6$-$C_{20}$-aryl substituted by one or more ($C_1$-$C_{12}$-alkylenyl)$_n$-NR$^e$C(O)R$^f$, wherein R$^e$ is H and R$^f$ is $C_1$-$C_{12}$-alkyl, $C_1$-$C_{12}$-haloalkyl, ($C_1$-$C_{12}$-alkylenyl)$_n$-$C_1$-$C_{12}$-alkoxy, $C_1$-$C_{12}$-hydroxyalkyl, ($C_1$-$C_{12}$-alkylenyl)-NH($C_1$-$C_{12}$-alkyl), ($C_1$-$C_{12}$-alkylenyl)-N($C_1$-$C_{12}$-alkyl)$_2$, ($C_1$-$C_{12}$-alkylenyl)$_n$-heterocyclyl unsubstituted or substituted by one or more R$^g$, or ($C_1$-$C_{12}$-alkylenyl)$_n$-$C_3$-$C_6$-cycloalkyl unsubstituted or substituted by one or more R$^g$;

Pyridine unsubstituted or substituted by one or more substituent(s) selected from the group consisting of: CN; $NH_2$; Halo; $C_1$-$C_{12}$-alkyl; $C_1$-$C_{12}$-haloalkyl; ($C_1$-$C_{12}$-alkylenyl)$_n$-NR$^a$R$^b$; wherein R$^a$ and R$^b$ are independently selected from: H, ($C_1$-$C_{12}$-alkylenyl)$_n$-heterocyclyl unsubstituted or substituted by one or more oxo, C(O)—$C_1$-$C_{12}$-alkyl, —C(O)O—$C_1$-$C_{12}$-alkyl and R$^g$, and $C_1$-$C_{12}$-alkylenyl-N($C_1$-$C_{12}$-alkyl)$_2$;

N-linked piperidine unsubstituted or substituted by $C_1$-$C_{12}$-alkyl, $C_1$-$C_{12}$-alkylenyl-$C_1$-$C_{12}$-alkoxy, $C_1$-$C_{12}$-alkoxy, $C_1$-$C_{12}$-hydroxyalkyl, $C_1$-$C_{12}$-haloalkyl, ($C_1$-$C_{12}$-alkylenyl)$_n$-heteroaryl unsubstituted or substituted by one or more substituent(s) selected from the group consisting of: OH, $C_1$-$C_{12}$-alkyl, $C_1$-$C_{12}$-haloalkyl, ($C_1$-$C_{12}$-alkylenyl)-$C_1$-$C_{12}$-alkoxy, —N($C_1$-$C_{12}$-alkyl)$_2$, —C(O)—$NH_2$, —C(O)—NH($C_1$-$C_{12}$-alkyl), —C(O)—N($C_1$-$C_{12}$-alkyl)$_2$, and —S(O)$_2$—$C_1$-$C_{12}$-alkyl, ($C_1$-$C_{12}$-alkylenyl)$_n$-C(O)NR$^c$R$^d$, wherein R$^c$ and R$^d$ are independently selected from: H, $C_1$-$C_{12}$-alkyl, ($C_1$-$C_{12}$-alkylenyl)$_n$-$C_1$-$C_{12}$-alkoxy, and ($C_1$-$C_{12}$-alkylenyl)$_n$-heterocyclyl, unsubstituted or substituted by one or more R$^g$, or R$^c$ and R$^d$ together with the nitrogen atom to which they are attached, form a 5 or 6 membered heterocyclyl comprising 1 or 2 additional heteroatom selected from N, O or S, or is ($C_1$-$C_{12}$-alkylenyl)$_n$-NR$^e$C(O)R$^f$, wherein R$^e$ is H and R$^f$ is ($C_1$-$C_{12}$-alkylenyl)$_n$-$C_1$-$C_{12}$-alkoxy, ($C_1$-$C_{12}$-alkylenyl)$_n$-heterocyclyl;

N-linked piperazine unsubstituted or substituted by one or more substituent(s) selected from the group consisting of: $C_1$-$C_{12}$-alkyl, —C(O)—$C_1$-$C_{12}$-alkyl, ($C_1$-$C_{12}$-alkylenyl)$_n$-C(O)OH, and ($C_1$-$C_{12}$-alkylenyl)$_n$-C(O)O—$C_1$-$C_{12}$-alkyl;

N-linked pyrrolidine unsubstituted or substituted by one or more substituent(s) selected from the group consisting of: $C_1$-$C_{12}$-haloalkyl, ($C_1$-$C_{12}$-alkylenyl)$_n$-heterocyclyl, ($C_1$-$C_{12}$-alkylenyl)$_n$-NR$^e$C(O)R$^f$, wherein R$^e$ is H or $C_1$-$C_{12}$-alkyl, R$^f$ is $C_1$-$C_{12}$-alkyl, ($C_1$-$C_{12}$-alkylenyl)$_n$-heteroaryl unsubstituted or substituted by one or more substituent(s) selected from the group consisting of: $C_1$-$C_{12}$-alkyl, $C_1$-$C_{12}$-hydroxyalkyl, —NH($C_1$-$C_{12}$-alkyl), and N($C_1$-$C_{12}$-alkyl)$_2$, ($C_1$-$C_{12}$-alkylenyl)$_n$-NR$^a$R$^b$, wherein R$^a$ and R$^b$ are independently selected from H and $C_1$-$C_{12}$-alkyl, ($C_1$-$C_{12}$-alkylenyl)$_n$-C(O)NR$^c$R$^d$, wherein R$^c$ and R$^d$ are independently selected from H and $C_1$-$C_{12}$-alkyl;

N-linked morpholine unsubstituted or substituted by heteroaryl or ($C_1$-$C_{12}$-alkylenyl)$_n$-C(O)NR$^c$R$^d$, wherein R$^c$ and R$^d$ are independently selected from H, $C_1$-$C_{12}$-alkyl, and ($C_1$-$C_{12}$-alkylenyl)$_n$-$C_3$-$C_6$-cycloalkyl unsubstituted or substituted by one or more R$^g$;

1H-pyrazol-4-yl unsubstituted or substituted by $C_1$-$C_{12}$-alkyl;

—O-phenyl unsubstituted or substituted by one or more substituent(s) selected from the group consisting of: halo, CN, $C_1$-$C_{12}$-alkyl and —C(O)—$NH_2$, —O-pyridine unsubstituted unsubstituted or substituted by one or more halo or $C_1$-$C_{12}$-alkyl;

—NH-cyclopentyl, or —NH-cyclohexyl unsubstituted or substituted by $C_1$-$C_{12}$-alkyl;

—NR—($C_1$-$C_{12}$-alkylenyl)$_n$-piperidine unsubstituted or substituted by —C(O)—$C_1$-$C_{12}$-alkyl or —C(O)O—$C_1$-$C_{12}$-alkyl;

—NR—($C_1$-$C_{12}$-alkylenyl)$_n$-phenyl unsubstituted or substituted by halo, $C_1$-$C_{12}$-alkyl, 5 or 6 membered heterocyclyl comprising 1, 2 or 3 heteroatom(s) selected from N, O and S;

—NR—($C_1$-$C_{12}$-alkylenyl)$_n$-pyridine or —NR—($C_1$-$C_{12}$-alkylenyl)$_n$-pyrimidine, each of which can be unsubstituted or substituted by $C_1$-$C_{12}$-alkyl;

—NR—($C_1$-$C_{12}$-alkylenyl)$_n$-O-phenyl unsubstituted or substituted by halo, —NR—$C_1$-$C_{12}$-hydroxyalkyl;

R$^2$ and R$^3$ are H; n is 0 or 1, R is H or $C_1$-$C_{12}$-alkyl and R$^g$ is; and stereoisomers, geometric isomers, tautomers, and pharmaceutically acceptable salts thereof.

In all embodiments herein, heterocyclyl can be selected from the following groups selected from the group consisting of 1,4-diazepane, piperazine, piperidine, pyrrolidine, azetidine, 1,4-oxazepane, 1,1-dioxo-tetrahydrothiophene, morpholine, oxetane, tetrahydropyrane, tetrahydropyrane, each of which is unsubstituted or substituted as described herein.

In one embodiment, the compound of Formula (I) is selected from the following compounds of examples 1 to 368:

| | |
|---|---|
| 1 | 6-(2-fluoro-4-pyridyl)pyrido[3,2-d]pyrimidin-4-amine |
| 2 | 4-(4-aminopyrido[3,2-d]pyrimidin-6-yl)pyridin-2(1H)-one |
| 3 | 3-(4-aminopyrido[3,2-d]pyrimidin-6-yl)-5-fluorobenzoic acid |
| 4 | 3-(4-aminopyrido[3,2-d]pyrimidin-6-yl)-5-fluoro-N-(1-hydroxy-2-methylpropan-2-yl) benzamide |
| 5 | 3-(4-aminopyrido[3,2-d]pyrimidin-6-yl)-5-fluoro-N-methylbenzamide |
| 6 | 3-(4-aminopyrido[3,2-d]pyrimidin-6-yl)-N-cyclobutyl-5-fluorobenzamide |
| 7 | 3-(4-aminopyrido[3,2-d]pyrimidin-6-yl)-5-fluoro-N-(2-hydroxyethyl)benzamide |
| 8 | 3-(4-aminopyrido[3,2-d]pyrimidin-6-yl)-5-fluoro-N-(3-hydroxycyclobutyl)benzamide |
| 9 | 3-(4-aminopyrido[3,2-d]pyrimidin-6-yl)-5-fluoro-N-(1-hydroxypropan-2-yl)benzamide |
| 10 | 3-(4-aminopyrido[3,2-d]pyrimidin-6-yl)-5-fluoro-N-((1-methylpiperidin-4-yl)methyl)benzamide |
| 11 | 3-(4-aminopyrido[3,2-d]pyrimidin-6-yl)-5-fluoro-N-(2-morpholinoethyl)benzamide |
| 12 | 3-(4-aminopyrido[3,2-d]pyrimidin-6-yl)-N-(2-(dimethylamino)ethyl)-5-fluorobenzamide |
| 13 | 3-(4-aminopyrido[3,2-d]pyrimidin-6-yl)-5-fluoro-N-(2-(pyrrolidin-1-yl)ethyl)benzamide |
| 14 | 3-(4-aminopyrido[3,2-d]pyrimidin-6-yl) benzoic acid |
| 15 | 3-(4-aminopyrido[3,2-d]pyrimidin-6-yl)-N-(3-hydroxycyclobutyl)benzamide |
| 16 | 3-(4-aminopyrido[3,2-d]pyrimidin-6-yl)-N-(2-hydroxyethyl)benzamide |
| 17 | 3-(4-aminopyrido[3,2-d]pyrimidin-6-yl)-N-(1-hydroxypropan-2-yl)benzamide |
| 18 | 3-(4-aminopyrido[3,2-d]pyrimidin-6-yl)-N-(1-hydroxy-2-methylpropan-2-yl)benzamide |
| 19 | 3-(4-aminopyrido[3,2-d]pyrimidin-6-yl)-N-cyclobutylbenzamide |
| 20 | 3-(4-aminopyrido[3,2-d]pyrimidin-6-yl)-N-methylbenzamide |
| 21 | 3-(4-aminopyrido[3,2-d]pyrimidin-6-yl)-N-(2-morpholinoethyl)benzamide |
| 22 | 3-(4-aminopyrido[3,2-d]pyrimidin-6-yl)-N-((1-methylpiperidin-4-yl)methyl)benzamide |
| 23 | 3-(4-aminopyrido[3,2-d]pyrimidin-6-yl)-N-(2-(dimethylamino)ethyl)benzamide |
| 24 | 3-(4-aminopyrido[3,2-d]pyrimidin-6-yl)-N-(2-(pyrrolidin-1-yl)ethyl)benzamide |
| 25 | 6-(3-fluorophenyl)-N-isopropylpyrido[3,2-d]pyrimidin-4-amine |
| 26 | 6-(3-fluorophenyl)-N-methylpyrido[3,2-d]pyrimidin-4-amine |
| 27 | N-(cyclobutyl)-6-(3-fluorophenyl)pyrido[3,2-d]pyrimidin-4-amine |
| 28 | N-(cyclopropylmethyl)-6-(3-fluorophenyl)pyrido[3,2-d]pyrimidin-4-amine |
| 29 | 6-(3-fluorophenyl)-N-ethylpyrido[3,2-d]pyrimidin-4-amine |
| 30 | Ethyl 4-(3-(4-aminopyrido[3,2-d]pyrimidin-6-yl)-5-fluorobenzylamino)piperidine-1-carboxylate |
| 31 | 6-(3-fluoro-5-(2-(pyrrolidin-1-yl)ethylamino)phenyl)pyrido[3,2-d]pyrimidin-4-amine |
| 32 | 6-(3-Fluoro-5-(3-(pyrrolidin-1-ylmethyl)oxetan-3-ylamino)phenyl)pyrido[3,2-d] pyrimidin-4-amine |
| 33 | N-(3-(4-aminopyrido[3,2-d]pyrimidin-6-yl)-5-fluorophenyl)pyrrolidine-1-sulfonamide |
| 34 | 2-Morpholin-4-yl-ethanesulfonic acid [3-(4-amino-pyrido[3,2-d]pyrimidin-6-yl)-5-fluoro-phenyl]-amide |
| 35 | N-(3-(4-aminopyrido[3,2-d]pyrimidin-6-yl)-5-fluorophenyl)-2-(piperidin-1-yl)ethanesulfonamide |
| 36 | N-(3-(4-aminopyrido[3,2-d]pyrimidin-6-yl)-5-fluorophenyl)-2-(4-methylpiperazin-1-yl)ethanesulfonamide |
| 37 | 6-[3-(2-Pyrrolidin-1-ylmethyl-cyclopropyl)-phenyl]-pyrido[3,2-d]pyrimidin-4-ylamine |
| 38 | 6-(3-(Pyridin-2-yloxy)phenyl)pyrido[3,2-d]pyrimidin-4-amine |
| 39 | 6-(3-Fluoro-5-(4-methyl-1H-pyrazol-3-yl)phenyl)pyrido[3,2-d]pyrimidin-4-amine |
| 40 | 6-(3-(4-methyl-1H-pyrazol-3-yl)phenyl)pyrido[3,2-d]pyrimidin-4-amine |
| 41 | 6-(3-(Cyclopentyloxy)phenyl)pyrido[3,2-d]pyrimidin-4-amine |
| 42 | 6-(3-(1H-imidazol-2-yl)piperidin-1-yl)pyrido[3,2-d]pyrimidin-4-amine |
| 43 | tert-butyl N-[(3S)-1-(4-aminopyrido[3,2-d]pyrimidin-6-yl)-3-piperidyl]carbamate |
| 44 | (S)-6-(3-aminopiperidin-1-yl)pyrido[3,2-d]pyrimidin-4-amine |
| 45 | N-[(3S)-1-(4-aminopyrido[3,2-d]pyrimidin-6-yl)-3-piperidyl]-3-methoxy-propanamide |
| 46 | N-[3-(4-aminoquinazolin-6-yl)-5-fluoro-phenyl]acetamide |
| 47 | N-[3-(4-aminoquinazolin-6-yl)-5-fluoro-phenyl]-2-morpholino-acetamide |
| 48 | N-(6-(3-amino-5-fluorophenyl)pyrido[3,2-d]pyrimidin-4-yl)-2-(pyrrolidin-1-yl)acetamide |
| 49 | N-(3-(4-aminopyrido[3,2-d]pyrimidin-6-yl)-5-fluorophenyl)-2-(pyrrolidin-1-yl)acetamide |
| 50 | N6-(2-methylbenzyl)pyrido[3,2-d]pyrimidine-4,6-diamine |
| 51 | 6-(o-tolyloxy)pyrido[3,2-d]pyrimidin-4-amine |
| 52 | 6-(3-chlorophenyl)-N-(pyridin-4-yl)quinazolin-4-amine |
| 53 | 6-(3-chlorophenyl)-N-cyclopropylquinazolin-4-amine |
| 54 | 4-amino-6-(3-fluorophenyl)quinazoline-8-carbonitrile |
| 55 | N-(2-acetamidoethyl)-4-amino-6-(3-fluorophenyl)quinazoline-8-carboxamide |
| 56 | 6-(2-(pyrrolidin-1-yl)ethylamino)pyridin-4-yl)quinazolin-4-amine |
| 57 | 6-(3-(2-(pyrrolidin-1-yl)ethoxyl)phenyl)pyrido[3,2-d]pyrimidin-4-amine |
| 58 | 1-(3-(4-aminoquinazolin-6-yl)phenyl)-3-cyclopentylurea |
| 59 | 6-(3-fluorophenyl)-N-isobutylpyrido[3,2-d]pyrimidin-4-amine |
| 60 | 1-[4-(4-aminopyrido[3,2-d]pyrimidin-6-yl)piperazin-1-yl]ethanone |
| 61 | 6-[3-(4-methyl-1H-pyrazol-3-yl)-1-piperidyl]pyrido[3,2-d]pyrimidin-4-amine |
| 62 | 6-(3-(1,4-dimethyl-1H-pyrazol-3-yl)piperidin-1-yl)pyrido[3,2-d]pyrimidin-4-amine |
| 63 | 6-(3-(1,4-dimethyl-1H-pyrazol-5-yl)piperidin-1-yl)pyrido[3,2-d]pyrimidin-4-amine |
| 64 | 1-(4-(3-(4-aminopyrido[3,2-d]pyrimidin-6-yl)-5-fluorobenzyl)-1,4-diazepan-1-yl)ethanone |
| 65 | 1-(4-(3-(4-aminopyrido[3,2-d]pyrimidin-6-yl)-5-fluorobenzyl)piperazin-1-yl)ethanone |
| 66 | 1-(3-(4-aminopyrido[3,2-d]pyrimidin-6-yl)-5-fluorobenzyl)piperidin-4-ol |
| 67 | 6-(3-fluoro-5-((methyl(1-methylpiperidin-4-yl)amino)methyl)phenyl)pyrido[3,2-d]pyrimidin-4-amine |
| 68 | (1-(3-(4-aminopyrido[3,2-d]pyrimidin-6-yl)-5-fluorobenzyl)piperidin-4-yl)methanol |
| 69 | 2-(4-(3-(4-aminopyrido[3,2-d]pyrimidin-6-yl)-5-fluorobenzyl)piperazin-1-yl)ethanol |
| 70 | 6-(3-fluoro-5-((4-(2-methoxyethyl)piperazin-1-yl)methyl)phenyl)pyrido[3,2-d]pyrimidin-4-amine |
| 71 | (S)-6-(3-((3-(dimethylamino)pyrrolidin-1-yl)methyl)-5-fluorophenyl)pyrido[3,2-d]pyrimidin-4-amine |

| | -continued |
|---|---|
| 72 | 4-(3-(4-aminopyrido[3,2-d]pyrimidin-6-yl)-5-fluorobenzyl)-N,N-dimethylpiperazine-1-carboxamide |
| 73 | 1-(3-(4-aminopyrido[3,2-d]pyrimidin-6-yl)-5-fluorobenzyl)piperidine-4-carboxamide |
| 74 | 6-(3-((3,3-difluoroazetidin-1-yl)methyl)-5-fluorophenyl)pyrido[3,2-d]pyrimidin-4-amine |
| 75 | 4-(3-(4-aminopyrido[3,2-d]pyrimidin-6-yl)-5-fluorobenzyl)-N,N-dimethylpiperazine-1-sulfonamide |
| 76 | 6-(3-((1,4-oxazepan-4-yl)methyl)-5-fluorophenyl)pyrido[3,2-d]pyrimidin-4-amine |
| 77 | 2-(4-(3-(4-aminopyrido[3,2-d]pyrimidin-6-yl)-5-fluorobenzyl)piperazin-1-yl)-N,N-dimethyl acetamide |
| 78 | 1-(4-(3-(4-aminopyrido[3,2-d]pyrimidin-6-yl)-5-fluorobenzyl)piperazin-1-yl)-2-methylpropan-1-one |
| 79 | 6-(3-fluoro-5-((4-(methylsulfonyl)piperazin-1-yl)methyl)phenyl)pyrido[3,2-d]pyrimidin-4-amine |
| 80 | 6-(3-fluoro-5-((methyl(1,1-dioxo-tetrahydrothiophen-3-yl)amino)methyl)phenyl)pyrido[3,2-d]pyrimidin-4-amine |
| 81 | 2-((3-(4-aminopyrido[3,2-d]pyrimidin-6-yl)-5-fluorobenzyl)(methyl)amino)-1-morpholinoethanone |
| 82 | N-(1-(3-(4-aminopyrido[3,2-d]pyrimidin-6-yl)-5-fluorobenzyl)pyrrolidin-3-yl)-N-methylacetamide |
| 83 | (1-(3-(4-aminopyrido[3,2-d]pyrimidin-6-yl)-5-fluorobenzyl)azetidin-3-yl)(4-methylpiperazin-1-yl)methanone |
| 84 | 6-(3-((4-(dimethylamino)piperidin-1-yl)methyl)-5-fluorophenyl)pyrido[3,2-d]pyrimidin-4-amine |
| 85 | 6-(3-fluoro-5-((4-methoxypiperidin-1-yl)methyl)phenyl)pyrido[3,2-d]pyrimidin-4-amine |
| 86 | 6-(3-fluoro-5-(pyrrolidin-1-ylmethyl)phenyl)pyrido[3,2-d]pyrimidin-4-amine |
| 87 | 6-(3-fluoro-5-((2-methylpyrrolidin-1-yl)methyl)phenyl)pyrido[3,2-d]pyrimidin-4-amine |
| 88 | 6-(3-fluoro-5-((methyl(1-methylpyrrolidin-3-yl)amino)methyl)phenyl)pyrido[3,2-d]pyrimidin-4-amine |
| 89 | 2-((3-(4-aminopyrido[3,2-d]pyrimidin-6-yl)-5-fluorobenzyl)(methyl)amino)-N,N-dimethylacetamide |
| 90 | 6-(3-fluoro-5-(((2-methoxyethyl)(methyl)amino)methyl)phenyl)pyrido[3,2-d]pyrimidin-4-amine |
| 91 | 4-(3-(4-aminopyrido[3,2-d]pyrimidin-6-yl)-5-fluorobenzyl)-N,1-dimethylpiperazine-2-carboxamide |
| 92 | 1-(3-(4-aminopyrido[3,2-d]pyrimidin-6-yl)-5-fluorobenzyl)azetidine-3-carboxamide |
| 93 | 1-(3-(4-aminopyrido[3,2-d]pyrimidin-6-yl)-5-fluorobenzyl)-N-methylpyrrolidine-3-carboxamide |
| 94 | 1-(3-(4-aminopyrido[3,2-d]pyrimidin-6-yl)-5-fluorobenzyl)-N,N-dimethylazetidine-3-carboxamide |
| 95 | 4-(3-(4-aminopyrido[3,2-d]pyrimidin-6-yl)-5-fluorobenzyl)-1-methylpiperazine-2-carboxamide |
| 96 | 1-(3-(4-aminopyrido[3,2-d]pyrimidin-6-yl)-5-fluorobenzyl)-N-methylazetidine-3-carboxamide |
| 97 | 2-(1-(3-(4-aminopyrido[3,2-d]pyrimidin-6-yl)-5-fluorobenzyl)piperidin-4-yl)-N,N-dimethyl acetamide |
| 98 | 4-(3-(4-aminopyrido[3,2-d]pyrimidin-6-yl)-5-fluorobenzyl)-N-methylmorpholine-2-carboxamide |
| 99 | 6-(3-((3-(dimethylamino)pyrrolidin-1-yl)methyl)-5-fluorophenyl)pyrido[3,2-d]pyrimidin-4-amine |
| 100 | (1-(3-(4-aminopyrido[3,2-d]pyrimidin-6-yl)-5-fluorobenzyl)piperidin-3-yl)methanol |
| 101 | 6-(3-fluoro-5-((3-morpholinopyrrolidin-1-yl)methyl)phenyl)pyrido[3,2-d]pyrimidin-4-amine |
| 102 | 6-(3-fluoro-5-((4-methylpiperazin-1-yl)methyl)phenyl)pyrido[3,2-d]pyrimidin-4-amine |
| 103 | 1-(3-(4-aminopyrido[3,2-d]pyrimidin-6-yl)-5-fluorobenzyl)piperidin-3-ol |
| 104 | (R)-1-(3-(4-aminopyrido[3,2-d]pyrimidin-6-yl)-5-fluorobenzyl)piperidin-3-ol |
| 105 | 6-(3-((cyclopropylamino)methyl)-5-fluorophenyl)pyrido[3,2-d]pyrimidin-4-amine |
| 106 | 2-(3-(4-aminopyrido[3,2-d]pyrimidin-6-yl)-5-fluorobenzylamino)ethanol |
| 107 | 6-(3-((cyclopropylmethylamino)methyl)-5-fluorophenyl)pyrido[3,2-d]pyrimidin-4-amine hydrochloride |
| 108 | 6-(3-((cyclobutylamino)methyl)-5-fluorophenyl)pyrido[3,2-d]pyrimidin-4-amine hydrochloride |
| 109 | 6-(3-fluoro-5-((oxetan-3-ylamino)methyl)phenyl)pyrido[3,2-d]pyrimidin-4-amine hydrochloride |
| 110 | 6-(3-fluoro-5-((isobutylamino)methyl)phenyl)pyrido[3,2-d]pyrimidin-4-amine |
| 111 | 2-(3-(4-aminopyrido[3,2-d]pyrimidin-6-yl)-5-fluorobenzylamino)propan-1-ol hydrochloride |
| 112 | 6-(3-((cyclopentylamino)methyl)-5-fluorophenyl)pyrido[3,2-d]pyrimidin-4-amine hydrochloride |
| 113 | N1-(3-(4-aminopyrido[3,2-d]pyrimidin-6-yl)-5-fluorobenzyl)-N2,N2-dimethylethane-1,2-diamine hydrochloride |
| 114 | 6-(3-fluoro-5-((isopropylamino)methyl)phenyl)pyrido[3,2-d]pyrimidin-4-amine hydrochloride |
| 115 | 6-(3-fluoro-5-((tetrahydro-2H-pyran-4-ylamino)methyl)phenyl)pyrido[3,2-d]pyrimidin-4-amine hydrochloride |
| 116 | 6-(3-fluoro-5-(((tetrahydrofuran-3-yl)methylamino)methyl)phenyl)pyrido[3,2-d]pyrimidin-4-amine |
| 117 | 2-(3-(4-aminopyrido[3,2-d]pyrimidin-6-yl)-5-fluorobenzylamino)-N,N-dimethylacetamide hydrochloride |
| 118 | 6-(3-fluoro-5-((4-methylcyclohexylamino)methyl)phenyl)pyrido[3,2-d]pyrimidin-4-amine hydrochloride |
| 119 | 6-(3-fluoro-5-((2-(pyrrolidin-1-yl)ethylamino)methyl)phenyl)pyrido[3,2-d]pyrimidin-4-amine hydrochloride |
| 120 | 6-(3-fluoro-5-((1-methylpiperidin-4-ylamino)methyl)phenyl)pyrido[3,2-d]pyrimidin-4-amine hydrochloride |

-continued

| | |
|---|---|
| 121 | 6-(3-((cyclopropylamino)methyl)phenyl)pyrido[3,2-d]pyrimidin-4-amine hydrochloride |
| 122 | 2-(3-(4-aminopyrido[3,2-d]pyrimidin-6-yl)benzylamino)ethanol hydrochloride |
| 123 | 6-(3-((cyclopropylmethylamino)methyl)phenyl)pyrido[3,2-d]pyrimidin-4-amine hydrochloride |
| 124 | 6-(3-((cyclobutylamino)methyl)phenyl)pyrido[3,2-d]pyrimidin-4-amine |
| 125 | 6-(3-((oxetan-3-ylamino)methyl)phenyl)pyrido[3,2-d]pyrimidin-4-amine |
| 126 | 6-(3-((isobutylamino)methyl)phenyl)pyrido[3,2-d]pyrimidin-4-amine hydrochloride |
| 127 | 2-(3-(4-aminopyrido[3,2-d]pyrimidin-6-yl)benzylamino)propan-1-ol hydrochloride |
| 128 | N1-(3-(4-aminopyrido[3,2-d]pyrimidin-6-yl)benzyl)-N2,N2-dimethylethane-1,2-diamine hydrochloride |
| 129 | 6-(3-((isopropylamino)methyl)phenyl)pyrido[3,2-d]pyrimidin-4-amine hydrochloride |
| 130 | 6-(3-(((tetrahydro-2H-pyran-4-ylamino)methyl)phenyl)pyrido[3,2-d]pyrimidin-4-amine hydrochloride |
| 131 | 6-(3-(((tetrahydrofuran-3-yl)methylamino)methyl)phenyl)pyrido[3,2-d]pyrimidin-4-amine hydrochloride |
| 132 | 6-(3-fluoro-5-(((tetrahydro-2H-pyran-4-yl)methylamino)methyl)phenyl)pyrido[3,2-d]pyrimidin-4-amine hydrochloride |
| 133 | 4-(3-(4-aminopyrido[3,2-d]pyrimidin-6-yl)-5-fluorobenzylamino)cyclohexanol |
| 134 | (1-(3-(4-aminopyrido[3,2-d]pyrimidin-6-yl)-5-fluorobenzylamino)cyclopropyl)methanol hydrochloride |
| 135 | 6-(3-fluoro-5-(((1-methylpiperidin-2-yl)methylamino)methyl)phenyl)pyrido[3,2-d]pyrimidin-4-amine hydrochloride |
| 136 | 6-(3-fluoro-5-(((1-methylpiperidin-4-yl)methylamino)methyl)phenyl)pyrido[3,2-d]pyrimidin-4-amine hydrochloride |
| 137 | 6-(3-fluoro-5-((2-morpholinoethylamino)methyl)phenyl)pyrido[3,2-d]pyrimidin-4-amine hydrochloride |
| 138 | 1-(4-(3-(4-aminopyrido[3,2-d]pyrimidin-6-yl)-5-fluorobenzylamino)piperidin-1-yl)ethanone hydrochloride |
| 139 | 6-(3-fluoro-5-((2-methyl-1-morpholinopropan-2-ylamino)methyl)phenyl)pyrido[3,2-d]pyrimidin-4-amine hydrochloride |
| 140 | 6-(3-fluoro-5-((1-methylazetidin-3-ylamino)methyl)phenyl)pyrido[3,2-d]pyrimidin-4-amine hydrochloride |
| 141 | ethyl 4-(3-(4-aminopyrido[3,2-d]pyrimidin-6-yl)-5-fluorobenzylamino)piperidine-1-carboxylate hydrochloride |
| 142 | 2-(3-(4-aminopyrido[3,2-d]pyrimidin-6-yl)benzylamino)propan-1-ol hydrochloride |
| 143 | 6-(3-((cyclopentylamino)methyl)phenyl)pyrido[3,2-d]pyrimidin-4-amine hydrochloride |
| 144 | 2-(3-(4-aminopyrido[3,2-d]pyrimidin-6-yl)benzylamino)-N,N-dimethylacetamide hydrochloride |
| 145 | 6-(3-((4-methylcyclohexylamino)methyl)phenyl)pyrido[3,2-d]pyrimidin-4-amine hydrochloride |
| 146 | 6-(3-((2-(pyrrolidin-1-yl)ethylamino)methyl)phenyl)pyrido[3,2-d]pyrimidin-4-amine hydrochloride |
| 147 | 6-(3-((1-methylpiperidin-4-ylamino)methyl)phenyl)pyrido[3,2-d]pyrimidin-4-amine hydrochloride |
| 148 | 6-(3-(((tetrahydro-2H-pyran-4-yl)methylamino)methyl)phenyl)pyrido[3,2-d]pyrimidin-4-amine hydrochloride |
| 149 | N1-(3-(4-aminopyrido[3,2-d]pyrimidin-6-yl)benzyl)cyclohexane-1,4-diamine hydrochloride |
| 150 | (1-(3-(4-aminopyrido[3,2-d]pyrimidin-6-yl)benzylamino)cyclopropyl)methanol hydrochloride |
| 151 | 6-(3-(((1-methylpiperidin-2-yl)methylamino)methyl)phenyl)pyrido[3,2-d]pyrimidin-4-amine hydrochloride |
| 152 | 6-(3-(((1-methylpiperidin-4-yl)methylamino)methyl)phenyl)pyrido[3,2-d]pyrimidin-4-amine hydrochloride |
| 153 | 6-(3-((2-morpholinoethylamino)methyl)phenyl)pyrido[3,2-d]pyrimidin-4-amine hydrochloride |
| 154 | 1-(4-(3-(4-aminopyrido[3,2-d]pyrimidin-6-yl)benzylamino)piperidin-1-yl)ethanone hydrochloride |
| 155 | 6-(3-((2-methyl-1-morpholinopropan-2-ylamino)methyl)phenyl)pyrido[3,2-d]pyrimidin-4-amine hydrochloride |
| 156 | 6-(3-((1-methylazetidin-3-ylamino)methyl)phenyl)pyrido[3,2-d]pyrimidin-4-amine hydrochloride |
| 157 | ethyl 4-(3-(4-aminopyrido[3,2-d]pyrimidin-6-yl)benzylamino)piperidine-1-carboxylate hydrochloride |
| 158 | 6-(3-chlorophenyl)quinazolin-4-amine |
| 159 | N-[3-(4-aminoquinazolin-6-yl)phenyl]acetamide |
| 160 | tert-butyl N-[4-(4-aminoquinazolin-6-yl)phenyl]carbamate |
| 161 | 5-(4-aminoquinazolin-6-yl)pyridine-3-carbonitrile |
| 162 | 6-(m-tolyl)quinazolin-4-amine |
| 163 | 6-(2-fluorophenyl)quinazolin-4-amine |
| 164 | 3-(4-aminoquinazolin-6-yl)benzonitrile |
| 165 | 4-(4-aminoquinazolin-6-yl)benzonitrile |
| 166 | 6-(4-methoxyphenyl)quinazolin-4-amine |
| 167 | 6-(3-methoxyphenyl)quinazolin-4-amine |
| 168 | 6-(2-methoxyphenyl)quinazolin-4-amine |
| 169 | 7-(3-chlorophenyl)quinazoline-2,4-diamine |
| 170 | 6-(3-chlorophenyl)isoquinolin-1-amine |
| 171 | 6-(3-chloro-5-fluoro-phenyl)quinazolin-4-amine |
| 172 | 6-(3-chlorophenyl)pyrido[3,2-d]pyrimidine-2,4-diamine |
| 173 | 6-(3-chlorophenyl)-N-cyclopropyl-quinazolin-4-amine |

| | |
|---|---|
| 174 | 6-(3-fluorophenyl)quinazolin-4-amine |
| 175 | 3-(4-aminoquinazolin-6-yl)-5-chloro-benzamide |
| 176 | 6-(3-chlorophenyl)-N-isobutyl-quinazolin-4-amine |
| 177 | 6-(3-chlorophenyl)-N-cyclobutyl-quinazolin-4-amine |
| 178 | 6-(3-chlorophenyl)-N-(2,2-difluoroethyl)quinazolin-4-amine |
| 179 | 6-(3-chlorophenyl)-N-ethyl-quinazolin-4-amine |
| 180 | 6-(3-chlorophenyl)-N-methyl-quinazolin-4-amine |
| 181 | 6-(3-chlorophenyl)pyrido[3,2-d]pyrimidin-4-amine |
| 182 | 6-(5-chloro-2-methyl-phenyl)quinazolin-4-amine |
| 183 | 6-(3,5-dichlorophenyl)quinazolin-4-amine |
| 184 | 6-(3-fluorophenyl)pyrido[3,2-d]pyrimidin-4-amine |
| 185 | 3-(4-aminoquinazolin-6-yl)-5-fluoro-benzonitrile |
| 186 | 6-(3,5-difluorophenyl)quinazolin-4-amine |
| 187 | 6-(3-amino-5-fluoro-phenyl)quinazolin-4-amine |
| 188 | N-[3-(4-aminoquinazolin-6-yl)-5-fluoro-phenyl]-2-tetrahydrofuran-2-yl-acetamide |
| 189 | N-[3-(4-aminoquinazolin-6-yl)-5-fluoro-phenyl]tetrahydropyran-4-carboxamide |
| 190 | 1-acetyl-N-[3-(4-aminoquinazolin-6-yl)-5-fluoro-phenyl]azetidine-3-carboxamide |
| 191 | N-[3-(4-aminoquinazolin-6-yl)-5-fluoro-phenyl]-2-pyrrolidin-1-yl-acetamide |
| 192 | N-[3-(4-aminoquinazolin-6-yl)-5-fluoro-phenyl]-3-(dimethylamino)propanamide |
| 193 | N-[3-(4-aminoquinazolin-6-yl)-5-fluoro-phenyl]cyclobutanecarboxamide |
| 194 | N-[3-(4-aminoquinazolin-6-yl)-5-fluoro-phenyl]-2-cyclopropyl-acetamide |
| 195 | N-[3-(4-aminoquinazolin-6-yl)-5-fluoro-phenyl]tetrahydrofuran-2-carboxamide |
| 196 | N-[3-(4-aminoquinazolin-6-yl)-5-fluoro-phenyl]-3-methoxy-propanamide |
| 197 | N-[3-(4-aminoquinazolin-6-yl)-5-fluoro-phenyl]-4-methyl-morpholine-2-carboxamide |
| 198 | 6-(3-methyl-1-piperidyl)pyrido[3,2-d]pyrimidin-4-amine |
| 199 | 6-(3-methoxy-1-piperidyl)pyrido[3,2-d]pyrimidin-4-amine |
| 200 | 6-[3-(trifluoromethyl)pyrrolidin-1-yl]pyrido[3,2-d]pyrimidin-4-amine |
| 201 | 6-[3-(trifluoromethyl)-1-piperidyl]pyrido[3,2-d]pyrimidin-4-amine |
| 202 | 6-[3-(methoxymethyl)-1-piperidyl]pyrido[3,2-d]pyrimidin-4-amine |
| 203 | [1-(4-aminopyrido[3,2-d]pyrimidin-6-yl)-3-piperidyl]methanol |
| 204 | 6-(4-pyridyl)quinazolin-4-amine |
| 205 | 6-(2-methyl-4-pyridyl)quinazolin-4-amine |
| 206 | N-[3-(4-aminoquinazolin-6-yl)phenyl]-2-cyclopropyl-acetamide |
| 207 | N-[3-(4-aminoquinazolin-6-yl)phenyl]cyclobutanecarboxamide |
| 208 | N-[3-(4-aminoquinazolin-6-yl)phenyl]propanamide |
| 209 | N-[3-(4-aminoquinazolin-6-yl)phenyl]-2,2-difluoro-acetamide |
| 210 | N-[3-(4-aminoquinazolin-6-yl)phenyl]-3,3,3-trifluoro-propanamide |
| 211 | N-[3-(4-aminoquinazolin-6-yl)phenyl]tetrahydropyran-4-carboxamide |
| 212 | N-[3-(4-aminoquinazolin-6-yl)phenyl]-4-methyl-morpholine-2-carboxamide |
| 213 | N-[3-(4-aminoquinazolin-6-yl)phenyl]-2,2-difluoro-cyclopropanecarboxamide |
| 214 | N-[3-(4-aminoquinazolin-6-yl)phenyl]tetrahydrofuran-2-carboxamide |
| 215 | N-[3-(4-aminoquinazolin-6-yl)phenyl]tetrahydrofuran-3-carboxamide |
| 216 | N-[3-(4-aminoquinazolin-6-yl)phenyl]-2-pyrrolidin-1-yl-acetamide |
| 217 | N-[3-(4-aminoquinazolin-6-yl)phenyl]-2-tetrahydrofuran-2-yl-acetamide |
| 218 | N-[3-(4-aminoquinazolin-6-yl)phenyl]-2,2-dimethyl-propanamide |
| 219 | N-[3-(4-aminoquinazolin-6-yl)phenyl]-3-methoxy-propanamide |
| 220 | N-[3-(4-aminoquinazolin-6-yl)phenyl]-2-morpholino-acetamide |
| 221 | 2-[3-(4-aminoquinazolin-6-yl)phenyl]-N-cyclopentyl-acetamide |
| 222 | N-[3-(4-aminoquinazolin-6-yl)phenyl]-2-pyrrolidin-1-yl-propanamide |
| 223 | 2-[3-(4-aminoquinazolin-6-yl)phenyl]-N-cyclopentyl-N-methyl-acetamide |
| 224 | N-[3-(4-aminoquinazolin-6-yl)phenyl]-2-(dimethylamino)acetamide |
| 225 | N6-[2-(4-fluorophenyl)ethyl]pyrido[3,2-d]pyrimidine-4,6-diamine |
| 226 | 6-(1-piperidyl)pyrido[3,2-d]pyrimidin-4-amine |
| 227 | [1-(4-aminopyrido[3,2-d]pyrimidin-6-yl)-4-piperidyl]-pyrrolidin-1-yl-methanone |
| 228 | 6-(3-morpholinopyrrolidin-1-yl)pyrido[3,2-d]pyrimidin-4-amine |
| 229 | 6-[4-(2-methoxyethyl)piperazin-1-yl]pyrido[3,2-d]pyrimidin-4-amine |
| 230 | N-[1-(4-aminopyrido[3,2-d]pyrimidin-6-yl)pyrrolidin-3-yl]-N-methyl-acetamide |
| 231 | 1-[4-(4-aminopyrido[3,2-d]pyrimidin-6-yl)piperazin-1-yl]ethanone |
| 232 | 1-[4-(4-aminopyrido[3,2-d]pyrimidin-6-yl)piperazin-1-yl]-2-methyl-propan-1-one |
| 233 | 6-[3-(4-methyl-1H-pyrazol-3-yl)-1-piperidyl]pyrido[3,2-d]pyrimidin-4-amine |
| 234 | tert-butyl 4-(4-aminopyrido[3,2-d]pyrimidin-6-yl)-2-methyl-piperazine-1-carboxylate |
| 235 | 2-[1-(4-aminopyrido[3,2-d]pyrimidin-6-yl)-4-piperidyl]-N-methyl-acetamide |
| 236 | 6-[4-(1H-pyrazol-5-yl)-1-piperidyl]pyrido[3,2-d]pyrimidin-4-amine |
| 237 | 6-[4-(6-methyl-2-pyridyl)-1-piperidyl]pyrido[3,2-d]pyrimidin-4-amine |
| 238 | 6-(3-morpholino-1-piperidyl)pyrido[3,2-d]pyrimidin-4-amine |
| 239 | 6-[3-(5-methyl-2-pyridyl)-1-piperidyl]pyrido[3,2-d]pyrimidin-4-amine |
| 240 | 6-[3-[(1-methylimidazol-2-yl)methyl]pyrrolidin-1-yl]pyrido[3,2-d]pyrimidin-4-amine |
| 241 | 6-[3-(5-methyl-1,2,4-oxadiazol-3-yl)-1-piperidyl]pyrido[3,2-d]pyrimidin-4-amine |
| 242 | 6-[4-(3-methylimidazol-4-yl)-1-piperidyl]pyrido[3,2-d]pyrimidin-4-amine |
| 243 | 6-(3-amino-5-fluoro-phenyl)pyrido[3,2-d]pyrimidin-4-amine |
| 244 | 6-[3-(4-pyridylmethyl)pyrrolidin-1-yl]pyrido[3,2-d]pyrimidin-4-amine |
| 245 | 6-[3-(3-methylimidazol-4-yl)pyrrolidin-1-yl]pyrido[3,2-d]pyrimidin-4-amine |
| 246 | 6-[3-(3-methyl-1,2,4-oxadiazol-5-yl)-1-piperidyl]pyrido[3,2-d]pyrimidin-4-amine |
| 247 | 1-(4-aminopyrido[3,2-d]pyrimidin-6-yl)-N-methyl-pyrrolidine-3-carboxamide |
| 248 | 6-[3-(2-pyridylmethyl)pyrrolidin-1-yl]pyrido[3,2-d]pyrimidin-4-amine |
| 249 | 6-[3-(3-methyl-1,2,4-oxadiazol-5-yl)pyrrolidin-1-yl]pyrido[3,2-d]pyrimidin-4-amine |
| 250 | 6-[3-(3-pyridylmethyl)pyrrolidin-1-yl]pyrido[3,2-d]pyrimidin-4-amine |
| 251 | 6-(4-methylpiperazin-1-yl)pyrido[3,2-d]pyrimidin-4-amine |

-continued

| | |
|---|---|
| 252 | 6-(4-methoxy-1-piperidyl)pyrido[3,2-d]pyrimidin-4-amine |
| 253 | 6-[3-(dimethylamino)pyrrolidin-1-yl]pyrido[3,2-d]pyrimidin-4-amine |
| 254 | ethyl 4-[(4-aminopyrido[3,2-d]pyrimidin-6-yl)amino]piperidine-1-carboxylate |
| 255 | 6-(3,4,6,7,8,8a-hexahydro-1H-pyrrolo[1,2-a]pyrazin-2-yl)pyrido[3,2-d]pyrimidin-4-amine |
| 256 | N6-cyclopentylpyrido[3,2-d]pyrimidine-4,6-diamine |
| 257 | 4-(4-aminopyrido[3,2-d]pyrimidin-6-yl)-N-cyclopentyl-morpholine-2-carboxamide |
| 258 | 6-[3-(6-methyl-2-pyridyl)-1-piperidyl]pyrido[3,2-d]pyrimidin-4-amine |
| 259 | tert-butyl 4-(4-aminopyrido[3,2-d]pyrimidin-6-yl)piperazine-1-carboxylate |
| 260 | 6-[4-(5-methyl-1,2,4-oxadiazol-3-yl)-1-piperidyl]pyrido[3,2-d]pyrimidin-4-amine |
| 261 | 1-[3-(4-aminoquinazolin-6-yl)phenyl]-3-cyclopentyl-urea |
| 262 | N-[3-(4-aminoquinazolin-6-yl)phenyl]-2-(2-oxopyrrolidin-1-yl)acetamide |
| 263 | N-[3-(4-aminopyrido[3,2-d]pyrimidin-6-yl)-5-fluoro-phenyl]-2-cyclopentyl-acetamide |
| 264 | 2-[3-(4-aminoquinazolin-6-yl)phenyl]ethanol |
| 265 | 3-(4-aminoquinazolin-6-yl)phenol |
| 266 | 6-(3-amino-4-fluoro-phenyl)quinazolin-4-amine |
| 267 | 6-(3-ethoxyphenyl)quinazolin-4-amine |
| 268 | 6-phenylquinazolin-4-amine |
| 269 | 6-(5-amino-2-fluoro-phenyl)quinazolin-4-amine |
| 270 | N6-benzylpyrido[3,2-d]pyrimidine-4,6-diamine |
| 271 | 6-[3-(4-methyl-1H-pyrazol-3-yl)-1-piperidyl]pyrido[3,2-d]pyrimidin-4-amine |
| 272 | 6-[3-(4-methyl-1H-pyrazol-3-yl)-1-piperidyl]pyrido[3,2-d]pyrimidin-4-amine |
| 273 | 6-[3-(4,6-dimethylpyrimidin-2-yl)-1-piperidyl]pyrido[3,2-d]pyrimidin-4-amine |
| 274 | 6-[1-(4-aminopyrido[3,2-d]pyrimidin-6-yl)-3-piperidyl]-N,N-dimethyl-pyridine-2-carboxamide |
| 275 | 6-[3-[(5-methyl-2-pyridyl)methyl]pyrrolidin-1-yl]pyrido[3,2-d]pyrimidin-4-amine |
| 276 | 6-[3-(pyrimidin-2-ylmethyl)pyrrolidin-1-yl]pyrido[3,2-d]pyrimidin-4-amine |
| 277 | 6-[3-[6-(dimethylamino)-2-pyridyl]-1-piperidyl]pyrido[3,2-d]pyrimidin-4-amine |
| 278 | 6-[3-(pyrimidin-2-ylmethyl)-1-piperidyl]pyrido[3,2-d]pyrimidin-4-amine |
| 279 | 6-[3-(4-methylsulfonyl-1H-pyrazol-5-yl)-1-piperidyl]pyrido[3,2-d]pyrimidin-4-amine |
| 280 | 6-[3-[6-(dimethylamino)pyrazin-2-yl]-1-piperidyl]pyrido[3,2-d]pyrimidin-4-amine |
| 281 | 6-[3-[[6-(methylamino)pyrimidin-4-yl]methyl]pyrrolidin-1-yl]pyrido[3,2-d]pyrimidin-4-amine |
| 282 | 6-[3-(2-methylpyrimidin-4-yl)pyrrolidin-1-yl]pyrido[3,2-d]pyrimidin-4-amine |
| 283 | 6-[3-[6-(dimethylamino)-2-methyl-pyrimidin-4-yl]pyrrolidin-1-yl]pyrido[3,2-d]pyrimidin-4-amine |
| 284 | 6-[3-[[6-(dimethylamino)pyrimidin-4-yl]methyl]-1-piperidyl]pyrido[3,2-d]pyrimidin-4-amine |
| 285 | 6-[3-(1H-pyrazol-3-yl)pyrrolidin-1-yl]pyrido[3,2-d]pyrimidin-4-amine |
| 286 | 6-[3-[[6-(dimethylamino)pyrimidin-4-yl]methyl]pyrrolidin-1-yl]pyrido[3,2-d]pyrimidin-4-amine |
| 287 | 6-[3-[2-(dimethylamino)pyrimidin-4-yl]-1-piperidyl]pyrido[3,2-d]pyrimidin-4-amine |
| 288 | 6-[1-(4-aminopyrido[3,2-d]pyrimidin-6-yl)-3-piperidyl]pyridine-2-carboxamide |
| 289 | 6-[3-[3-(dimethylamino)pyrazin-2-yl]-1-piperidyl]pyrido[3,2-d]pyrimidin-4-amine |
| 290 | 6-[3-(2-methylpyrimidin-4-yl)-1-piperidyl]pyrido[3,2-d]pyrimidin-4-amine |
| 291 | 6-(3-pyrimidin-4-yl-1-piperidyl)pyrido[3,2-d]pyrimidin-4-amine |
| 292 | 6-[3-[5-(trifluoromethyl)-1H-pyrazol-3-yl]-1-piperidyl]pyrido[3,2-d]pyrimidin-4-amine |
| 293 | 6-(3-pyrazin-2-yl-1-piperidyl)pyrido[3,2-d]pyrimidin-4-amine |
| 294 | 6-[3-(pyrazin-2-ylmethyl)-1-piperidyl]pyrido[3,2-d]pyrimidin-4-amine |
| 295 | 6-[3-[5-(dimethylamino)-2-pyridyl]-1-piperidyl]pyrido[3,2-d]pyrimidin-4-amine |
| 296 | 6-[3-(4-methylpyrimidin-2-yl)-1-piperidyl]pyrido[3,2-d]pyrimidin-4-amine |
| 297 | 6-[3-(2-pyridyl)-1-piperidyl]pyrido[3,2-d]pyrimidin-4-amine |
| 298 | 6-[3-(4-methyl-1,2,4-triazol-3-yl)-1-piperidyl]pyrido[3,2-d]pyrimidin-4-amine |
| 299 | 6-[3-[5-(methoxymethyl)-1,2,4-oxadiazol-3-yl]-1-piperidyl]pyrido[3,2-d]pyrimidin-4-amine |
| 300 | 6-[1-(4-aminopyrido[3,2-d]pyrimidin-6-yl)-3-piperidyl]-N-methyl-pyridine-2-carboxamide |
| 301 | 6-[3-(5-methylsulfonylpyrimidin-4-yl)-1-piperidyl]pyrido[3,2-d]pyrimidin-4-amine |
| 302 | 6-[3-(4-pyridyl)pyrrolidin-1-yl]pyrido[3,2-d]pyrimidin-4-amine |
| 303 | 4-amino-6-(3-fluorophenyl)-N-methyl-N-(1-methylpyrrolidin-3-yl)quinazoline-8-carboxamide |
| 304 | 4-amino-6-(3-fluorophenyl)-N-(2-methoxyethyl)-N-methyl-quinazoline-8-carboxamide |
| 305 | 4-amino-6-(3-fluorophenyl)-N-(2-pyrrolidin-1-ylethyl)quinazoline-8-carboxamide |
| 306 | 6-(2-ethyl-4-pyridyl)pyrido[3,2-d]pyrimidin-4-amine |
| 307 | 6-(2-methyl-4-pyridyl)pyrido[3,2-d]pyrimidin-4-amine |
| 308 | [4-amino-6-(3-fluorophenyl)quinazolin-8-yl]-[3-(dimethylamino)pyrrolidin-1-yl]methanone |
| 309 | [4-amino-6-(3-fluorophenyl)quinazolin-8-yl]-[4-(dimethylamino)-1-piperidyl]methanone |
| 310 | [4-amino-6-(3-fluorophenyl)quinazolin-8-yl]-(3-hydroxyazetidin-1-yl)methanone |
| 311 | 4-amino-6-(3-fluorophenyl)-N-(oxetan-3-yl)quinazoline-8-carboxamide |
| 312 | [4-amino-6-(3-fluorophenyl)quinazolin-8-yl]-(4-methylpiperazin-1-yl)methanone |
| 313 | 6-[3-[(1-methylimidazol-2-yl)methyl]-1-piperidyl]pyrido[3,2-d]pyrimidin-4-amine |
| 314 | N-[3-(4-aminopyrido[3,2-d]pyrimidin-6-yl)-5-fluoro-phenyl]-2-pyrrolidin-1-yl-acetamide |
| 315 | N-[6-(3-amino-5-fluoro-phenyl)pyrido[3,2-d]pyrimidin-4-yl]-2-pyrrolidin-1-yl-acetamide |
| 316 | 3-(4-aminopyrido[3,2-d]pyrimidin-6-yl)phenol |
| 317 | 6-[6-(1-methyl-3-piperidyl)-3-pyridyl]quinazolin-4-amine |
| 318 | 5-[1-(4-aminopyrido[3,2-d]pyrimidin-6-yl)-3-piperidyl]-2-methyl-pyrazol-3-ol |
| 319 | 6-[2-(2-pyrrolidin-1-ylethylamino)-4-pyridyl]quinazolin-4-amine |
| 320 | 6-[3-(2-pyrrolidin-1-ylethoxy)phenyl]pyrido[3,2-d]pyrimidin-4-amine |
| 321 | 6-[3-(1H-pyrazol-3-yl)-1-piperidyl]pyrido[3,2-d]pyrimidin-4-amine |
| 322 | 6-[2-(1H-pyrazol-3-yl)morpholin-4-yl]pyrido[3,2-d]pyrimidin-4-amine |

-continued 323 6-[3-(1H-imidazol-2-yl)-1-piperidyl]pyrido[3,2-d]pyrimidin-4-amine
324 N-[4-(4-aminoquinazolin-6-yl)-2-pyridyl]-N',N'-dimethyl-ethane-1,2-diamine
325 tert-butyl N-[(3R)-1-(4-aminopyrido[3,2-d]pyrimidin-6-yl)-3-piperidyl]carbamate
326 6-[(3S)-3-amino-1-piperidyl]pyrido[3,2-d]pyrimidin-4-amine
327 6-[(3R)-3-amino-1-piperidyl]pyrido[3,2-d]pyrimidin-4-amine
328 N-[(3S)-1-(4-aminopyrido[3,2-d]pyrimidin-6-yl)-3-piperidyl]-3-pyrrolidin-1-yl-propanamide
329 N-[(3S)-1-(4-aminopyrido[3,2-d]pyrimidin-6-yl)-3-piperidyl]-2-(4-methylpiperazin-1-yl)acetamide
330 N-[(3R)-1-(4-aminopyrido[3,2-d]pyrimidin-6-yl)-3-piperidyl]-3-methoxy-propanamide
331 N-[(3R)-1-(4-aminopyrido[3,2-d]pyrimidin-6-yl)-3-piperidyl]-3-pyrrolidin-1-yl-propanamide
332 N-[(3R)-1-(4-aminopyrido[3,2-d]pyrimidin-6-yl)-3-piperidyl]-2-(4-methylpiperazin-1-yl)acetamide
333 N6-[(2-fluorophenyl)methyl]pyrido[3,2-d]pyrimidine-4,6-diamine
334 N6-(1-phenylethyl)pyrido[3,2-d]pyrimidine-4,6-diamine
335 6-[2-(trifluoromethyl)-4-pyridyl]pyrido[3,2-d]pyrimidin-4-amine
336 6-(2-methylphenoxy)pyrido[3,2-d]pyrimidin-4-amine
337 6-(3-methylphenoxy)pyrido[3,2-d]pyrimidin-4-amine
338 6-(4-pyridyloxy)pyrido[3,2-d]pyrimidin-4-amine
339 6-(4-methylphenoxy)pyrido[3,2-d]pyrimidin-4-amine
340 6-(3-fluorophenoxy)pyrido[3,2-d]pyrimidin-4-amine
341 2-(4-aminopyrido[3,2-d]pyrimidin-6-yl)oxybenzonitrile
342 6-[(6-methyl-3-pyridyl)oxy]pyrido[3,2-d]pyrimidin-4-amine
343 6-[(2-methyl-3-pyridyl)oxy]pyrido[3,2-d]pyrimidin-4-amine
344 6-phenoxypyrido[3,2-d]pyrimidin-4-amine
345 6-(3-pyridyloxy)pyrido[3,2-d]pyrimidin-4-amine
346 4-(4-aminopyrido[3,2-d]pyrimidin-6-yl)oxybenzamide
347 4-(4-aminopyrido[3,2-d]pyrimidin-6-yl)oxybenzonitrile
348 3-(4-aminopyrido[3,2-d]pyrimidin-6-yl)oxybenzonitrile
349 6-(2-chlorophenoxy)pyrido[3,2-d]pyrimidin-4-amine
350 6-(4-methoxyphenoxy)pyrido[3,2-d]pyrimidin-4-amine
351 6-(4-chlorophenoxy)pyrido[3,2-d]pyrimidin-4-amine
352 6-(3-chlorophenoxy)pyrido[3,2-d]pyrimidin-4-amine
353 6-(2,4-difluorophenoxy)pyrido[3,2-d]pyrimidin-4-amine
354 6-(3,4-difluorophenoxy)pyrido[3,2-d]pyrimidin-4-amine
355 N6-[(2-chlorophenyl)methyl]pyrido[3,2-d]pyrimidine-4,6-diamine
356 6-(2-fluorophenoxy)pyrido[3,2-d]pyrimidin-4-amine
357 N6-[(3-chlorophenyl)methyl]pyrido[3,2-d]pyrimidine-4,6-diamine
358 N6-[(4-chlorophenyl)methyl]pyrido[3,2-d]pyrimidine-4,6-diamine
359 N6-(o-tolylmethyl)pyrido[3,2-d]pyrimidine-4,6-diamine
360 N6-[1-(6-methyl-2-pyridyl)ethyl]pyrido[3,2-d]pyrimidine-4,6-diamine
361 N6-[(3-pyrrolidin-1-ylphenyl)methyl]pyrido[3,2-d]pyrimidine-4,6-diamine
362 N6-(pyrazin-2-ylmethyl)pyrido[3,2-d]pyrimidine-4,6-diamine
363 6-[3-(difluoromethoxy)phenyl]pyrido[3,2-d]pyrimidin-4-amine
364 6-(3-(6-methylpyridin-2-yloxy)phenyl)pyrido[3,2-d]pyrimidin-4-amine
365 6-(3-isopropoxyphenyl)pyrido[3,2-d]pyrimidin-4-amine
366 6-(1H-indazol-4-yl)pyrido[3,2-d]pyrimidin-4-amine
367 6-(3-methoxyphenyl)pyrido[3,2-d]pyrimidin-4-amine
368 N1-(3-(4-aminopyrido[3,2-d]pyrimidin-6-yl)-5-fluorophenyl)-N3,N3-dimethylpropane-1,3-diamine formate free bases and pharmaceutical salts thereof as described herein and stereoisomers thereof.

In one embodiment, the invention relates to a compound according to the invention for use as therapeutically active substance.

In one embodiment, the invention relates to a pharmaceutical composition comprising a compound according to the invention and a therapeutically inert carrier.

In one embodiment, the invention relates to a compound according to the invention for the treatment or prophylaxis of cancer.

In one embodiment, the invention relates to the use of a compound according to the invention for the preparation of a medicament for the treatment or prophylaxis of cancer.

In one embodiment, the invention relates to a compound according to the invention for the treatment or prophylaxis of cancer.

In one embodiment, the invention relates to a method for the treatment or prophylaxis of cancer which method comprises administering an effective amount of a compound according to the invention.

In one embodiment, the invention cancer is selected from the groups consisting of the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma Pharmaceutical Formulations In order to use a Formula (I) compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of compounds of Formula (I) may be prepared. Suitable examples of sustained-release preparations include semipermeable matrices of solid hydrophobic polymers containing a compound of Formula (I), which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I). Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxy groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I) may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula (I) may be employed alone or in combination with other therapeutic agents for the treatment of a disease or disorder described herein, such as inflammation or a hyperproliferative disorder (e.g., cancer). In certain embodiments, a compound of Formula (I) is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula (I) such that they do not adversely affect each other. Such compounds are suitably present in combination in amounts that are effective for the purpose intended. In one embodiment, a composition of this invention comprises a compound of Formula (I), or a stereoisomer, tautomer, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula (I), or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula (I), or a stereoisomer, tautomer, or pharmaceutically acceptable salt or prodrug thereof, and the use of at least one other cancer treatment method. The amounts of the compound(s) of Formula (I) and the other pharmaceutically active chemotherapeutic agent(s) and the relative timings of administration will be selected in order to achieve the desired combined therapeutic effect.

Metabolites of Compounds of Formula (I)

Also falling within the scope of this invention are the in vivo metabolic products of Formula (I) described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula (I), including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula (I). The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula (I) or a formulation thereof which is effective for treating the condition and may have a sterile access port (for example, the container may be an intravenous solution bag or a vial having a stopper pierceable by a hypodermic injection needle). At least one active agent in the composition is a compound of Formula (I). The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula (I) can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula (I) and, if present, the second pharmaceutical formulation. For example, if the kit comprises a first composition comprising a compound of Formula (I) and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula (I), such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula (I) contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula (I) and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Biological Evaluation

Within the scope of the present invention the inventors have identified MAP4K4 as a key regulator of endothelial membrane dynamics during migration. Loss of MAP4K4 expression or MAP4K4 kinase activity in vitro reduces retraction of subcellular membrane protrusions, leading to the lengthening of these protrusions and persistent subcellular membrane branching, which ultimately impairs cell motility. The inventors have discovered that vascular-specific MAP4K4 knockout in mice results in severe hemorrhage and edema by E14.5 that culminates in embryonic lethality at ~E16.5. Embryonic endothelial cells have long aberrant protrusions, increased subcellular membrane branches, and delayed migration, with decreased vascular coverage in multiple organs.

The inventors have discovered that MAP4K4 in endothelial cells regulates the endothelial cell membrane dynamics during sprouting angiogenesis. The inventors discovered that inhibition of MAP4K4 kinase activity with small molecule inhibitors reduced cancer cell migration without affecting their proliferation or survival. Inhibition of MAP4K4 can therefore be useful for treating cancer by both reducing the tumor blood supply to decrease tumor growth, and by decreasing invasion/metastasis—the main cause of cancer fatality. The inventors have developed MAP4K4 antagonists that can be useful for the treatment of angiogenesis and cancer.

The relative efficacies of Formula (I) compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective MAP4K4 inhibitor" can be understood to refer to a compound that exhibits a 50% inhibitory concentration ($IC_{50}$) with respect to MAP4K4 that is at least at least 10-fold lower than the $IC_{50}$ value with respect to any or all of the other MAP4K4 family members.

Determination of the activity of MAP4K4 kinase activity of Formula (I) compounds is possible by a number of direct and indirect detection methods. The range of IC50 values for inhibition of MAP4K4 was less than 1 nM (nanomolar) to about 10 µM (micromolar). Certain exemplary compounds of the invention had MAP4K4 inhibitory $IC_{50}$ values less than 10 nM. Certain Formula (I) compounds may have antiangiogenesis activity to treat hyperproliferative disorders such as cancer. The Formula (I) compounds may inhibit angiogenesis in mammals and may be useful for treating human cancer patients.

The Example section of this patent application herein shows Formula (I) compounds that were made, characterized, and tested for inhibition of MAP4K4 and selectivity according to the methods of this invention, and have the corresponding structures and names (ChemBioDraw Ultra, Version 11.0, Cambridge Soft Corp., Cambridge Mass.).

Preparation of Formula (I) Compounds

The compounds of Formula (I) may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula (I) compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula (I) may be prepared singly or as compound libraries comprising at least 2, for example 5 to 1,000 compounds, or 10 to 100 compounds. Libraries of compounds of Formula (I) may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

For illustrative purposes, the following schemes show general methods for preparing compounds of Formula (I) according to the invention, as well as key intermediates. For a more detailed description of the individual reaction steps, see the Examples sections. Those skilled in the art will appreciate that other synthetic routes may be used to synthesize the inventive compounds. Although specific starting materials and reagents are depicted and discussed in the General Procedures, Examples, and schemes, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

GENERAL METHOD A

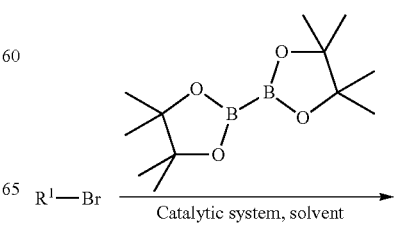

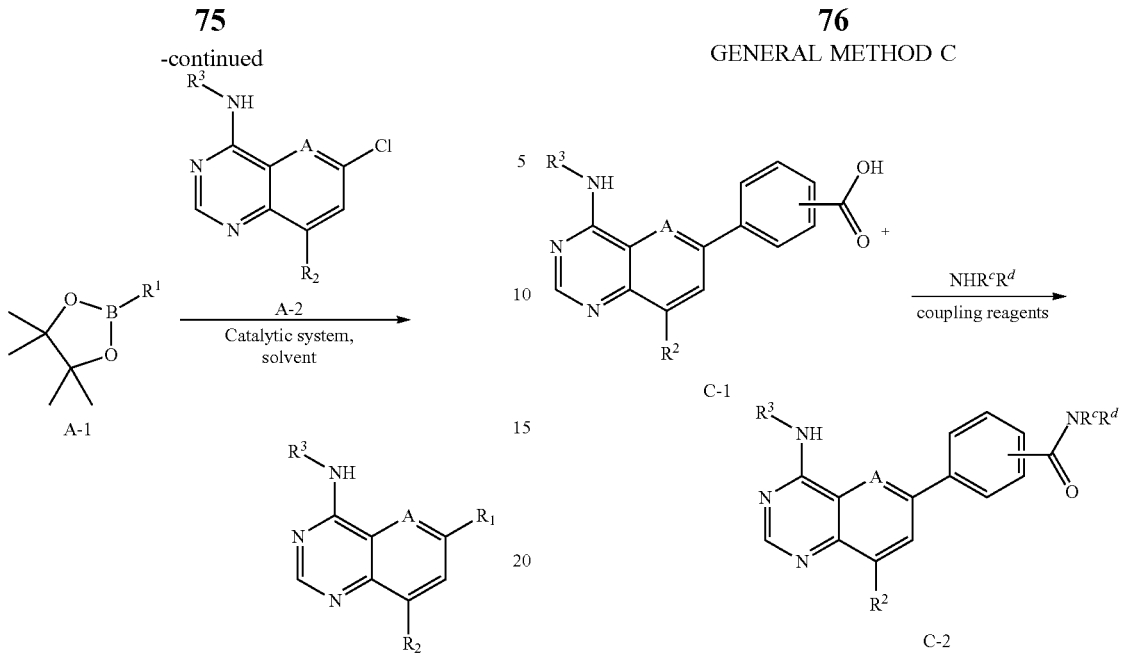

The compound of Formula I wherein A, R¹, R² and R³ are as defined herein, can be made according to the two step method of General Method A:

Step 1: a compound R¹—Br is treated in a suspension with 4,4,4',4',5,5,5',5'-octamethyl-2,2'-Bi-1,3,2-dioxaborolane (CAS 73183-34-3, about 1.2 eq), with a catalytic system such as e.g. Pd(dppf)Cl₂ and KOAc (about 2 eq) in a solvent, e.g. DMSO, heated (e.g. about 90 C for about 3 h). The reaction solution can then be partitioned between EtOAc and brine. The combined organic layer can be washed with water, concentrated and used in next step without further purification.

Step 2: the compound of Formula I can be obtained by reacting a compound A-1 (excess) with a compound of formula A-2 in a catalytic system, such as Pd(PPh₃)₄ and Cs₂CO₃ in an appropriate solvent, e.g. dioxane/H2O by heating (e.g. about 90 C for about 2 hours). The reaction solution can be partitioned between EtOAc and brine. The combined organic layer can be washed with water concentrated and purified by prep-HPLC.

GENERAL METHOD B

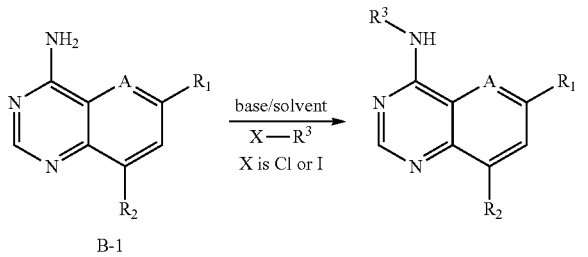

A method for adding a group R³ to the compounds of Formula I is shown in General Method B. According to this method, a compound of Formula B-1 in a solvent (e.g. DMF) is treated with a base e.g. sodium hydride dispersed in mineral oil and then reacted with a compound of Formula X—R³ (or X—R⁴) wherein X is halogen, e.g. Cl or I.

GENERAL METHOD C

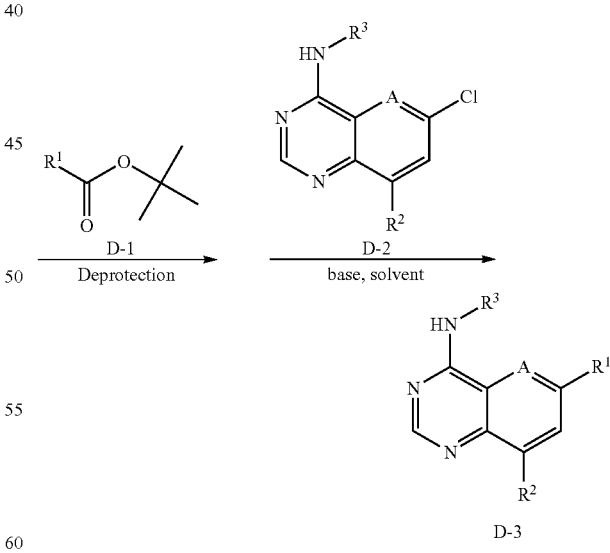

General Method C provides for the preparation of compounds of Formula C-2, which are compounds of Formula I wherein R¹ is a phenyl group substituted by an amide group. In this scheme R², R³, R$^c$ and R$^d$ are as defined herein. According to this method, a compound of Formula C-1 in a solvent (e.g. DMF) is coupled with an amine NH₂—R with coupling reagents such as DIPEA/HATU. The person skilled in the art will recognize that the same procedure could be used for compounds of Formula I wherein R¹ is heteroaryl substituted by an amido group.

GENERAL METHOD D

General Method D is useful for preparing compounds of Formula I wherein R¹ is an nitrogen linked group so that D-1 is a carbamate. R¹ can for example be —NR—C₁-C₁₂-hydroxyalkyl, —NR—(C₁-C₁₂-alkylenyl)$_n$-C₃-C₆-cycloalkyl, —NR—(C₁-C₁₂-alkylenyl)$_n$-heterocyclyl, —NR—(C₁-C₁₂-alkylenyl)$_n$-C₆-C₂₀-aryl, —NR—(C₁-C₁₂- alkylenyl)$_n$-heteroaryl, —NR—(C$_1$-C$_{12}$-alkylenyl)$_n$-C$_6$-C$_{20}$-aryloxy, C$_6$-C$_{20}$-aryl, pyridine, N-linked piperidine, N-linked pyrrolidine, N-linked morpholine, 1H-pyrazol-4-yl. These heterocycles can be substituted. Possible substituents for this heterocycle group are as defined herein. A, R$^2$ and R$^3$ are as defined herein. According to General Method D, the esters can be deprotected and reacted with a compound of Formula D-1 in appropriate media, e.g. base and solvent such as e.g. triethylamine and DMA.

GENERAL METHOD E

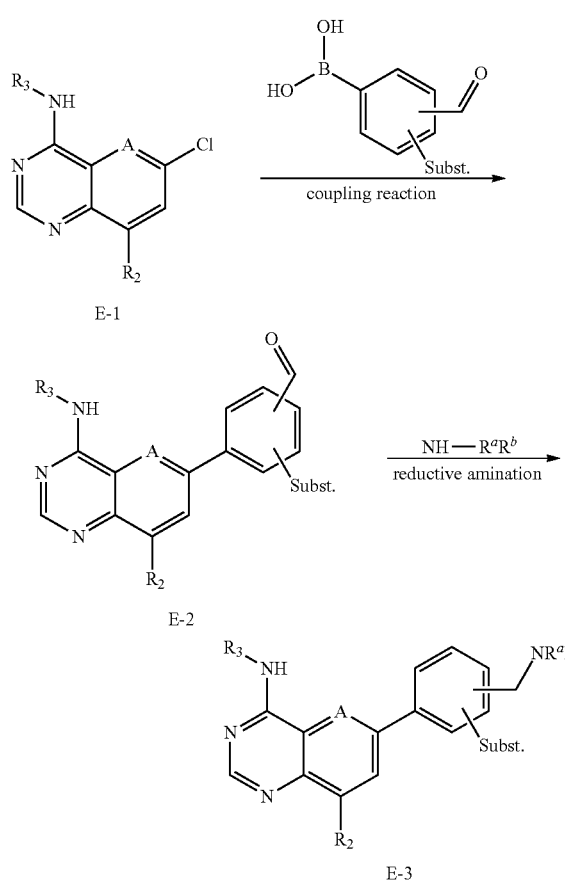

GENERAL METHOD F

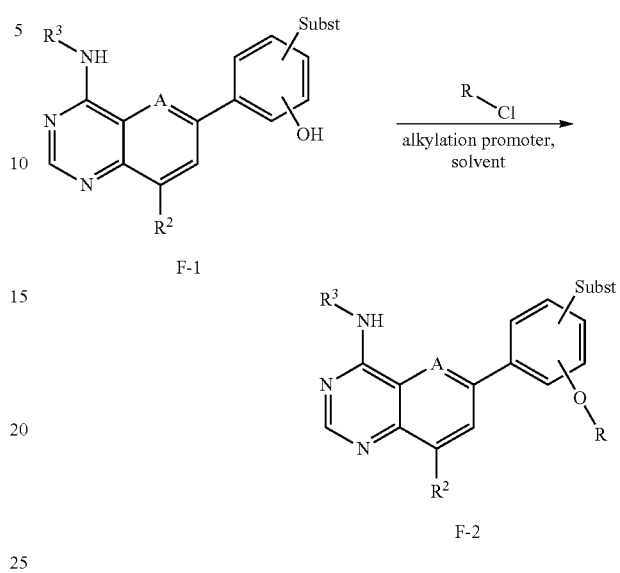

General Method F is useful to prepare compounds of Formula F-2 which are compounds of Formula I, wherein R$^1$ is a phenyl group substituted by an oxygen-linked group of formula —OR, wherein R is any group linked through O as defined herein, such as for example alkyl, haloalkyl. In this scheme A, R$^2$ and R$^3$ are as defined herein. A compound of Formula F-1 is reacted with a compound of Formula R—Cl in a suitable medium, e.g. in dimethylformamide in the presence of cesium carbonate or potassium carbonate as a promoter for the alkylation of the alcool. Non-limiting examples of such reaction can be found in the examples below. The person skilled in the art will recognize that the same procedure could be used for compounds of Formula I wherein R$^1$ is heteroaryl substituted by the —OR group.

GENERAL METHOD G

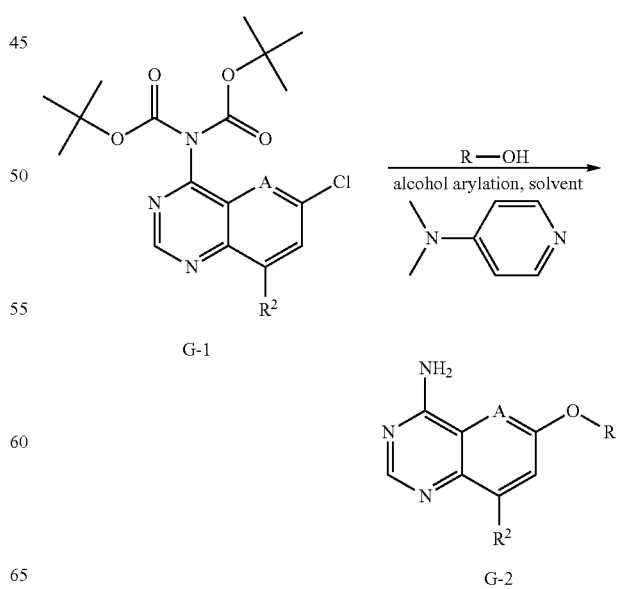

General Method E is useful to prepare compounds of Formula I wherein R$^1$ is a phenyl group that is optionally substituted and bears a —(CH$_2$)—NR$^a$R$^b$, wherein R$^a$ and R$^b$ are as defined herein. In this scheme A, R$^2$ and R$^3$ are as defined herein. In a first step, Compound of Formula E-1 can be coupled with the phenyl derivative depicted in the scheme above with suitable coupling reagents such as a palladium catalyst e.g. Pd(PPh$_3$)$_4$ in an appropriate solvent. In a second step, a reductive amination is performed, for example using sodium cyanoborohydride. Non-limiting examples of such reaction can be found in the examples below. The person skilled in the art will recognize that the same procedure could be used for compounds of Formula I wherein R$^1$ is heteroaryl substituted by the —(CH$_2$)—NR$^a$R$^b$ group.

General Method G is a variant of the General Method F useful to prepare compounds of Formula G-2 which correspond to compounds of Formula I, wherein $R^1$ is a group of formula —OR. In this scheme A and $R_2$ are as defined herein and R is aryl or heteroaryl which is optionally substituted. The reaction conditions are similar to those described in General Method F. Non-limiting examples of such reaction can be found in the examples below. The person skilled in the art will recognize that a group $R^3$ can be added to the compounds of Formula G-2 by using General Method B.

GENERAL METHOD H

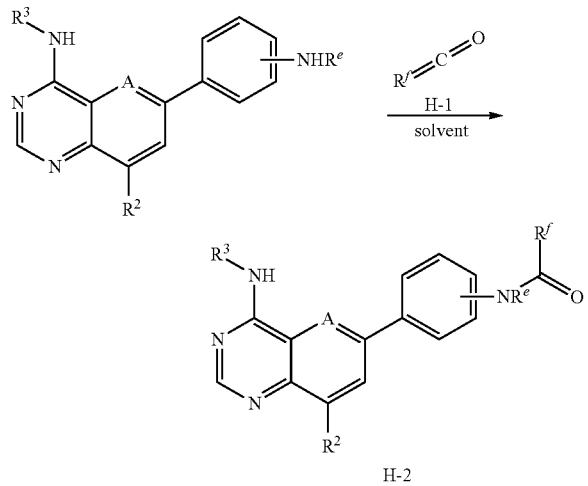

General Method H is useful to prepare compounds of Formula H-2, which correspond to compounds of Formula I, wherein $R^1$ is phenyl group substituted by an urea group of formula —$NR^e(CO)R^f$. In this urea, $R^e$ and $R^f$ are as defined herein for the compounds of Formula I. In this scheme, A, $R^2$ and $R^3$ are as defined herein. The person skilled in the art will recognize that the same procedure could be used for compounds of Formula I wherein $R^1$ is heteroaryl substituted by an urea group.

GENERAL METHOD I

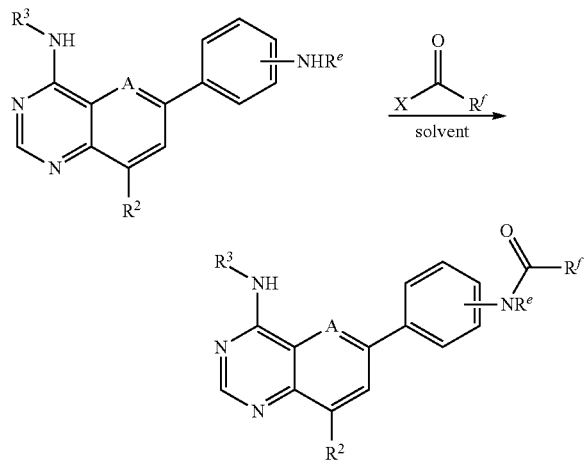

General Method I is useful to prepare compounds of Formula I wherein $R^1$ is a phenyl group substituted by an amido group. In this amido group, $R^e$ and W are as defined herein for the compounds of Formula I and X is halo. The person skilled in the art will recognize that the same procedure could be used for compounds of Formula I wherein $R^1$ is heteroaryl substituted by an amido group.

GENERAL METHOD J

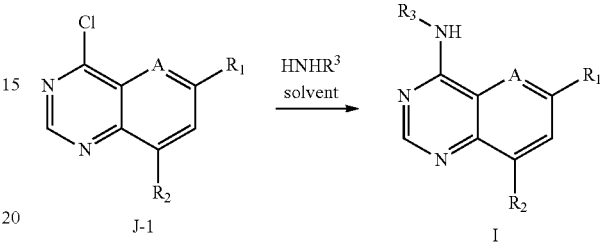

According to General Method J, a compound of Formula J-1 in a solvent (e.g. DMF) is treated with a base e.g. triethylamine and then reacted with a compound of Formula HN—$R^3$. In this scheme A, $R^1$, $R^2$ and $R^3$ are as defined herein.

GENERAL METHOD K

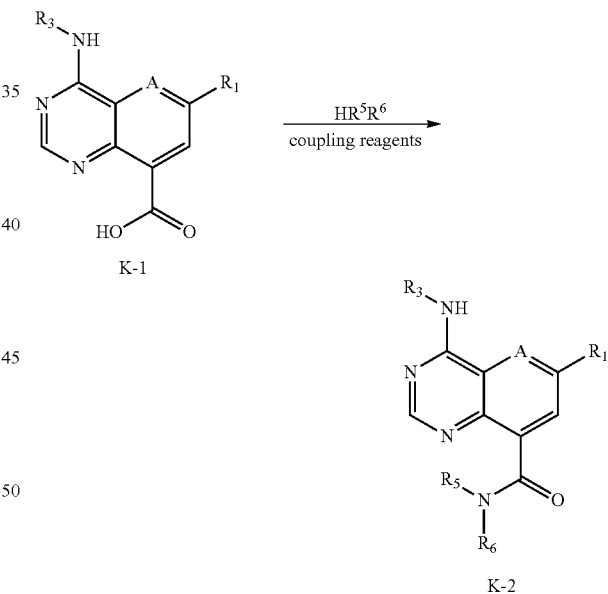

General Method K provides for the preparation of compounds of Formula K-2, which are compounds of Formula I wherein $R^2$ is —C(O)—NH($C_1$-$C_{12}$-alkyl)-NH—C(O)—$C_1$-$C_{12}$-alkyl, —C(O)—N($C_1$-$C_{12}$-alkyl)$_2$-$C_1$-$C_{12}$-alkoxy, —C(O)—N($C_1$-$C_{12}$-alkyl)-heterocyclyl, —C(O)-heterocyclyl, which heterocyclyl groups are unsubstituted or substituted by one or more $R^g$ or —N($C_1$-$C_{12}$-alkyl)-C(O)—$C_1$-$C_{12}$-alkyl, and —N($C_1$-$C_{12}$-alkyl)$_2$ group, as represented by the group —(CO)—$NR^5R^6$. According to this method, a compound of Formula K-1 in a solvent (e.g. DMF) is coupled with an amine $HNR^5R^6$ with coupling reagents such as DIPEA/HATU.

GENERAL METHOD L

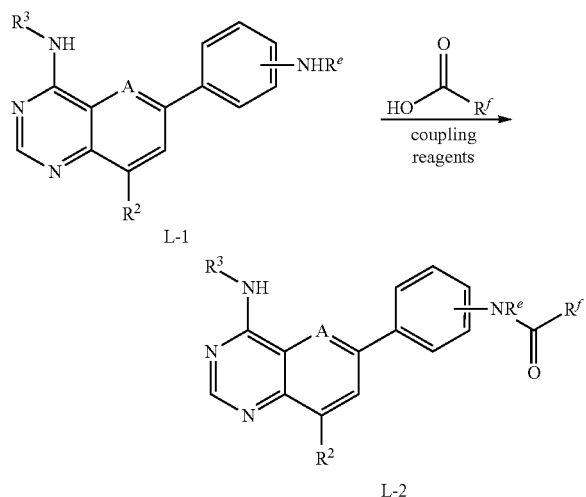

General Method L provides for the preparation of compounds of Formula L-2, which are compounds of Formula I wherein $R^1$ is a phenyl group substituted by an amide group. In this scheme A, $R^2$, $R^3$, $R^e$ and $R^f$ are as defined herein. According to this method, a compound of Formula L-1 in a solvent (e.g. DMF) is coupled with an acid $R^f$—$CO_2H$ with coupling reagents such as DIPEA/HATU.

GENERAL METHOD M

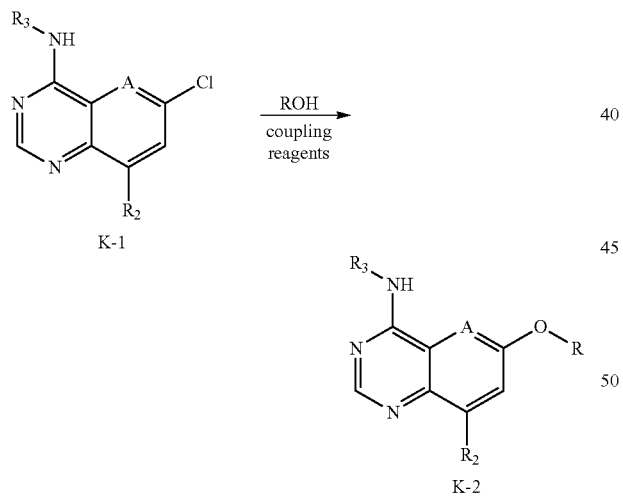

General Method K is useful to prepare compounds of Formula K-2, which correspond to compounds of Formula I wherein $R^1$ is aryloxy or heteroaryloxy as defined herein. A compound of Formula K-1 in a solvent (e.g. DMA) is treated with a base e.g. potassium carbonate and then reacted with a compound of Formula ROH.

EXAMPLES

The invention will be more fully understood by reference to the following examples. They should not, however, be construed as limiting the scope of the invention.

The chemical reactions described in the Examples may be readily adapted to prepare a number of other MAP4K4 inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

$^1$H NMR spectra were recorded at ambient temperature using an NMR spectrometer, including a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography/Mass Spectrometry (LCMS) experiments to determine retention times ($R_T$) and associated mass ions may be performed. The spectrometers may have an electrospray source operating in positive and negative ion mode. Additional detection is achieved using a evaporative light scattering detector.

Unless otherwise stated, all reactions were performed under an inert, i.e. argon or nitrogen, atmosphere.

Abbreviations

AcOH: Acetic acid; BOC: Di-tert-butyl dicarbonate; DCM: Dichloromethane; DIPEA: Diisopropylethylamine; DMAP: 4-Dimethylaminopyridine; EtOAc: Ethyl acetate; HATU: (2-(7-Aza-1H-benzotriazole-1-yl)-1,1,3,3-tetramethyluronium hexafluorophosphate); HCl: Hydrochloric acid; MeOH: Methanol; NaBH$_4$: Sodium borohydride, NBS: N-Bromosuccinimide; NH$_4$Cl: Ammonium chloride; NMR: Nuclear magnetic resonance; Pd(dppf)Cl$_2$: [1,1'-Bis(diphenylphosphino)ferrocene]dichloropalladium(II), complex with dichloromethane; RT: Room temperature; TFA: Trifluoroacetic acid; THF: Tetrahydrofuran.

Example 1

6-(2-fluoro-4-pyridyl)pyrido[3,2-d]pyrimidin-4-amine

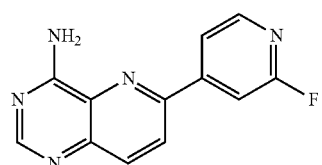

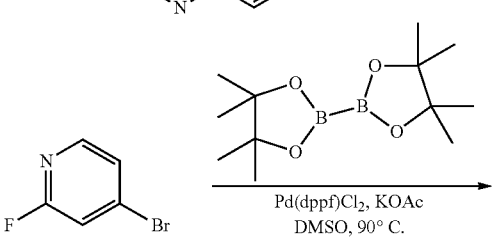

Example 3

3-(4-aminopyrido[3,2-d]pyrimidin-6-yl)-5-fluorobenzoic acid

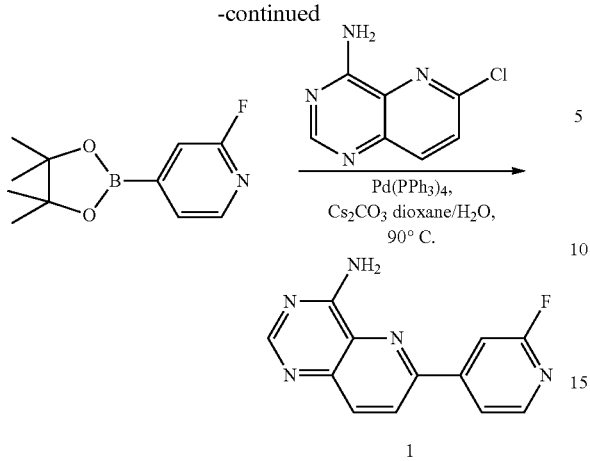

1H NMR (400 MHz, DMSO) δ 8.62-8.57 (d, J=8.8 Hz, 1H), 8.48-8.43 (s, 2H), 8.43-8.40 (d, J=5.3 Hz, 1H), 8.39-8.35 (d, J=5.3 Hz, 1H), 8.35-8.33 (s, 1H), 8.24-8.20 (d, J=8.8 Hz, 1H), 8.15-8.09 (s, 1H).

Example 2

4-(4-aminopyrido[3,2-d]pyrimidin-6-yl)pyridin-2(1H)-one

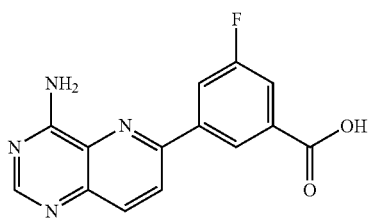

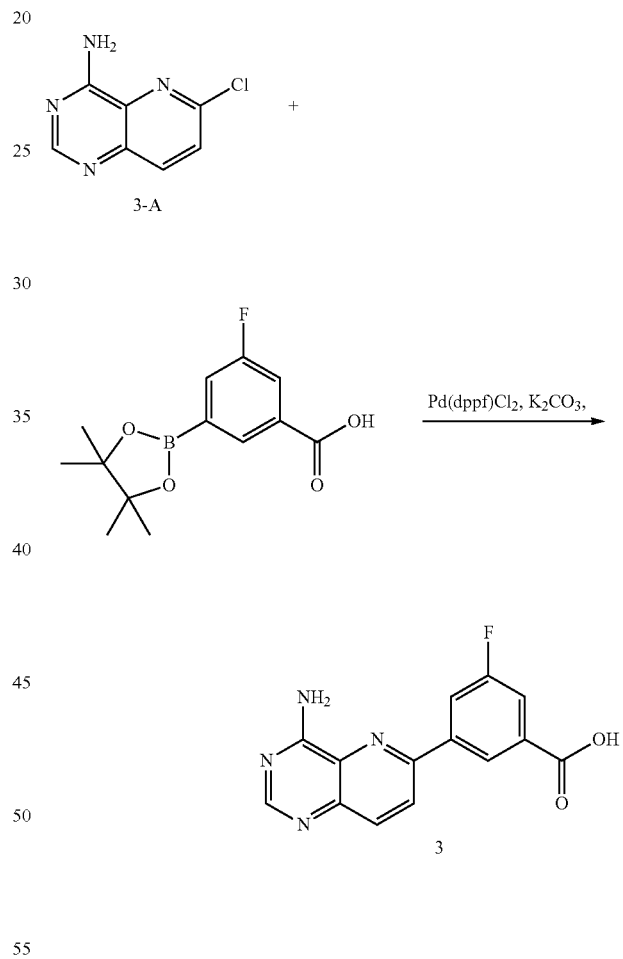

6-(2-fluoro-4-pyridyl)pyrido[3,2-d]pyrimidin-4-amine (50 mg, 0.21 mmol) 1 was treated with hydrogen chloride (4 mol/L) in 1,4-dioxane. The mixture was heated to 80° C. for 1 hour. Cooled to room temperature and basified with 4 N NaOH. Yellow precipitate was collected, and purified with Prep HPLC, 30 mg of 4-(4-aminopyrido[3,2-d]pyrimidin-6-yl)pyridin-2(1H)-one 2 was obtained (yield 60%). LC/MS (ESI+): m/z 240 (M+H). 1H NMR (400 MHz, DMSO) δ 8.39 (d, J=8.7 Hz, 1H), 8.18 (s, 1H), 8.15 (d, J=8.6 Hz, 1H), 7.52 (d, J=6.9 Hz, 1H), 7.11 (d, J=1.6 Hz, 1H), 7.00 (dd, J=6.9, 1.8 Hz, 1H).

6-chloropyrido[3,2-d]pyrimidin-4-amine (500 mg, 2.8 mmol) 3-A in acetonitrile (5 mL) was treated with 3-borono-5-fluoro-benzoic acid (CAS 269404-73-6) (560 mg, 3 mL), PDCL₂(DPPF) (202 mg, 0.28 mmol) and 1 M potassium carbonate solution (8 mL). The reaction vial was purged with nitrogen, and heated to 80° C. for 1 hour. LCMS showed 100% conversion to desired product. Yellow precipitate was collected and LCMS indicated it is pure product 3-(4-aminopyrido[3,2-d]pyrimidin-6-yl)-5-fluorobenzoic acid 3. The filtrate was concentrate and purified by prep HPLC. LC/MS (ESI+): m/z 285 (M+H).

Example 4

3-(4-aminopyrido[3,2-d]pyrimidin-6-yl)-5-fluoro-N-(1-hydroxy-2-methylpropan-2-yl)benzamide

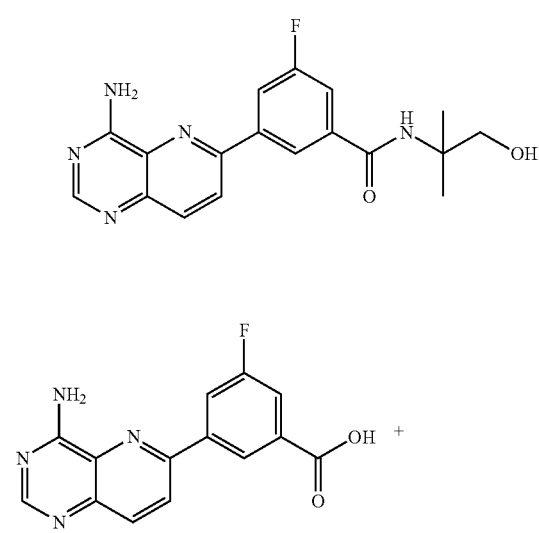

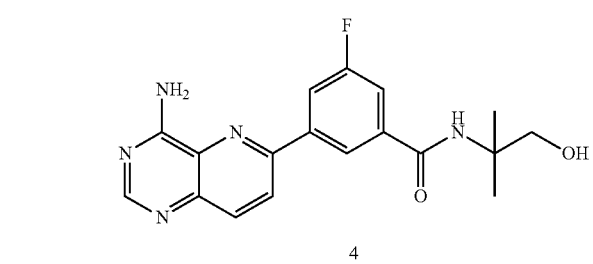

3-(4-aminopyrido[3,2-d]pyrimidin-6-yl)-5-fluoro-benzoic acid (100 mg, 0.35 mmol) 3 in DMF was treated with DIPEA (0.3 mL, 1.76 mmol) followed by HATU (279 mg, 0.7 mmol). The mixture was stirred at room temperature for 10 minutes, then 2-amino-2-methyl-propan-1-ol (CAS-124-68-5) (0.07 mL, 0.7 mmol) was added and continue stirred at room temperature overnight. Saturated sodium bicarbonate was added, and the mixture was extracted with EtOAc. The combined organics were dried over sodium sulfate and concentrated. The crude was purified by Prep HPLC to give 15 mg of 3-(4-aminopyrido[3,2-d]pyrimidin-6-yl)-5-fluoro-N-(1-hydroxy-2-methylpropan-2-yl)benzamide 4. LC/MS (ESI+): m/z 356 (M+H). 1H NMR (400 MHz, DMSO) δ 8.55 (t, J=8.7 Hz, 1H), 8.47 (s, 1H), 8.44 (d, J=7.1 Hz, 1H), 8.18 (t, J=8.8 Hz, 1H), 7.82 (d, J=24.4 Hz, 1H), 7.71 (d, J=9.4 Hz, 1H), 4.87 (t, J=6.0 Hz, 1H), 3.58 (d, J=5.8 Hz, 2H), 2.07 (s, 2H), 1.36 (s, 6H).

Example 5

3-(4-aminopyrido[3,2-d]pyrimidin-6-yl)-5-fluoro-N-methylbenzamide

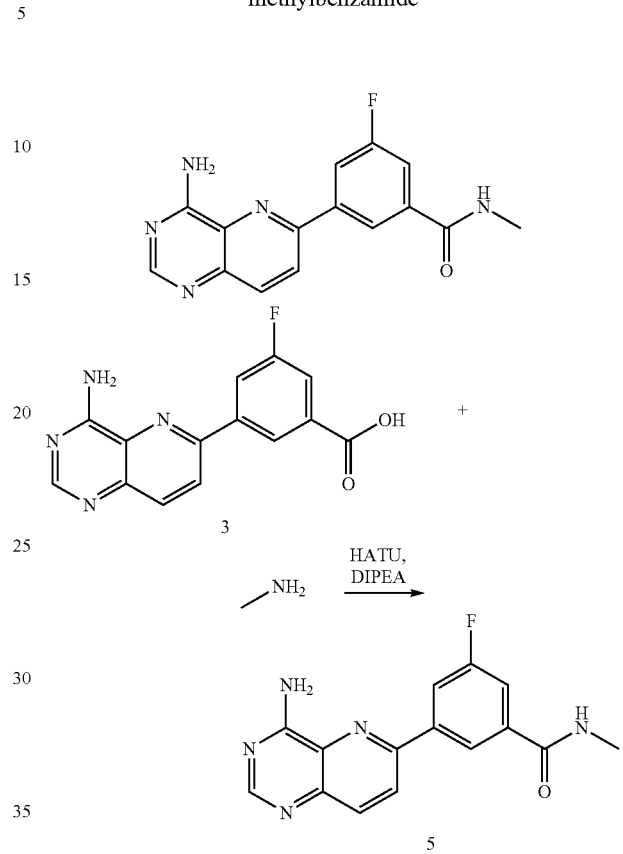

Following the same reaction and purification procedure, the acid 3 (50 mg, 0.18 mmol) was reacted with methyl amine 2M in THF (0.18 mL, 0.35 mmol), HATU (103 mg, 0.6 mmol) and DIPEA (0.15 mL, 0.88 mmol) in DMF (1 mL) at room temperature to provide 3-(4-aminopyrido[3,2-d]pyrimidin-6-yl)-5-fluoro-N-methylbenzamide 5. LC/MS (ESI+): m/z 298 (M+H). 1H NMR (400 MHz, DMSO) δ 8.71 (d, J=4.5 Hz, 1H), 8.59 (dd, J=7.4, 4.0 Hz, 2H), 8.54 (d, J=8.9 Hz, 1H), 8.47 (s, 1H), 8.28 (s, 1H), 8.20 (d, J=8.8 Hz, 1H), 8.06 (s, 1H), 7.72 (d, J=9.2 Hz, 1H), 2.87 (d, J=4.5 Hz, 3H).

Example 6

3-(4-aminopyrido[3,2-d]pyrimidin-6-yl)-N-cyclobutyl-5-fluorobenzamide

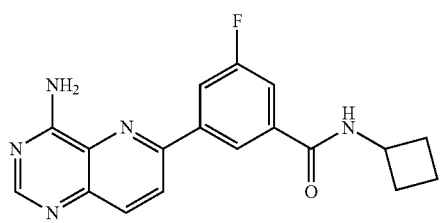

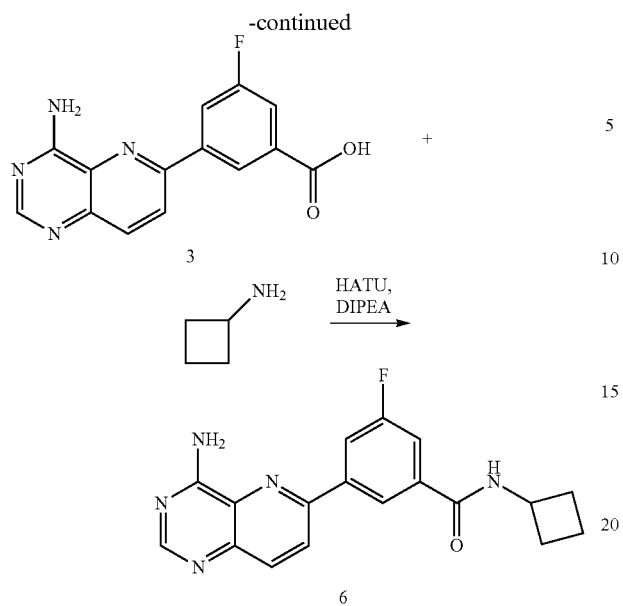

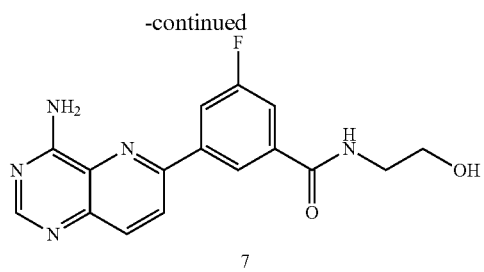

Following the same reaction and purification procedure as above, the acid 3 (50 mg, 0.18 mmol) was reacted with cyclobutanamine (CAS-2516-34-9) (0.03 mL, 0.35 mmol), HATU (103 mg, 0.35 mmol) and DIPEA (0.15 mL, 0.88 mmol) in DMF (1 mL) at room temperature to provide 3-(4-aminopyrido[3,2-d]pyrimidin-6-yl)-N-cyclobutyl-5-fluorobenzamide 6. LC/MS (ESI+): m/z 338 (M+H). 1H NMR (400 MHz, DMSO) δ 8.84 (d, J=7.3 Hz, 1H), 8.63 (d, J=10.3 Hz, 1H), 8.55 (dd, J=7.6, 5.1 Hz, 2H), 8.47-8.40 (m, 1H), 8.29 (d, J=12.0 Hz, 1H), 8.19 (dd, J=15.7, 10.5 Hz, 1H), 8.04 (s, 1H), 7.73 (d, J=9.2 Hz, 1H), 4.47 (dq, J=15.8, 7.9 Hz, 1H), 2.36-2.21 (m, 2H), 2.21-2.03 (m, 2H), 1.84-1.61 (m, 2H).

Example 7

3-(4-aminopyrido[3,2-d]pyrimidin-6-yl)-5-fluoro-N-(2-hydroxyethyl)benzamide

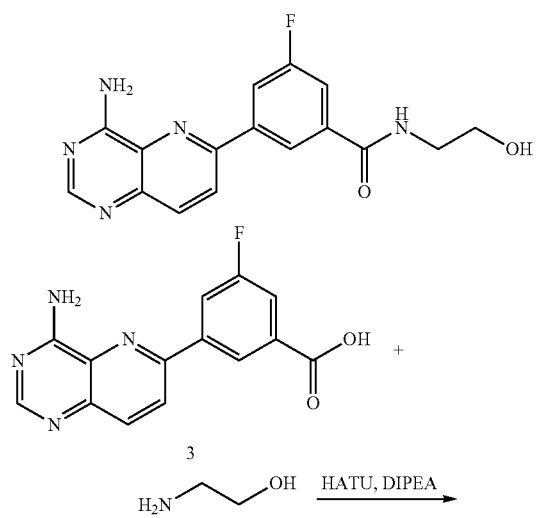

Following the same reaction and purification procedure, the acid 3 (100 mg, 0.35 mmol) was reacted with 2-aminoethanol (CAS 141-43-5) (43 mg, 0.7 mmol), HATU (276 mg, 0.7 mmol) and DIPEA (0.30 mL, 1.8 mmol) in DMF (1 mL) at room temperature to provide 3-(4-aminopyrido[3,2-d]pyrimidin-6-yl)-5-fluoro-N-(2-hydroxyethyl)benzamide 7. LC/MS (ESI+): m/z 328 (M+H).

Example 8

3-(4-aminopyrido[3,2-d]pyrimidin-6-yl)-5-fluoro-N-(3-hydroxycyclobutyl)benzamide

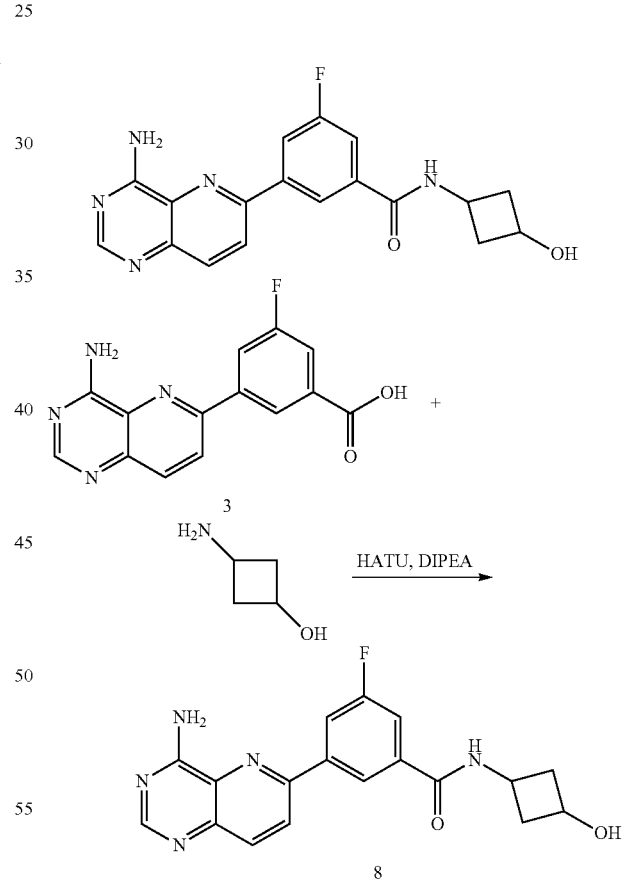

Following the same reaction and purification procedure, the acid 3 (50 mg, 0.17 mmol) was reacted with 2-aminocyclobutanol (CAS 4640-44-2) (30 mg, 0.35 mmol), HATU (135 mg, 0.35 mmol) and DIPEA (0.15 mL, 0.9 mmol) in DMF (1 mL) at room temperature to provide 3-(4-aminopyrido[3,2-d]pyrimidin-6-yl)-5-fluoro-N-(3-hydroxycyclobutyl)benzamide 8 as a mixture of cis and trans isomer. LC/MS (ESI+): m/z 354 (M+H). 1H NMR (400 MHz, DMSO) δ 8.81 (d, J=6.9 Hz, 1H), 8.63 (d, J=10.2 Hz, 1H), 8.54 (dd, J=10.1, 8.9 Hz, 3H), 8.44 (s, 1H), 8.31 (s, 1H), 8.20 (d, J=8.8 Hz, 1H), 8.03 (s, 1H), 7.73 (d, J=8.2 Hz, 2H), 5.15 (d, J=5.4 Hz, 1H), 5.05 (d, J=5.2 Hz, 1H), 4.48 (d, J=6.2 Hz, 1H), 4.37 (d, J=4.7 Hz, 1H), 4.04-3.84 (m, 2H), 2.96-2.84 (m, 1H), 2.69-2.54 (m, 2H), 2.39-2.28 (m, 1H), 2.21 (ddd, J=12.6, 8.1, 4.7 Hz, 1H), 1.97 (ddd, J=17.2, 8.7, 2.7 Hz, 2H).

Example 9

3-(4-aminopyrido[3,2-d]pyrimidin-6-yl)-5-fluoro-N-(1-hydroxypropan-2-yl)benzamide

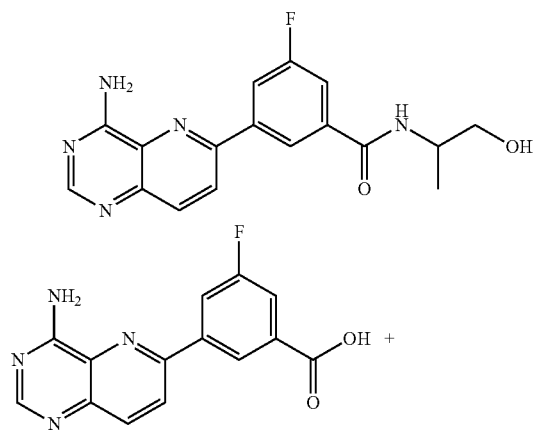

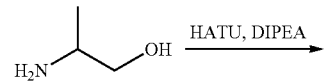

9

Following the same reaction and purification procedure as above, the acid 3 (60 mg, 0.21 mmol) was reacted with 2-aminopropan-1-ol (CAS 78-91-1) (0.03 mL, 0.42 mmol), HATU (166 mg, 0.42 mmol) and DIPEA (0.18 mL, 1.1 mmol) in DMF (1 mL) at room temperature to provide 3-(4-aminopyrido[3,2-d]pyrimidin-6-yl)-5-fluoro-N-(1-hydroxypropan-2-yl)benzamide 9. LC/MS (ESI+): m/z 342 (M+H). 1H NMR (400 MHz, DMSO) δ 8.64 (d, J=10.3 Hz, 1H), 8.56 (d, J=8.7 Hz, 2H), 8.43 (d, J=5.5 Hz, 1H), 8.38 (d, J=7.9 Hz, 1H), 8.30 (s, 1H), 8.21 (d, J=8.8 Hz, 1H), 8.03 (s, 1H), 7.75 (d, J=9.4 Hz, 1H), 4.77 (t, J=5.8 Hz, 1H), 4.17-3.99 (m, 1H), 3.52 (dt, J=11.2, 5.7 Hz, 1H), 3.46-3.36 (m, 1H), 1.19 (d, J=6.7 Hz, 3H).

Example 10

3-(4-aminopyrido[3,2-d]pyrimidin-6-yl)-5-fluoro-N-((1-methylpiperidin-4-yl)methyl)benzamide

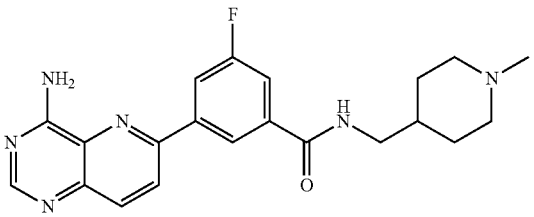

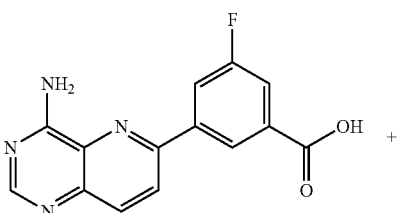

3

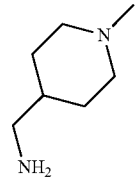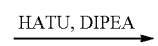

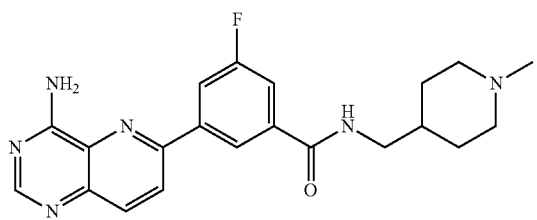

10

Following the same reaction and purification procedure as above, the acid 3 (60 mg, 0.21 mmol) was reacted with (1-methyl-4-piperidyl)methanamine (CAS 7149-42-0) (54 mg, 0.42 mmol), HATU (166 mg, 0.42 mmol) and DIPEA (0.18 mL, 1.1 mmol) in DMF (1 mL) at room temperature to provide 3-(4-aminopyrido[3,2-d]pyrimidin-6-yl)-5-fluoro-N-((1-methylpiperidin-4-yl)methyl)benzamide 10. LC/MS (ESI+): m/z 395 (M+H). 1H NMR (400 MHz, DMSO) δ 8.53 (d, J=8.8 Hz, 1H), 8.48 (d, J=10.6 Hz, 1H), 8.46-8.38 (m, 1H), 8.32 (s, 1H), 8.22 (s, 1H), 8.14 (d, J=8.8 Hz, 1H), 7.99 (s, 1H), 7.33 (d, J=8.5 Hz, 1H), 2.90 (d, J=7.8 Hz, 2H), 2.84-2.63 (m, 4H), 2.19 (s, 1H), 2.03 (s, 3H), 1.82 (s, 2H), 1.66 (s, 2H).

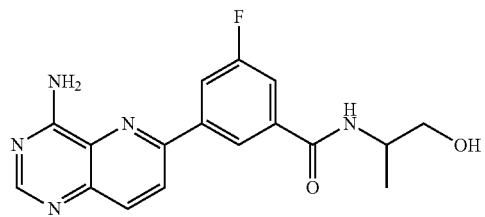

Example 11

3-(4-aminopyrido[3,2-d]pyrimidin-6-yl)-5-fluoro-N-(2-morpholinoethyl)benzamide

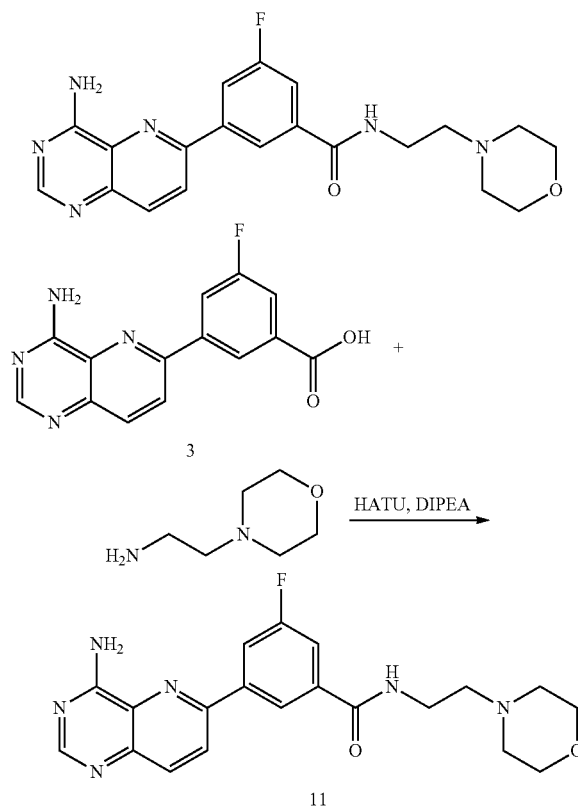

Following the same reaction and purification procedure, the acid 3 (60 mg, 0.21 mmol) was reacted with 2-morpholinoethanamine (CAS 2038-03-1) (55 mg, 0.42 mmol), HATU (166 mg, 0.42 mmol) and DIPEA (0.18 mL, 1.1 mmol) in DMF (1 mL) at room temperature to provide 3-(4-aminopyrido[3,2-d]pyrimidin-6-yl)-5-fluoro-N-(2-morpholinoethyl)benzamide 11. LC/MS (ESI+): m/z 397 (M+H). 1H NMR (400 MHz, DMSO) δ 8.70 (t, J=5.6 Hz, 1H), 8.62 (d, J=10.2 Hz, 1H), 8.54 (dd, J=17.5, 8.6 Hz, 2H), 8.44 (s, 1H), 8.28 (s, 1H), 8.20 (d, J=8.8 Hz, 1H), 8.05 (s, 1H), 7.72 (d, J=9.3 Hz, 1H), 3.67-3.52 (m, 4H), 3.46 (dd, J=13.1, 6.6 Hz, 2H), 2.55-2.51 (m, 2H), 2.47-2.41 (m, 4H).

Example 12

3-(4-aminopyrido[3,2-d]pyrimidin-6-yl)-N-(2-(dimethylamino)ethyl)-5-fluorobenzamide

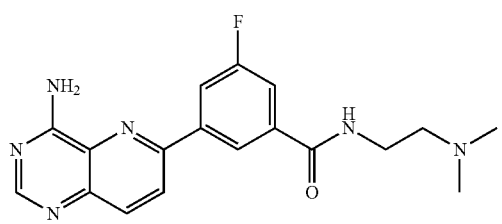

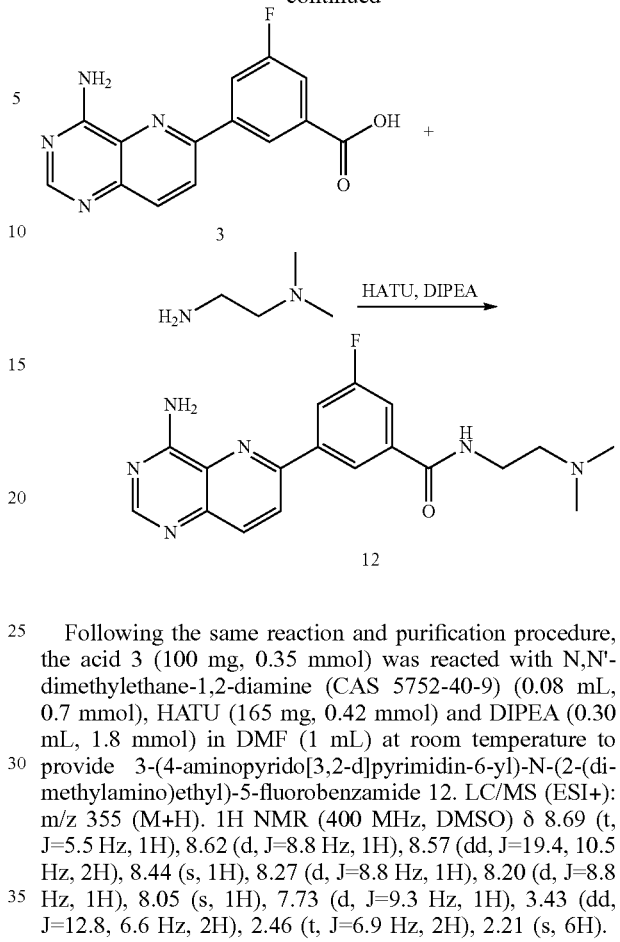

Following the same reaction and purification procedure, the acid 3 (100 mg, 0.35 mmol) was reacted with N,N'-dimethylethane-1,2-diamine (CAS 5752-40-9) (0.08 mL, 0.7 mmol), HATU (165 mg, 0.42 mmol) and DIPEA (0.30 mL, 1.8 mmol) in DMF (1 mL) at room temperature to provide 3-(4-aminopyrido[3,2-d]pyrimidin-6-yl)-N-(2-(dimethylamino)ethyl)-5-fluorobenzamide 12. LC/MS (ESI+): m/z 355 (M+H). 1H NMR (400 MHz, DMSO) δ 8.69 (t, J=5.5 Hz, 1H), 8.62 (d, J=8.8 Hz, 1H), 8.57 (dd, J=19.4, 10.5 Hz, 2H), 8.44 (s, 1H), 8.27 (d, J=8.8 Hz, 1H), 8.20 (d, J=8.8 Hz, 1H), 8.05 (s, 1H), 7.73 (d, J=9.3 Hz, 1H), 3.43 (dd, J=12.8, 6.6 Hz, 2H), 2.46 (t, J=6.9 Hz, 2H), 2.21 (s, 6H).

Example 13

3-(4-aminopyrido[3,2-d]pyrimidin-6-yl)-5-fluoro-N-(2-(pyrrolidin-1-yl)ethyl)benzamide

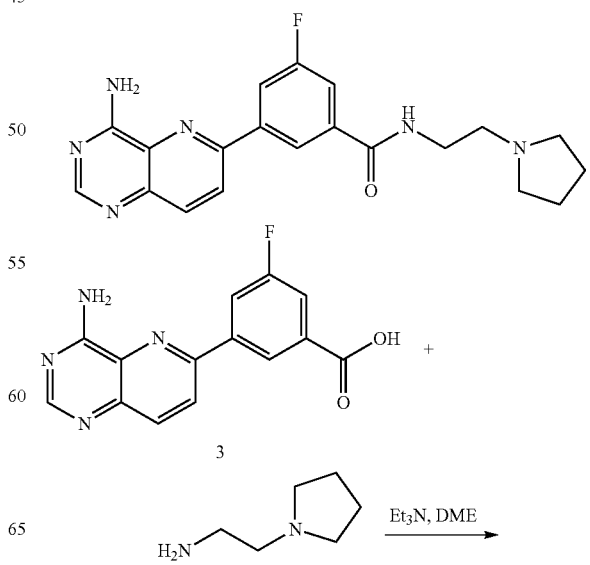

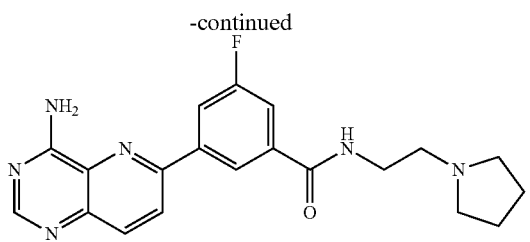

3-(4-aminopyrido[3,2-d]pyrimidin-6-yl)-5-fluoro-benzoic acid 3 (110 mg, 0.39 mmol) in DME (2 mL) was treated with triethylamine (0.11 mL, 0.77 mmol) and cooled in ice bath with salt, methanolsulfonyl chloride (0.05 mL, 0.58 mmol) was added, and continue stirred for 1 hour in ice bath, then 2-pyrrolidin-1-ylethanamine (CAS 7154-73-6) (0.07 mL, 0.58 mmol) was added, the reaction was stirred overnight. The reaction mixture was purified with prep HPLC to give pure 3-(4-aminopyrido[3,2-d]pyrimidin-6-yl)-5-fluoro-N-(2-(pyrrolidin-1-yl)ethyl)benzamide 13. LC/MS (ESI+): m/z 381 (M+H). 1H NMR (400 MHz, DMSO) δ 8.75 (t, J=5.6 Hz, 1H), 8.66-8.49 (m, 3H), 8.44 (s, 1H), 8.29 (s, 1H), 8.20 (t, J=4.4 Hz, 2H), 8.05 (s, 1H), 7.73 (d, J=9.4 Hz, 1H), 3.62-3.39 (m, 2H), 2.65 (t, J=7.0 Hz, 2H), 2.54 (s, 4H), 1.82-1.59 (m, 4H).

Example 14

3-(4-aminopyrido[3,2-d]pyrimidin-6-yl)benzoic acid

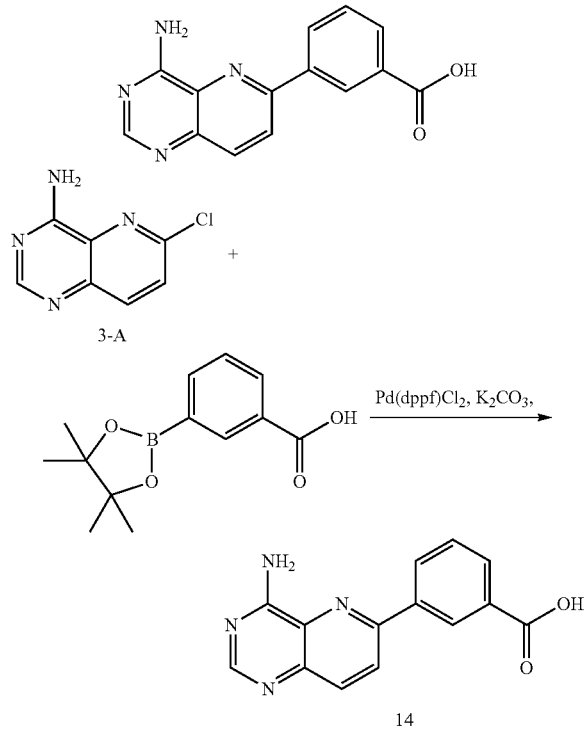

6-chloropyrido[3,2-d]pyrimidin-4-amine 3-A (500 mg, 2.8 mmol) in acetonitrile (5 mL) was treated with 3-boronobenzoic acid (CAS 269404-73-6) (560 mg, 3 mL), PDCL₂(DPPF) (202 mg, 0.28 mmol) and 1 M POTASSIUM CARBONATE solution (8 mL). The reaction vial was purged with nitrogen, and heated to 80° C. for 1 hour. LCMS showed 100% conversion to desired product. Yellow ppt. was filtered and LCMS indicated it is pure product 3-(4-aminopyrido[3,2-d]pyrimidin-6-yl)benzoic acid 14. The filtrate was concentrate and purified with reverse phase C-18 column to provide more product. LC/MS (ESI+): m/z 267 (M+H).

Example 15

3-(4-aminopyrido[3,2-d]pyrimidin-6-yl)-N-(3-hydroxycyclobutyl)benzamide

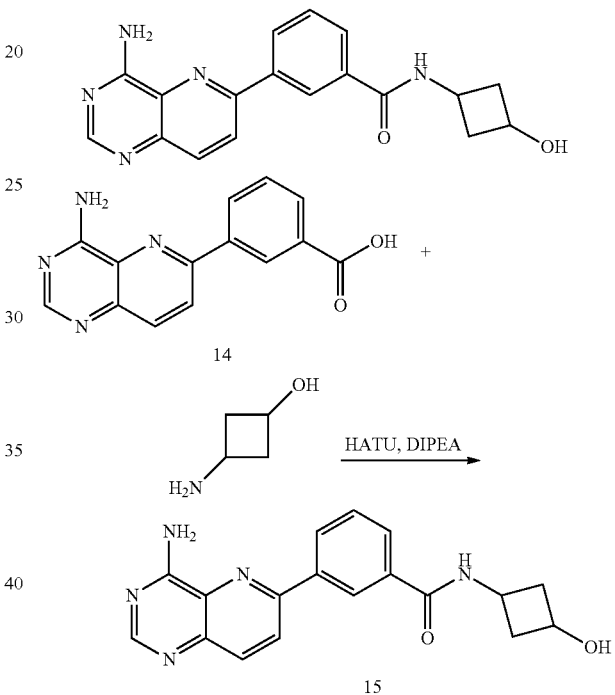

Following the same reaction and purification procedure, the acid 14 (90 mg, 0.34 mmol) was reacted with 2-aminocyclobutanol (CAS 4640-44-2) (59 mg, 0.68 mmol), HATU (145 mg, 0.38 mmol) and DIPEA (0.3 mL, 1.7 mmol) in DMF (1 mL) at room temperature to provide 3-(4-aminopyrido[3,2-d]pyrimidin-6-yl)-N-(3-hydroxycyclobutyl)benzamide 15 as a mixture of cis and trans isomer. LC/MS (ESI+): m/z 336 (M+H). 1H NMR (400 MHz, DMSO) δ 8.80-8.66 (m, 2H), 8.61 (d, J=7.8 Hz, 1H), 8.56-8.47 (m, 1H), 8.43 (s, 1H), 8.19 (d, J=8.8 Hz, 1H), 8.06 (d, J=32.4 Hz, 2H), 8.01-7.91 (m, 1H), 7.63 (t, J=7.8 Hz, 1H), 5.12 (d, J=5.4 Hz, 1H), 5.03 (d, J=5.3 Hz, 1H), 4.50 (d, J=6.5 Hz, 1H), 4.37 (s, 1H), 4.03-3.81 (m, 2H), 2.95-2.78 (m, 1H), 2.62 (ddd, J=12.7, 11.7, 8.9 Hz, 1H), 2.40-2.27 (m, 1H), 2.20 (ddd, J=12.4, 8.0, 4.5 Hz, 1H), 1.97 (ddd, J=17.3, 8.6, 2.8 Hz, 2H).

Example 16

3-(4-aminopyrido[3,2-d]pyrimidin-6-yl)-N-(2-hydroxyethyl)benzamide

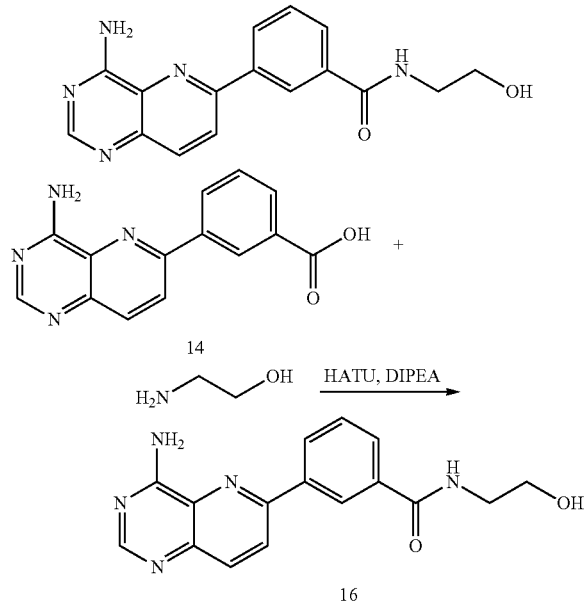

Following the same reaction and purification procedure, the acid 14 (80 mg, 0.30 mmol) was reacted with 2-aminoethanol (CAS 141-43-5) (36 mg, 0.6 mmol), HATU (141 mg, 0.36 mmol) and DIPEA (0.26 mL, 1.5 mmol) in DMF (1 mL) at room temperature to provide 3-(4-aminopyrido[3,2-d]pyrimidin-6-yl)-N-(2-hydroxyethyl)benzamide 16. LC/MS (ESI+): m/z 309 (M+H). 1H NMR (400 MHz, DMSO) δ 8.76 (s, 1H), 8.64 (t, J=5.5 Hz, 1H), 8.60 (d, J=7.9 Hz, 1H), 8.51 (d, J=8.9 Hz, 1H), 8.43 (s, 1H), 8.17 (t, J=12.9 Hz, 1H), 8.07 (d, J=24.4 Hz, 2H), 7.98 (d, J=7.7 Hz, 1H), 7.68-7.56 (m, 1H), 4.76 (t, J=5.6 Hz, 1H), 3.57 (q, J=6.0 Hz, 2H), 3.41 (q, J=6.0 Hz, 2H).

Example 17

3-(4-aminopyrido[3,2-d]pyrimidin-6-yl)-N-(1-hydroxypropan-2-yl)benzamide

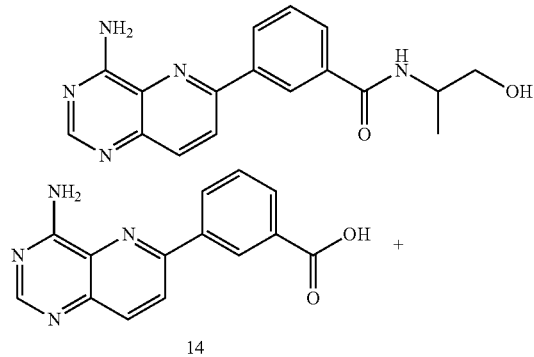

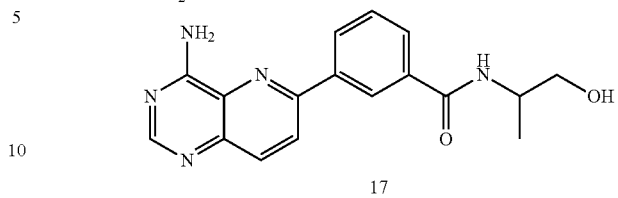

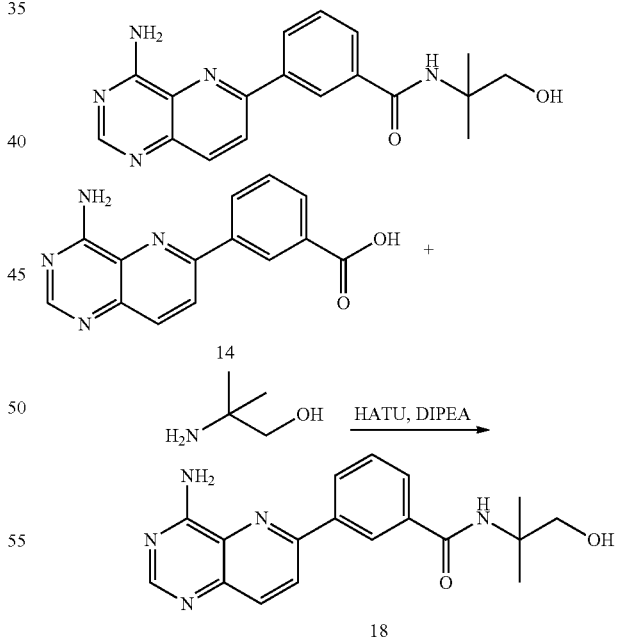

Following the same reaction and purification procedure, the acid 14 (80 mg, 0.30 mmol) was reacted with 2-aminopropan-1-ol (CAS 78-91-1) (0.05 mL, 0.6 mmol), HATU (141 mg, 0.36 mmol) and DIPEA (0.26 mL, 1.5 mmol) in DMF (1 mL) at room temperature to provide 3-(4-aminopyrido[3,2-d]pyrimidin-6-yl)-N-(1-hydroxypropan-2-yl)benzamide 17. LC/MS (ESI+): m/z 323 (M+H). 1H NMR (400 MHz, DMSO) δ 8.70 (s, 1H), 8.61 (t, J=13.5 Hz, 1H), 8.57-8.48 (m, 1H), 8.43 (s, 1H), 8.29 (d, J=7.9 Hz, 1H), 8.19 (dd, J=8.8, 3.1 Hz, 1H), 8.05 (d, J=30.8 Hz, 2H), 7.97 (d, J=7.7 Hz, 1H), 7.63 (t, J=7.8 Hz, 1H), 4.76 (s, 1H), 4.18-4.00 (m, 1H), 3.52 (dd, J=10.5, 5.7 Hz, 1H), 3.46-3.35 (m, 1H), 1.19 (d, J=6.7 Hz, 3H).

Example 18

3-(4-aminopyrido[3,2-d]pyrimidin-6-yl)-N-(1-hydroxy-2-methylpropan-2-yl)benzamide Following the same reaction and purification procedure, the acid 14 (80 mg, 0.30 mmol) was reacted with 2-amino-2-methylpropan-1-ol (CAS 124-68-5) (53 mg, 0.6 mmol), HATU (129 mg, 0.3 mmol) and DIPEA (0.26 mL, 1.5 mmol) in DMF (1 mL) at room temperature to provide 3-(4-aminopyrido[3,2-d]pyrimidin-6-yl)-N-(1-hydroxy-2-methylpropan-2-yl)benzamide 18. LC/MS (ESI+): m/z 338

(M+H). 1H NMR (400 MHz, DMSO) δ 8.69-8.55 (m, 2H), 8.51 (d, J=8.9 Hz, 1H), 8.43 (s, 1H), 8.18 (d, J=8.8 Hz, 1H), 8.05 (d, J=39.6 Hz, 2H), 7.91 (d, J=7.7 Hz, 1H), 7.76 (s, 1H), 7.61 (t, J=7.7 Hz, 1H), 4.90 (t, J=6.0 Hz, 1H), 3.57 (d, J=6.0 Hz, 2H), 1.36 (s, 6H).

Example 19

3-(4-aminopyrido[3,2-d]pyrimidin-6-yl)-N-cyclobutylbenzamide

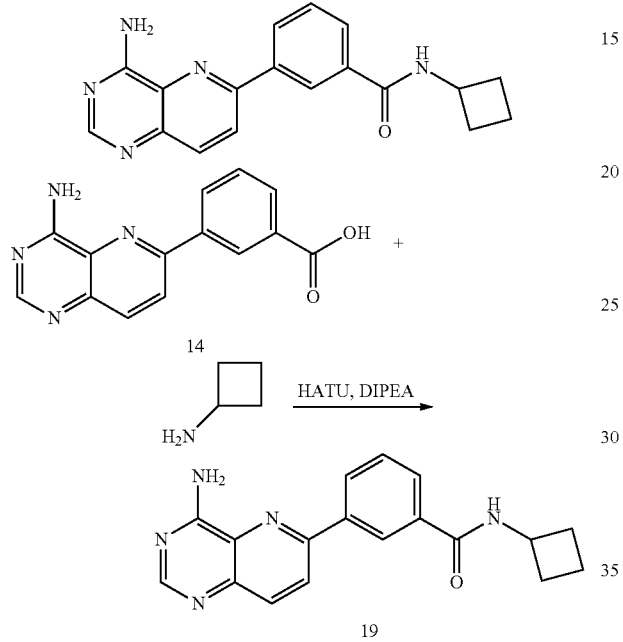

Following the same reaction and purification procedure, the acid 14 (90 mg, 0.34 mmol) was reacted with cyclobutanamine (CAS-2516-34-9) (48 mg, 0.68 mmol), HATU (146 mg, 0.38 mmol) and DIPEA (0.3 mL, 1.7 mmol) in DMF (1 mL) at room temperature to provide 3-(4-aminopyrido[3,2-d]pyrimidin-6-yl)-N-cyclobutylbenzamide 19. LC/MS (ESI+): m/z 320 (M+H). 1H NMR (400 MHz, DMSO) δ 8.76 (d, J=7.4 Hz, 1H), 8.70 (s, 1H), 8.59 (t, J=12.2 Hz, 1H), 8.51 (d, J=8.9 Hz, 1H), 8.43 (s, 1H), 8.19 (d, J=8.8 Hz, 1H), 8.06 (d, J=33.2 Hz, 1H), 7.95 (d, J=7.8 Hz, 1H), 7.63 (t, J=7.8 Hz, 1H), 4.48 (dq, J=16.3, 8.2 Hz, 1H), 2.37-2.22 (m, 2H), 2.22-1.99 (m, 2H), 1.79-1.60 (m, 2H).

Example 20

3-(4-aminopyrido[3,2-d]pyrimidin-6-yl)-N-methylbenzamide

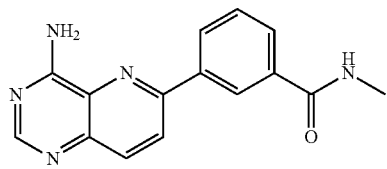

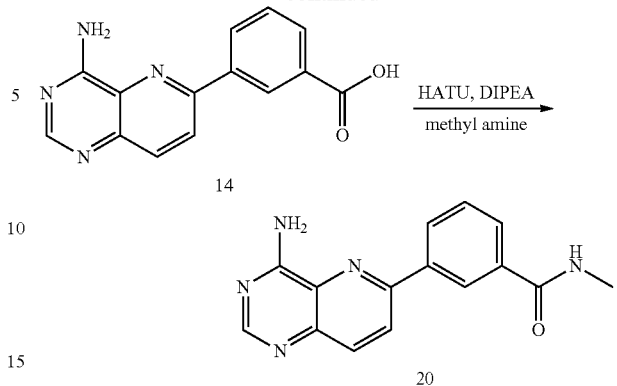

Following the same reaction and purification procedure, the acid 14 (50 mg, 0.18 mmol) was reacted with methyl amine 2M in THF (0.18 mL, 0.35 mmol), HATU (103 mg, 0.6 mmol) and DIPEA (0.15 mL, 0.88 mmol) in DMF (1 mL) at room temperature to provide 3-(4-aminopyrido[3,2-d]pyrimidin-6-yl)-N-methylbenzamide 20. LC/MS (ESI+): m/z 280 (M+H). 1H NMR (400 MHz, DMSO) δ 8.76 (s, 1H), 8.59 (dd, J=10.4, 6.2 Hz, 2H), 8.49 (d, J=8.9 Hz, 1H), 8.43 (d, J=5.3 Hz, 1H), 8.18 (d, J=8.8 Hz, 1H), 8.07 (d, J=17.7 Hz, 2H), 7.96 (d, J=7.7 Hz, 1H), 7.63 (t, J=7.8 Hz, 1H), 2.83 (t, J=24.6 Hz, 3H).

Example 21

3-(4-aminopyrido[3,2-d]pyrimidin-6-yl)-N-(2-morpholinoethyl)benzamide

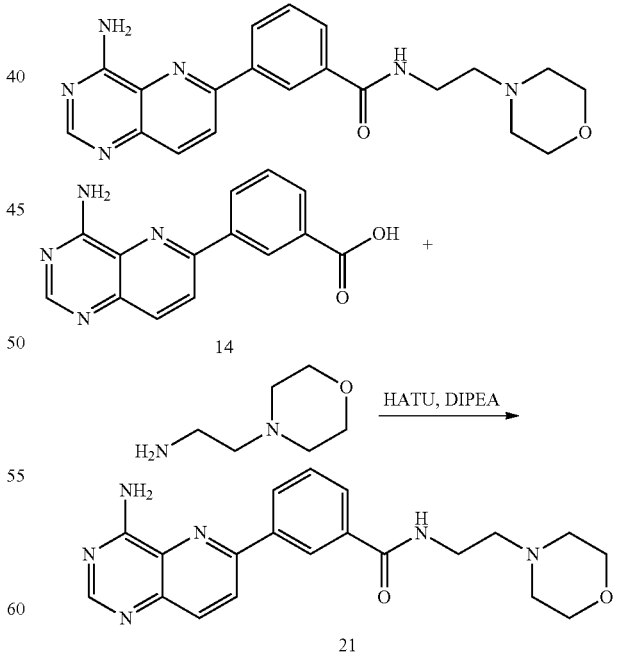

Following the same reaction and purification procedure, the acid 14 (80 mg, 0.3 mmol) was reacted with 2-morpholinoethanamine (CAS 2038-03-1) (78 mg, 0.6 mmol), HATU (129 mg, 0.33 mmol) and DIPEA (0.26 mL, 1.5 mmol) in DMF (1 mL) at room temperature to provide 3-(4-aminopyrido[3,2-d]pyrimidin-6-yl)-N-(2-morpholinoethyl)benzamide 21. LC/MS (ESI+): m/z 379 (M+H). 1H NMR (400 MHz, DMSO) δ 8.73 (s, 1H), 8.60 (d, J=7.5 Hz, 2H), 8.50 (d, J=8.9 Hz, 1H), 8.43 (d, J=4.9 Hz, 1H), 8.19 (d, J=8.8 Hz, 1H), 8.06 (d, J=13.7 Hz, 2H), 7.96 (d, J=7.8 Hz, 1H), 7.64 (t, J=7.8 Hz, 1H), 3.67-3.53 (m, 4H), 3.47 (dd, J=13.2, 6.6 Hz, 2H), 2.53 (d, J=7.1 Hz, 2H), 2.48-2.40 (m, 4H).

Example 22

3-(4-aminopyrido[3,2-d]pyrimidin-6-yl)-N-((1-methylpiperidin-4-yl)methyl)benzamide

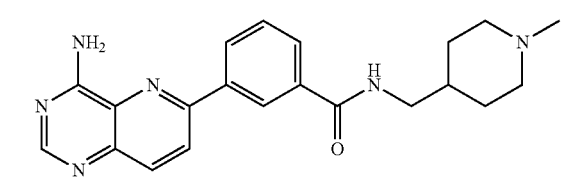

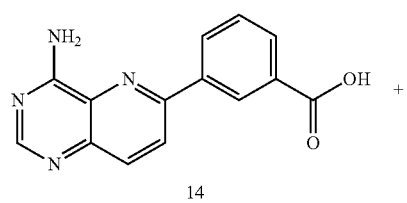

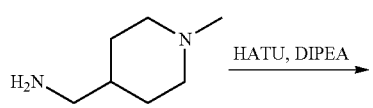

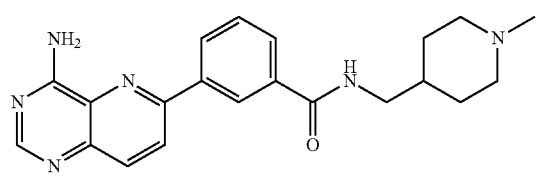

22

Following the same reaction and purification procedure, the acid 14 (80 mg, 0.30 mmol) was reacted with (1-methyl-4-piperidyl)methanamine (CAS 7149-42-0) (77 mg, 0.6 mmol), HATU (129 mg, 0.33 mmol) and DIPEA (0.26 mL, 1.5 mmol) in DMF (1 mL) at room temperature to provide 3-(4-aminopyrido[3,2-d]pyrimidin-6-yl)-N-((1-methylpiperidin-4-yl)methyl)benzamide 22. LC/MS (ESI+): m/z 377 (M+H). 1H NMR (400 MHz, DMSO) δ 8.48 (d, J=8.8 Hz, 2H), 8.42 (s, 2H), 8.23 (s, 1H), 8.14 (d, J=8.8 Hz, 2H), 7.96 (s, 1H), 7.59 (t, J=7.7 Hz, 1H), 7.45 (d, J=6.9 Hz, 1H), 2.90 (s, 2H), 2.73 (d, J=52.3 Hz, 4H), 2.19 (s, 1H), 2.04 (s, 3H), 1.83 (s, 2H), 1.64 (s, 2H).

Example 23

3-(4-aminopyrido[3,2-d]pyrimidin-6-yl)-N-(2-(dimethylamino)ethyl)benzamide

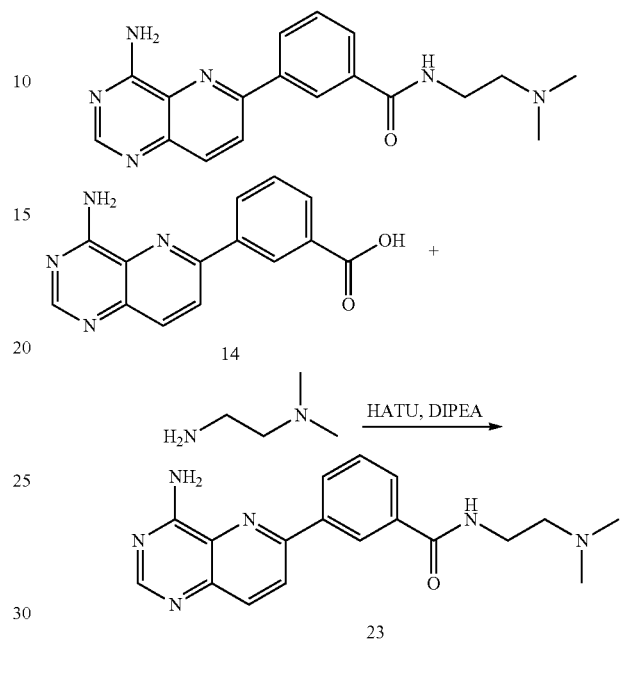

Following the same reaction and purification procedure, the acid 14 (100 mg, 0.38 mmol) was reacted with N,N'-dimethylethane-1,2-diamine (CAS 5752-40-9) (0.08 mL, 0.75 mmol), HATU (177 mg, 0.45 mmol) and DIPEA (0.33 mL, 1.9 mmol) in DMF (1 mL) at room temperature to provide 3-(4-aminopyrido[3,2-d]pyrimidin-6-yl)-N-(2-(dimethylamino)ethyl)benzamide 23. LC/MS (ESI+): m/z 337 (M+H). $^1$H NMR (400 MHz, DMSO) δ 8.74 (s, 1H), 8.60 (d, J=6.6 Hz, 2H), 8.50 (d, J=8.9 Hz, 1H), 8.43 (s, 1H), 8.28-8.14 (m, 1H), 8.06 (d, J=19.6 Hz, 2H), 7.97 (d, J=7.8 Hz, 1H), 7.64 (t, J=7.8 Hz, 1H), 3.44 (dd, J=12.9, 6.6 Hz, 2H), 2.47 (d, J=6.9 Hz, 2H), 2.22 (s, 6H).

Example 24

3-(4-aminopyrido[3,2-d]pyrimidin-6-yl)-N-(2-(pyrrolidin-1-yl)ethyl)benzamide

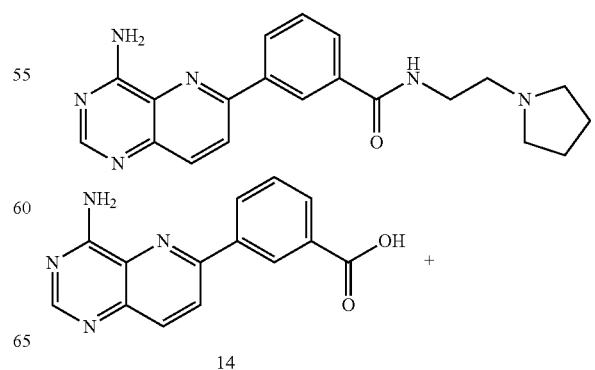

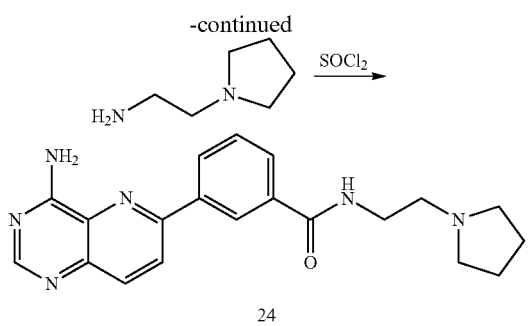

3-(4-aminopyrido[3,2-d]pyrimidin-6-yl)-benzoic acid 14 (100 mg, 0.39 mmol) in DCM (2 mL) was heated with thionyl chloride (0.11 mL, 0.77 mmol) at 80° C. for 1 hour, the mixture was cooled to room temperature and concentrated to dry, 2-pyrrolidin-1-ylethanamine (CAS 7154-73-6) (0.05 mL, 0.58 mmol) was then added, and was stirred overnight. The reaction mixture was purified with prep HPLC to give pure 3-(4-aminopyrido[3,2-d]pyrimidin-6-yl)-N-(2-(pyrrolidin-1-yl)ethyl)benzamide 24. LC/MS (ESI+): m/z 363 (M+H).

1H NMR (400 MHz, DMSO) δ 8.74 (s, 1H), 8.65 (t, J=5.7 Hz, 1H), 8.60 (d, J=7.9 Hz, 1H), 8.50 (d, J=8.9 Hz, 1H), 8.43 (d, J=5.6 Hz, 1H), 8.25-8.13 (m, 2H), 8.07 (d, J=19.9 Hz, 2H), 7.97 (d, J=7.8 Hz, 1H), 7.64 (t, J=7.8 Hz, 1H), 3.46 (dt, J=18.6, 9.4 Hz, 2H), 2.67 (t, J=7.0 Hz, 2H), 2.61-2.52 (m, 4H), 1.78-1.60 (m, 4H).

Example 25

6-(3-fluorophenyl)-N-isopropylpyrido[3,2-d]pyrimidin-4-amine

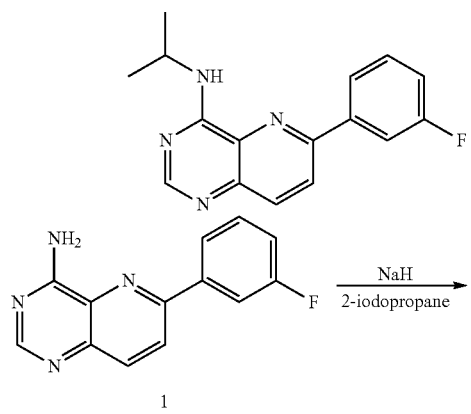

6-(3-fluorophenyl)pyrido[3,2-d]pyrimidin-4-amine 1 (100 mg, 0.42 mmol) in DMF was treated with sodium hydride 60% dispersion in mineral oil (25 mg, 0.63 mmol) followed by 2-iodopropane (0.04 mL, 0.42 mmol), stirred at room temperature for 2 hrs. The reaction mixture was poured on ice, and extracted with EtOAc three times. The combined organic layers were dried with sodium sulfate and concentrated to dry. The crude was purified by ISCO eluting with 100% EtOAc to give pure 6-(3-fluorophenyl)-N-isopropylpyrido[3,2-d]pyrimidin-4-amine 25. LC/MS (ESI+): m/z 283 (M+H). 1H NMR (400 MHz, DMSO) δ 8.53-8.43 (m, 2H), 8.37 (d, J=10.8 Hz, 1H), 8.21 (t, J=8.4 Hz, 2H), 8.15 (d, J=8.8 Hz, 1H), 7.60 (dd, J=14.2, 8.0 Hz, 1H), 7.34 (td, J=8.5, 2.5 Hz, 1H), 4.56 (dq, J=13.3, 6.7 Hz, 1H), 1.35 (d, J=6.6 Hz, 6H).

Example 26

6-(3-fluorophenyl)-N-methylpyrido[3,2-d]pyrimidin-4-amine

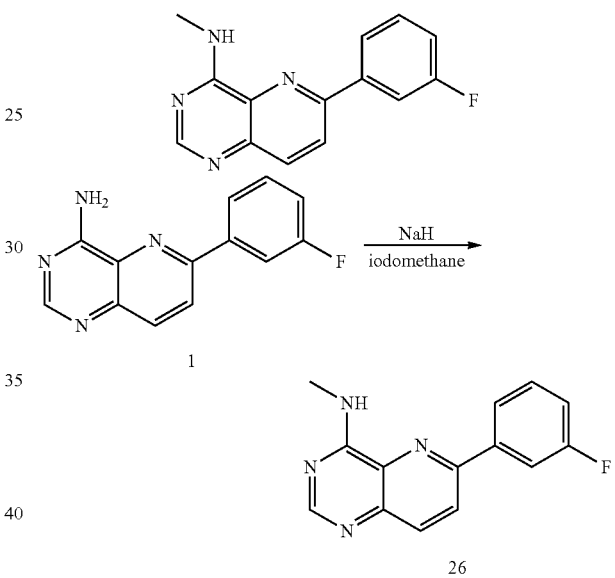

Following the same reaction and purification procedure, the amine 1 (150 mg, 0.62 mmol) was treated with sodium hydride 60% dispersion in mineral oil (37 mg, 0.94 mmol) and iodomethane (0.04 mL, 0.62 mmol) to provide 6-(3-fluorophenyl)-N-methylpyrido[3,2-d]pyrimidin-4-amine 26. LC/MS (ESI+): m/z 255 (M+H). 1H NMR (400 MHz, DMSO) δ 8.89 (s, 1H), 8.38-8.19 (m, 1H), 8.19-8.03 (m, 3H), 7.96 (d, J=8.5 Hz, 1H), 7.58 (dd, J=14.3, 7.8 Hz, 1H), 7.32 (dd, J=10.1, 8.0 Hz, 1H), 3.49 (s, 3H).

Examples 27 and 28

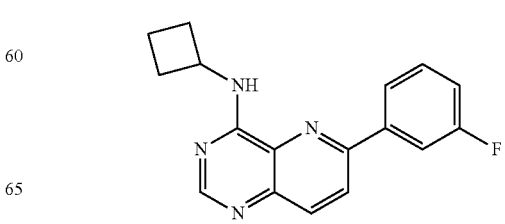

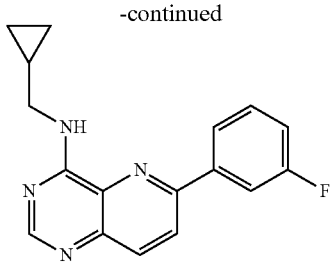

N-(cyclopropylmethyl)-6-(3-fluorophenyl)pyrido[3,2-d]pyrimidin-4-amine

N-(cyclobutyl)-6-(3-fluorophenyl)pyrido[3,2-d]pyrimidin-4-amine

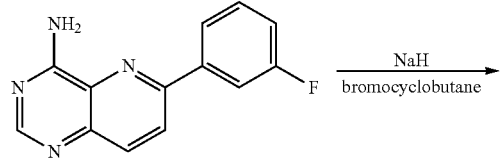

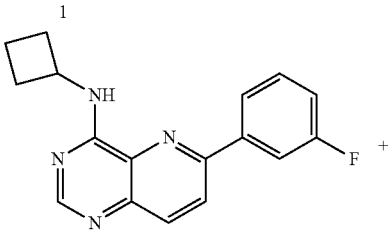

27

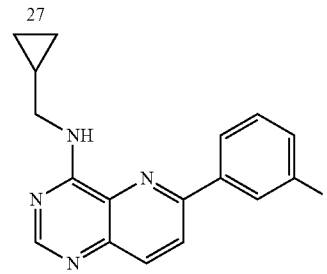

28

Following the same reaction and purification procedure, the amine 1 (100 mg, 0.42 mmol) was treated with sodium hydride 60% dispersion in mineral oil (25 mg, 0.62 mmol) and bromocyclobutane (56 mg, 0.42 mmol) to provide N-cyclobutyl-6-(3-fluorophenyl)pyrido[3,2-d]pyrimidin-4-amine 27 and N-(cyclopropylmethyl)-6-(3-fluorophenyl)pyrido[3,2-d]pyrimidin-4-amine 28. LC/MS (ESI+): m/z 295 (M+H). 1H NMR (400 MHz, DMSO) δ 8.80 (t, J=6.1 Hz, 1H), 8.48 (d, J=7.2 Hz, 2H), 8.39 (d, J=10.9 Hz, 1H), 8.22 (d, J=7.9 Hz, 1H), 8.15 (d, J=8.8 Hz, 1H), 7.60 (dd, J=14.3, 7.9 Hz, 1H), 7.34 (td, J=8.5, 2.4 Hz, 1H), 3.50 (t, J=6.5 Hz, 2H), 1.27 (dd, J=13.4, 6.1 Hz, 1H), 0.52-0.42 (m, 2H), 0.42-0.31 (m, 2H).

1H NMR (400 MHz, DMSO) δ 8.80 (t, J=6.1 Hz, 1H), 8.48 (d, J=7.2 Hz, 2H), 8.39 (d, J=10.9 Hz, 1H), 8.22 (d, J=7.9 Hz, 1H), 8.15 (d, J=8.8 Hz, 1H), 7.60 (dd, J=14.3, 7.9 Hz, 1H), 7.34 (td, J=8.5, 2.4 Hz, 1H), 3.50 (t, J=6.5 Hz, 2H), 1.27 (dd, J=13.4, 6.1 Hz, 1H), 0.55-0.41 (m, 2H), 0.41-0.28 (m, 2H).

Example 29

6-(3-fluorophenyl)-N-ethylpyrido[3,2-d]pyrimidin-4-amine

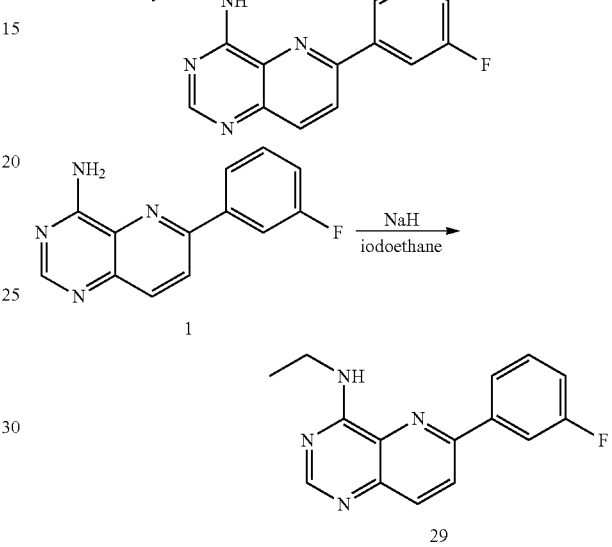

Following the same reaction and purification procedure, the amine 1 (150 mg, 0.62 mmol) was treated with sodium hydride 60% dispersion in mineral oil (37 mg, 0.94 mmol) and iodoethane (0.05 mL, 0.62 mmol) to provide 6-(3-fluorophenyl)-N-ethylpyrido[3,2-d]pyrimidin-4-amine 29.

LC/MS (ESI+): m/z 269 (M+H).

1H NMR (400 MHz, DMSO) δ 8.74 (t, J=5.8 Hz, 1H), 8.47 (d, J=8.2 Hz, 2H), 8.40 (d, J=10.9 Hz, 1H), 8.22 (d, J=7.8 Hz, 1H), 8.14 (d, J=8.8 Hz, 1H), 7.59 (dd, J=14.3, 7.9 Hz, 1H), 7.34 (td, J=8.5, 2.4 Hz, 1H), 3.65 (p, J=7.0 Hz, 2H), 1.27 (t, J=7.1 Hz, 3H).

Example 30

Ethyl 4-(3-(4-aminopyrido[3,2-d]pyrimidin-6-yl)-5-fluorobenzylamino)piperidine-1-carboxylate

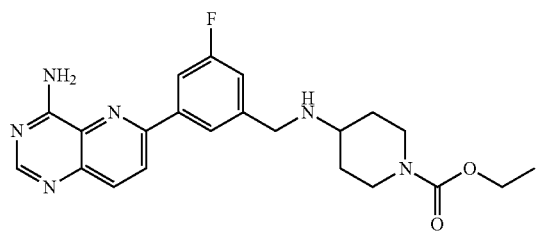

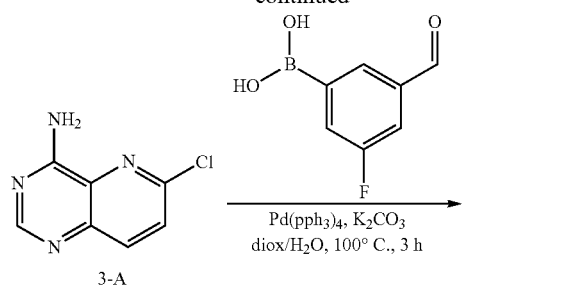

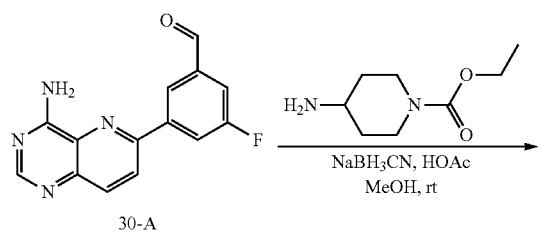

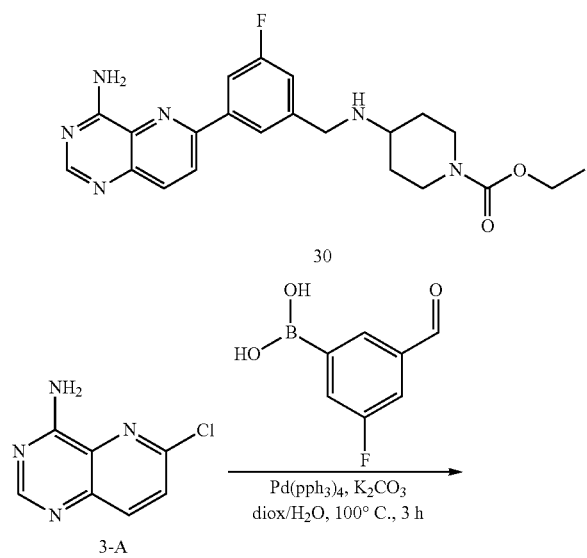

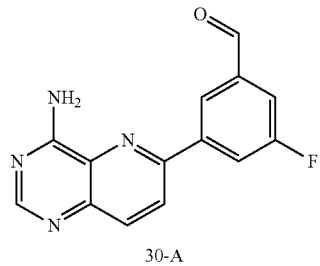

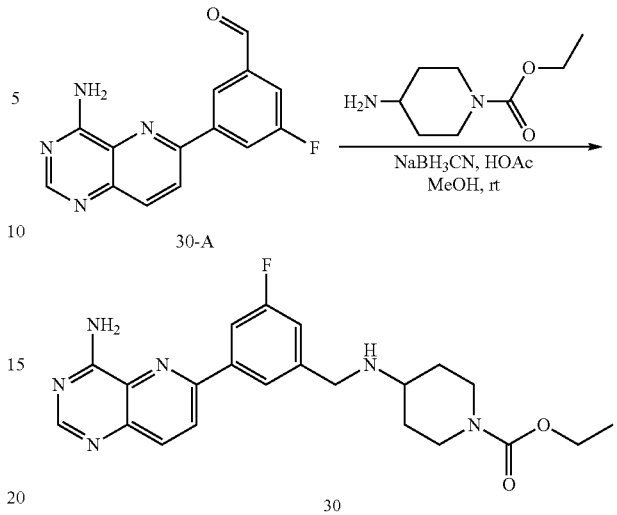

Step 1: 3-(4-Aminopyrido[3,2-d]pyrimidin-6-yl)-5-fluorobenzaldehyde (3).

A suspension of 6-chloropyrido[3,2-d]pyrimidin-4-amine (1) (3.61 g, 20 mmol), 3-fluoro-5-formylphenylboronic acid (CAS 328956-60-1) (4.03 g, 24 mmol, 1.2 eq), Pd(PPh$_3$)$_4$ (1.16 g, 1.0 mmol, 0.05 eq), and K$_2$CO$_3$ (5.53 g, 40 mmol, 2.0 eq) in a mixture of dioxane (100 mL) and H$_2$O (10 mL) was heated at 100° C. for 3 h. After it was cooled to r.t., the reaction was extracted with EtOAc (100 mL) and water (60 mL). The organic layer were washed with water and concentrated. The yellow solid was recrystallized in MeCN to give the titled product (4.8 g, yield: 90%).

Step 2: Ethyl 4-(3-(4-aminopyrido[3,2-d]pyrimidin-6-yl)-5-fluorobenzylamino)piperidine-1-carboxylate.

After a solution of compound 30-A (110 mg, 0.4 mmol), ethyl 4-aminopiperidine-1-carboxylate (CAS 58859-46-4) (100 mg, 0.6 mmol) and HOAc (0.3 ml) in MeOH (5 mL) were stirred at r.t. for 30 min, NaBH$_3$CN (76 mg, 1.2 mmol) was added to solution. The reaction mixture was stirred at r.t. overnight. MeOH was removed by reduced pressure and the residue was partitioned between EtOAc (10 mL) and aqueous NaHCO$_3$ solution (0.5 M, 10 mL). The organic layer was concentrated, and purified by pre-HPLC to give the title product (55 mg, 32%).

LCMS (ESI, 0-60AB, 2 min), RT=0.942, M+H=446.9

$^1$H NMR (400 MHz, DMSO-d$_6$) δ 10.05-9.93 (m, 4H), 8.92 (s, 1H), 8.85 (s, 1H), 8.77 (d, J=8.8 Hz, 1H), 8.47 (d, J=10.4 Hz, 1H), 8.38 (d, J=8.8 Hz, 1H), 7.66 (d, J=8.4 Hz, 1H), 4.32 (m, 1H), 4.07-4.02 (m, 4H), 3.30 (s, 1H), 2.84-2.80 (m, 2H), 2.19-2.17 (m 2H), 1.68-1.59 (m, 2H), 1.19 (t, J=7.2 Hz, 3H).

Example 31

6-(3-fluoro-5-(2-(pyrrolidin-1-yl)ethylamino)phenyl)pyrido[3,2-d]pyrimidin-4-amine

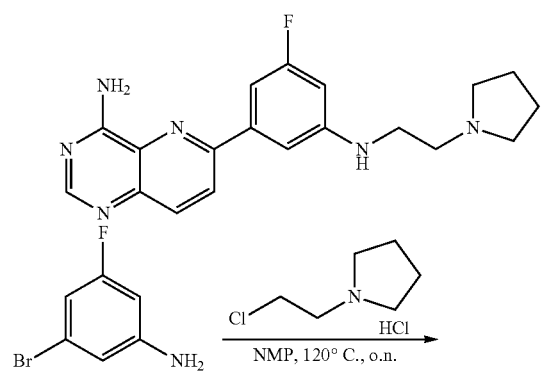

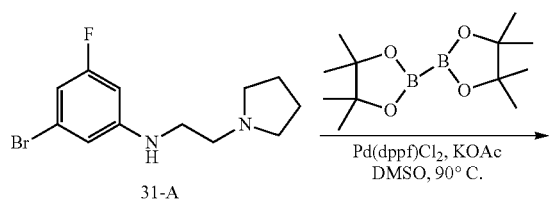

Step 1: 3-Bromo-5-fluoro-N-(2-(pyrrolidin-1-yl)ethyl)aniline (31-A)

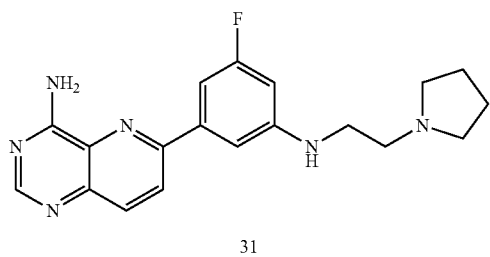

A solution of 3-bromo-5-fluoroaniline (CAS 134168-97-1) (380 mg, 2.0 mmol) and 1-(2-chloroethyl)pyrrolidine (CAS 5050-41-9) (380 mg, 2.2 mmol) in NMP (20 mL) was heated to 120° C. overnight. The solution was diluted with EtOAc (100 mL) and washed with saturated $Na_2CO_3$ aqueous solution (3×40 mL). The combined organic layer were dried over $Na_2SO_4$, concentrated and purified by prep-TLC (DCM:MeOH=10:1) to give the titled product (290 mg, 50%). LCMS (0-60 AB), RT=1.076 min, M+H: 289.0

Step 2: 3-Fluoro-N-(2-(pyrrolidin-1-yl)ethyl)-5-(4,4,5,5-tetramethyl-1,3,2-dioxaborolan-2-yl)aniline (31-B):

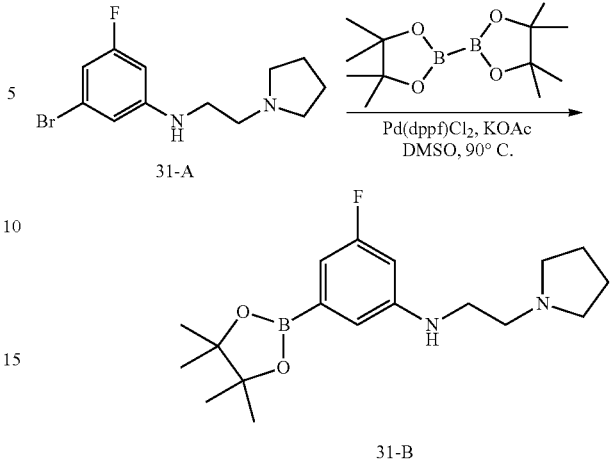

A suspension of 31-A (290 mg, 1.0 mmol), 4,4,4',4',5,5,5',5'-octamethyl-2,2'-Bi-1,3,2-dioxaborolane (CAS 73183-34-3), (300 mg, 1.2 mmol), $Pd(dppf)Cl_2$ (30 mg) and KOAc (200 mg, 2.0 mmol) in DMSO (6 mL) was heated at 90° C. for 3 h. The reaction solution was partitioned between EtOAc (100 mL) and brine (35 mL). The combined organic layer was washed with water (3×30 mL), concentrated and used in next step without further purification.

Step 3: 6-(3-Fluoro-5-(2-(pyrrolidin-1-yl)ethylamino)phenyl)pyrido[3,2-d]pyrimidin-4-amine (31)

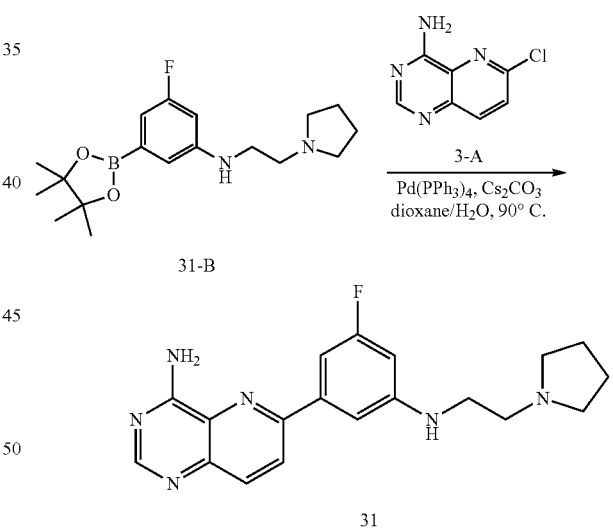

A suspension of crude 31-B (300 mg, 1.0 mmol), 3-A (150 mg, 0.80 mmol), $Pd(PPh_3)_4$ (30 mg) and $Cs_2CO_3$ (600 mg, 1.8 mmol) in dioxane/$H_2O$ (10 mL/1.0 mL) was stirred at 90° C. for 2 h. The reaction solution was partitioned between EtOAc (100 mL) and brine (35 mL). The combined organic layer was washed with water (3×30 mL), concentrated and purified by prep-HPLC (25 mg, 8.9%). LCMS (0-60AB), RT=0.904 min, M+H 352.9 $^1$H-NMR (Methanol-d4, 400 MHz): δ 8.53 (s, 1H), 8.35 (s, 1H), 8.23 (d, J=8.8 Hz, 1H), 8.03 (d, J=8.8 Hz, 1H)), 7.33 (s, 1H), 7.24 (d, J=10.4 Hz, 1H), 6.49 (d, J=11.2 Hz, 1H), 3.60-3.57 (m, 2H), 3.37-3.28 (m, 6H), 2.07-2.04 (m, 2H).

Example 32

6-(3-Fluoro-5-(3-(pyrrolidin-1-ylmethyl)oxetan-3-ylamino)phenyl)pyrido[3,2-d]pyrimidin-4-amine

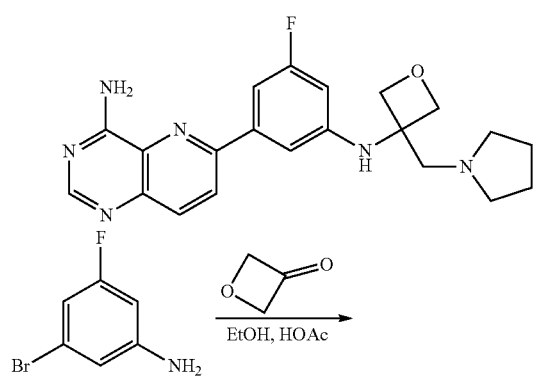

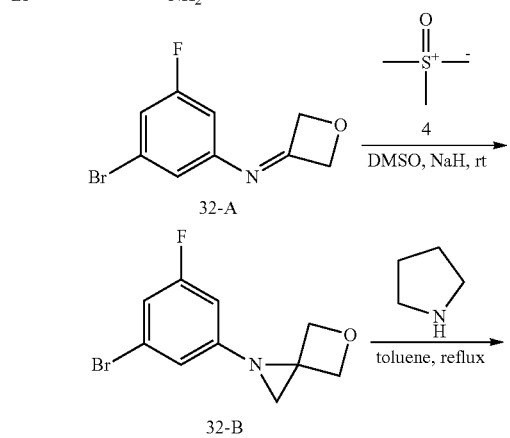

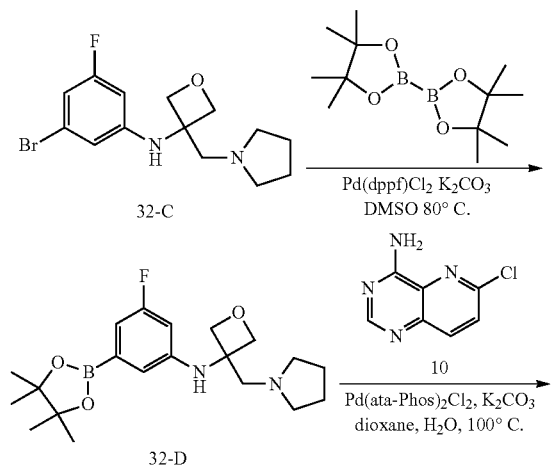

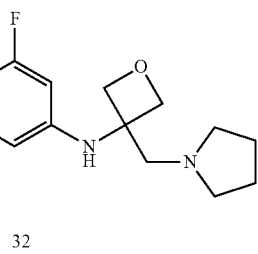

Step 1: 3-Bromo-5-fluoro-N-(oxetan-3-ylidene)aniline (3).

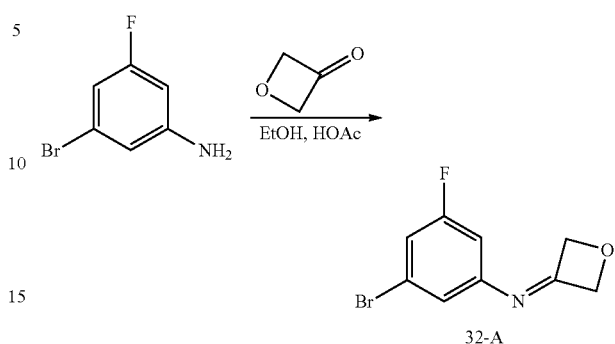

To a solution of 3-bromo-5-fluoroaniline (CAS 134168-97-1) (3.0 g, 16 mmol) in EtOH (50 mL), was added HOAc (900 mg, 16 mmol), and oxetan-3-one (CAS 6704-31-0) (2.4 g, 32 mmol). The mixture was stirred at reflux for overnight. It was poured into water (100 mL) and extract with EtOAc (100 mL×2). The combined organic layers was dried over Na$_2$SO$_4$ and concentrated in vacuum to give the crude product (3.0 g, 77%).

Step 2: 1-(3-bromo-5-fluorophenyl)-5-oxa-1-azaspiro[2.3]hexane

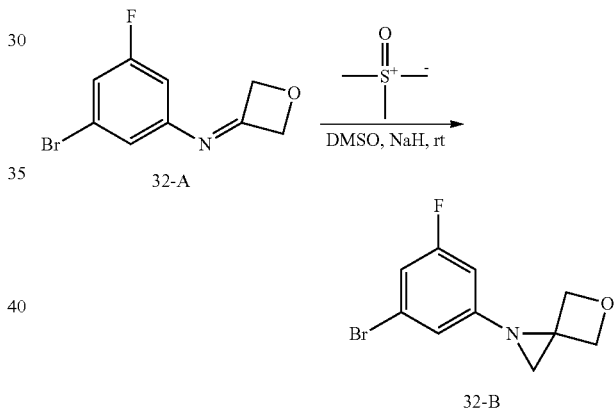

To a solution of 32-A (8.1 g, 36 mmol) in DMSO (50 mL), was added NaH (1.9 g, 48 mmol) slowly, and the mixture was stirred at r.t. for 30 min. dimethyl-sulfoxonium methylide (commercially available) (3.0 g, 12 mmol) in DMSO (10 mL) was added dropwise to the mixture at r.t. After the mixture was stirred at r.t. overnight, it was poured into water (100 mL) and extracted with EtOAc (100 mL×2), and the combined organic layer was washed with sat. NaCl (50 mL×2), dried over Na$_2$SO$_4$ and concentrated in vacuum to give the crude product (3.0 g, 95%).

Step 3: N-(3-bromo-5-fluorophenyl)-3-(pyrrolidin-1-ylmethyl)oxetan-3-amine

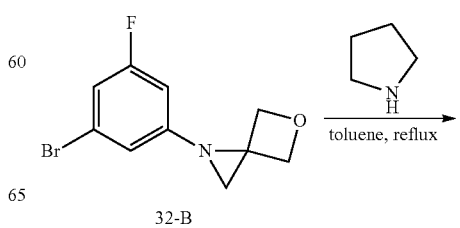

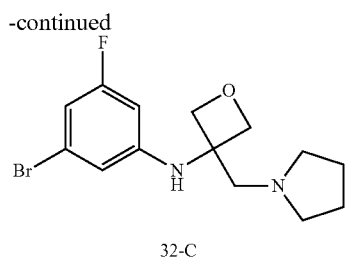

32-C

To a solution of 32-B (3.0 g, crude) in toluene (50 mL), was added pyrrolidine (commercially available) (3 g, 42 mmol), and the mixture was stirred at reflux overnight under N₂. It was poured into water (100 mL) and extract with EtOAc (100 mL×2). The combined organic layers was dried over Na₂SO₄ and concentrated in vacuum and purified by column chromatography (PE:EtOAc=1:2 to 1:4) to give the product as yellow oil (1.6 g, yield 30% for 3 steps).

Step 4: N-(3-fluoro-5-(4,4,5,5-tetramethyl-1,3,2-dioxaborolan-2-yl)phenyl)-3-(pyrrolidin-1-yl methyl)oxetan-3-amine

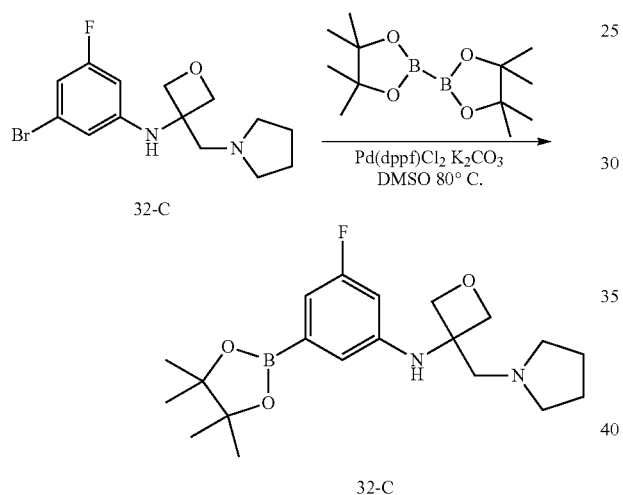

To a solution of 32-C (600 mg, 1.8 mmol) in DMSO (20 mL), was added 4,4,4',4',5,5,5',5'-octamethyl-2,2'-Bi-1,3,2-dioxaborolane (CAS 73183-34-3), (930 mg, 3.6 mmol), K₂CO₃ (500 mg, 3.6 mmol), and Pd(dppf)Cl₂ (135 mg, 0.18 mmol). The mixture was stirred at 80° C. for 2 h under N₂, and poured into water (50 mL). The mixture was extract by EtOAc (100 mL×2) and the combined organic layers was dried over Na₂SO₄ and concentrated in vacuum to give the crude product (600 mg, about 50%).

Step 5: 6-(3-Fluoro-5-(3-(pyrrolidin-1-ylmethyl)oxetan-3-ylamino)phenyl)pyrido[3,2-d]pyrimidin-4-amine

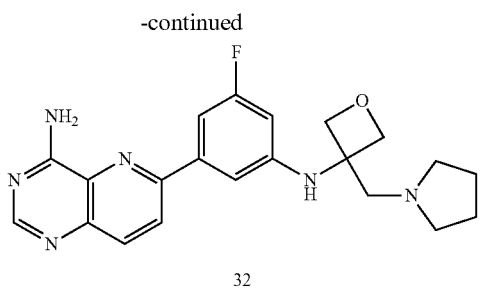

32

To a solution of 32-C (250 mg, 0.66 mmol) in a mixture of DMSO and H₂O (20/5 mL), was added 3-A (150 mg, 0.79 mmol), K₂CO₃ (270 mg, 2.0 mmol), and Pd(ata-Phos)₂Cl₂ (60 mg, 0.07 mmol). The mixture was stirred at 80° C. overnight under N₂, and poured into water (50 mL). It was extract with EtOAc (100 mL×3) and the combined organic layers was dried over Na₂SO₄ and concentrated in vacuum and purified by prep-HPLC to give product as white solid (70 mg, yield 10%, over 2 steps). LCMS (0-60, AB, 2 min), 0.818 min, MH+=395.2; ¹H NMR (400 MHz, DMSO-d₆) δ 8.39 (s, 1H), 8.26 (d, J=8.8 Hz, 1H), 8.12 (t, J=2.0 Hz, 1H), 8.00 (s, 1H), 7.95 (s, 1H), 7.54 (d, J=10.4 Hz, 1H), 7.14 (s, 1H), 6.66 (s, 1H), 6.31 (d, J=11.2 Hz, 2H).

Example 33

N-(3-(4-aminopyrido[3,2-d]pyrimidin-6-yl)-5-fluorophenyl)pyrrolidine-1-sulfonamide

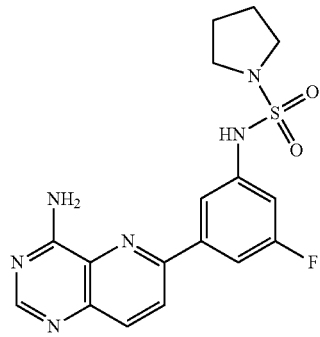

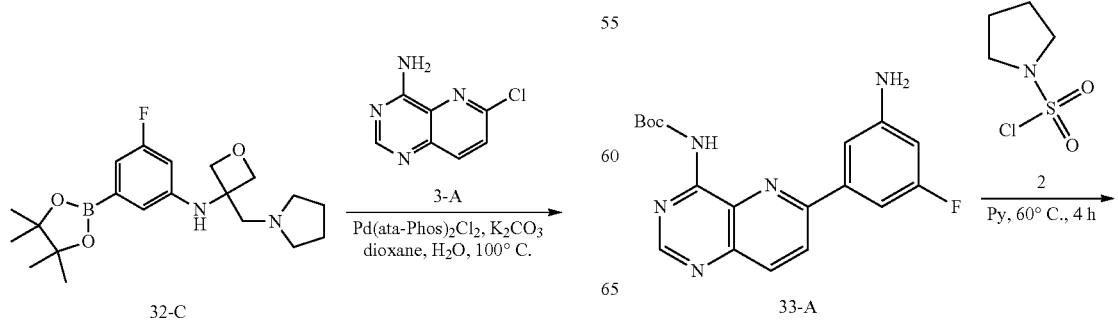

33-A

113

-continued

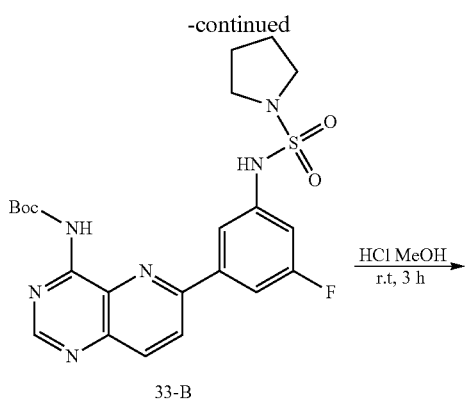

33-B

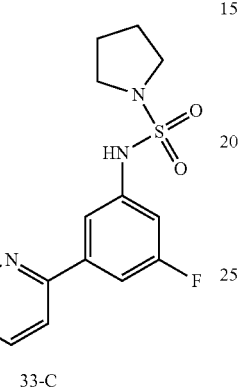

33-C

Step 1: tert-Butyl 6-(3-fluoro-5-(pyrrolidine-1-sulfonamido)phenyl)pyrido3,2-d]yrimidin-4-ylcarbamate

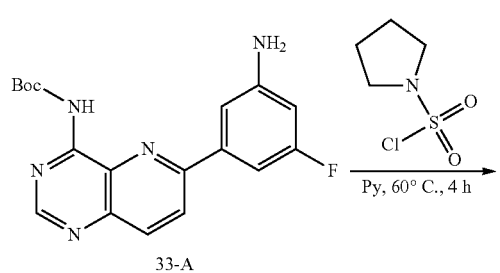

Pyrrolidine-1-sulfonyl chloride (CAS 1689-02-7) (56 mg, 0.92 mmol) was added to a solution of tert-butyl 6-(3-amino-5-fluorophenyl)pyrido[3,2-d]pyrimidin-4-ylcarbamate (33-A) (300 mg, 0.84 mmol) in pyridine at ice bath. After the reaction mixture was stirred at 60° C. for 4 h, it was partitioned between water and EtOAc and purified by prep-TLC (PE:EtOAc=2:1) to give title product (250 mg, 61%).

114

Step 2: N-(3-(4-aminopyrido[3,2-d]pyrimidin-6-yl)-5-fluorophenyl)pyrrolidine-1-sulfonamide

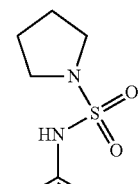

33-B

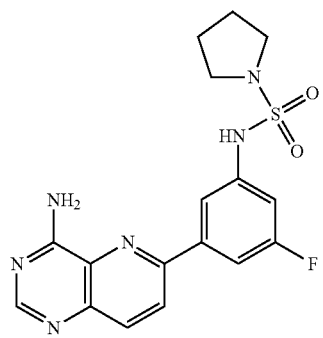

33

To a solution of compound 33-B (250 mg, 0.51 mmol) in MeOH was added HCl-MeOH. The reaction mixture was stirred at r.t. for 3 h. The mixture was partitioned between water and EtOAc. The solvent was removed and the crude product was purified by prep-HPLC to give the title product (6 mg, 3%). $^1$H NMR (400 MHz, MeOH-$d_4$) δ 8.72 (s, 1H), 8.51 (d, J=9.2 Hz, 1H), 8.25 (d, J=8.8 Hz, 1H), 7.94-7.91 (m, 1H), 7.83 (t, J=1.8 Hz, 1H), 7.15 (dt, J=10.4, 2.2 Hz, 1H), 3.35-3.29 (m, 4H), 1.88-1.85 (m, 4H).

Example 34

2-Morpholin-4-yl-ethanesulfonic acid[3-(4-amino-pyrido[3,2-d]pyrimidin-6-yl)-5-fluoro-phenyl]-amide

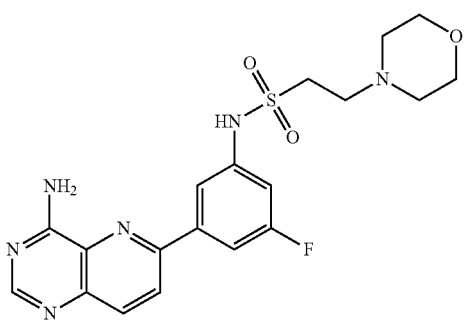

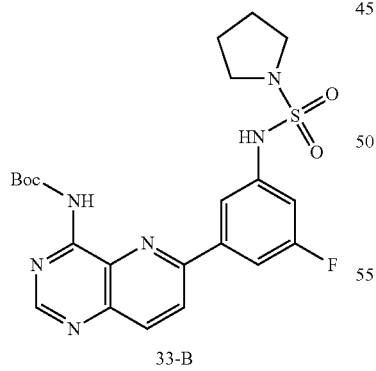

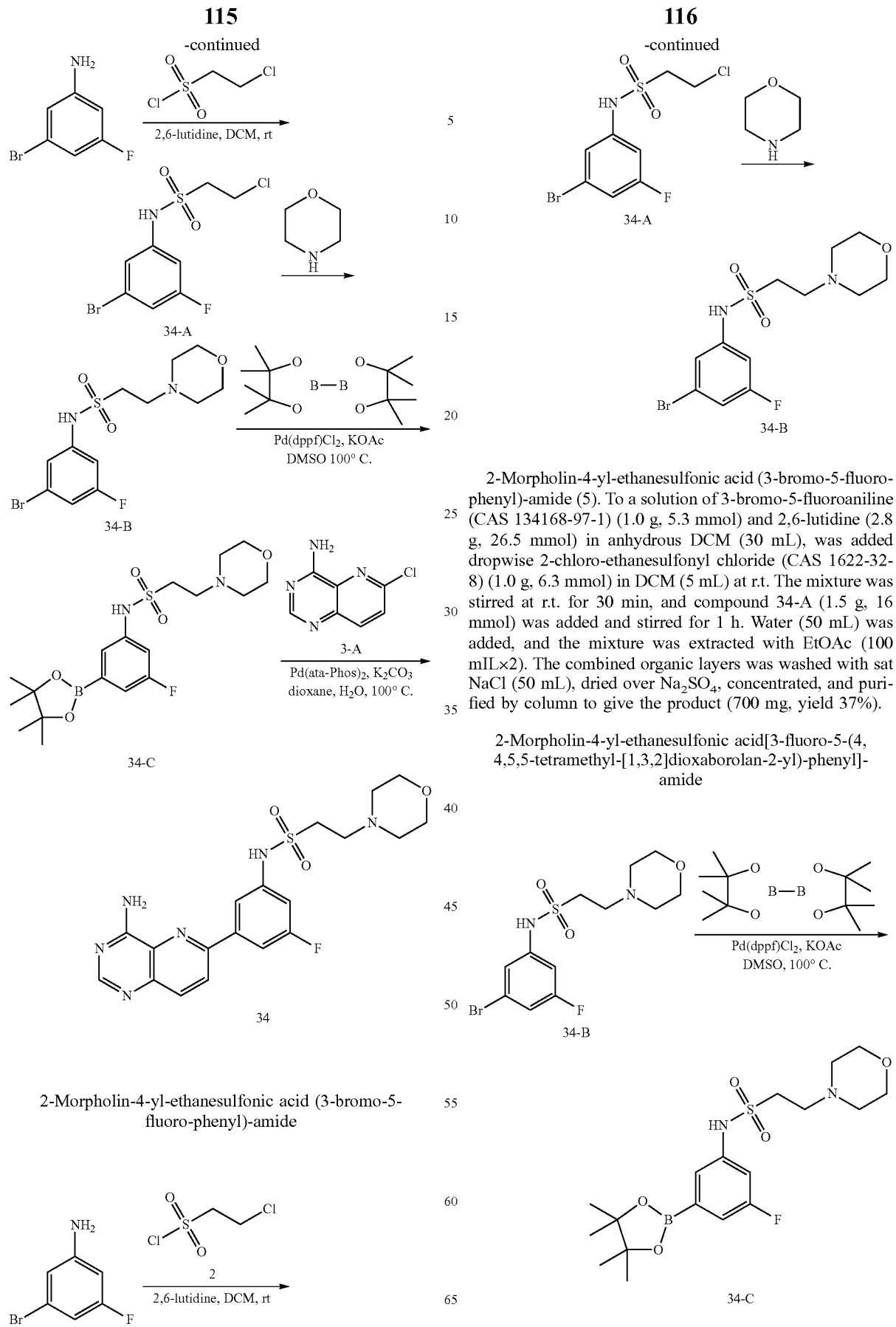

2-Morpholin-4-yl-ethanesulfonic acid (3-bromo-5-fluoro-phenyl)-amide (5). To a solution of 3-bromo-5-fluoroaniline (CAS 134168-97-1) (1.0 g, 5.3 mmol) and 2,6-lutidine (2.8 g, 26.5 mmol) in anhydrous DCM (30 mL), was added dropwise 2-chloro-ethanesulfonyl chloride (CAS 1622-32-8) (1.0 g, 6.3 mmol) in DCM (5 mL) at r.t. The mixture was stirred at r.t. for 30 min, and compound 34-A (1.5 g, 16 mmol) was added and stirred for 1 h. Water (50 mL) was added, and the mixture was extracted with EtOAc (100 mIL×2). The combined organic layers was washed with sat NaCl (50 mL), dried over $Na_2SO_4$, concentrated, and purified by column to give the product (700 mg, yield 37%).

2-Morpholin-4-yl-ethanesulfonic acid[3-fluoro-5-(4,4,5,5-tetramethyl-[1,3,2]dioxaborolan-2-yl)-phenyl]-amide A mixture of Compound 34-B (500 mg, 1.3 mmol), BIS(PINACOLATO)DIBORON (CAS 73183-34-3) (680 mg, 2.6 mmol), KOAc (400 mg, 4.3 mmol), and Pd(dppf)Cl₂ (110 mg, 0.14 mmol) in DMSO (20 mL) was stirred at 80° C. for 3 h under N₂. It was poured into water (50 mL). The resulting mixture was extract by EtOAc (100 mL×2) and the combined organic layers was washed with sat NaCl (50 mL), dried over Na₂SO₄ and concentrated in vacuum to give the crude product. (400 mg, crude, 55%).

2-Morpholin-4-yl-ethanesulfonic acid[3-(4-amino-pyrido[3,2-d]pyrimidin-6-yl)-5-fluoro-phenyl]-amide

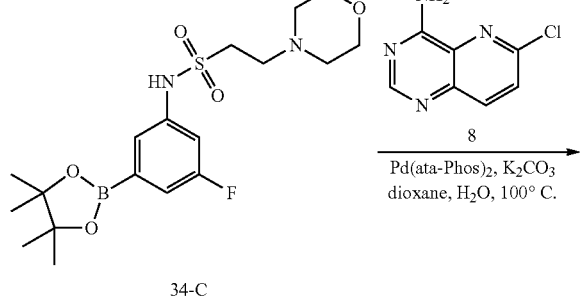

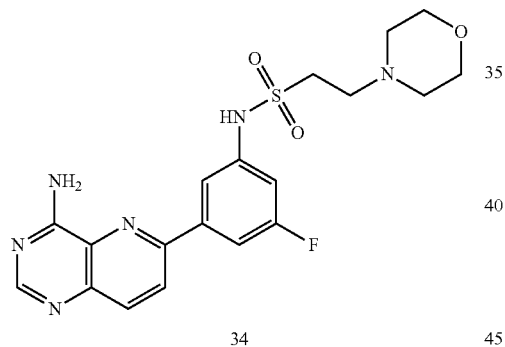

To a solution of compound 7 (250 mg, 0.66 mmol) in a mixture of DMSO (20 mL) and H₂O (5 mL), was added compound 8 (150 mg, 0.79 mmol), K₂CO₃ (270 mg, 2.0 mmol), and Pd(ata-Phos)₂Cl₂ (60 mg, 0.07 mmol). The mixture was stirred at 80° C. overnight under N₂, and poured into water (50 mL).

The resulting mixture was extract with EtOAc (100 mL×3) and the combined organic layers was dried over Na₂SO₄, concentrated in vacuum and purified by prep-HPLC to give product as white solid (35 mg, yield 12%). LCMS (0-60AB, 2 min) 1.037 min, M+H=432.8; ¹H NMR (400 MHz, DMSO-d₆) δ 8.46 (s, 1H), 8.39 (d, J=7.2 Hz, 1H), 8.16 (d, J=9.2 Hz, 1H), 7.48 (t, J=2.0 Hz, 1H), 7.05-7.37 (m, 1H), 6.58-6.54 (m, 1H), 3.77-3.72 (m, 6H), 3.38-3.24 (m, 6H).

Example 35

N-(3-(4-aminopyrido[3,2-d]pyrimidin-6-yl)-5-fluorophenyl)-2-(piperidin-1-yl)ethanesulfonamide

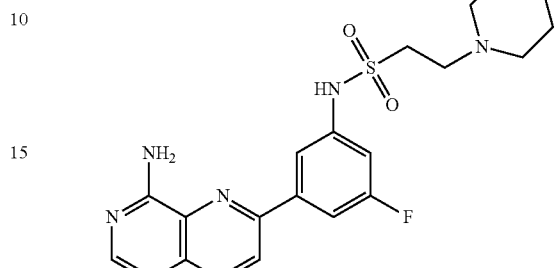

N-(3-(4-aminopyrido[3,2-d]pyrimidin-6-yl)-5-fluorophenyl)-2-(piperidin-1-yl)ethanesulfonamide was prepared according to the procedure described in example 34 in which in step 2, the reaction was performed with piperidine instead of morpholine. Yield, 9%, LCMS 1.112 min, 430.9, 0-60AB 1H NMR (400 MHz, MeOD-d4) δ 8.74 (s, 1H), 8.59 (d, J=9.2 Hz, 1H), 8.25 (d, J=8.8 Hz, 1H), 7.75 (t, J=1.6 Hz, 1H), 7.43-7.40 (m, 1H), 6.62-6.58 (m, 1H), 3.77 (t, J=6.4 Hz, 2H), 3.30-3.26 (m, 6H), 1.69-1.58 (m, 6H).

Example 36

N-(3-(4-aminopyrido[3,2-d]pyrimidin-6-yl)-5-fluorophenyl)-2-(4-methylpiperazin-1-yl)ethane sulfonamide N-(3-(4-aminopyrido[3,2-d]pyrimidin-6-yl)-5-fluorophenyl)-2-(4-methylpiperazin-1-yl)ethanesulfonamide was prepared according to the procedure described in example 34 in which in step 2, the reaction was performed with piperidine instead of morpholine. Yield, 10%, LCMS 1.096 min, 446.0, 0-60AB, ¹H NMR (400 MHz, MeOD-d₄) δ 8.42 (s, 1H), 8.36 (d, J=9.4 Hz, 1H), 8.14 (d, J=6.4 Hz, 1H), 7.51 (m, 1H), 7.37-7.30 (m, 1H), 6.55 (d, J=4.8 Hz, 1H), 3.77 (t, J=6.4 Hz, 2H), 3.43-3.37 (m, 6H), 2.75 (m, 4H), 2.46 (s, 3H).

Example 37

6-[3-(2-Pyrrolidin-1-ylmethyl-cyclopropyl)-phenyl]-pyrido[3,2-d]pyrimidin-4-ylamine

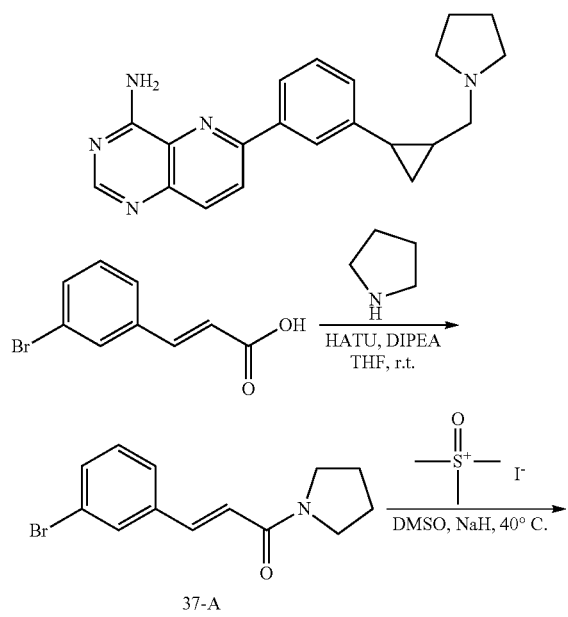

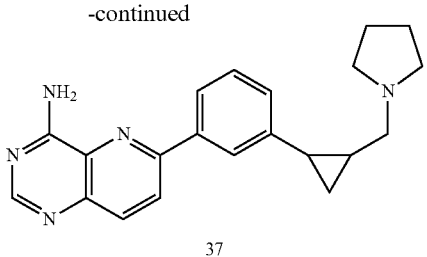

37

Step 1: 3-(3-Bromo-phenyl)-1-pyrrolidin-1-yl-propenone

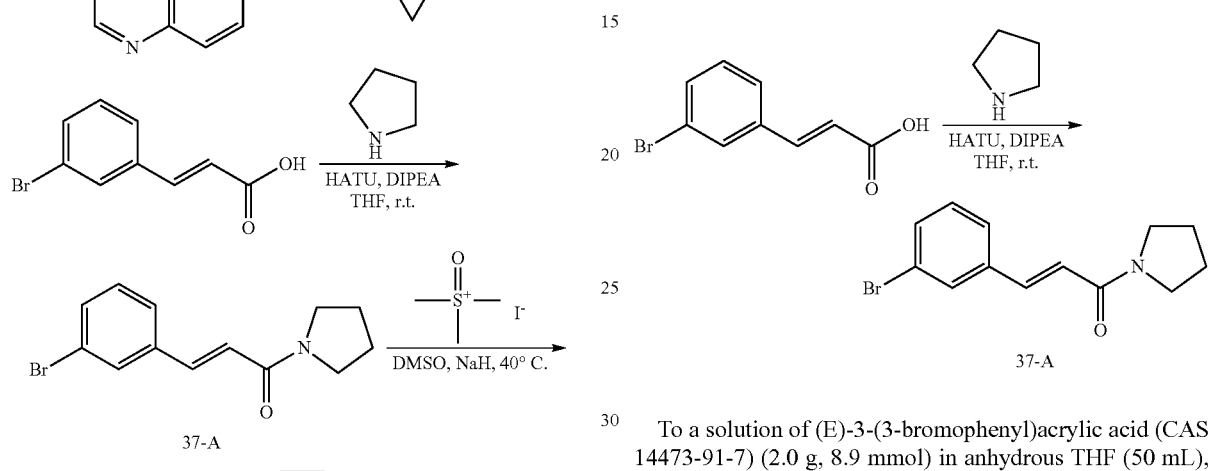

37-A

To a solution of (E)-3-(3-bromophenyl)acrylic acid (CAS 14473-91-7) (2.0 g, 8.9 mmol) in anhydrous THF (50 mL), was added DIPEA (3.5 g, 26.5 mmol), HATU (4.7 g, 13.3 mmol), and pyrrolidine (1.4 g, 19.0 mmol). After the mixture was stirred at r.t. for 4 h, it was poured into water (100 mL) and the resulting mixture was extract by EtOAc (100 mL×2). The combined organic layers was washed with HCl (0.5 M, 30 mL), sat NaCl (50 mL), dried over Na$_2$SO$_4$ and concentrated in vacuum to give the crude product (2.0 g, yield 80%).

Step 2: [2-(3-Bromo-phenyl)-cyclopropyl]-pyrrolidin-1-yl-methanone

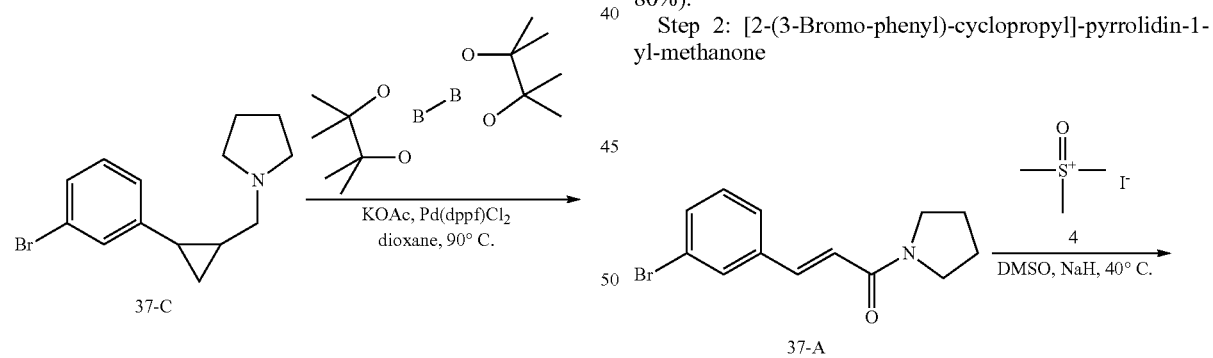

37-A

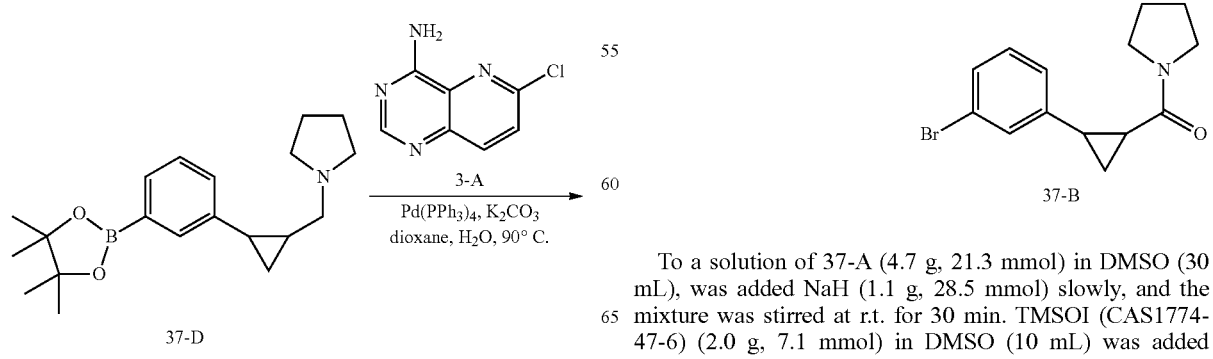

37-B

To a solution of 37-A (4.7 g, 21.3 mmol) in DMSO (30 mL), was added NaH (1.1 g, 28.5 mmol) slowly, and the mixture was stirred at r.t. for 30 min. TMSOI (CAS1774-47-6) (2.0 g, 7.1 mmol) in DMSO (10 mL) was added dropwise to the mixture at r.t. After the mixture was stirred at r.t. overnight, it was poured into water (100 mL). The mixture was extracted with EtOAc (100 mL×2), and the combined organic layer was washed sat NaCl (50 mL×2), dried over Na$_2$SO$_4$ and concentrated in vacuum and purified by column chromatography (PE:EtOAc=3:1 to 10:1) to give the desired product (1.2 g, yield 60%).

Step 3: 1-[2-(3-Bromo-phenyl)-cyclopropylmethyl]-pyrrolidine

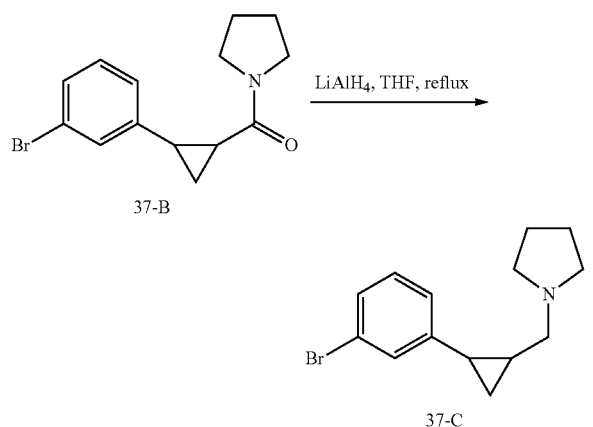

Compound 3 (1.2 g, 4.1 mmol) in dry THF (30 mL) was added dropwise to a suspension of LiAlH$_4$ (460 mg, 13 mmol) in dry THF (10 mL) carefully at r.t. The mixture was stirred at 40-50° C. for 2 h under N$_2$, and cooled to 0° C. MeOH (10 mL) was added dropwise to the mixture carefully, and then the mixture was poured into water (50 mL). The mixture was extracted with EtOAc (100 mL×2), and the combined organic layer was washed with sat NaCl (50 mL×2), and dried over Na$_2$SO$_4$ and concentrated in vacuum to give the crude product. The crude product was purified by column chromatography on silica gel (PE:EtOAc=1:3 to 1:6) to give the desired product (500 mg, yield 45%).

Step 4: 1-{2-[3-(4,4,5,5-Tetramethyl-[1,3,2]dioxaborolan-2-yl)-phenyl]-cyclopropylmethyl}-pyrrolidine

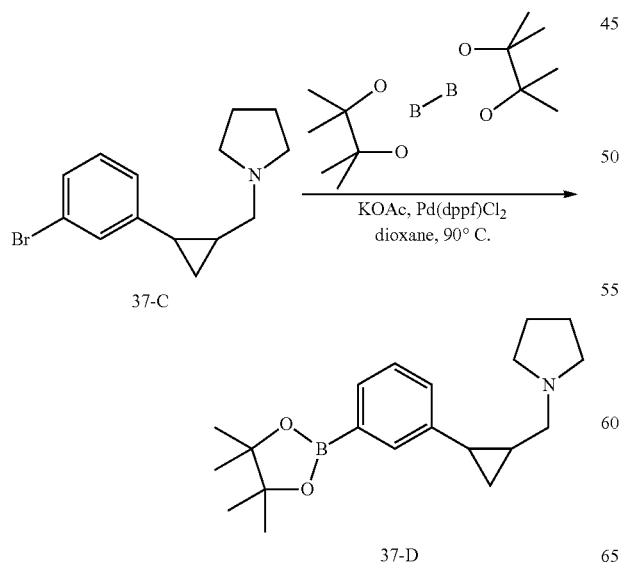

(8). To a solution of Compound 6 (400 mg, 1.4 mmol) in DMSO (20 mL) was added Bis(pinacolato)doboron (CAS18183-34-3) (720 mg, 2.8 mmol), KOAc (400 mg, 4.3 mmol), and Pd(dppf)Cl$_2$ (110 mg, 0.14 mmol). After the mixture was stirred at 80° C. for 3 h under N$_2$, it was poured into water (50 mL). The resulting mixture was extract with EtOAc (100 mL×2) and the combined organic layers was washed with sat NaCl (50 mL), dried over Na$_2$SO$_4$ and concentrated in vacuum to give the crude product (400 mg, crude, 45%).

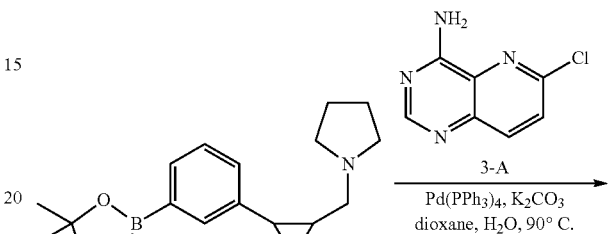

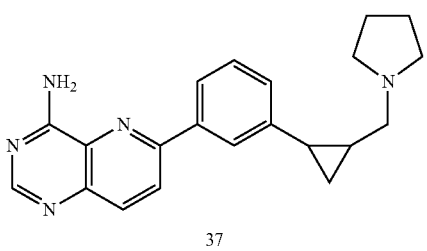

6-[3-(2-Pyrrolidin-1-ylmethyl-cyclopropyl)-phenyl]-pyrido[3,2-d]pyrimidin-4-ylamine To solution of compound 37-D (200 mg, 0.6 mmol) in a mixture of DMSO-H$_2$O (20/5 mL), were added compound 3-A (130 mg, 7.2 mmol), K$_2$CO$_3$ (250 mg, 1.8 mmol), and Pd(PPh$_3$)$_4$ (110 mg, 0.14 mmol). After the mixture was stirred at 100° C. for 5 h under N$_2$, it was poured into water (50 mL). The resulting mixture was extract with EtOAc (100 mL×2) and the combined organic layers was sat NaCl (50 mL), dried over Na$_2$SO$_4$ concentrated in vacuum, and purified by prep-HPLC to give the product as white solid (13 mg, yield 6.3%). LCMS (0-60AB, 2 min) 0.919 min, M+H=345.9; $^1$H NMR (400 MHz, DMSO-d$_6$) δ 8.74 (s, 1H), 8.66 (d, J=8.8 Hz, 1H), 8.27 (d, J=9.2 Hz, 1H), 8.21 (m, 2H), 7.54 (t, J=8.4 Hz, 1H), 7.36 (d, J=7.6 Hz, 1H), 3.75-3.65 (m, 1H), 3.32-3.15 (m, 3H), 2.30-2.03 (m, 6H), 1.66 (m, 1H), 1.42-1.24 (m, 2H).

Example 38

6-(3-(Pyridin-2-yloxy)phenyl)pyrido[3,2-d]pyrimidin-4-amine

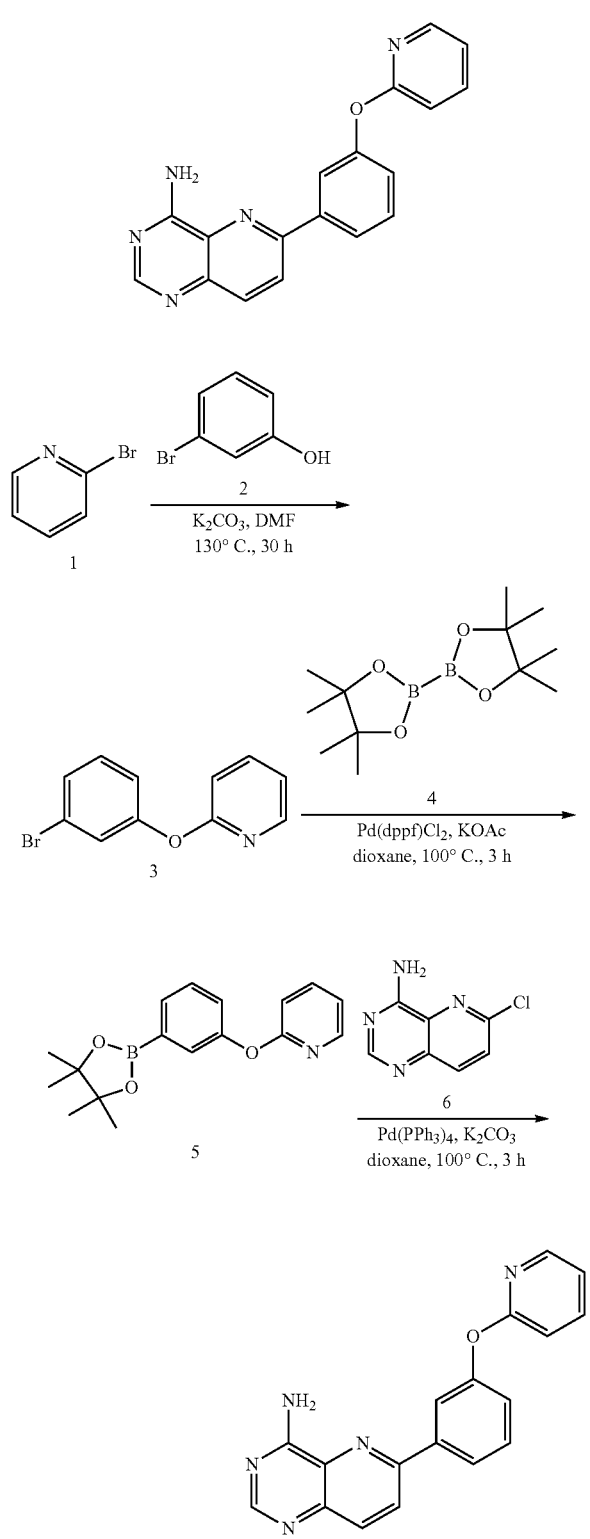

Step 1: 2-(3-Bromophenoxy)pyridine

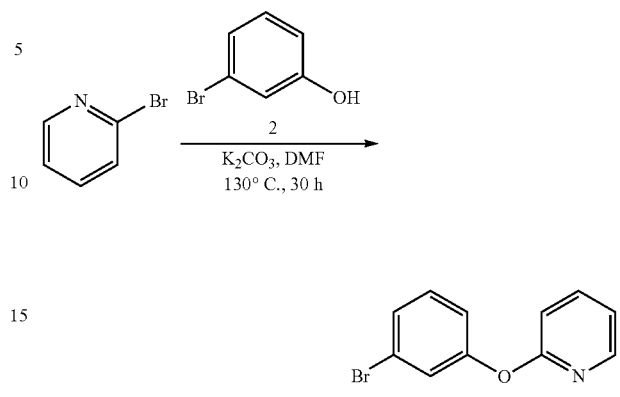

A suspension of 2-bromopyridine (commercially available) (2.0 g, 13.6 mmol), 3-bromophenol (CAS591-20-8) (4.4 g, 24.9 mmol), K₂CO₃ (5.2 g, 40 mmol) in DMF (30 mL) was stirred at 130° C. for 30 h. The mixture was filtered, concentrated, and purified by column chromatography to give titled compound (1.0 g, 30.3%).

Step 2: 2-(3-(4,4,5,5-Tetramethyl-1,3,2-dioxaborolan-2-yl)phenoxy)pyridine

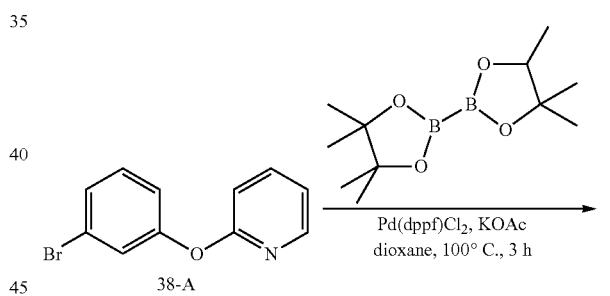

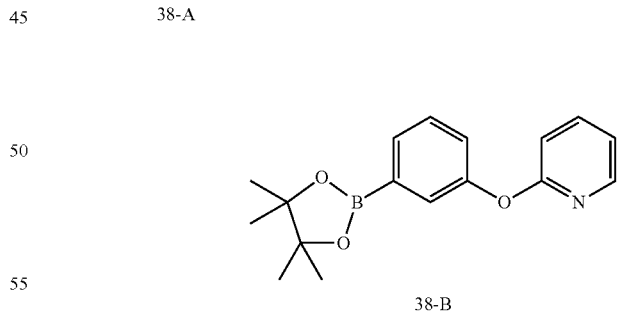

A suspension of 38-A (1.0 g, 4.0 mmol), bis(pinacolato)diboron (CAS 78183-34-3) (1.27 g, 5.5 mmol), Pd(dpppf)Cl₂ (290 mg, 0.40 mmol), and KOAc (1.2 g, 12 mmol) in dioxane (50 mL) was stirred at 100° C. under N₂ for 3 h. The mixture was filtered, concentrated, and purified by column chromatography to give the title compound (800 mg, 67.8%).

Step 3: 6-(3-(Pyridin-2-yloxy)phenyl)pyrido[3,2-d]pyrimidin-4-amine

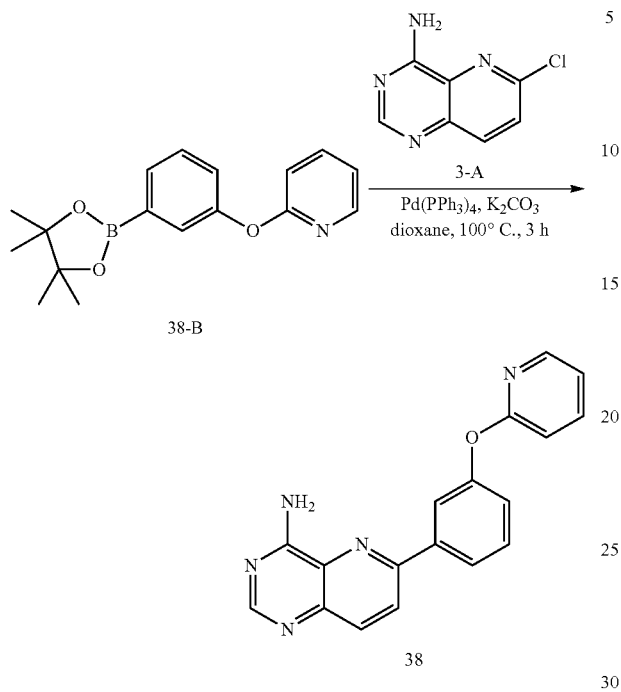

A suspension of 38-B (300 mg, 1.66 mmol), 3-A (740 mg, 2.5 mmol), Pd(PPh$_3$)$_4$ (196 mg, 0.17 mmol), K$_2$CO$_3$ (690 mg, 4.98 mmol) in dioxane (30 mL) was stirred at 100° C. for 3 h under N$_2$. The mixture was filtered, concentrated, and purified by column chromatography to give (330 mg, 63.2%). LCMS (0-60AB, 2 min), 0.938 min, MH+=315.9; $^1$H-NMR (DMSO-d6, 400 MHz): δ 8.44 (d, J=8.8 Hz, 1H), 8.67 (s, 1H), 8.38 (s, 1H), 8.28 (s, 1H), 8.23-8.05 (m, 4H), 7.75 (s, 1H), 7.90-7.86 (m, 1H), 7.55 (t, J=8.0 Hz, 1H), 7.26-7.20 (m, 1H), 7.18-7.05 (m, 2H).

Example 39

6-(3-Fluoro-5-(4-methyl-1H-pyrazol-3-yl)phenyl)pyrido[3,2-d]pyrimidin-4-amine

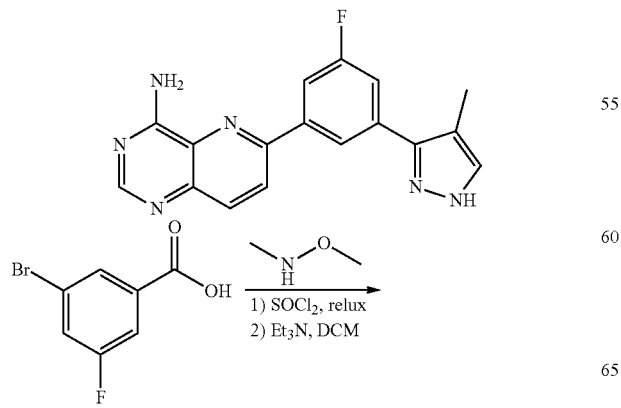

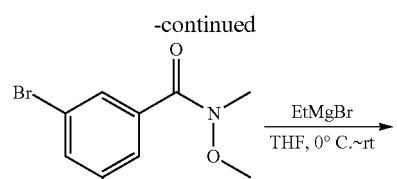

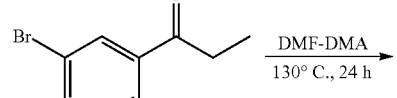

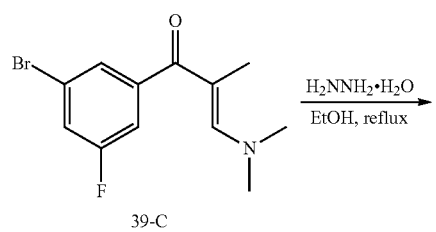

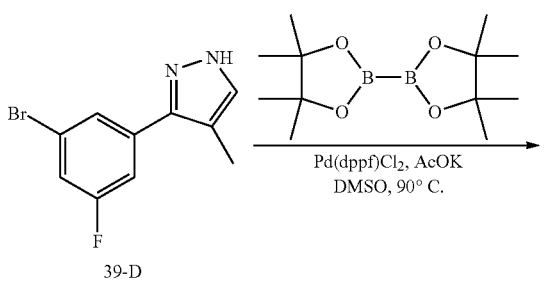

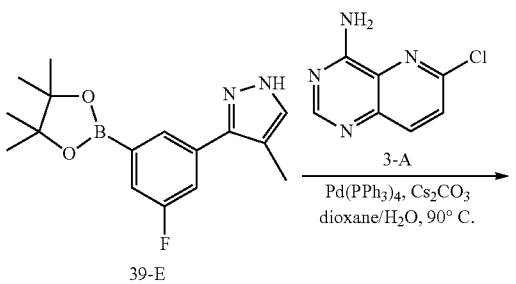

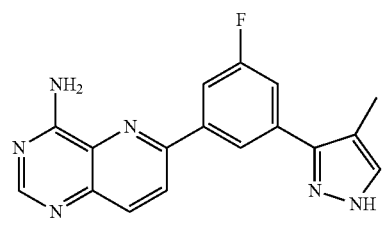

Step 1: 3-Bromo-5-fluoro-N-methoxy-N-methylbenzamide

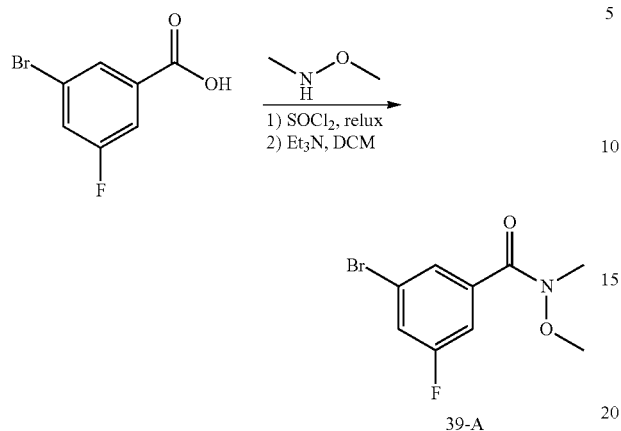

A solution of 3-bromo-5-fluorobenzoic acid (commercially available) (10.0 g, 45.7 mmol) in thionyl chloride (80 mL) was heated at reflux for 2 hours. Thionyl chloride was removed under reduced pressure and the residue was added to solution of N,O-dimethylhydroxylamine hydrochloride (5.32 g, 54.8 mmol) and Et₃N (10.1 g, 0.1 mol) in DCM (300 mL) dropwise at 0° C. After the reaction mixture was stirred at r.t. overnight, it was washed with water (3×100 mL), brine, dried over anhydrous Na₂SO₄ and concentrated. The colorless oil was used in next step without further purification (11.0 g, yield: 95%).

Step 2: 1-(3-Bromo-5-fluorophenyl)propan-1-one

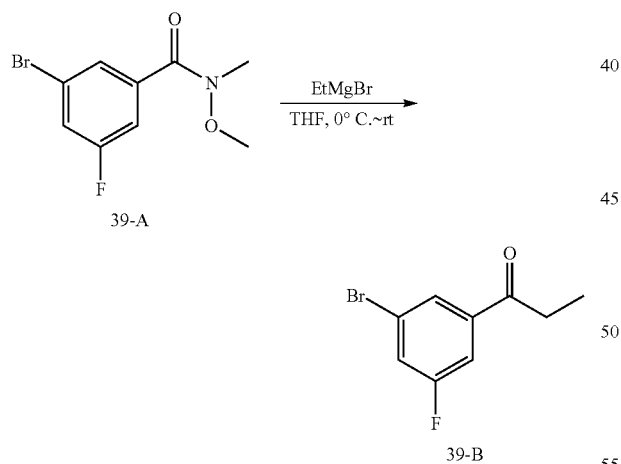

Ethyl magnesium bromide (3.0 M, 16.5 mL, 49.5 mmol) was added to a solution of 39-A (11.0 g, 45.1 mmol) in anhydrous THF (250 mL) dropwise at 0° C. and maintained the temperature below 5° C. After addition, the reaction warmed to r.t. and stirred over night. The reaction was quenched with a NH₄Cl solution. The organic layer was washed with water, brine, dried over anhydrous Na₂SO₄, concentrated and purified by column chromatography (PE: EtOAc=20:1) to give the title compound as a colorless oil (8.0 g, yield: 83%).

Step 3: (E)-1-(3-bromo-5-fluorophenyl)-3-(dimethylamino)-2-methylprop-2-en-1-one

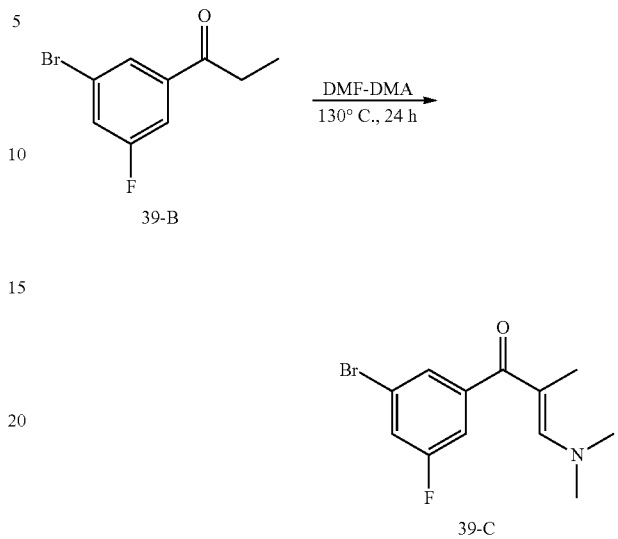

A solution of 39-B (7.9 g, 37.1 mmol) in DMF-DMA (30 mL) was heated at 130° C. and stirred over night. The solvent was removed and the residue was used in next step without further purification.

Step 4: 3-(3-Bromo-5-fluorophenyl)-4-methyl-1H-pyrazole

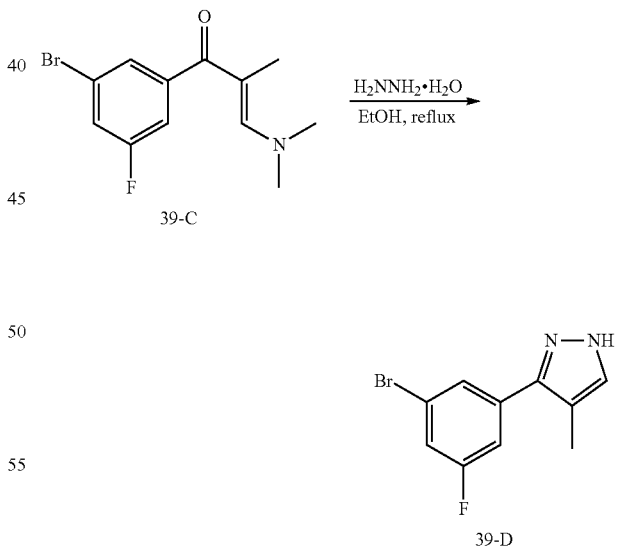

A solution of crude 39-C (10. g, 37.0 mmol) and hydrazine hydrate (5 mL) in ethanol (40 mL) was heated at reflux for 2 h. Ethanol was removed and the residue was partitioned between EtOAc (200 mL) and brine (70 mL). The organic layer was dried over anhydrous Na₂SO₄, concentrated and purified by column (PE:EtOAc=10:1) to give the titled product as a yellow solid (4.5 g, 48%).

Step 5: 3-(3-Fluoro-5-(4,4,5,5-tetramethyl-1,3,2-dioxaborolan-2-yl)phenyl)-4-methyl-1H-pyrazole

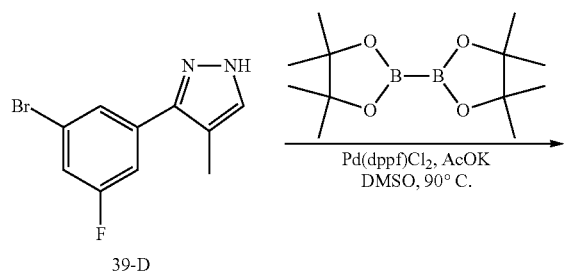

A suspension of 39-D (255 mg, 1.0 mmol), Bis(pinacolato)biboron (CAS 78183-34-3) (300 mg, 1.2 mmol), Pd(dppf)Cl₂ (30 mg) and KOAc (200 mg, 2.0 mmol) in DMSO (6.0 mL) was heated at 90° C. for 3 h. The reaction solution was partitioned between EtOAc (100 mL) and brine (35 mL). The combined organic layer was washed with water (3×30 mL), concentrated and used in next step without further purification.

Step 6: 6-(3-Fluoro-5-(4-methyl-1H-pyrazol-3-yl)phenyl)pyrido[3,2-d]pyrimidin-4-amine

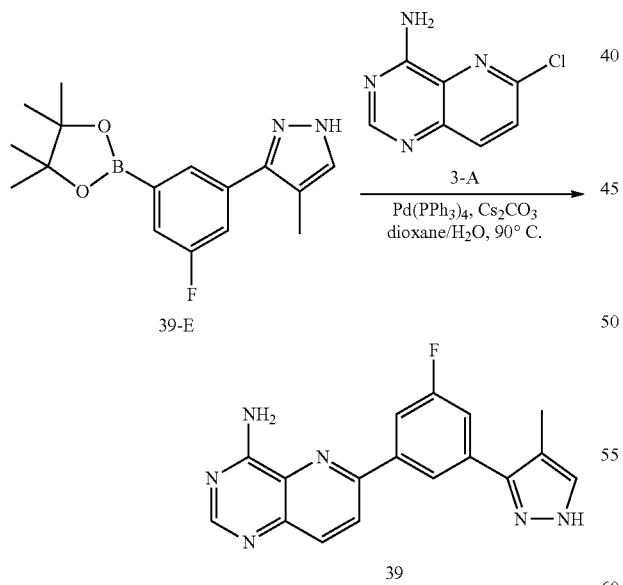

A suspension of crude 39-E (350 mg, 1.0 mmol), 3-A (150 mg, 0.80 mmol), Pd(PPh₃)₄ (30 mg) and Cs₂CO₃ (600 mg, 1.8 mmol) in a mixture of dioxane/H₂O (10 mL/1 mL) was heated to 90° C. for 2 h. The reaction solution was partitioned between EtOAc (100 mL) and brine (35 mL). The combined organic layer was washed with water (3×30 mL), concentrated and purified by prep-HPLC (49 mg, 19%). LCMS (ESI, 10-80AB, 2 min): RT=0.858 min, M+H=321.1. ¹H NMR (DMSO-d6, 400 MHz): 12.87-12.80 (bs, 1H), 8.55-8.52 (d, J=8.8 Hz, 1H), 8.48-8.37 (m, 4H), 8.24 (s, 1H), 8.18 (d, J=8.8 Hz, 1H), 8.15 (s, 1H), 7.59 (s, 1H), 7.53 (d, J=10 Hz, 1H), 2.26 (s, 3H).

Example 40

6-(3-(4-methyl-1H-pyrazol-3-yl)phenyl)pyrido[3,2-d]pyrimidin-4-amine 6-(3-(4-methyl-1H-pyrazol-3-yl)phenyl)pyrido[3,2-d]pyrimidin-4-amine was prepared according to the procedure described in example 39. Yield 18%, LCMS 10-80AB, 303.1, 8.838 min, ¹H-NMR (DMSO-d6, 400 MHz): 12.92-12.76 (bs, 1H), 8.56 (s, 1H), 8.52-8.49 (m, 2H), 8.39 (d, J=10.4 Hz, 1H)), 8.35-8.28 (m, 2H), 8.19-8.17 (d, J=8.8 Hz, 1H), 7.75 (d, J=8.0 Hz, 1H), 7.63 (t, J=8.0 Hz, 1H), 7.55 (s, 1H), 2.27 (s, 3H).

Example 41

6-(3-(Cyclopentyloxy)phenyl)pyrido[3,2-d]pyrimidin-4-amine

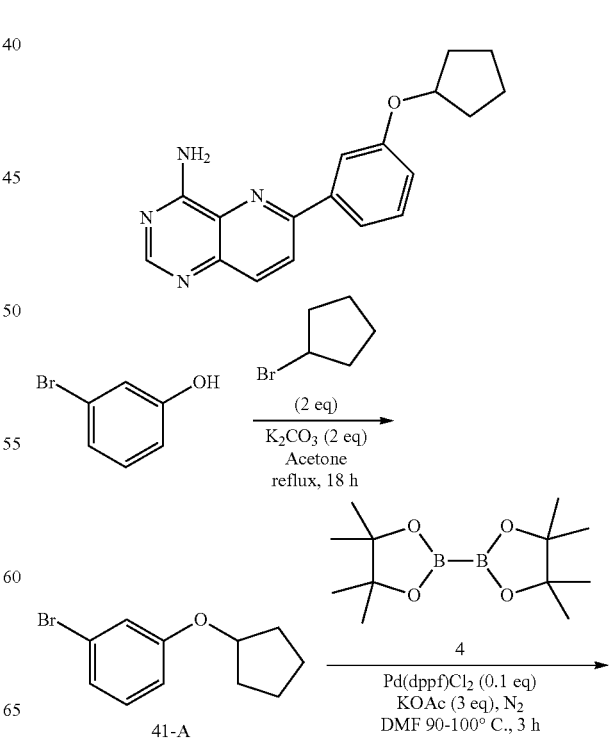

-continued

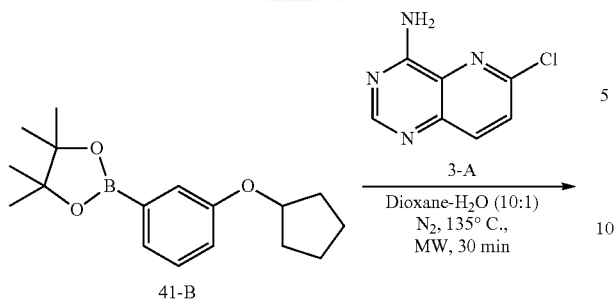

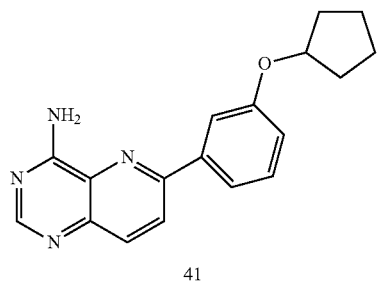

41

Step 1: 1-Bromo-3-(cyclopentyloxy)benzene (41-A)

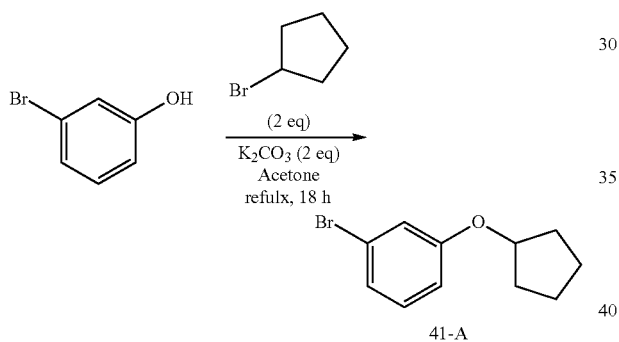

A mixture of 3-bromophenol (commercially available) (1.72 g, 10 mmol), bromocyclopentane (commercially available) (2.96 g, 20 mmol), and $K_2CO_3$ (2.56 g, 20 mmol) in acetone (30 mL) was stirred at 80° C. for 18 h. The solvent was removed under reduced pressure and the mixture was extracted with EtOAc (100 mL×2). The combined organic layers was washed with sat NaCl (50 mL), dried over $Na_2SO_4$, concentrated, and purified by column to give the title product (1.8 g, yield 75%).

Step 2: 2-(3-(Cyclopentyloxy)phenyl)-4,4,5,5-tetramethyl-1,3,2-dioxaborolane (41-B).

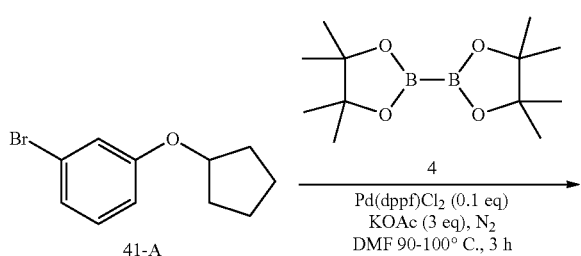

-continued

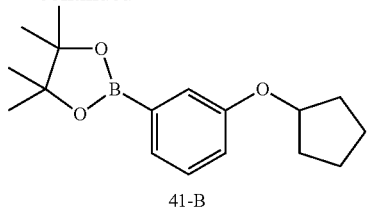

41-B

A mixture of 41-A (1.2 g, 5 mmol), 4,4,4',4',5,5,5',5'-octamethyl-2,2'-Bi-1,3,2-dioxaborolane (CAS 73183-34-3) (2.54 g, 10 mmol), KOAc (980 mg, 10 mmol), and Pd(dppf)Cl$_2$ (366 mg, 0.5 mmol) in DMF (20 mL) was purged 3 times and heated at 110° C. for 2 h at $N_2$. It was poured into water (50 mL) and extract with EtOAc (100 mL×2). The combined organic layers was washed with sat NaCl (50 mL), dried over $Na_2SO_4$ and concentrated in vacuum to give the crude title product (1.0 g, yield 71.4%).

Step 3: 6-(3-(Cyclopentyloxy)phenyl)pyrido[3,2-d]pyrimidin-4-amine

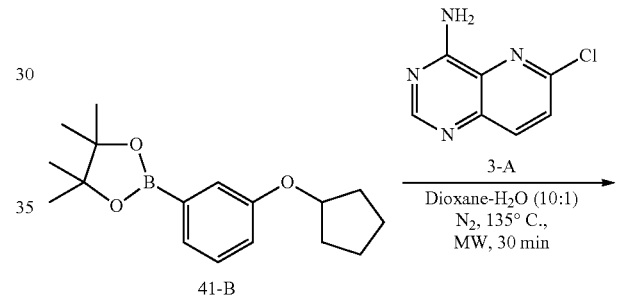

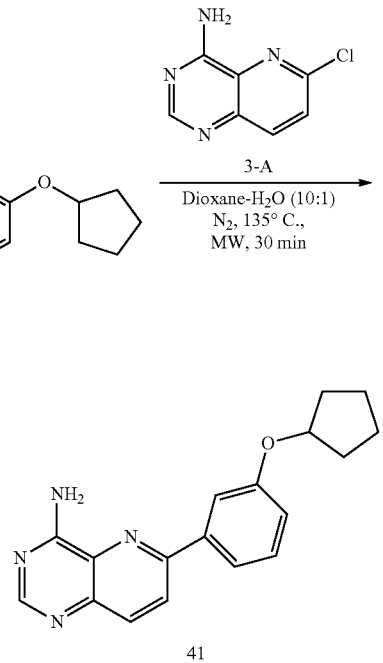

A mixture of 41-B (500 mg, 1.74 mmol), 3-A (312 mg, 1.74 mmol), Cs$_2$CO$_3$ (1.13 g, 3.48 mmol) and Pd(dppf)Cl$_2$ (127.3 mg, 0.174 mmol) in a mixture of dioxane-H$_2$O (10-1 mL) was heated under a irradiation of MW, at 130° C. for 30 min under $N_2$. It was filtered, concentrated and purified by pre-HPLC to give the title compound 41 (47.6 mg, 8.9%). LCMS (0-60AB, ESI): RT=1.129 min, M+H$^+$=307.1; $^1$H NMR (400 MHz, DMSO-d6) δ8.41 (d, J=8.8 Hz, 2H), 8.10 (d, J=8.8 Hz, 2H), 7.97 (s, 1H), 7.90 (s, 2H), 7.41 (t, J=8.0 Hz, 1H), 7.021 (s, J=8.4 Hz, 1H), 5.02 (s, 1H), 1.96 (s, 2H), 1.74 (s, 4H), 1.61 (s, 2H).

Example 42

6-(3-(1H-imidazol-2-yl)piperidin-1-yl)pyrido[3,2-d]pyrimidin-4-amine

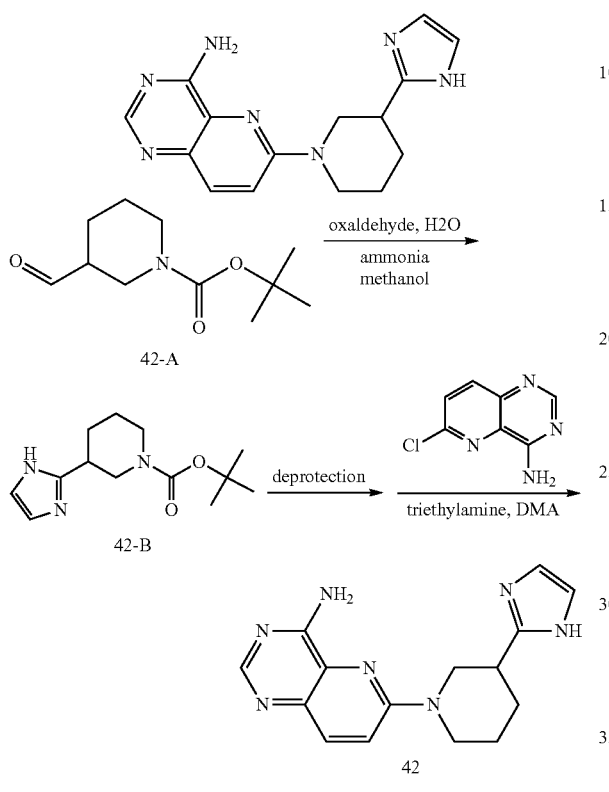

Step 1: tert-butyl 3-(1H-imidazol-2-yl)piperidine-1-carboxylate (42-B)

To an 8 mL screw-cap vial was added tert-butyl 3-formylpiperidine-1-carboxylate 42-A (200 mg, 0.94 mmol, commercially available) and oxaldehyde, 40% in water (0.8 equiv., 0.75022 mmol, 108.9 mg). The reaction was cooled to 0° C., then ammonia (7 mol/L) in methanol (10 equiv., 9.4 mmol, 1.3397 mL) was slowly added. The reaction was then capped and shaken over for 72 h at room temperature. The reaction was mostly concentrated, then partitioned with dichloromethane:water. Organic phase was extracted, dried over sodium sulfate, filtered, and concentrated. Recovered tert-butyl 3-(1H-imidazol-2-yl)piperidine-1-carboxylate was carried directly on to the deprotection step.

Step 2: Deprotection

To an 8 mL screw-cap vial was added tert-butyl 3-(1H-imidazol-2-yl)piperidine-1-carboxylate 42-B (172 mg, 0.68 mmol), methanol (2 mL), and HCl/dioxane (4 mol/L) (8 mmol, 2 mL). The reaction was capped and shaken at room temperature for 4 h. The reaction was then concentrated, then azeotroped with methanol. 6-chloropyrido[3,2-d]pyrimidin-4-amine was carried directly forward to the N-alkylation step without purification.

Step 3: 6-(3-(1H-imidazol-2-yl)piperidin-1-yl)pyrido[3,2-d]pyrimidin-4-amine (42)

To an 8 mL screw-cap vial was added 6-chloropyrido[3,2-d]pyrimidin-4-amine 10 (1 equiv., 0.68 mmol, 123 mg), 3-(1H-imidazol-2-yl)piperidine hydrochloride (1 equiv., 0.68 mmol, 128 mg), triethylamine (3 equiv., 2.05 mmol, 0.287 mL) and DMA (2 mL). The reaction was capped and shaken at 100° C. overnight. The reaction was then cooled to room temperature, diluted with dichloromethane, and washed with water. The organic was then concentrated, then purified by reverse phase HPLC, yielding 16 mg of product. $^1$H NMR (400 MHz, DMSO) δ 8.20-8.14 (m, 3H), 7.82-7.77 (m, 1H), 7.54-7.49 (d, J=9.4 Hz, 1H), 7.38-7.28 (d, J=8.1 Hz, 2H), 6.96-6.94 (s, 2H), 4.79-4.71 (d, J=12.7 Hz, 1H), 4.53-4.46 (d, J=17.4 Hz, 1H), 3.17-3.07 (m, 1H), 3.07-2.96 (m, 1H), 2.96-2.84 (m, 1H), 2.18-2.08 (m, 1H), 1.91-1.77 (m, 2H), 1.66-1.51 (m, 1H). LCMS M/Z (M+H)=296.

Example 43 tert-butyl N-[(3S)-1-(4-aminopyrido[3,2-d]pyrimidin-6-yl)-3-piperidyl]carbamate

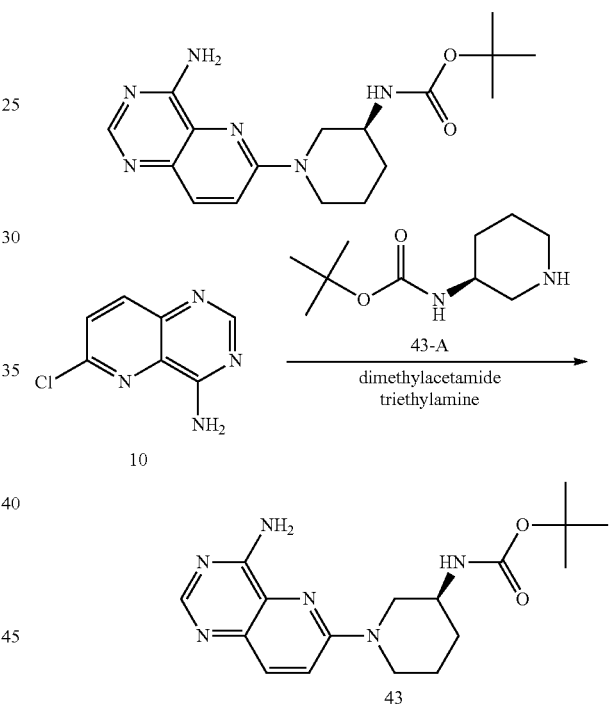

To 40 mL screw-cap vials was added 6-chloropyrido[3,2-d]pyrimidin-4-amine (2.00 g, 11.1 mmol) followed by tert-butyl N-[(3S)-3-piperidyl]carbamate (1.1 equiv., 12.2 mmol, 2.44 g) then dimethylacetamide (10 mL) and triethylamine (3 equiv., 33.2 mmol, 4.65 mL). The reaction was capped and shaken at 100° C. for 42 h, then an additional 24 h at 115° C. The reaction was cooled to room temperature, then partitioned with ethyl acetate:water. Residual chloride starting material was removed by filtration. The filtrate phases were separated, and the organics dried over sodium sulfate, filtered and concentrated, yielding 2.53 g of product. $^1$H NMR (400 MHz, DMSO) δ 8.19-8.13 (s, 1H), 7.81-7.74 (d, J=9.3 Hz, 1H), 7.43-7.39 (d, J=9.1 Hz, 1H), 6.95-6.85 (d, J=6.6 Hz, 1H), 4.32-4.19 (m, 2H), 3.50-3.38 (m, 1H), 3.19-3.04 (m, 1H), 2.96-2.85 (m, 1H), 1.90-1.80 (m, 1H), 1.80-1.67 (m, 1H), 1.60-1.34 (m, 11H). LCMS M/Z (M+H)=345.

Example 44

(S)-6-(3-aminopiperidin-1-yl)pyrido[3,2-d]pyrimidin-4-amine

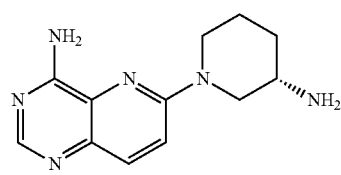 [SMILES: Nc1ncnc2ccc(N3CCC[C@H](N)C3)nc12]

To a 40 mL screw-cap vial was added tert-butyl N-[(3S)-1-(4-aminopyrido[3,2-d]pyrimidin-6-yl)-3-piperidyl]carbamate 43 (2.53 g, 7.35 mmol) followed by methanol (7 mL), then HCl in dioxane (4 mol/L, 7.5 equiv., 55.1 mmol, 13.8 mL). The reaction was stirred at room temperature for 2 hours. Resulting precipitate was collected by filtration, and washed 2× with ethyl acetate, yielding 1.93 g of product as an orange solid, 3×HCl salt. 25 mg was purified by reverse phase HPLC, yielding 5 mg of neutralized product. $^1$H NMR (400 MHz, DMSO) δ 8.17-8.13 (s, 1H), 7.77-7.73 (d, J=9.3 Hz, 1H), 7.46-7.39 (d, J=9.4 Hz, 1H), 7.39-7.07 (s, 2H), 4.48-4.26 (m, 2H), 3.03-2.90 (m, 1H), 2.73-2.62 (m, 2H), 1.93-1.82 (m, 1H), 1.82-1.67 (m, 1H), 1.52-1.36 (m, 1H), 1.34-1.16 (m, 1H). LCMS M?Z (M+H)=245.

Example 45

N-[(3S)-1-(4-aminopyrido[3,2-d]pyrimidin-6-yl)-3-piperidyl]-3-methoxy-propanamide

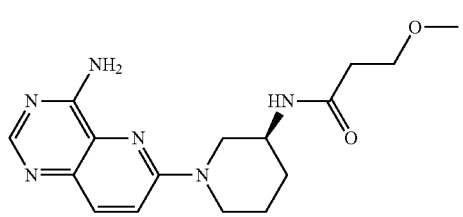 [SMILES: COCCC(=O)N[C@H]1CCCN(c2ccc3ncnc(N)c3n2)C1]

To an 8 mL screw-cap vial was added (S)-6-(3-aminopiperidin-1-yl)pyrido[3,2-d]pyrimidin-4-amine trihydrochloride 44 (0.15 mmol, 53 mg) followed by 3-methoxypropanoic acid (1.2 equiv., 0.18 mmol, 19 mg), HATU (1.2 equiv., 0.18 mmol, 68 mg), dimethylformamide (1 mL), then triethylamine (6 equiv., 0.90 mmol, 0.13 mL). The reaction was capped and shaken at room temperature overnight. The reaction was diluted with 3 mL DCM, and washed with 2 mL water. Organic was concentrated via GeneVac, then purified by reverse phase HPLC, yielding 15 mg of desired product. $^1$H NMR (400 MHz, DMSO) δ 8.19-8.14 (s, 1H), 7.91-7.83 (d, J=7.0 Hz, 1H), 7.82-7.73 (d, J=9.3 Hz, 1H), 7.44-7.38 (d, J=9.3 Hz, 1H), 7.38-7.18 (m, 2H), 4.25-4.17 (d, J=12.7 Hz, 1H), 4.17-4.08 (d, J=13.8 Hz, 1H), 3.85-3.72 (m, 1H), 3.58-3.48 (m, 2H), 3.23-3.18 (s, 3H), 3.10-2.99 (m, 1H), 2.37-2.28 (m, 2H), 1.90-1.81 (m, 1H), 1.81-1.70 (m, J=8.7 Hz, 1H), 1.63-1.40 (m, 2H). LCMS M/Z (M+H)=331.

Example 46

N-[3-(4-aminoquinazolin-6-yl)-5-fluoro-phenyl]acetamide

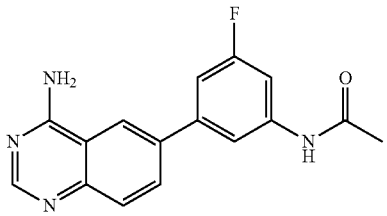 [SMILES: CC(=O)Nc1cc(F)cc(-c2ccc3ncnc(N)c3c2)c1]

To a 4 mL screw-cap vial was added 6-(3-amino-5-fluoro-phenyl)quinazolin-4-amine, 25 mg; 0.10 mmol) followed by DCM (0.5 mL), TEA (2 equiv., 0.20 mmol, 0.0277 mL), and acetyl chloride (2 equiv., 0.20 mmol, 15.43 mg). The reaction was capped and shaken at room temperature for 2 h. Reaction was then diluted with 2 mL dichloromethane, and washed with water. Resultant precipitate was collected by filtration, then purified by reverse phase HPLC. Purification recovered 6 mg of desired product. 1H NMR (400 MHz, DMSO) δ 10.35-10.24 (s, 1H), 8.61-8.49 (d, J=1.7 Hz, 1H), 8.43-8.36 (s, 1H), 8.05-7.97 (dd, J=8.7, 1.8 Hz, 1H), 7.98-7.82 (bs, 1H), 7.77-7.73 (d, J=8.7 Hz, 1H), 7.71-7.67 (s, 1H), 7.65-7.56 (d, J=11.2 Hz, 1H), 7.42-7.30 (d, J=10.0 Hz, 1H), 2.11-2.08 (s, 3H). LCMS M/Z (M+H) 297.

Example 47

N-[3-(4-aminoquinazolin-6-yl)-5-fluoro-phenyl]-2-morpholino-acetamide

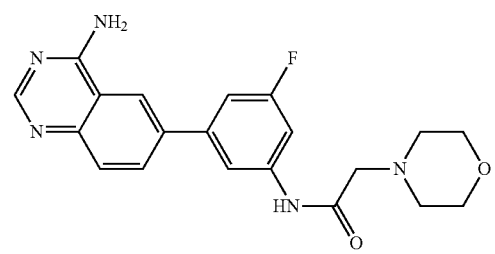 [SMILES: Nc1ncnc2ccc(-c3cc(F)cc(NC(=O)CN4CCOCC4)c3)cc12]

To 2-morpholinoacetic acid (0.175 mmol, 25 mg) in a 4 mL vial was added HATU (0.175 mmol, 69 mg), 6-(3-amino-5-fluoro-phenyl)quinazolin-4-amine, 0.15 mmol, 38 mg), and TEA (0.30 mmol, 0.042 mL). The vial was capped and shaken overnight at room temperature. The reaction was then diluted with 3 mL DCM, then washed with 2 mL water. Organic phase was concentrated, and then purified by reverse phase HPLC yielding 20 mg of desired product. $^1$H NMR (400 MHz, DMSO) δ 10.07-9.93 (s, 1H), 8.60-8.52 (d, J=1.8 Hz, 1H), 8.42-8.39 (s, 1H), 8.08-8.03 (dd, J=8.7, 1.9 Hz, 1H), 7.93-7.66 (m, 4H), 7.44-7.35 (d, J=10.0 Hz, 1H), 3.71-3.63 (m, 4H), 3.20-3.17 (s, 2H), 2.56-2.51 (m, 4H). LCMS M/Z (M+H) 382.

Examples 48 and 49

N-(6-(3-amino-5-fluorophenyl)pyrido[3,2-d]pyrimidin-4-yl)-2-(pyrrolidin-1-yl)acetamide

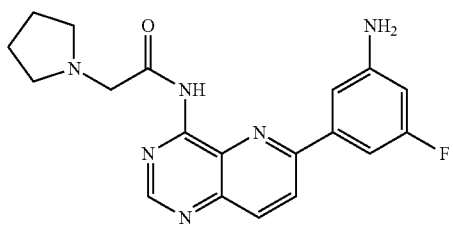 [SMILES: Nc1cc(F)cc(-c2ccc3ncnc(NC(=O)CN4CCCC4)c3n2)c1]

N-(3-(4-aminopyrido[3,2-d]pyrimidin-6-yl)-5-fluorophenyl)-2-(pyrrolidin-1-yl)acetamide

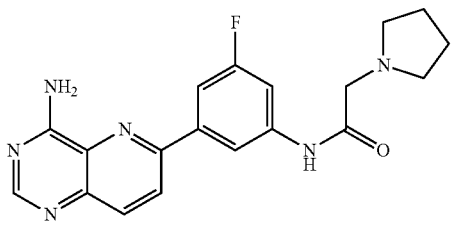 [SMILES: Nc1ncnc2ccc(-c3cc(F)cc(NC(=O)CN4CCCC4)c3)nc12]

To a 4 mL vial was added 6-(3-amino-5-fluoro-phenyl)pyrido[3,2-d]pyrimidin-4-amine, 50 mg; 0.20 mmol) followed by HATU (1.1 equiv., 0.22 mmol, 84.48 mg), 2-pyrrolidin-1-ylacetic acid, (1.1 equiv.; 0.22 mmol, 28 mg), DMF (0.5 mL), and triethylamine (2 equiv., 0.40 mmol, 0.055 mL). The reactions were capped and shaken at room temperature overnight. The following morning the reaction was diluted with 2 mL DCM, and washed with 1 mL water. The organic was concentrated in vacuo, the crude was then purified by reverse phase HPLC, yielding 4.5 mg of Example 166, N-(6-(3-amino-5-fluorophenyl)pyrido[3,2-d]pyrimidin-4-yl)-2-(pyrrolidin-1-yl)acetamide, 1H NMR (400 MHz, DMSO) δ 11.83-11.71 (s, 1H), 9.01-8.93 (s, 1H), 8.48-8.38 (m, 2H), 7.30-7.20 (m, 2H), 6.54-6.49 (d, J=11.3 Hz, 1H), 5.69-5.60 (s, 2H), 3.51-3.47 (s, 2H), 2.81-2.71 (m, 4H), 1.93-1.83 (m, 4H), LCMS M/Z (M+H)=367, and 3 mg of Example 167, N-(3-(4-aminopyrido[3,2-d]pyrimidin-6-yl)-5-fluorophenyl)-2-(pyrrolidin-1-yl)acetamide, 1H NMR (400 MHz, DMSO) δ 9.97-9.91 (s, 1H), 8.44-8.41 (s, 1H), 8.37-8.33 (d, J=8.9 Hz, 1H), 8.31-8.26 (s, 1H), 8.21-8.07 (m, 3H), 8.07-7.99 (s, 1H), 7.91-7.86 (d, J=11.1 Hz, 1H), 2.67-2.59 (m, 4H), 1.83-1.76 (m, 4H). LCMS M/Z (M+H)=367.

Example 50

N6-(2-methylbenzyl)pyrido[3,2-d]pyrimidine-4,6-diamine

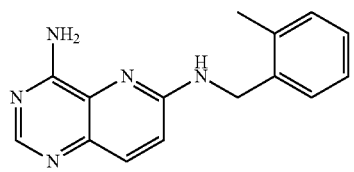

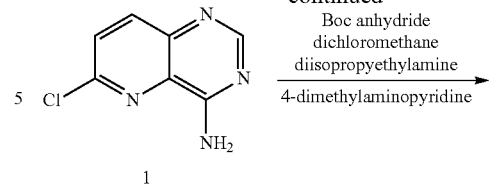

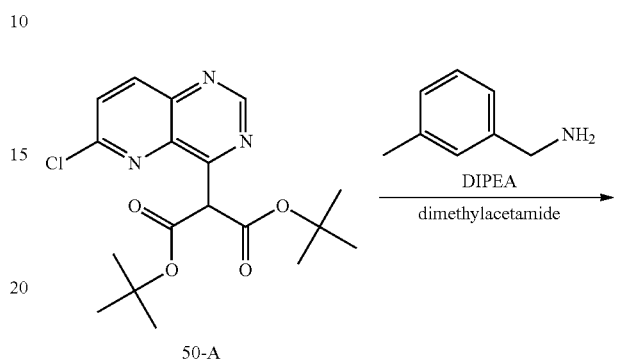

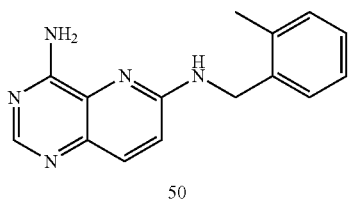

Step 1: tert-butyl N-tert-butoxycarbonyl-N-(6-chloropyrido[3,2-d]pyrimidin-4-yl)carbamate (50-A)

To a round bottom flask was added 6-chloropyrido[3,2-d]pyrimidin-4-amine 1 (5.00 g, 27.7 mmol) followed by Boc anhydride (2.1 equiv., 58.1 mmol, 12.6 g), dichloromethane (200 mL), diisopropylethylamine (3 equiv., 83.1 mmol, 10.8 g) and catalytic 4-dimethylaminopyridine (0.05 equiv., 1.38 mmol, 173 mg). The reaction was stirred at 40° C. overnight. Reaction was then concentrated. Crude product was purified by flash chromatography, 15-50% EA: Heptane, yielding 6.74 g of product. LCMS M/Z (M+H)=381

Step 2: N6-(2-methylbenzyl)pyrido[3,2-d]pyrimidine-4,6-diamine (50)

To a microwave vial was added tert-butyl N-tert-butoxycarbonyl-N-(6-chloropyrido[3,2-d]pyrimidin-4-yl)carbamate 50-A (0.20 mmol, 76 mg) followed by 3-methylbenzyl amine (2 equiv., 0.4 mmol, 48 mg), DIPEA (3 equiv., 0.6 mmol, 78 mg), and dimethylacetamide (0.5 mL). The reactions were capped and stirred under microwave irradiation for 30 minutes at 130° C. The reaction was then transferred to an 8 ml vial, and concentrated via GeneVac. To the crude material was added dichloromethane (0.25 mL) followed by trifluoroacetic acid (0.5 mL). The reaction was capped and shaken at room temperature for one hour. The reaction was then concentrated, and the crude purified by reverse phase HPLC to yield 11 mg of product. 1H NMR (400 MHz, DMSO) δ 8.16-8.11 (s, 1H), 7.69-7.62 (d, J=9.1 Hz, 1H), 7.53-7.46 (t, J=5.5 Hz, 1H), 7.40-7.33 (m, 1H), 7.22-7.11 (m, 3H), 7.11-7.07 (d, J=9.1 Hz, 1H), 4.70-4.62 (d, J=5.5 Hz, 2H), 2.37-2.33 (s, 3H). LCMS M/Z (M+H)=266.

Example 51

6-(o-tolyloxy)pyrido[3,2-d]pyrimidin-4-amine

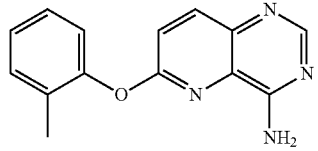 [SMILES: Cc1ccccc1Oc1ccc2ncnc(N)c2n1]

To an 8 mL screw-cap vial was added tert-butyl N-tert-butoxycarbonyl-N-(6-chloropyrido[3,2-d]pyrimidin-4-yl)carbamate 50-A (0.20 mmol, 76 mg) followed by 2-methylphenol (2 equiv., 0.40 mmol, 43 mg), potassium carbonate (2 equiv., 0.40 mmol, 55 mg) and dimethylacetamide (0.4 mL), and 4-dimethylaminopyridine, 0.05 equiv., 0.01 mmol, 1 mg). The reactions were capped and shaken at 80° C. for 2 h. The reaction was filtered, and concentrated via GeneVac. Crude was then taken up in dichloromethane (0.25 mL), followed by trifluoroacetic acid (0.5 mL). The reaction was capped and shaken for 1 h, then concentrated. Crude was purified by reverse phase HPLC to yield 27 mg of product. $^1$H NMR (400 MHz, DMSO) δ 8.40-8.33 (s, 1H), 8.17-8.11 (d, J=9.0 Hz, 1H), 7.44-7.35 (dd, J=13.1, 8.3 Hz, 2H), 7.32-7.26 (m, 1H), 7.26-7.17 (m, 2H), 2.17-2.13 (s, 3H). LCMS M/Z (M+H)=253.

Example 52

6-(3-chlorophenyl)-N-(pyridin-4-yl)quinazolin-4-amine

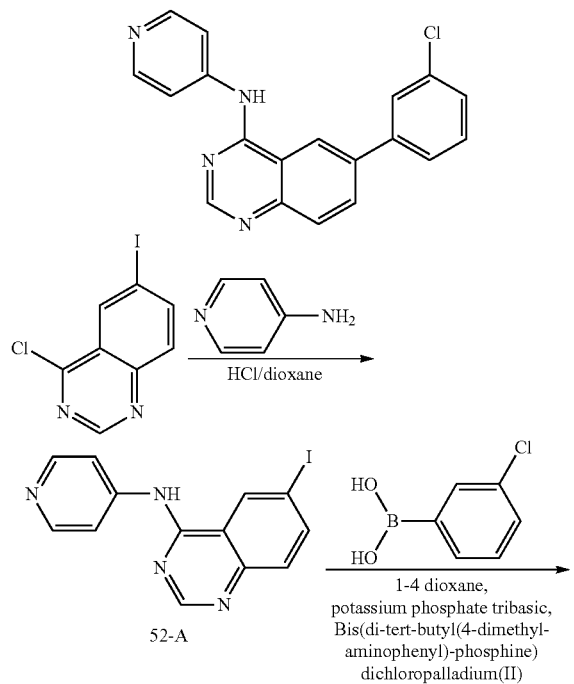

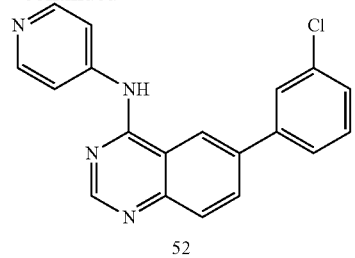

Step 1: 6-iodo-N-(4-pyridyl)quinazolin-4-amine 52-A

To a vial was added 4-chloro-6-iodo-quinazoline (100 mg; 0.34 mmol, commercially available), pyridin-4-amine (3 equiv., 1.03 mmol, 97.19 mg, commercially available), and 2 drops of 4M HCl/dioxane. The reaction vial was heated until solids melted. LCMS of resultant solution showed clean product formation. Upon cooling the product re-solidified. The solid was suspended in dichloromethane:water, and collected by filtration. 95 mg of 6-iodo-N-(4-pyridyl)quinazolin-4-amine was recovered as an orange solid, which was carried on directly to the Suzuki step. LCMS M/Z (M+H)=350.

Step 2: 6-(3-chlorophenyl)-N-(pyridin-4-yl)quinazolin-4-amine 52

To an 8 mL screw-cap vial was added 6-iodo-N-(4-pyridyl)quinazolin-4-amine (95 mg, 0.2729 mmol), (3-chlorophenyl)boronic acid, (1.2 equiv., 0.33 mmol, 51.21 mg), 1-4 dioxane (0.8 mL), potassium phosphate tribasic, (2M in H2O, 3 equiv., 0.82 mmol, 0.41 mL), and Bis(di-tert-butyl (4-dimethylaminophenyl)phosphine)dichloropalladium(II) (0.05 equiv.; 0.014 mmol, 10 mg). The reaction was capped and shaken at 60° C. for 1 h. The reaction was then diluted with 4 mL dichloromethane and washed with water. Organic phase was then concentrated. Crude was purified by reverse phase HPLC yielding 31 mg of product. $^1$H NMR (400 MHz, DMSO) δ 10.22-10.07 (s, 1H), 8.92-8.86 (s, 1H), 8.82-8.75 (s, 1H), 8.56-8.49 (d, J=5.4 Hz, 2H), 8.31-8.25 (m, 1H), 8.05-7.97 (m, 3H), 7.97-7.91 (d, J=8.7 Hz, 1H), 7.90-7.84 (d, J=7.7 Hz, 1H), 7.64-7.57 (t, J=7.8 Hz, 1H), 7.57-7.50 (d, J=8.0 Hz, 1H). LCMS M/Z (M+H)=333.

Example 53

6-(3-chlorophenyl)-N-cyclopropylquinazolin-4-amine

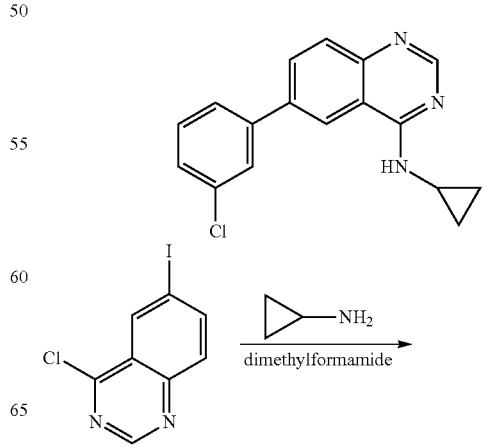

-continued

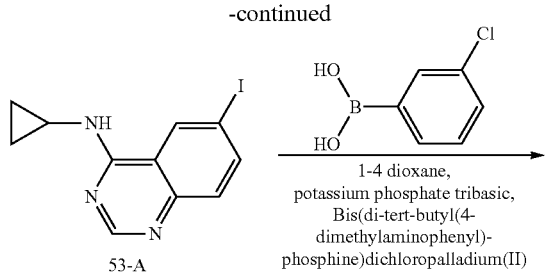

Step 1: N-cyclopropyl-6-iodo-quinazolin-4-amine

To 8 mL screw-cap vials was added 4-chloro-6-iodo-quinazoline (0.25 mmol, 73 mg), cyclopropyl amine 3 equiv., 0.75 mmol, 43 mg), and dimethylformamide (0.5 mL). The reaction was capped and shaken at 60° C. for 3 h. The crude N-cyclopropyl-6-iodo-quinazolin-4-amine was then cooled to room temperature, concentrated via GeneVac, and then carried on to the Suzuki step. LCMS M/Z (M+H)=312.

Step 2: 6-(3-chlorophenyl)-N-cyclopropylquinazolin-4-amine

To an 8 mL screw-cap vial was added N-cyclopropyl-6-iodo-quinazolin-4-amine (0.25 mmol 78 mg), (3-chlorophenyl)boronic acid, (1.2 equiv., 0.30 mmol, 47 mg), 1-4 dioxane (0.6 mL), potassium phosphate tribasic, (2M in H2O, 3 equiv., 0.75 mmol, 0.0.38 mL), and Bis(di-tert-butyl (4-dimethylaminophenyl)phosphine)dichloropalladium(II) (0.05 equiv.; 0.013 mmol, 9 mg). The reaction was capped and shaken at 60° C. for 1 h. The reaction was cooled to room temperature and the phases separated. Organic phase was then concentrated. Crude was purified by reverse phase HPLC yielding 35 mg of product. $^1$H NMR (400 MHz, DMSO) δ 8.60-8.49 (m, 2H), 8.44-8.35 (s, 1H), 8.18-8.05 (d, J=8.7, 1H), 7.93-7.87 (s, 1H), 7.84-7.71 (m, 2H), 7.62-7.51 (t, J=7.9 Hz, 1H), 7.51-7.43 (d, J=8.4 Hz, 1H), 3.12-2.98 (m, 1H), 0.90-0.78 (m, 2H), 0.72-0.64 (m, 2H). LCMS M/Z (M+H)=296.

Example 54

4-amino-6-(3-fluorophenyl)quinazoline-8-carbonitrile

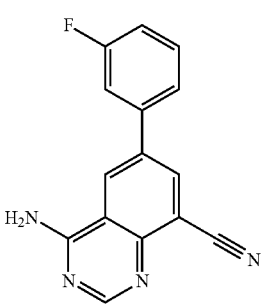

-continued

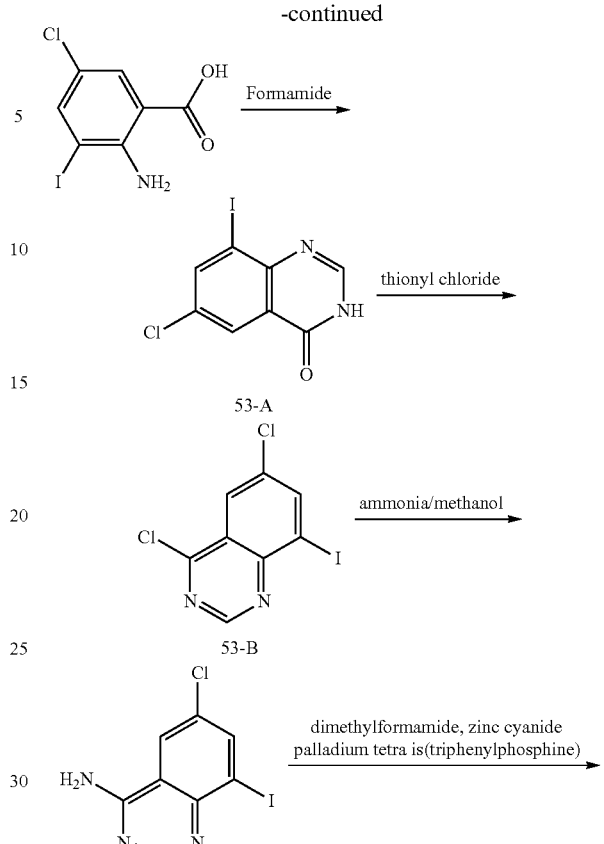

Step 1: 6-chloro-8-iodo-3H-quinazolin-4-one 53-A

To a round bottom flask was added formamide (4 equiv., 13.5 mmol, 605 mg) and 2-amino-5-chloro-3-iodo-benzoic acid (1000 mg, 3.4 mmol). The reaction was capped and shaken at 130° C. for 72 h. The reaction was cooled to room temperature, then the precipitate was collected by filtration and washed 3× with water. The precipitate was dried under vacuum, yielding 881 mg of 6-chloro-8-iodo-3H-quinazolin-4-one as a purple solid. $^1$H NMR (400 MHz, DMSO) δ

12.66-12.49 (s, 1H), 8.40-8.37 (d, J=2.4 Hz, 1H), 8.24-8.21 (s, 1H), 8.09-8.05 (d, J=2.4 Hz, 1H). LCMS M/Z (M+H)=307.

Step 2: 4,6-dichloro-8-iodo-quinazoline 53-B

To a round bottom flask was added 6-chloro-8-iodo-3H-quinazolin-4-one (1000 mg, 3.3 mmol) and thionyl chloride (50 mL). DMF (0.1 mL) was then added, and the reaction was stirred at reflux for 2 h. The reaction was cooled to room temperature, then concentrated via rotovap. The product was then azeotroped 2× with DCM, then dried under vacuum yielding 4,6-dichloro-8-iodo-quinazoline, carried immediately to the next step. $^1$H NMR (400 MHz, DMSO) δ 9.24-9.20 (s, 1H), 8.77-8.73 (d, J=2.2 Hz, 1H), 8.36-8.31 (d, J=2.2 Hz, 1H).

Step 3: 6-chloro-8-iodo-quinazolin-4-amine 53-C

To 4,6-dichloro-8-iodo-quinazoline (1.00 g, 3.08 mmol) was added 2.4 mL of 7N ammonia/methanol. The mixture was capped and shaken overnight at room temperature. The rxn was then concentrated via rotovap yielding product as a white solid. The product was purified by flash column (2.5-10% Methanol:Dichloromethane), yielding 450 mg of 6-chloro-8-iodo-quinazolin-4-amine. $^1$H NMR (400 MHz, DMSO) δ 8.51-8.45 (s, 1H), 8.45-8.41 (d, J=2.0 Hz, 1H), 8.41-8.35 (d, J=1.9 Hz, 1H), 8.12-7.92 (bs, 2H). LCMS M/Z (M+H)=306.

Step 4: 4-amino-6-chloro-quinazoline-8-carbonitrile 53-D

To an 8 mL screw-cap vial was added 6-chloro-8-iodo-quinazolin-4-amine (450 mg, 1.47 mmol), dimethylformamide (2 mL), zinc cyanide (0.65 equiv., 1.0 mmol, 115 mg), and palladium tetra is (triphenylphosphine), (0.1 equiv., 0.15 mmol), 179 mg). The reaction was capped and shaken at 110° C. overnight. The reaction was cooled to room temperature, diluted with 3 mL of dichloromethane, and 2 mL of water was added. The precipitate that followed was collected by filtration, and washed with water, then dichloromethane yielding 240 mg of 4-amino-6-chloro-quinazoline-8-carbonitrile as a light yellow solid. $^1$H NMR (400 MHz, DMSO) δ 8.72-8.67 (d, J=2.2 Hz, 1H), 8.54-8.50 (s, 1H), 8.50-8.46 (d, J=2.1 Hz, 1H), 8.29-8.22 (bs, 2H). LCMS M/Z (M+H)=205.

Step 5: 4-amino-6-(3-fluorophenyl)quinazoline-8-carbonitrile 53

To an 8 mL vial was added 4-amino-6-chloro-quinazoline-8-carbonitrile (100 mg, 0.49 mmol) followed by (3-fluorophenyl)boronic acid (2 equiv., 1.0 mmol, 0.13676 g), potassium phosphate tribasic (2M in water, 4 equiv., 2.0 mmol, 1 mL), Bis(di-tert-butyl(4-dimethylaminophenyl)phosphine)dichloropalladium(II) (0.05 equiv., 0.024 mmol, 17 mg) and dioxane (2 mL). The reaction was capped and shaken at 100° C. for 2 h. The reaction was cooled to room temperature, then diluted with 4 mL ethyl acetate and 3 mL water. The resulting precipitate was collected by filtration, yielding 72 mg of desired product. $^1$H NMR (400 MHz, DMSO) δ 8.94-8.89 (d, J=1.5 Hz, 1H), 8.77-8.72 (d, J=1.4 Hz, 1H), 8.55-8.50 (s, 1H), 8.43-8.13 (s, 2H), 7.83-7.74 (t, J=8.5 Hz, 2H), 7.63-7.55 (dd, J=14.5, 8.0 Hz, 1H), 7.33-7.25 (dd, J=12.5, 4.5 Hz, 1H). LCMS M/Z (M+H)=265.

Examples 55

N-(2-acetamidoethyl)-4-amino-6-(3-fluorophenyl)quinazoline-8-carboxamide

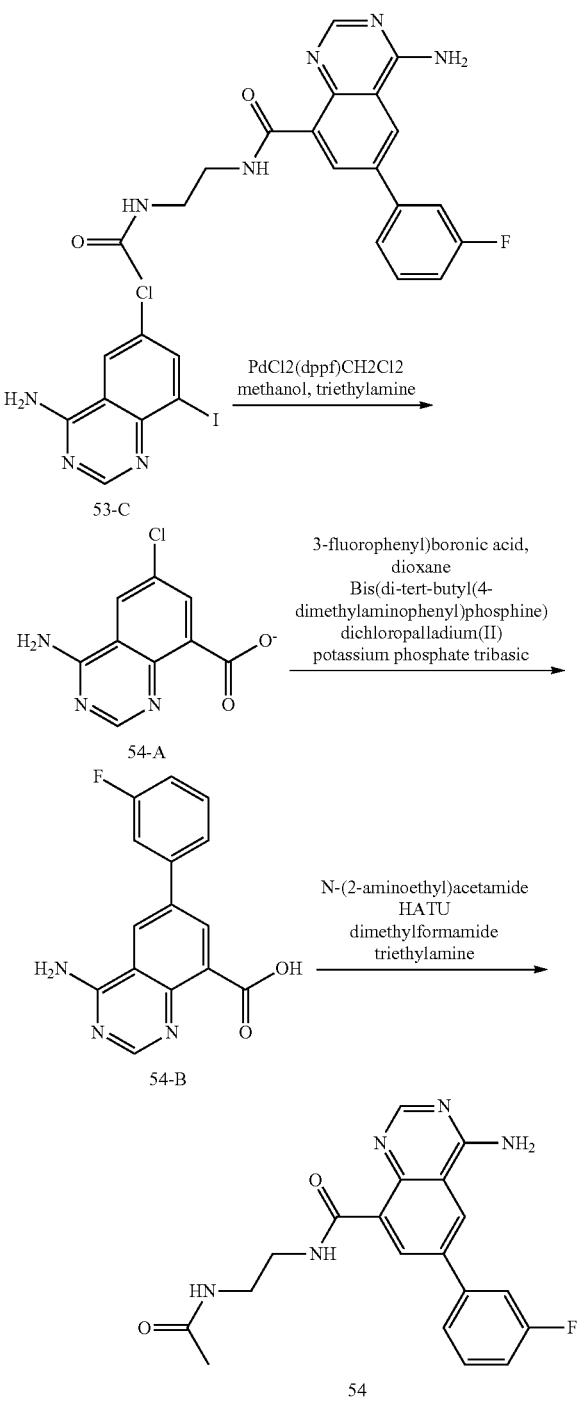

Step 1: 4-amino-6-chloro-quinazoline-8-carboxylate 54-A

To a 50 mL round bottom flask was added 6-chloro-8-iodo-quinazolin-4-amine 53-C (250 mg, 0.81833 mmol), PdCl2(dppf)CH2Cl2 (0.1 equiv., 0.08) mmol, 66 mg), methanol (1 mL), and triethylamine (3 equiv., 2.46 mmol, 0.3459 mL). The reaction was vacuum purged, and backfilled with 1 atm of carbon monoxide. The purge was repeated 3×, then the reaction was stirred at 40° C. for 4 h. The reaction was concentrated. The reaction was repeated 4 times on 1 g, 1.55 g, 1.55 g, and 0.5 g scale as above, with reaction temperatures of room temperature to 40° C. The reactions were combined, concentrated, then partitioned with ethyl acetate and water. Solids were removed by filtration, and the filtrate phases separated. The organic was dried over sodium sulfate, filtered, and concentrated. Crude was purified by flash chromatography (0-10% methanol:dichloromethane) yielding 640 mg of 4-amino-6-chloro-quinazoline-8-carboxylate. LCMS M/Z (M+H)=265.

Step 2: 4-amino-6-(3-fluorophenyl)quinazoline-8-carboxylic acid 54-B

To a 20 mL screw-cap vial was added methyl 4-amino-6-chloro-quinazoline-8-carboxylate (640 mg; 1.8 mmol), (3-fluorophenyl)boronic acid (2 equiv., 3.6 mmol, 0.49753 g), dioxane (10 mL), Bis(di-tert-butyl(4-dimethylaminophenyl)phosphine)dichloropalladium(II) (0.05 equiv. 0.09 mmol, 0.062945 g), and potassium phosphate tribasic (2M in water, 4 equiv., 7.2 mmol, 3.6 mL). The reaction was capped and shaken at 100° C. for 4 h. LCMS showed complete Suzuki coupling, as well as saponified ester. The Reaction was cooled to room temperature, and partitioned with water and ethyl acetate. The organic was extracted 2 additional times with water. The combined aqueous was acidified to pH 2 with conc. HCl. The resulting precipitate was collected via filtration, yielding 350 mg of 4-amino-6-(3-fluorophenyl)quinazoline-8-carboxylic acid, ~85% pure. Product was carried directly on to the amide formation. LCMS M/Z (M+H)=284.

Step 3: N-(2-acetamidoethyl)-4-amino-6-(3-fluorophenyl)quinazoline-8-carboxamide 54

To a 4 mL screw-cap vial was added 4-amino-6-(3-fluorophenyl)quinazoline-8-carboxylic acid (0.10 mmol, 28 mg) followed by N-(2-aminoethyl)acetamide (2 equiv., 0.20 mmol, 20 mg), HATU (1.1 equiv., 0.11 mmol, 43 mg), dimethylformamide (0.5 mL), and triethylamine (3 equiv., 0.30 mmol, 0.042 mL). The reaction was capped and shaken at 50° C. for 4 h. The reaction was cooled to room temperature, diluted with 2.5 ml dichloromethane and washed with 1 ml water. Organic was concentrated, then the crude was purified by reverse phase HPLC, yielding 6 mg of desired product. $^1$H NMR (400 MHz, DMSO) δ 11.17-11.07 (t, J=5.6 Hz, 1H), 8.89-8.75 (m, 2H), 8.54-8.50 (s, 1H), 8.44-8.06 (m, 2H), 8.06-7.99 (t, J=5.5 Hz, 1H), 7.75-7.64 (m, 2H), 7.64-7.53 (m, 1H), 7.35-7.22 (m, 1H), 3.53-3.44 (m, 2H), 3.32-3.26 (m, 2H), 1.85-1.82 (s, 3H). LCMS M/Z (M+H)=368.

Examples 56

6-(2-(2-(pyrrolidin-1-yl)ethylamino)pyridin-4-yl)quinazolin-4-amine

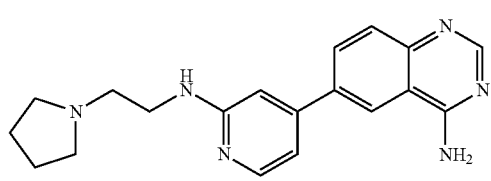

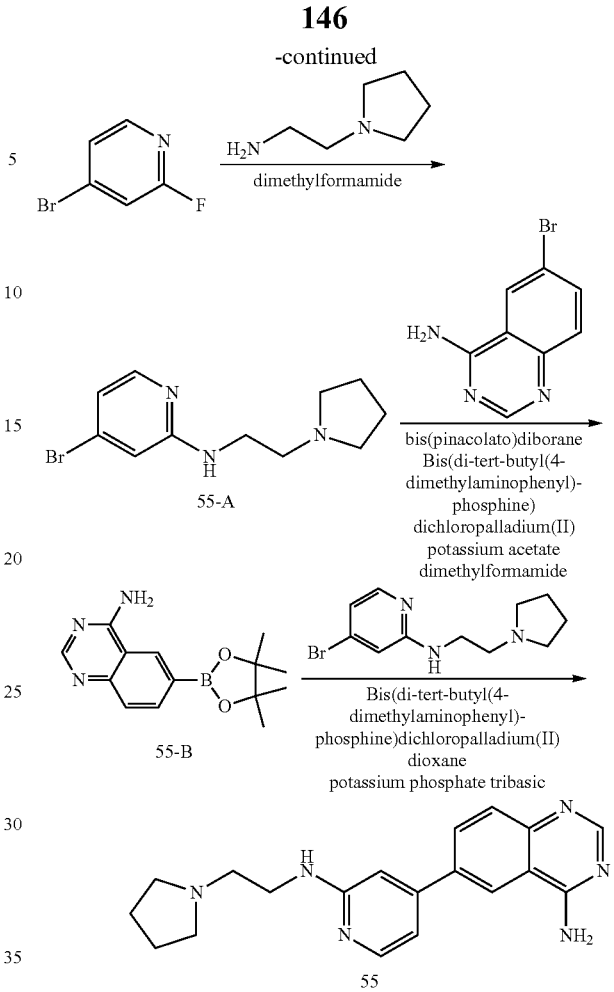

Step 1: 4-bromo-N-(2-pyrrolidin-1-ylethyl)pyridin-2-amine 55-A To a 4 mL screw-cap vial was added 4-bromo-2-fluoro-pyridine (100 mg, 0.57 mmol), 2-pyrrolidin-1-ylethanamine (1.1 equiv., 0.63 mmol, 71 mg), and dimethylformamide (0.25 mL). The reaction was capped and shaken at 100° C. for 3 h. TLC showed new spot, with no starting material present. The reaction was concentrated, and 4-bromo-N-(2-pyrrolidin-1-ylethyl)pyridin-2-amine was carried directly on to the Suzuki cross-coupling step.

Step 2: 6-(4,4,5,5-tetramethyl-1,3,2-dioxaborolan-2-yl)quinazolin-4-amine 55-B

To a 40 mL screw-cap vial was added 6-bromoquinazolin-4-amine (1000 mg, 4.5 mmol), bis(pinacolato)diborane (2 equiv., 8.9 mmol, 2390 mg), Bis(di-tert-butyl(4-dimethylaminophenyl)phosphine)dichloropalladium(II) (0.05 equiv., 0.22 mmol, 158 mg), potassium acetate (3 equiv., 13.4 mmol, 2.00 mol/L, 6.69 mL), and dimethylformamide (12 mL, 153 mmol, 11300 mg). The reaction was capped and shaken at 90° C. overnight. The reaction was cooled to room temperature, then partitioned with ethyl acetate:water. Solids were filtered off (palladium+by-product). Phases were separated. Organic was dried over sodium sulfate, filtered, and concentrated, yielding 6-(4,4,5,5-tetramethyl-1,3,2-dioxaborolan-2-yl)quinazolin-4-amine. The boronic ester was carried directly to the cross coupling step due to potential instability.

Step 3: 6-(2-(2-(pyrrolidin-1-yl)ethylamino)pyridin-4-yl)quinazolin-4-amine 55

To an 8 mL screw-cap vial was added 6-(4,4,5,5-tetramethyl-1,3,2-dioxaborolan-2-yl)quinazolin-4-amine (26 mg;

0.096 mmol, 26 mg) followed by 4-bromo-N-(2-pyrrolidin-1-ylethyl)pyridin-2-amine (2 equiv., 0.19 mmol, 52 mg, Bis(di-tert-butyl(4-dimethylaminophenyl)phosphine)dichloropalladium(II) (0.05 equiv., 0.005 mmol, 4 mg, dioxane (0.4 mL), and potassium phosphate tribasic (2M in water, 4 equiv., 0.38 mmol, 0.19 mL). The reaction was capped and shaken for 1 h at 100° C. The reaction was then cooled to room temperature, then extracted. The aqueous was further extracted with dichloromethane, and combined with the dioxane extract and concentrated. The crude was purified by reverse phase HPLC, yielding 5 mg of desired product. $^1$H NMR (400 MHz, DMSO) δ 8.62-8.56 (s, 1H), 8.42-8.38 (s, 1H), 8.32-8.16 (m, 2H), 8.11-8.02 (m, 2H), 7.77-7.72 (d, J=8.7 Hz, 1H), 6.98-6.92 (d, J=5.4 Hz, 1H), 6.90-6.84 (s, 1H), 6.53-6.44 (t, J=5.4 Hz, 1H), 3.49-3.40 (t, J=6.7 Hz, 2H), 2.73-2.65 (t, J=6.7 Hz, 2H), 2.64-2.55 (m, 4H), 1.80-1.63 (m, 4H). LCMS M/Z (M+H)=335.

Examples 57

6-(3-(2-(pyrrolidin-1-yl)ethoxy)phenyl)pyrido[3,2-d]pyrimidin-4-amine

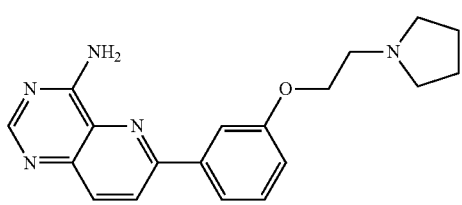 [SMILES: Nc1ncnc2ccc(-c3cccc(OCCN4CCCC4)c3)nc12]

To a 4 mL screw-cap vial was added 3-(4-aminopyrido[3,2-d]pyrimidin-6-yl)phenol (100 mg; 0.32 mmol) followed by 1-(2-chloroethyl)pyrrolidine hydrochloride (CAS 7050-67-1) (1.1 equiv., 0.35 mmol, 59 mg) cesium carbonate (5 equiv., 1.57 mmol, 513 mg) and dimethylformamide (0.6 mL). The reaction was capped at shaken at 80° C. overnight. The reaction was cooled to room temperature, diluted with dichloromethane, and washed with water. Organic phase was concentrated, then purified by reverse phase HPLC yielding 16 mg of desired product. $^1$H NMR (400 MHz, DMSO) δ 8.48-8.39 (m, 2H), 8.15-8.08 (m, 2H), 8.00-7.89 (m, 3H), 7.47-7.40 (t, J=7.9 Hz, 1H), 7.12-7.03 (dd, J=8.1, 2.3 Hz, 1H), 4.27-4.18 (t, J=5.9 Hz, 2H), 2.90-2.81 (t, J=5.9 Hz, 2H), 2.59-2.53 (m, 4H), 1.76-1.66 (m, 4H). LCMS M/Z (M+H)=336.

Examples 58

1-(3-(4-aminoquinazolin-6-yl)phenyl)-3-cyclopentylurea

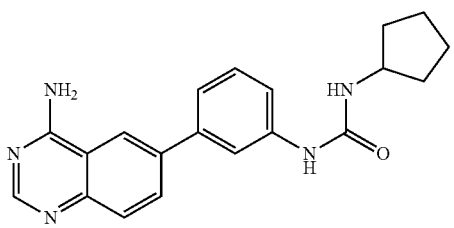

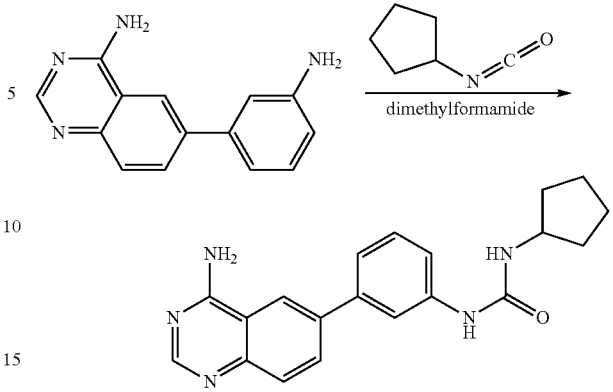

To a 4 mL screw-cap vial was added 6-(3-aminophenyl)quinazolin-4-amine (35 mg; 0.15 mmol) followed by dimethylformamide (0.5 mL) and isocyanatocyclopentane (1.1 equiv., 0.16 mmol, 18 mg). The reaction was stirred at room temperature overnight. The following morning the crude reaction mix was directly purified by reverse phase HPLC, yielding 19 mg of desired product. $^1$H NMR (400 MHz, DMSO) δ 8.51-8.45 (d, J=1.8 Hz, 1H), 8.45-8.40 (s, 1H), 8.40-8.37 (s, 1H), 8.03-7.95 (dd, J=8.7, 1.9 Hz, 1H), 7.95-7.76 (s, 2H), 7.76-7.70 (d, J=8.7 Hz, 1H), 7.43-7.28 (m, 3H), 6.33-6.20 (d, J=7.2 Hz, 1H), 4.04-3.90 (dd, J=13.4, 6.7 Hz, 1H), 1.93-1.80 (m, 2H), 1.74-1.46 (m, 4H), 1.46-1.32 (m, 2H). LCMS M/Z (M+H)=348.

Example 59

6-(3-fluorophenyl)-N-isobutylpyrido[3,2-d]pyrimidin-4-amine

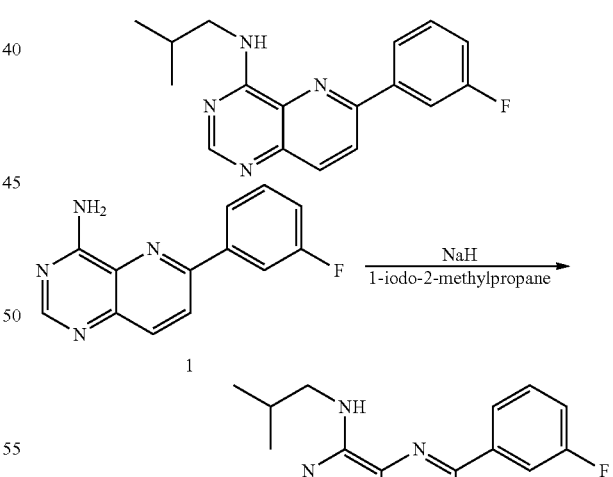

The amine 1 (50 mg, 0.21 mmol) was treated with sodium hydride 60% dispersion in mineral oil (13 mg, 0.31 mmol) and iodoethane (57 mg, 0.31 mmol) to provide 6-(3-fluorophenyl)-N-isobutylpyrido[3,2-d]pyrimidin-4-amine.
LC/MS (ESI+): m/z 297 (M+H). 1H NMR (400 MHz, DMSO) δ 8.73 (t, J=6.1 Hz, 1H), 8.47 (d, J=7.0 Hz, 2H), 8.40 (d, J=10.9 Hz, 1H), 8.22 (d, J=7.8 Hz, 1H), 8.15 (d, J=8.8 Hz, 1H), 7.59 (dd, J=14.3, 7.9 Hz, 1H), 7.34 (td, J=8.5, 2.4 Hz, 1H), 3.45 (t, J=6.7 Hz, 2H), 2.12 (dp, J=13.5, 6.8 Hz, 1H), 0.96 (d, J=6.7 Hz, 6H).

Example 60

1-[4-(4-aminopyrido[3,2-d]pyrimidin-6-yl)piperazin-1-yl]ethanone

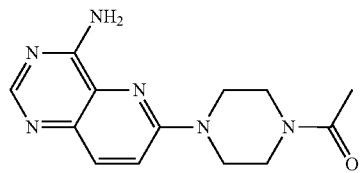 [SMILES: CC(=O)N1CCN(c2ccc3ncnc(N)c3n2)CC1]

To 1-[4-(4-aminopyrido[3,2-d]pyrimidin-6-yl)piperazin-1-yl]ethanone (1.5 equiv., 0.3 mmol, 38 mg) in an 8 mL screw-cap vial was added 6-chloropyrido[3,2-d]pyrimidin-4-amine (0.2 mmol, 36 mg), DMA; 0.25 mL, and triethylamine (3 equiv., 0.6 mmol, 0.084 mL).

The reaction was capped and shaken overnight at 100° C. The following morning the reaction was cooled to room temperature, and partitioned with water and dichloromethane. The organic was concentrated via GeneVac, then purified by reverse phase HPLC, yielding 6 mg of desired product. 1H NMR (400 MHz, DMSO) δ 8.22-8.15 (s, 1H), 7.85-7.78 (d, J=9.3 Hz, 1H), 7.51-7.45 (d, J=9.3 Hz, 1H), 7.45-7.26 (bs, 2H), 3.82-3.74 (m, 2H), 3.74-3.67 (m, 2H), 3.63-3.49 (m, 4H), 2.09-2.01 (s, 3H). LCMS M/Z (M+H) 273.

Example 61

6-[3-(4-methyl-1H-pyrazol-3-yl)-1-piperidyl]pyrido[3,2-d]pyrimidin-4-amine

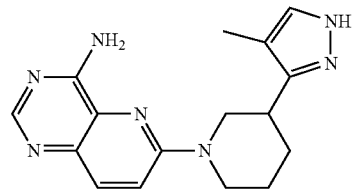 [SMILES: Cc1c[nH]nc1C1CCCN(c2ccc3ncnc(N)c3n2)C1]

The racemic 6-[3-(4-methyl-1H-pyrazol-3-yl)-1-piperidyl]pyrido[3,2-d]pyrimidin-4-amine was synthesized as exemplified in Example 42, on 75 mg scale. The product was purified by chiral HPLC, yielding 35 mg of peak 1 ($^1$H NMR (400 MHz, DMSO) δ 12.49-12.14 (m, 1H), 8.22-8.10 (s, 1H), 7.84-7.71 (d, J=9.3 Hz, 1H), 7.56-7.47 (d, J=9.4 Hz, 1H), 7.43-7.16 (bs, 2H), 4.75-4.51 (m, 2H), 3.08-2.88 (m, 2H), 2.88-2.68 (s, 1H), 1.97-1.73 (m, 3H), 1.67-1.50 (m, 1H). LCMS M/Z (M+H) 310, and 33 mg of peak 2, ($^1$H NMR (400 MHz, DMSO) δ 12.49-12.14 (m, 1H), 8.22-8.10 (s, 1H), 7.84-7.71 (d, J=9.3 Hz, 1H), 7.56-7.47 (d, J=9.4 Hz, 1H), 7.43-7.16 (bs, 2H), 4.75-4.51 (m, 2H), 3.08-2.88 (m, 2H), 2.88-2.68 (s, 1H), 1.97-1.73 (m, 3H), 1.67-1.50 (m, 1H). LCMS M/Z (M+H) 310

Examples 62 and 63

6-(3-(1,4-dimethyl-1H-pyrazol-3-yl)piperidin-1-yl)pyrido[3,2-d]pyrimidin-4-amine

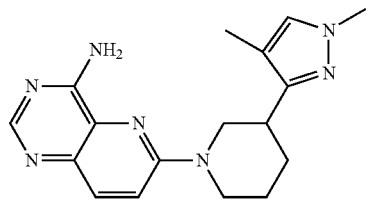 [SMILES: Cc1cn(C)nc1C1CCCN(c2ccc3ncnc(N)c3n2)C1]

6-(3-(1,4-dimethyl-1H-pyrazol-5-yl)piperidin-1-yl)pyrido[3,2-d]pyrimidin-4-amine

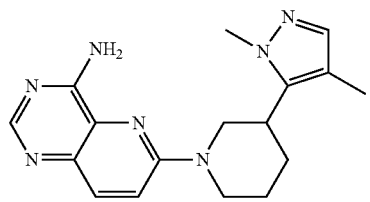 [SMILES: Cc1cnn(C)c1C1CCCN(c2ccc3ncnc(N)c3n2)C1]

To an 8 mL screw-cap vial was added +/−6-[3-(4-methyl-1H-pyrazol-3-yl)-1-piperidyl]pyrido[3,2-d]pyrimidin-4-amine (172 mg; 0.56 mmol) and DMF (2 mL). Sodium hydride (60% in oil; 1.3 equiv.; 0.73 mmol; 60 mass %; 29 mg) was then slowly added. The reaction was then loosely capped and shaken for 15 minutes. Iodomethane; (1.1 equiv., 0.61 mmol, 86.80 mg) was then added. The reaction was capped and shaken at room temperature overnight. The following morning the reactions were diluted with DCM and washed with water. Aqueous was extracted 2× with DCM, then organics were combined, dried over sodium sulfate, filtered, and concentrated. The crude product was purified by reverse phase HPLC. Mixture of diastereomers were then separated by SCF chiral chromatography. All 4 diastereomers were isolated. 6-(3-(1,4-dimethyl-1H-pyrazol-3-yl)piperidin-1-yl)pyrido[3,2-d]pyrimidin-4-amine, peak 1, 9 mg, $^1$H NMR (400 MHz, DMSO) δ 8.18-8.14 (s, 1H), 7.79-7.73 (d, J=9.3 Hz, 1H), 7.52-7.43 (d, J=9.4 Hz, 1H), 7.39-7.33 (s, 1H), 4.74-4.64 (d, J=12.9 Hz, 1H), 4.64-4.51 (d, J=12.6 Hz, 1H), 3.76-3.70 (s, 3H), 3.07-2.86 (m, 2H), 2.79-2.66 (m, 1H), 2.02-1.98 (s, 3H), 1.98-1.90 (d, J=10.1 Hz, 1H), 1.86-1.73 (m, 2H), 1.64-1.52 (m, 1H). LCMS M/Z (M+H)=324.

6-(3-(1,4-dimethyl-1H-pyrazol-3-yl)piperidin-1-yl)pyrido[3,2-d]pyrimidin-4-amine, peak 2, 10 mg, $^1$H NMR (400 MHz, DMSO) δ 8.18-8.14 (s, 1H), 7.79-7.73 (d, J=9.3 Hz, 1H), 7.52-7.43 (d, J=9.4 Hz, 1H), 7.39-7.33 (s, 1H), 4.74-4.64 (d, J=12.9 Hz, 1H), 4.64-4.51 (d, J=12.6 Hz, 1H), 3.76-3.70 (s, 3H), 3.07-2.86 (m, 2H), 2.79-2.66 (m, 1H), 2.02-1.98 (s, 3H), 1.98-1.90 (d, J=10.1 Hz, 1H), 1.86-1.73 (m, 2H), 1.64-1.52 (m, 1H). LCMS M/Z (M+H)=324.

6-(3-(1,4-dimethyl-1H-pyrazol-5-yl)piperidin-1-yl)pyrido[3,2-d]pyrimidin-4-amine, peak 1, 4 mg, $^1$H NMR (400 MHz, DMSO) δ 8.17-8.14 (s, 1H), 7.81-7.74 (d, J=9.3 Hz, 1H), 7.57-7.51 (d, J=9.4 Hz, 1H), 7.44-7.27 (bs, 2H), 7.14-7.10 (s, 1H), 4.79-4.68 (d, J=12.4 Hz, 1H), 4.64-4.55

(d, J=12.9 Hz, 1H), 3.79-3.75 (s, 3H), 3.19-3.07 (t, J=12.3 Hz, 1H), 3.07-2.88 (m, 2H), 2.14-2.10 (s, 3H), 2.10-1.95 (m, 1H), 1.95-1.86 (m, 1H), 1.86-1.75 (m, 1H), 1.65-1.48 (m, 1H). LCMS M/Z (M+H)=324.

Example 219

6-(3-(1,4-dimethyl-1H-pyrazol-5-yl)piperidin-1-yl)pyrido[3,2-d]pyrimidin-4-amine, peak 2, 4 mg, ¹H NMR (400 MHz, DMSO) δ 8.17-8.14 (s, 1H), 7.81-7.74 (d, J=9.3 Hz, 1H), 7.57-7.51 (d, J=9.4 Hz, 1H), 7.44-7.27 (bs, 2H), 7.14-7.10 (s, 1H), 4.79-4.68 (d, J=12.4 Hz, 1H), 4.64-4.55 (d, J=12.9 Hz, 1H), 3.79-3.75 (s, 3H), 3.19-3.07 (t, J=12.3 Hz, 1H), 3.07-2.88 (m, 2H), 2.14-2.10 (s, 3H), 2.10-1.95 (m, 1H), 1.95-1.86 (m, 1H), 1.86-1.75 (m, 1H), 1.65-1.48 (m, 1H). LCMS M/Z (M+H)=324.

Compounds of examples 64 to 368 below have been prepared according to the General Methods described herein, or methods known in the art.

| Ex. No. | General Method | Structure/Name | IUPAC name | Isolated Yield | LCMS $R_T$ (min), M + H⁺, method | ¹H NMR (ppm) |
|---|---|---|---|---|---|---|
| 64 | E | | 1-(4-(3-(4-aminopyrido[3,2-d]pyrimidin-6-yl)-5-fluorobenzyl)-1,4-diazepan-1-yl)ethanone | 35% | 0.830 395.0 0-60AB | ¹H NMR (400 MHz, Methanol-d₄) δ 8.41 (s, 1H), 8.36 (d, J = 8.0 Hz, 1H), 8.12 (d, J = 8.0 Hz, 1H), 8.07 (d, J = 8.0 Hz, 1H), 7.98 (d, J = 8.0 Hz, 1H), 7.27-7.24 (m, 1H), 3.79 (d, J = 8.0 Hz, 2H), 3.68-3.62 (m, 4H), 2.83-2.81 (m, 1H), 2.78-2.70 (m, 3H), 2.13 (d, J = 8.0 Hz, 3H), 1.97-1.89 (m, 2H). |
| 65 | E | | 1-(4-(3-(4-aminopyrido[3,2-d]pyrimidin-6-yl)-5-fluorobenzyl)piperazin-1-yl)ethanone | 43% | 0.829 381.1 0-60AB | / |
| 66 | E | | 1-(3-(4-aminopyrido[3,2-d]pyrimidin-6-yl)-5-fluorobenzyl)piperidin-4-ol | 23% | 0.826 354.0 0-60AB | ¹H NMR (400 MHz, DMSO-d₆) δ 8.46-8.42 (t, J = 8.0 Hz, 2H), 8.27-8.25 (m, 2H), 8.14 (d, J = 8.0 Hz, 2H), 8.10 (s, 1H), 8.0 (s, 1H), 7.22 (d, J = 8.0 Hz, 1H), 4.54 (m, 1H), 3.59 (s, 1H), 3.50 (m, 1H), 2.73-2.70 (m, 2H), 2.11 (m, 2H), 1.71 (m, 2H), 1.44-1.42 (m, 2H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 67 | E | | 6-(3-fluoro-5-((methyl(1-methylpiperidin-4-yl)amino)methyl)phenyl)pyrido[3,2-d]pyrimidin-4-amine | 16% | 0.767 381.1 0-60AB | / |
| 68 | E | | (1-(3-(4-amino-pyrido[3,2-d]pyrimidin-6-yl)-5-fluoro-benzyl)piperidin-4-yl)methanol | 33% | 0.842 368.1 0-60AB | $^1$H NMR (400 MHz, DMSO-d$_6$) δ 8.45 (d, J = 8.0 Hz, 1H), 8.42 (s, 1H), 8.27 (s, 1H), 8.25 (s, 1H), 8.14 (d, J = 8.0 Hz, 1H), 8.10 (s, 1H), 8.0 (s, 1H), 7.24 (d, J = 8.0 Hz, 1H), 4.4 (m, 1H), 3.58 (s, 2H), 3.25 (d, J = 8.0 Hz, 2H), 2.85 (d, J = 8.0 Hz, 2H), 1.96 (t, J = 8.0 Hz, 2H), 1.64 (d, J = 8.0 Hz, 2H), 1.4-1.3 (m, 1H), 1.18-1.15 (m, 2H). |
| 69 | E | | 2-(4-(3-(4-aminopyrido[3,2-d]pyrimidin-6-yl)-5-fluoro-benzyl)piperazin-1-yl)ethanol | 44% | 0.864 383.0 0-60AB | / |
| 70 | E | | 6-(3-fluoro-5-((4-(2-methoxy-ethyl)piperazin-1-yl)methyl)phenyl)pyrido[3,2-d]pyrimidin-4-amine | 33% | 0.883 397.0 0-60AB | / |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 71 | E | 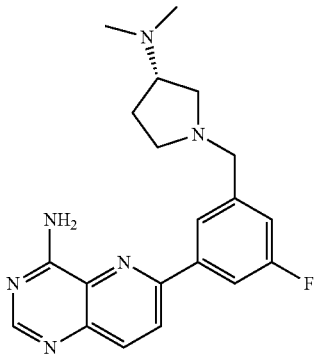 [SMILES: CN(C)[C@H]1CCN(Cc2cc(F)cc(-c3ccc4ncnc(N)c4n3)c2)C1] | (S)-6-(3-((3-(dimethylamino)pyrrolidin-1-yl)methyl)-5-fluorophenyl)pyrido[3,2-d]pyrimidin-4-amine | 28% | 0.817 367.0 0-60AB | / |
| 72 | E | 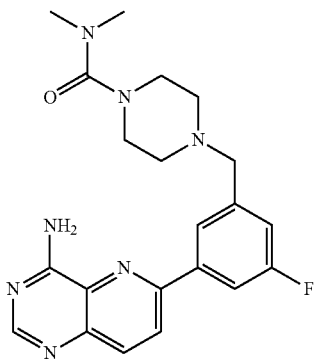 [SMILES: CN(C)C(=O)N1CCN(Cc2cc(F)cc(-c3ccc4ncnc(N)c4n3)c2)CC1] | 4-(3-(4-amino-pyrido[3,2-d]pyrimidin-6-yl)-5-fluoro-benzyl)-N,N-dimethyl-piperazine-1-carboxamide | 31% | 0.861 410.1 0-60AB | / |
| 73 | E | 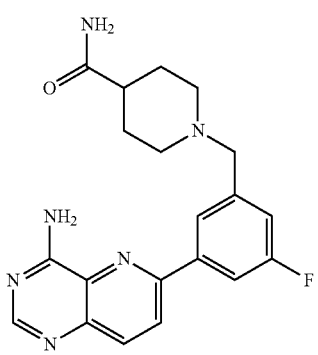 [SMILES: NC(=O)C1CCN(Cc2cc(F)cc(-c3ccc4ncnc(N)c4n3)c2)CC1] | 1-(3-(4-amino-pyrido[3,2-d]pyrimidin-6-yl)-5-fluoro-benzyl)piperidine-4-carboxamide | 57% | 0.818 381.0 0-60AB | $^1$H NMR (400 MHz, DMSO-d$_6$) δ 8.45 (d, J = 8.0 Hz, 1H), 8.42 (s, 1H), 8.30-8.25 (m, 3H), 8.14 (d, J = 8.0 Hz, 1H), 8.12 (s, 1H), 8.0 (s, 1H), 7.25 (d, J = 8.0 Hz, 1H), 7.21 (s, 1H), 6.72 (s, 1H), 3.61 (m, 2H), 2.87 (m, 2H), 2.2-1.9 (m, 3H), 1.71-1.59 (m, 4H). |
| 74 | E | 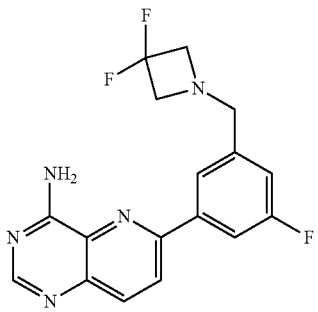 [SMILES: Nc1ncnc2ccc(-c3cc(F)cc(CN4CC(F)(F)C4)c3)nc12] | 6-(3-((3,3-difluoro-azetidin-1-yl)methyl)-5-fluorophenyl)pyrido[3,2-d]pyrimidin-4-amine | 36% | 0.887 346.0 0-60AB | $^1$H NMR (400 MHz, DMSO-d$_6$) δ 8.47 (d, J = 8.0 Hz, 1H), 8.42 (s, 1H), 8.29 (d, J = 8.0 Hz, 1H), 8.25 (s, 1H), 8.14 (d, J = 8.0 Hz, 1H), 8.01 (s, 1H), 7.26 (d, J = 8.0 Hz, 1H), 3.86 (s, 2H), 3.68 (t, J = 12 Hz, 4H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 75 | E | | 4-(3-(4-amino-pyrido[3,2-d]pyrimidin-6-yl)-5-fluoro-benzyl)-N,N-dimethyl-piperazine-1-sulfonamide | 63% | 0.896 446.1 0-60AB | / |
| 76 | E | | 6-(3-((1,4-oxazepan-4-yl)methyl)-5-fluorophenyl)pyrido[3,2-d]pyrimidin-4-amine | 41% | 0.839 353.9 0-60AB | / |
| 77 | E | | 2-(4-(3-(4-aminopyrido[3,2-d]pyrimidin-6-yl)-5-fluoro-benzyl)piperazin-1-yl)-N,N-dimethyl-acetamide | 55% | 0.881 424.0 0-60AB | $^1$H NMR (400 MHz, DMSO-$d_6$) δ 8.45 (d, J = 8.0 Hz, 1H), 8.42 (s, 1H), 8.29-8.25 (m, 2H), 8.15 (s, 1H), 8.12 (d, J = 8.0 Hz, 1H), 8.0 (s, 1H), 7.24 (d, J = 8.0 Hz, 1H), 3.61 (s, 2H), 3.12 (s, 2H), 3.01 (m, 3H), 2.80 (s, 3H), 2.46 (m, 8H). |
| 78 | E | | 1-(4-(3-(4-amino-pyrido[3,2-d]pyrimidin-6-yl)-5-fluoro-benzyl)piperazin-1-yl)-2-methyl-propan-1-one | 46% | 0.875 409.1 0-60AB | / |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 79 | E | 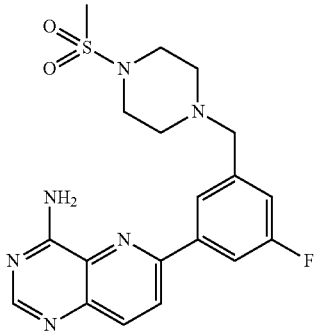 [SMILES: CS(=O)(=O)N1CCN(Cc2cc(F)cc(-c3ccc4ncnc(N)c4n3)c2)CC1] | 6-(3-fluoro-5-((4-(methyl-sulfonyl)piperazin-1-yl)methyl)phenyl)pyrido[3,2-d]pyrimidin-4-amine | 71% | 0.854 416.9 0-60AB | / |
| 80 | E | 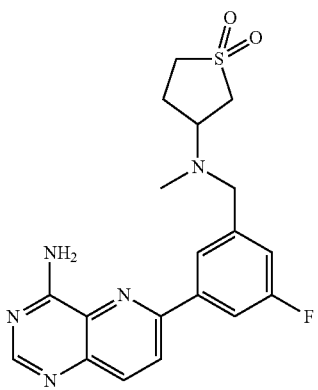 [SMILES: CN(Cc1cc(F)cc(-c2ccc3ncnc(N)c3n2)c1)C1CCS(=O)(=O)C1] | 6-(3-fluoro-5-((methyl(1,1-dioxo-tetrahydro-thiophen-3-yl)amino)methyl)phenyl)pyrido[3,2-d]pyrimidin-4-amine | 36% | 0.971 402.0 0-30AB | / |
| 81 | E | 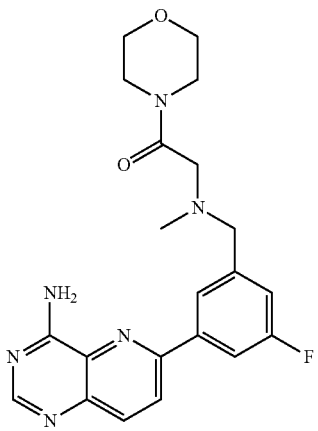 [SMILES: CN(CC(=O)N1CCOCC1)Cc1cc(F)cc(-c2ccc3ncnc(N)c3n2)c1] | 2-((3-(4-amino-pyrido[3,2-d]pyrimidin-6-yl)-5-fluoro-benzyl)(methyl)amino)-1-morpholino-ethanone | 38% | 0.863 411.1 0-60AB | $^1$H NMR (400 MHz, DMSO-d$_6$) δ 8.46-8.42 (m, 2H), 8.29 (d, J = 8.0 Hz, 1H), 8.22 (s, 1H), 8.16-8.14 (m, 2H), 8.01 (s, 1H), 7.25 (d, J = 8.0 Hz, 1H), 3.70 (s, 2H), 3.56 (m, 6H), 3.45-3.44 (m, 2H), 3.31 (m, 2H), 2.22 (s, 3H). |
| 82 | E | 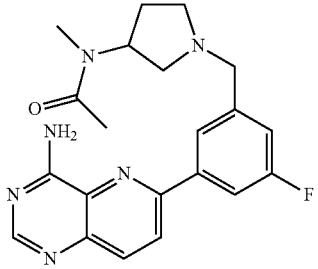 [SMILES: CC(=O)N(C)C1CCN(Cc2cc(F)cc(-c3ccc4ncnc(N)c4n3)c2)C1] | N-(1-(3-(4-amino-pyrido[3,2-d]pyrimidin-6-yl)-5-fluoro-benzyl)pyrrolidin-3-yl)-N-methylacetamide | 47% | 0.869 395.1 0-60AB | / |

| Ex. No. | General Method | Structure/Name | IUPAC name | Isolated Yield | LCMS $R_T$ (min), $M + H^+$, method | $^1$H NMR (ppm) |
|---|---|---|---|---|---|---|
| 83 | E | | (1-(3-(4-amino-pyrido[3,2-d]pyrimidin-6-yl)-5-fluoro-benzyl)azetidin-3-yl)(4-methyl piperazin-1-yl)methanone | 35% | 0.783 436.1 0-60AB | / |
| 84 | E | | 6-(3-((4-(dimethyl-amino)piperidin-1-yl)methyl)-5-fluorophenyl)pyrido[3,2-d]pyrimidin-4-amine | 23% | 0.781 381.0 0-60AB | / |
| 85 | E | | 6-(3-fluoro-5-((4-methoxy-piperidin-1-yl)methyl)phenyl)pyrido[3,2-d]pyrimidin-4-amine | 30% | 0.880 368.1 0-60AB | / |
| 86 | E | | 6-(3-fluoro-5-(pyrrolidin-1-ylmethyl)phenyl)pyrido[3,2-d]pyrimidin-4-amine | 8% | 0.844 323.9 0-60AB | / |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 87 | E | | 6-(3-fluoro-5-((2-methyl-pyrrolidin-1-yl)methyl)phenyl)pyrido[3,2-d]pyrimidin-4-amine | 2% | 0.882 337.9 0-60AB | / |
| 88 | E | | 6-(3-fluoro-5-((methyl(1-methylpyrrolidin-3-yl)amino)methyl)phenyl)pyrido[3,2-d]pyrimidin-4-amine | 7% | 0.823 367.1 0-60AB | / |
| 89 | E | | 2-((3-(4-amino-pyrido[3,2-d]pyrimidin-6-yl)-5-fluoro-benzyl)(methyl)amino)-N,N-dimethyl-acetamide | 37% | 0.859 369.1 0-60AB | / |
| 90 | E | | 6-(3-fluoro-5-(((2-methoxy-ethyl)(methyl)amino)methyl)phenyl)pyrido[3,2-d]pyrimidin-4-amine | 31% | 0.862 342.0 0-60AB | / |

| Ex. No. | General Method | Structure/Name | IUPAC name | Isolated Yield | LCMS $R_T$ (min), M + H+, method | 1H NMR (ppm) |
|---|---|---|---|---|---|---|
| 91 | E | | 4-(3-(4-amino-pyrido[3,2-d]pyrimidin-6-yl)-5-fluoro-benzyl)-N,1-dimethyl-piperazine-2-carboxamide | 36% | 0.895 410.0 0-60AB | / |
| 92 | E | | 1-(3-(4-amino-pyrido[3,2-d]pyrimidin-6-yl)-5-fluoro-benzyl) azetidine-3-carboxamide | 25% | 0.803 352.9 0-60AB | / |
| 93 | E | | 1-(3-(4-amino-pyrido[3,2-d] pyrimidin-6-yl)-5-fluorobenzyl)-N-methylpyrrolidine-3-carboxamide | 16% | 0.849 381.1 0-60AB | / |
| 94 | E | | 1-(3-(4-amino-pyrido[3,2-d]pyrimidin-6-yl)-5-fluoro-benzyl)-N,N-dimethyl-azetidine-3-carboxamide | 29% | 0.854 381.0 0-60AB | / |
| 95 | E | | 4-(3-(4-amino-pyrido[3,2-d]pyrimidin-6-yl)-5-fluoro-benzyl)-1-methyl-piperazine-2-carboxamide | 8% | 0.876 418.0 0-60AB | / |

| Ex. No. | General Method | Structure/Name | IUPAC name | Isolated Yield | LCMS $R_T$ (min), M + H+, method | $^1$H NMR (ppm) |
|---|---|---|---|---|---|---|
| 96 | E | 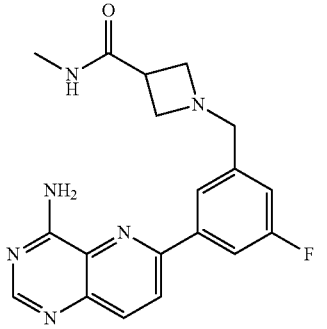 [SMILES: CNC(=O)C1CN(Cc2cc(F)cc(-c3ccc4ncnc(N)c4n3)c2)C1] | 1-(3-(4-amino-pyrido[3,2-d]pyrimidin-6-yl)-5-fluoro-benzyl)-N-methylazetidine-3-carboxamide | 22% | 0.837 366.9 0-60AB | / |
| 97 | E | 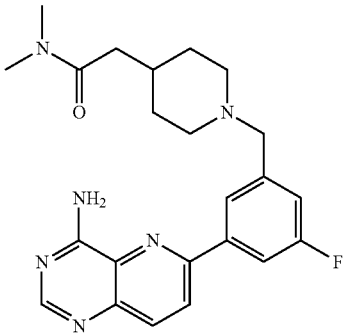 [SMILES: CN(C)C(=O)CC1CCN(Cc2cc(F)cc(-c3ccc4ncnc(N)c4n3)c2)CC1] | 2-(1-(3-(4-aminopyrido[3,2-d]pyrimidin-6-yl)-5-fluoro-benzyl)piperidin-4-yl)-N,N-dimethyl-acetamide | 17% | 0.887 445.1 0-60AB | / |
| 98 | E | 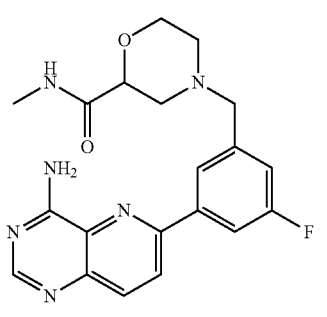 [SMILES: CNC(=O)C1CN(Cc2cc(F)cc(-c3ccc4ncnc(N)c4n3)c2)CCO1] | 4-(3-(4-amino-pyrido[3,2-d]pyrimidin-6-yl)-5-fluoro-benzyl)-N-methyl-morpholine-2-carboxamide | 45% | 0.836 397.1 0-60AB | / |
| 99 | E | 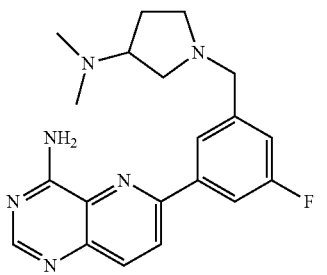 [SMILES: CN(C)C1CCN(Cc2cc(F)cc(-c3ccc4ncnc(N)c4n3)c2)C1] | 6-(3-((3-(dimethyl-amino)pyrrolidin-1-yl)methyl)-5-fluorophenyl)pyrido[3,2-d]pyrimidin-4-amine | 25% | 0.799 367.1 0-60AB | / |

| Ex. No. | General Method | Structure/Name | IUPAC name | Isolated Yield | LCMS $R_T$ (min), M + H+, method | $^1$H NMR (ppm) |
|---|---|---|---|---|---|---|
| 100 | E | | (1-(3-(4-amino-pyrido[3,2-d]pyrimidin-6-yl)-5-fluoro-benzyl)piperidin-3-yl)methanol | 24% | 0.848 368.0 0-60AB | / |
| 101 | E | | 6-(3-fluoro-5-((3-morpholino-pyrrolidin-1-yl)methyl)phenyl)pyrido[3,2-d]pyrimidin-4-amine | 29% | 0.830 409.2 0-60AB | $^1$H NMR (400 MHz, Methanol-$d_4$) δ 8.77-8.76 (m, 3H), 8.33 (d, J = 8.0 Hz, 2H), 7.63 (d, J = 8.0 Hz, 1H), 4.76 (s, 2H), 4.4-4.3 (m, 1H), 4.15-3.9 (m, 6H), 3.9-3.4 (m, 6H), 2.8-2.6 (m, 2H). |
| 102 | E | | 6-(3-fluoro-5-((4-methyl-piperazin-1-yl)methyl)phenyl)pyrido[3,2-d]pyrimidin-4-amine | 23% | 0.867 353.1 0-60AB | / |
| 103 | E | | 1-(3-(4-amino-pyrido[3,2-d]pyrimidin-6-yl)-5-fluoro-benzyl)piperidin-3-ol | 44% | 0.831 353.9 0-60AB | / |
| 104 | E | | (R)-1-(3-(4-aminopyrido[3,2-d]pyrimidin-6-yl)-5-fluoro-benzyl)piperidin-3-ol | 45% | 0.824 354.1 0-60AB | / |

| Ex. No. | General Method | Structure/Name | IUPAC name | Isolated Yield | LCMS $R_T$ (min), M + H+, method | $^1$H NMR (ppm) |
|---|---|---|---|---|---|---|
| 105 | E | 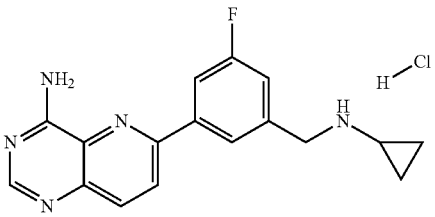 | 6-(3-((cyclo-propylamino)methyl)-5-fluoro-phenyl)pyrido[3,2-d]pyrimidin-4-amine | 18% | 0.870 310.1 0-60AB | $^1$H NMR (400 MHz, DMSO-$d_6$) δ 8.19 (d, J = 15.2 Hz, 1H), 8.12 (s, 1H), 7.96-7.84 (m, 6H), 7.72 (s, 1H), 7.00 (d, J = 9.6 Hz, 1H), 3.57 (3, 2H), 1.82-1.77 (m, 1H), 0.11-0.014 (m, 4H). |
| 106 | E | 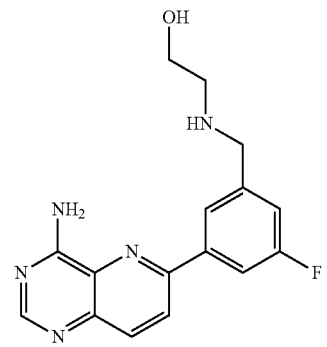 [SMILES: Nc1ncnc2ccc(-c3cc(F)cc(CNCCO)c3)nc12] | 2-(3-(4-amino-pyrido[3,2-d]pyrimidin-6-yl)-5-fluoro-benzyl-amino)ethanol | 6.6% | 0.836 313.9 0-60AB | $^1$H NMR (400 MHz, DMSO-$d_6$) δ 9.89 (s, 1H), 9.52 (s, 2H), 8.83 (s, 1H), 8.73-8.70 (m, 2H), 8.51 (d, J = 10.0 Hz, 1H), 8.37 (d, J = 9.2 Hz, 1H), 7.61 (d, J = 9.2 Hz, 1H), 4.31 (s, 1H), 3.74 (t, J = 5.2 Hz, 2H), 3.03 (s, 2H). |
| 107 | E | 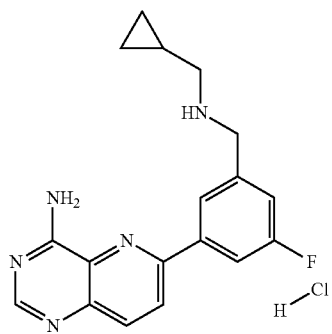 | 6-(3-((cyclo-propylmethyl-amino)methyl)-5-fluorophenyl)pyrido[3,2-d]pyrimidin-4-amine hydrochloride | 11% | 0.898 323.9 0-60AB | $^1$H NMR (400 MHz, DMSO-$d_6$) δ 10.19 (s, 1H), 10.13 (s, 1H), 9.89 (s, 2H), 8.91 (s, 1H), 8.97 (s, 1H), 8.79 (d, J = 9.2 Hz, 1H), 8.45 (t, J = 9.2 Hz, 2H), 7.64 (d, J = 8.8 Hz, 1H), 4.29 (d, J = 5.6 Hz, 2H), 2.86 (d, J = 5.2 Hz, 2H), 1.22-1.18 (m, 1H), 0.59 (dd, J = 12.8 6.4 Hz 2H), 0.42 (dd, J = 10.0, 4.8 Hz 2H). |
| 108 | E | 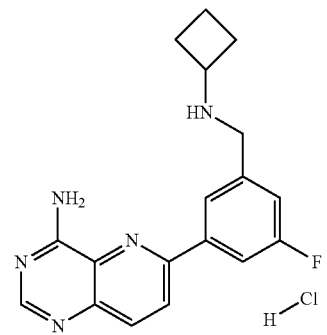 | 6-(3-((cyclo-butylamino)methyl)-5-fluoro-phenyl)pyrido[3,2-d]pyrimidin-4-amine hydrochloride | 12.7% | 0.896 324.2 0-60AB | $^1$H NMR (400 MHz, DMSO-$d_6$) δ 10.04-9.99 (m, 4H), 8.83 (d, J = 8.8 Hz, 2H), 8.76 (d, J = 8.8 Hz, 1H), 8.47 (d, J = 8.8 Hz, 1H), 8.39 (d, J = 8.8 Hz, 1H), 7.62 (d, J = 9.2 Hz, 1H), 4.16 (t, J = 6.0 Hz, 2H), 3.72 (t, J = 7.2 Hz, 1H), 2.347-2.270 (m, 2H), 2.190-2.128 (m, 2H), 1.83-1.73 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 109 | E | | 6-(3-fluoro-5-((oxetan-3-ylamino)methyl)phenyl)pyrido[3,2-d]pyrimidin-4-amine hydrochloride | 5.5% | 0.845 326.0 0-60AB | $^1$H NMR (400 MHz, Methanol-d$_4$) δ 8.74-8.69 (m, 2H), 8.50 (s, 1H), 8.38 (d, J = 10.8 Hz, 1H), 8.31 (d, J = 7.0 Hz, 1H), 7.50 (d, J = 10.0, 1H), 4.96-4.89 (m, 2H), 4.74 (t, J = 4.8 Hz, 2H), 4.59-4.58 (m, 1H), 4.36 (s, 2H), 2.66 (s, 1H). |
| 110 | E | | 6-(3-fluoro-5-((isobutylamino)methyl)phenyl)pyrido[3,2-d]pyrimidin-4-amine | 10.7% | 0.903 326.1 0-60AB | $^1$H NMR (400 MHz, DMSO-d$_6$) δ 8.47-8.42 (m, 2H), 8.28-8.23 (m, 3H), 8.15 (d, J = 8.8 Hz, 1H), 8.06-8.02 (m, 1H), 7.33 (d, J = 8.0 Hz, 1H), 3.89 (s, 2H), 2.40 (d, J = 6.8 Hz, 2H), 1.78-1.70 (m, 1H), 0.93-0.89 (m, 6H). |
| 111 | E | | 2-(3-(4-amino-pyrido[3,2-d]pyrimidin-6-yl)-5-fluoro-benzylamino)propan-1-ol hydrochloride | 5.2% | 0.877 328.1 0-60AB | $^1$H NMR (400 MHz, Methanol-d$_4$) δ 8.75-8.68 (m, 2H), 8.47 (s, 1H), 8.38 -8.29 (m, 2H), 7.51 (d, J = 8.4 Hz, 1H), 4.42 (d, J = 10.4 Hz, 2H), 4.15-4.10 (m, 1H), 3.18-3.14 (m, 1H), 2.97-2.91 (m, 1H), 1.25 (d, J = 6.4 Hz, 3H). |
| 112 | E | | 6-(3-((cyclo-pentylamino)methyl)-5-fluorophenyl)pyrido[3,2-d]pyrimidin-4-amine hydrochloride | 20% | 0.926 337.9 0-60AB | $^1$H NMR (400 MHz, DMSO-d$_6$) δ 10.04 (s, 1H), 10.00 (s, 1H), 9.76 (s, 2H), 8.89 (d, J = 12.8 Hz, 2H), 8.79 (d, J = 8.8 Hz, 1H), 8.51 (d, J = 10.4 Hz, 1H), 8.41 (d, J = 8.8 Hz, 1H), 7.68 (d, J = 8.8 Hz, 1H), 4.30 (t, J = 5.6 Hz, 2H), 2.06-1.54 (m, 9H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 113 | E | | N1-(3-(4-amino-pyrido[3,2-d]pyrimidin-6-yl)-5-fluoro-benzyl)-N2,N2-dimethylethane-1,2-diamine hydrochloride | 20% | 0.804 340.9 0-60AB | $^1$H NMR (400 MHz, DMSO-d$_6$) δ 10.97 (s, 1H), 10.35 (s, 1H), 10.11 (d, J = 4.8 Hz, 2H), 8.87 (s, 1H), 8.84 (s, 1H), 8.78 (d, J = 9.2 Hz, 1H), 8.48-8.44 (m, 2H), 7.64 (d, J = 8.8 Hz, 1H), 4.37 (s, 2H), 3.59-3.49 (m, 4H), 2.86 (s, 6H). |
| 114 | E | | 6-(3-fluoro-5-((isopropylamino)methyl)phenyl)pyrido[3,2-d]pyrimidin-4-amine hydrochloride | 7% | 0.877 312.1 0-60AB | $^1$H NMR (400 MHz, DMSO-d$_6$) δ 10.03 (s, 1H), 9.94 (s, 1H), 9.63 (s, 2H), 8.899 (s, 1H), 8.82 (s, 1H), 8.76 (d, J = 8.8 Hz, 1H), 8.46 (d, J = 10.4 Hz, 1H), 8.38 (d, J = 8.8 Hz, 1H), 7.65 (d, J = 8.8 Hz, 2H), 4.27 (t, J = 5.6 Hz, 2H), 2.58 (m, 1H), 1.35 (d, J = 6.8 Hz, 6H). |
| 115 | E | | 6-(3-fluoro-5-((tetrahydro-2H-pyran-4-ylamino)methyl)phenyl)pyrido[3,2-d]pyrimidin-4-amine hydrochloride | 19% | 0.873 353.9 0-60AB | $^1$H NMR (400 MHz, DMSO-d$_6$) δ 10.07 (s, 1H), 10.02 (s, 1H), 9.89 (s, 2H), 8.93 (s, 1H), 8.85 (s, 1H), 8.74 (d, J = 7.2 Hz, 1H), 8.49 (d, J = 10.4 Hz, 1H), 8.40 (d, J = 8.8 Hz, 1H), 7.68 (d, J = 9.6 Hz, 2H), 4.31 (d, J = 5.2 Hz, 2H), 3.96 (m, 2H), 3.29 (m, 2H), 2.51 (m, 1H), 2.12 (m, 2H), 1.84-1.75 (m, 2H). |
| 116 | E | | 6-(3-fluoro-5-(((tetrahydro-furan-3-yl)methyl-amino)methyl)phenyl)pyrido[3,2-d]pyrimidin-4-amine | 9.5% | 0.880 353.9 0-60AB | $^1$H NMR (400 MHz, Methanol-d$_4$) δ 8.75-8.72 (m, 2H), 8.64 (s, 1H), 8.35-8.30 (m, 2H), 7.52 (d, J = 8.8 Hz, 1H), 4.41 (s, 1H), 3.94-3.80 (m, 2H), 3.78-3.74 (m, 1H), 3.61-3.58 (m, 1H), 3.20 (d, J = 7.6 Hz, 2H), 2.75-2.68 (m, 1H), 2.66 (s, 2H), 2.24-2.18 (m, 1H), 1.83-1.75 (m, 1H). |

| Ex. No. | General Method | Structure/Name | IUPAC name | Isolated Yield | LCMS $R_T$ (min), $M + H^+$, method | $^1$H NMR (ppm) |
|---|---|---|---|---|---|---|
| 117 | E | 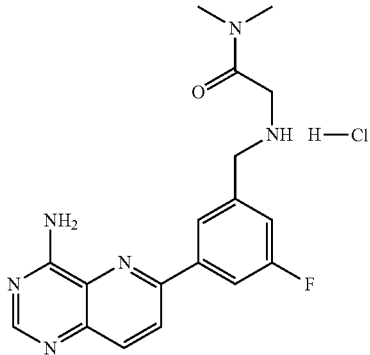 | 2-(3-(4-amino-pyrido[3,2-d]pyrimidin-6-yl)-5-fluorobenzyl-amino)-N,N-dimethylacetamide hydrochloride | 10% | 0.864 354.9 0-60AB | $^1$H NMR (400 MHz, DMSO-$d_6$) δ 10.14 (s, 2H), 9.79 (s, 2H), 8.88 (s, 1H), 8.74 (m, 2H), 8.52-8.46 (m, 2H), 7.60 (d, J = 8.0 Hz, 1H), 4.29 (m, 2H), 4.07 (m, 2H), 2.93 (s, 3H), 2.89 (s, 3H). |
| 118 | E | 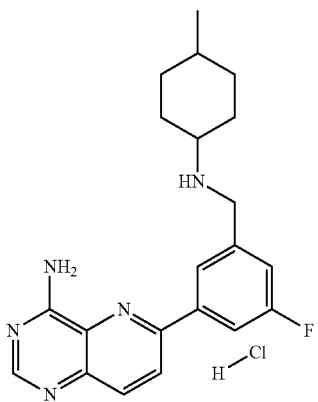 | 6-(3-fluoro-5-((4-methylcyclo-hexylamino)methyl)phenyl)pyrido[3,2-d]pyrimidin-4-amine hydrochloride | 20% | 1.050 366.0 0-60AB | $^1$H NMR (400 MHz, DMSO-$d_6$) δ 8.47 (d, J = 8.8 Hz, 1H), 8.42 (s, 1H), 8.37 (m, 1H), 8.35 (s, 1H), 8.329 (s, 1H), 8.23 (s, 2H), 8.05 (m, 1H), 7.44 (d, J = 9.2 Hz, 1H), 4.06 (s, 2H), 2.87 (m, 1H), 1.65 (m, 5H), 1.43 (m, 4H), 0.91 (d, J = 6.8 Hz, 3H). |
| 119 | E | 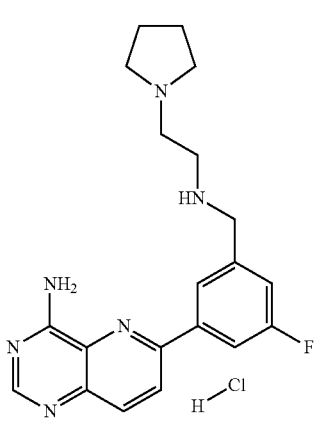 | 6-(3-fluoro-5-((2-(pyrrolidin-1-yl)ethyl amino)methyl)phenyl)pyrido[3,2-d]pyrimidin-4-amine hydrochloride | 10% | 0.821 366.9 0-60AB | $^1$H NMR (400 MHz, DMSO-$d_6$) δ 11.11 (m, 1H), 10.25 (s, 1H), 9.96 (s, 1H), 8.82 (m, 1H), 8.76 (d, J = 8.8 Hz, 2H), 8.40 (d, J = 8.8 Hz, 1H), 7.63 (d, J = 8.8 Hz, 1H), 4.38 (s, 1H), 3.63 (m, 3H), 3.45 (m, 3H), 3.07 (m, 2H), 2.00 (m, 4H). |

-continued

| Ex. No. | General Method | Structure/Name | IUPAC name | Isolated Yield | LCMS $R_T$ (min), M + H+, method | $^1$H NMR (ppm) |
|---|---|---|---|---|---|---|
| 120 | E | 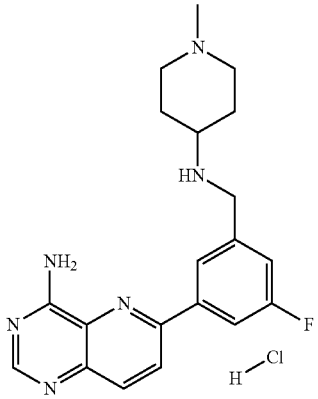 | 6-(3-fluoro-5-((1-methyl-piperidin-4-ylamino)methyl)phenyl)pyrido[3,2-d]pyrimidin-4-amine hydrochloride | 5.5% | 0.811 367.0 0-60AB | $^1$H NMR (400 MHz, Methanol-$d_4$) δ 8.76-8.73 (m, 2H), 8.36-8.29 (m, 2H), 7.54 (d, J = 8.8 Hz, 1H), 4.47 (s, 2H), 3.72-3.66 (m, 2H), 3.23-3.13 (m, 2H), 2.92 (s, 3H), 2.66 (s, 1H), 2.57 (d, J = 14.4 Hz, 2H), 2.25-2.18 (m, 2H). |
| 121 | E | 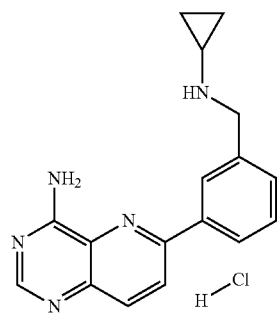 | 6-(3-((cyclo-propylamino)methyl)phenyl)pyrido[3,2-d]pyrimidin-4-amine hydrochloride | 80% | 0.854 292.2 0-60AB | $^1$H NMR (400 MHz, DMSO-$d_6$) δ 10.04 (m, 4H), 9.09 (s, 1H), 8.85 (s, 1H), 8.74 (d, J = 8.8 Hz, 1H), 8.43 (m, 2H), 7.71 (d, J = 7.2 Hz, 1H), 7.60 (m, 1H), 4.34 (s, 1H), 2.67 (s, 1H), 1.03 (m, 2H), 0.73 (m, 2H). |
| 122 | E | 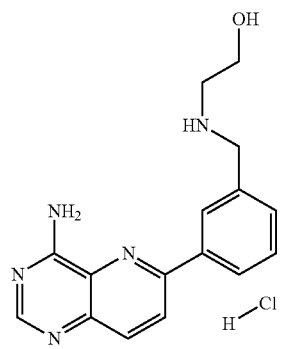 | 2-(3-(4-amino-pyrido[3,2-d]pyrimidin-6-yl)benzylamino)ethanol hydrochloride | 30% | 0.821 296.2 0-60AB | $^1$H NMR (400 MHz, DMSO-$d_6$) δ 9.99 (m, 2H), 9.61 (s, 1H), 8.99 (s, 1H), 8.85 (s, 1H), 8.73 (d, J = 8.8 Hz, 1H), 8.46 (d, J = 8.0 Hz, 1H), 8.38 (d, J = 8.8 Hz, 1H), 7.69 (d, J = 7.2 Hz, 1H), 7.62 (t, J = 8.0 Hz, 1H), 4.30 (m, 2H), 3.75 (m, 2H), 3.00 (m, 2H). |
| 123 | E | 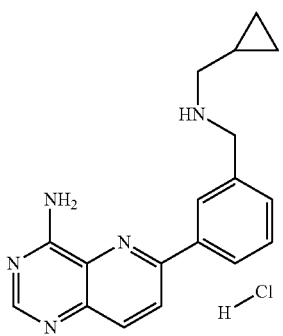 | 6-(3-((cyclo-propylmethyl-amino)methyl)phenyl)pyrido[3,2-d]pyrimidin-4-amine hydrochloride | 32% | 0.875 306.3 0-60AB | $^1$H NMR (400 MHz, DMSO-$d_6$) δ 10.00 (m, 2H), 9.76 (s, 1H), 9.10 (s, 1H), 8.84 (s, 1H), 8.74 (d, J = 9.2 Hz, 1H), 8.45 (d, J = 8.0 Hz, 1H), 8.38 (d, J = 8.8 Hz, 1H), 7.63 (m, 2H), 4.28 (m, 2H), 2.86 (m, 2H), 1.20 (m, 21H), 0.59 (m, 2H), 0.43 (m, 2H). |

-continued

| Ex. No. | General Method | Structure/Name | IUPAC name | Isolated Yield | LCMS $R_T$ (min), M + H+, method | $^1$H NMR (ppm) |
|---|---|---|---|---|---|---|
| 124 | E | 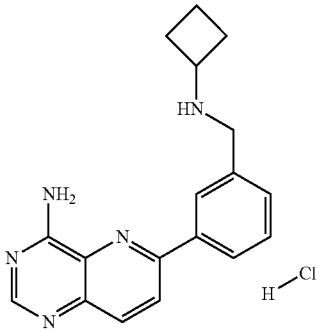 | 6-(3-((cyclobutylamino)methyl)phenyl)pyrido[3,2-d]pyrimidin-4-amine | 53% | 0.879 306.1 0-60AB | $^1$H NMR (400 MHz, DMSO-d$_6$) δ 10.00 (d, J = 9.2 Hz, 4H), 9.05 (s, 1H), 8.82 (s, 1H), 8.73 (d, J = 8.8 Hz, 1H), 8.43 (d, J = 8.0 Hz, 1H), 8.38 (d, J = 8.8 Hz, 1H), 7.66 (d, J = 7.6 Hz, 1H), 7.59 (t, J = 7.6 Hz, 1H), 4.12 (d, J = 6.0 Hz, 2H), 3.71-3.65 (m, 1H), 2.37-3.27 (m, 2H), 2.16-2.12 (m, 2H), 1.83-1.70 (m, 2H). |
| 125 | E | 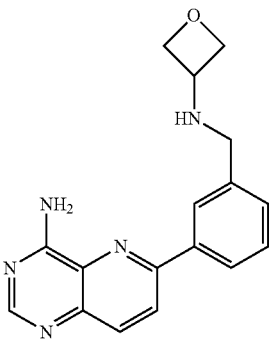 [SMILES: Nc1ncnc2ccc(-c3cccc(CNC4COC4)c3)nc12] | 6-(3-((oxetan-3-ylamino)methyl)phenyl)pyrido[3,2-d]pyrimidin-4-amine | 11% | 0.821 308.1 0-60AB | $^1$H NMR (400 MHz, DMSO-d$_6$) δ 8.44 (s, 1H), 8.42 (m, 1H), 8.41 (s, 1H), 8.27 (m, 1H), 8.13 (d, J = 8.8 Hz, 1H), 8.08 (s, 1H), 8.02 (s, 1H), 7.45 (m, 2H), 4.56 (m, 2H), 4.32 (t, J = 7.2 Hz, 2H), 3.92 s, 1H), 3.74 (s, 1H), 3.01 (m, 1H). |
| 126 | E | 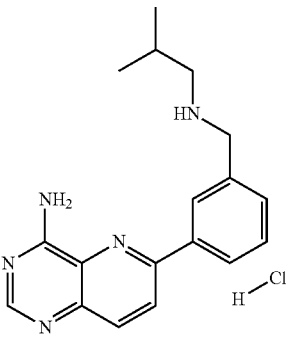 | 6-(3-((isobutylamino)methyl)phenyl)pyrido[3,2-d]pyrimidin-4-amine hydrochloride | 22% |  | $^1$H NMR (400 MHz, DMSO-d$_6$) δ 10.00 (s, 2H), 9.60 (s, 2H), 9.12 (s, 1H), 8.83 (s, 1H), 8.72 (d, J = 8.8 Hz, 1H), 8.44 (d, J = 8.0 Hz, 1H), 8.37 (d, J = 8.8 Hz, 1H), 7.69 (d, J = 7.6 Hz, 1H), 7.60 (t, J = 7.6 Hz, 1H), 4.24 (s, 2H), 2.72 (t, J = 6.0 Hz, 2H), 2.15-2.08 (m, 1H), 0.94 (d, J = 6.8 Hz, 6H). |
| 127 | E | 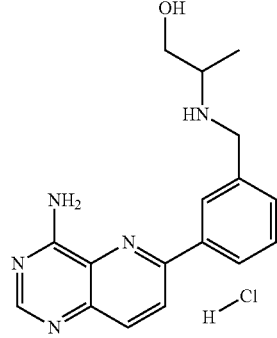 | 2-(3-(4-aminopyrido[3,2-d]pyrimidin-6-yl)benzylamino)propan-1-ol hydrochloride | 16% | 0.842 310.0 0-60AB | $^1$H NMR (400 MHz, DMSO-d$_6$) δ 10.01 (s, 1H), 9.97 (s, 1H), 9.74 (s, 1H), 9.39 (s, 1H), 9.00 (s, 1H), 8.85 (s, 1H), 8.73 (d, J = 8.8 Hz, 1H), 8.46 (d, J = 8.4 Hz, 1H), 7.69 (d, J = 8.0 Hz, 1H), 7.63 (m, 1H), 4.29 (m, 2H), 4.10 (m, 1H), 2.93 (m, 1H), 2.76 (m, 1H), 1.10 (m, 3H). |

| Ex. No. | General Method | Structure/Name | IUPAC name | Isolated Yield | LCMS $R_T$ (min), M + H+, method | 1H NMR (ppm) |
|---|---|---|---|---|---|---|
| 128 | E | | N1-(3-(4-amino-pyrido[3,2-d]pyrimidin-6-yl)benzyl)-N2,N2-dimethylethane-1,2-diamine hydrochloride | 33% | 0.796 323.0 0-60AB | 1H NMR (400 MHz, DMSO-$d_6$) δ 11.02 (s, 1H), 10.24 (s, 2H), 10.17 (s, 1H), 10.09 (s, 1H), 9.07 (s, 1H), 8.88 (s, 1H), 8.77 (d, J = 9.2 Hz, 1H), 8.45 (m, 2H), 7.71 (d, J = 7.6 Hz, 1H), 7.63 (m, 1H), 4.35 (s, 2H), 3.59 (m, 2H), 3.50 (m, 2H), 2.85 (m, 6H). |
| 129 | E | | 6-(3-((isopropyl-amino)methyl)phenyl)pyrido[3,2-d]pyrimidin-4-amine hydrochloride | 12% | 0.871 294.3 0-60AB | 1H NMR (400 MHz, DMSO-$d_6$) δ 10.13 (s, 1H), 10.07 (s, 1H), 9.71 (s, 2H), 9.20 (s, 1H), 8.85 (s, 1H), 8.77 (d, J = 8.8 Hz, 1H), 8.43 (m, 2H), 7.72 (d, J = 7.6 Hz, 1H), 7.61 (m, 1H), 4.26 (m, 2H), 3.31 (m, 1H), 1.38 (s, 3H), 1.37 (s, 3H). |
| 130 | E | | 6-(3-((tetrahydro-2H-pyran-4-ylamino)methyl)phenyl)pyrido[3,2-d]pyrimidin-4-amine hydrochloride | 26% | 0.858 335.9 0-60AB | 1H NMR (400 MHz, DMSO-$d_6$) δ 10.11 (s, 1H), 10.08 (s, 1H), 9.94 (s, 2H), 9.20 (s, 1H), 8.85 (s, 1H), 8.76 (d, J = 8.8 Hz, 1H), 8.42 (m, 2H), 7.71 (d J = 7.6 Hz, 1H), 7.60 (m, 1H), 4.29 (m, 2H), 3.93 (m, 2H), 3.30 (m, 3H), 2.12 (m, 2H), 1.84 (m, 2H). |
| 131 | E | | 6-(3-(((tetrahydro-furan-3-yl)methyl-amino)methyl)phenyl)pyrido[3,2-d]pyrimidin-4-amine hydrochloride | 91% | 0.846 336.0 0-60AB | 1H NMR (400 MHz, DMSO-$d_6$) δ 10.09 (m, 2H), 9.86 (m, 2H), 9.17 (s, 1H), 8.86 (s, 1H), 8.76 (d, J = 9.2 Hz, 1H), 8.45 (m, 2H), 7.70 (d, J = 7.6 Hz, 1H), 7.61 (t, J = 7.6 Hz, 1H), 4.28 (m, 2H), 3.76 (m, 2H), 3.62 (m, 1H), 2.95 (m, 2H), 2.74 (m, 1H), 2.05 (m, 1H), 1.68 (m, 1H). |

| Ex. No. | General Method | Structure/Name | IUPAC name | Isolated Yield | LCMS R_T (min), M + H+, method | $^1$H NMR (ppm) |
|---|---|---|---|---|---|---|
| 132 | E | [structure: 4-amino-pyrido[3,2-d]pyrimidine linked to 3-fluorophenyl with CH2-NH-CH2-tetrahydropyran, HCl salt] | 6-(3-fluoro-5-(((tetrahydro-2H-pyran-4-yl)methylamino)methyl)phenyl)pyrido[3,2-d]pyrimidin-4-amine hydrochloride | 7% | 0.883 367.9 0-60AB | $^1$H NMR (400 MHz, Methanol-d$_4$) δ 8.75-8.72 (m, 2H), 8.64 (s, 1H), 8.37-8.36 (m, 2H), 7.52 (d, J = 8.8 Hz, 2H), 4.40 (s, 2H), 3.96 (dd, J = 14.4 Hz, 2.8 Hz, 2H), 3.48-3.41 (m, 2H), 3.05 (d, J = 7.2 Hz, 2H), 2.66 (s, 1H), 2.16-2.11 (m, 1H), 1.77 (dd, J = 14.4, 1.6 Hz, 2H), 1.44-1.33 (m, 2H). |
| 133 | E | [structure: 4-amino-pyrido[3,2-d]pyrimidine linked to 3-fluorophenyl with CH2-NH-cyclohexanol] | 4-(3-(4-amino-pyrido[3,2-d]pyrimidin-6-yl)-5-fluorobenzyl-amino)cyclohexanol | 7% | 0.861 367.9 0-60AB | $^1$H NMR (400 MHz, DMSO-d$_6$) δ 9.85-9.81 (m, 1H), 9.51 (s, 2H), 8.80 (d, J = 5.2 Hz, 2H), 8.72 (d, J = 9.2 Hz, 1H), 8.50 (d, J = 10.4 HZ, 1H), 8.34 (d, J = 8.8 Hz, 1H), 7.62 (d, J = 9.2 Hz, 1H), 4.29 (s, 2H), 3.10-3.02 (m, 1H), 2.54 (s, 1H), 2.17 (d, J = 12.4 Hz, 2H), 1.90 (d, J = 10 Hz, 2H), 1.57-1.48 (m, 2H), 1.22-1.14 (m, 2H). |
| 134 | E | [structure: 4-amino-pyrido[3,2-d]pyrimidine linked to 3-fluorophenyl with CH2-NH-cyclopropyl-CH2OH, HCl salt] | (1-(3-(4-amino-pyrido[3,2-d]pyrimidin-6-yl)-5-fluorobenzyl-amino)cyclopropyl)methanol hydrochloride | 41% | 0.863 339.9 0-60AB | $^1$H NMR (400 MHz, DMSO-d$_6$) δ 10.04 (m, 2H), 9.92 (m, 2H), 8.84 (m, 2H), 8.76 (d, J = 8.8 Hz, 1H), 8.42 (m, 2H), 7.67 (d, J = 9.2 Hz, 1H), 4.45 (s, 2H), 3.71 (s, 2H), 1.22 (m, 2H), 0.79 (m, 2H). |
| 135 | E | [structure: 4-amino-pyrido[3,2-d]pyrimidine linked to 3-fluorophenyl with CH2-NH-CH2-(1-methylpiperidin-2-yl), HCl salt] | 6-(3-fluoro-5-(((1-methyl-piperidin-2-yl)methyl-amino)methyl)phenyl)pyrido[3,2-d]pyrimidin-4-amine hydrochloride | 21% | 0.829 381.0 0-60AB | $^1$H NMR (400 MHz, DMSO-d$_6$) δ 11.30 (m, 1H), 10.43 (s, 2H), 10.18 (m, 2H), 8.92 (d, J = 8.8 Hz, 1H), 8.88 (s, 1H), 8.79 (d, J = 9.2 Hz, 1H), 8.47 (m, 2H), 8.67 (d, J = 8.8 Hz, 2H), 4.40 (s, 2H), 3.67 (m, 2H), 3.44 (m, 1H), 3.31 (s, 1H), 3.12 (m, 1H), 3.00 (m, 3H), 2.33 (m, 1H), 2.00 (s, 1H), 1.51 (m, 3H), 1.46 (m, 1H). |

| Ex. No. | General Method | Structure/Name | IUPAC name | Isolated Yield | LCMS $R_T$ (min), M+H+, method | ¹H NMR (ppm) |
|---|---|---|---|---|---|---|
| 136 | E | | 6-(3-fluoro-5-(((1-methyl-piperidin-4-yl)methyl-amino)methyl)phenyl)pyrido[3,2-d]pyrimidin-4-amine hydrochloride | 7.2% | 0.807 381.0 0-60AB | ¹H NMR (400 MHz, MeOD-d₄) δ 8.75-8.71 (m, 3H), 8.33-8.30 (m, 2H), 7.54 (d, J = 7.6 Hz, 1H), 4.42 (s, 2H), 3.57 (s, 1H), 3.54 (s, 1H), 3.15-3.04 (m, 3H), 2.86 (s, 2H), 2.66 (s, 2H), 2.27 (d, J = 7.2 Hz, 1H), 2.18 (s, 1H), 2.14 (s, 1H), 1.69-1.60 (m, 2H). |
| 137 | E | | 6-(3-fluoro-5-((2-morpholino-ethylamino)methyl)phenyl)pyrido[3,2-d]pyrimidin-4-amine hydrochloride | 12.2% | 0.824 382.9 0-60AB | ¹H NMR (400 MHz, DMSO-d₆) δ 10.31 (s, 2H), 10.18 (s, 1H), 10.15 (s, 1H), 8.88 (s, 1H), 8.85 (s, 1H), 8.80 (d, J = 8.8 Hz, 1H), 8.47 (t, J = 8.8 Hz, 2H), 7.65 (d, J = 8.4 Hz, 1H), 4.38 (s, 2H), 3.66-3.56 (m, 10H), 3.19 (s, 1H). |
| 138 | E | | 1-(4-(3-(4-amino-pyrido[3,2-d]pyrimidin-6-yl)-5-fluorobenzyl-amino)piperidin-1-yl)ethanone hydrochloride | 6.0% | 0.866 395.0 0-60AB | ¹H NMR (400 MHz, DMSO-d₆) δ 10.17 (s, 1H), 10.12 (s, 1H), 10.00 (d, J = 6.4 Hz, 2H), 8.95 (s, 7H), 8.85 (s, 1H), 8.78 (d, J = 8.8 Hz, 1H), 8.46-8.40 (m, 2H), 7.66 (d, J = 8.8 Hz, 1H), 4.43 (d, J = 12.0 Hz, 1H), 4.30 (t, J = 6.4 Hz, 2H), 3.91 (d, J = 14.4 Hz, 1H), 3.35-3.32 (m, 1H), 3.04 (t, J = 12.0 Hz, 1H), 2.60-2.57 (m, 1H), 2.19 (m, 2H), 2.00 (s, 1H), 1.70-1.54 (m, 2H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 139 | E | 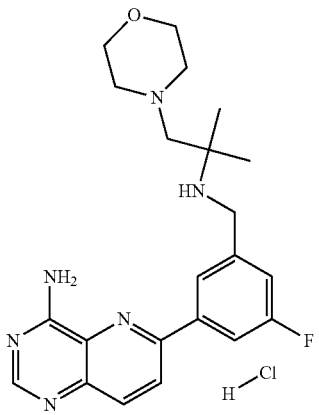 | 6-(3-fluoro-5-((2-methyl-1-morpholino-propan-2-ylamino)methyl)phenyl)pyrido[3,2-d]pyrimidin-4-amine hydrochloride | 53% | 0.904 411.0 0-60AB | 1H NMR (400 MHz, DMSO-d6) δ 11.31 (s, 1H), 10.47 (s, 1H), 10.12 (s, 2H), 8.90-8.87 (m, 2H), 8.79 (d, J = 8.8 Hz, 1H), 8.48-8.43 (m, 2H), 7.71 (d, J = 9.2 Hz, 1H), 4.39 (s, 2H), 3.88 (s, 6H), 3.28-3.21 (m, 4H), 1.67 (s, 6H). |
| 140 | E | 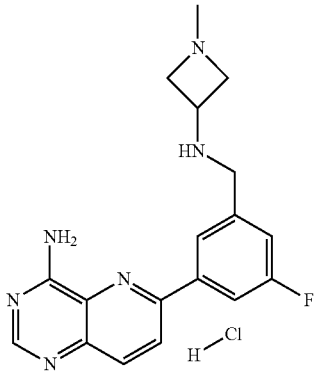 | 6-(3-fluoro-5-((1-methylazetidin-3-ylamino)methyl)phenyl)pyrido[3,2-d]pyrimidin-4-amine hydrochloride | 52% | 0.821 338.9 0-60AB | 1H NMR (400 MHz, DMSO-d6) δ 10.25 (s, 2H), 8.88 (s, 1H), 8.79 (m, 3H), 8.45 (m, 2H), 7.61 (m, 1H), 4.70 (m, 1H), 4.46 (m, 2H), 4.34 (m, 4'H), 2.93 (m, 3H). |
| 141 | E | 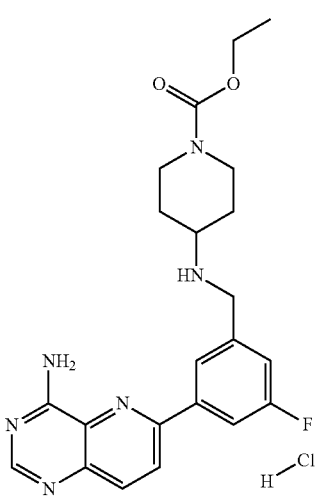 | ethyl 4-(3-(4-amino-pyrido[3,2-d]pyrimidin-6-yl)-5-fluorobenzyl-amino)piperidine-1-carboxylate hydrochloride | 15.7% | 0.942 446.9 (M + Na) 0-60AB | 1H NMR (400 MHz, DMSO-d6) δ 10.05 (s, 1H), 9.99 (s, 1H), 9.93 (s, 2H), 8.92 (s, 1H), 8.85 (s, 1H), 8.77 (d, J = 8.8 Hz, 1H), 8.48 (d, J = 10.4 Hz, 1H), 8.38 (d, J = 8.8 Hz, 1H), 7.76 (d, J = 8.4 Hz, 1H), 4.32 (s, 2H), 4.07-4.02 (m, 4H), 3.42 (s, 1H), 2.84-2.80 (m, 2H), 2.18 (d, J = 10.0 Hz, 2H), 1.68-1.59 (m, 2H), 2.00 (s, 1H), 1.19 (t, J = 6.8 Hz, 3H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 142 | E | | 2-(3-(4-amino-pyrido[3,2-d]pyrimidin-6-yl)benzylamino)propan-1-ol hydrochloride | 15% | 0.842 310.0 0-60AB | $^1$H NMR (400 MHz, DMSO-d$_6$) δ 10.01 (s, 1H), 9.97 (s, 1H), 9.74 (s, 1H), 9.39 (s, 1H), 9.00 (s, 1H), 8.85 (s, 1H), 8.73 (d, J = 8.8 Hz, 1H), 8.46 (d, J = 8.4 Hz, 1H), 7.69 (d, J = 8.0 Hz, 1H), 7.63 (m, 1H), 4.29 (m, 2H), 4.10 (m, 1H), 2.93 (m, 1H), 2.76 (m, 1H), 1.10 (m, 3H). |
| 143 | E | | 6-(3-((cyclopentyl-amino)methyl)phenyl)pyrido[3,2-d]pyrimidin-4-amine hydrochloride | 29% | 0.904 320.1 0-60AB | $^1$H NMR (400 MHz, DMSO-d$_6$) δ 10.04 (s, 1H), 10.00 (s, 1H), 9.73 (s, 2H), 9.12 (s, 1H), 8.84 (s, 1H), 8.75 (d, J = 8.8 Hz, 1H), 8.45 (d, J = 8.0 Hz, 1H), 8.38 (d, J = 9.2 Hz, 1H), 7.71 (d, J = 8.0 Hz, 1H), 7.62 (m, 1H), 4.26 (m, 2H), 3.48 (m, 1H), 2.03 (m, 2H), 1.80 (m, 4H), 1.54 (m, 2H). |
| 144 | E | | 2-(3-(4-amino-pyrido[3,2-d]pyrimidin-6-yl)benzyl-amino)-N,N-dimethylacetamide hydrochloride | 43% | 0.852 337.0 0-60AB | $^1$H NMR (400 MHz, DMSO-d$_6$) δ 10.15 (s, 1H), 10.10 (s, 1H), 9.79 (m, 2H), 9.01 (s, 1H), 8.86 (s, 2H), 8.73 (d, J = 8.0 Hz, 1H), 8.47 (d, J = 8.0 Hz, 1H), 7.68 (d, J = 8.0 Hz, 1H), 7.60 (t, J = 8.0 Hz, 1H), 4.28 (m, 2H), 4.06 (m, 2H), 2.92 (s, 3H), 2.88 (s, 3H). |
| 145 | E | | 6-(3-((4-methyl-cyclohexylamino)methyl)phenyl)pyrido[3,2-d]pyrimidin-4-amine hydrochloride | 12% | 1.038 348.0 0-60AB | $^1$H NMR (400 MHz, DMSO-d$_6$) δ 8.57 (s, 1H), 8.43 (m, 2H), 8.34 (m, 2H), 8.15 (d, J = 8.8 Hz, 2H), 8.04 (s, 1H), 7.55 (m, 2H), 4.07 (s, 2H), 2.89 (s, 1H), 1.69 (m, 5H), 1.44 (t, J = 5.6 Hz, 4H), 0.91 (d, J = 6.8 Hz, 3H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 146 | E | | 6-(3-((2-pyrrolidin-1-yl)ethyl-amino)methyl) phenyl)pyrido[3,2-d]pyrimidin-4-amine hydrochloride | 33% | 0.800 348.9 0-60AB | $^1$H NMR (400 MHz, DMSO-d$_6$) δ 11.25 (m, 1H), 10.25 (s, 1H), 10.07 (s, 1H), 9.99 (s, 1H), 9.06 (s, 1H), 8.85 (s, 1H), 8.75 (d, J = 8.8 Hz, 1H), 8.44 (m, 2H), 7.71 (d, J = 8.0 Hz, 1H), 7.62 (m, 1H), 4.36 (s, 2H), 3.67 (m, 3H), 3.48 (m, 3H), 3.13 (s, 2H), 2.05 (m, 4H). |
| 147 | E | | 6-(3-((1-methyl-piperidin-4-ylamino)methyl) phenyl)pyrido [3,2-d]pyrimidin-4-amine hydrochloride | 36% | 0.783 348.9 0-60AB | $^1$H NMR (400 MHz, DMSO-d$_6$) δ 10.59 (m, 1H), 10.10 (s, 4H), 9.14 (s, 1H), 8.87 (s, 1H), 8.77 (m, 1H), 8.47 (m, 1H), 8.38 (m, 1H), 7.74 (m, 1H), 7.63 (m, 1H), 4.30 (m, 2H), 3.34 (m, 1H), 3.27 (m, 2H), 2.82 (m, 2H), 2.12 (m, 1H), 1.73 (m, 2H), 1.20 (m, 2H). |
| 148 | E | | 6-(3-(((tetrahydro-2H-pyran-4-yl)methylamino) methyl)phenyl) pyrido[3,2-d] pyrimidin-4-amine hydrochloride | 75% | 0.863 349.9 0-60AB | $^1$H NMR (400 MHz, DMSO-d$_6$) δ 10.11 (s, 1H), 10.08 (s, 1H), 9.78 (s, 2H), 9.17 (s, 1H), 8.86 (s, 1H), 8.75 (d, J = 9.2 Hz, 1H), 8.43 (m, 2H), 7.70 (d, J = 8.0 Hz, 1H), 7.61 (t, J = 7.2 Hz, 1H), 4.27 (m, 2H), 3.83 (m, 2H), 3.27 (m, 2H), 2.82 (m, 2H), 2.12 (m, 1H), 1.73 (m, 2H), 1.20 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 149 | E | | N1-(3-(4-amino-pyrido[3,2-d]pyrimidin-6-yl)benzyl)cyclohexane-1,4-diamine hydrochloride | 65% | 0.846 349.9 0-60AB | $^1$H NMR (400 MHz, DMSO-d$_6$) δ 10.01 (m, 2H), 9.65 (s, 2H), 9.14 (s, 1H), 8.84 (s, 1H), 8.75 (d, J = 9.2 Hz, 1H), 8.45 (d, J = 8.0 Hz, 1H), 8.37 (d, J = 9.2 Hz, 1H), 7.69 (m, 1H), 7.63 (m, 1H), 4.27 (s, 2H), 3.40 (m, 1H), 3.00 (m, 1H), 1.92 (m, 2H), 1.61 (m, 2H), 1.18 (m, 2H). |
| 150 | E | | (1-(3-(4-amino-pyrido[3,2-d]pyrimidin-6-yl)benzylamino)cyclopropyl)methanol hydrochloride | 26% | 0.854 322.1 0-60AB | $^1$H NMR (400 MHz, DMSO-d$_6$) δ 9.99 (s, 2H), 9.81 (s, 2H), 9.05 (s, 1H), 8.83 (s, 1H), 8.73 (d, J = 8.4 Hz, 1H), 8.43 (d, J = 7.6 Hz, 1H), 8.37 (d, J = 8.8 Hz, 1H), 7.71 (d, J = 7.6 Hz, 1H), 7.59 (t, J = 7.6 Hz, 1H), 4.43 (s, 2H), 3.71 (s, 2H), 1.20 (m, 2H), 0.78 (m, 2H). |
| 151 | E | | 6-(3-(((1-methyl-piperidin-2-yl)methylamino)methyl)phenyl)pyrido[3,2-d]pyrimidin-4-amine hydrochloride | 33% | 0.808 363.0 0-60AB | $^1$H NMR (400 MHz, DMSO-d$_6$) δ 10.34 (m, 2H), 10.13 (m, 2H), 10.11 (s, 1H), 9.16 (m, 1H), 8.86 (s, 1H), 8.87 (d, J = 8.8 Hz, 1H), 8.45 (m, 2H), 7.73 (m, 1H), 7.61 (m, 1H), 4.38 (s, 2H), 3.67 (m, 2H), 3.45 (m, 1H), 3.31 (m, 1H), 3.05 (m, 1H), 2.85 (m, 3H), 2.33 (m, 1H), 2.00 (m, 1H), 1.75 (m, 3H), 1.43 (m, 1H). |
| 152 | E | | 6-(3-(((1-methyl-piperidin-4-yl)methylamino)methyl)phenyl)pyrido[3,2-d]pyrimidin-4-amine hydrochloride | 22% | 0.800 363.0 0-60AB | $^1$H NMR (400 MHz, DMSO-d$_6$) δ 10.84 (m, 1H), 10.15 (s, 1H), 10.11 (s, 1H), 9.99 (s, 2H), 9.24 (s, 1H), 9.20 (s, 1H), 8.86 (s, 1H), 8.77 (m, 2H), 8.43 (m, 2H), 7.71 (d, J = 7.6 Hz, 1H), 7.60 (t, J = 7.6 Hz, 1H), 4.27 (m, 2H), 3.37 (m, 2H), 3.14 (m, 1H), 2.92 (m, 4H), 2.67 (m, 3H), 2.05 (m, 2H), 1.57 (m, 2H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 153 | E | | 6-(3-((2-morpholinoethylamino)methyl)phenyl)pyrido[3,2-d]pyrimidin-4-amine hydrochloride | 41% | 0.808 365.0 0-60AB | 1H NMR (400 MHz, DMSO-d6) δ 11.53 (m, 1H), 10.28 (s, 2H), 10.16 (s, 1H), 10.07 (s, 1H), 9.08 (s, 1H), 8.87 (s, 1H), 8.76 (d, J = 8.8 Hz, 1H), 8.45 (m, 2H), 7.71 (d, J = 7.6 Hz, 1H), 7.61 (d, J = 7.6 Hz, 1H), 4.36 (s, 2H), 3.97 (m, 2H), 3.81 (m, 2H), 3.66 (m, 2H), 3.57 (s, 4H), 3.17 (m, 2H). |
| 154 | E | | 1-(4-(3-(4-aminopyrido[3,2-d]pyrimidin-6-yl)benzylamino)piperidin-1-yl)ethanone hydrochloride | 16% | 0.896 M + Na+ 398.9 0-60AB | 1H NMR (400 MHz, DMSO-d6) δ 8.56 (s, 1H), 8.45 (s, 1H), 8.42 (s, 1H), 8.39 (d, J = 7.6 Hz, 1H), 8.26 (s, 2H), 8.16 (d, J = 8.8 Hz, 2H), 8.05 (s, 1H), 7.55 (m, 2H), 4.31 (m, 1H), 4.10 (s, 2H), 3.02 (m, 2H), 2.63 (m, 1H), 2.03 (m, 5H), 1.41 (m, 1H), 1.32 (m, 1H). |
| 155 | E | | 6-(3-((2-methyl-1-morpholinopropan-2-ylamino)methyl)phenyl)pyrido[3,2-d]pyrimidin-4-amine hydrochloride | 9% | 0.896 393.0 0-60AB | 1H NMR (400 MHz, DMSO-d6) δ 11.37 (m, 1H), 10.32 (s, 1H), 10.15 (s, 1H), 10.04 (s, 1H), 9.09 (s, 1H), 8.77 (d, J = 9.2 Hz, 1H), 8.44 (t, J = 9.2 Hz, 2H), 7.76 (d, J = 7.6 Hz, 1H), 7.61 (t, J = 7.6 Hz, 1H), 4.38 (s, 2H), 3.90 (m, 6H), 3.40 (m, 4H), 1.70 (s, 6H). |

| Ex. No. | General Method | Structure/Name | IUPAC name | Isolated Yield | LCMS $R_T$ (min), M + H$^+$, method | $^1$H NMR (ppm) |
|---|---|---|---|---|---|---|
| 156 | E | | 6-(3-((1-methyl-azetidin-3-ylamino)methyl)phenyl)pyrido[3,2-d]pyrimidin-4-amine hydrochloride | 34% | 0.800 321.0 0-60AB | $^1$H NMR (400 MHz, DMSO-d$_6$) δ 11.20 (m, 2H), 10.17 (s, 1H), 10.09 (d, J = 10 Hz, 1H), 9.04 (d, J = 8.4 Hz, 1H), 8.87 (s, 1H), 8.76 (d, J = 8.8 Hz, 1H), 8.43 (t, J = 8.8 Hz, 2H), 7.65 (m, 2H), 4.65 (m, 1H), 4.46 (m, 2H), 4.29 (m, 4H), 2.93 (m, 3H). |
| 157 | E | | ethyl 4-(3-(4-amino-pyrido[3,2-d]pyrimidin-6-yl)benzylamino)piperidine-1-carboxylate hydrochloride | 8.0% | 0.921 406.9 0-60AB | $^1$H NMR (400 MHz, DMSO-d$_6$) δ 10.05 (d, J = 10.0 Hz, 1H), 9.95 (d, J = 4.4 Hz, 1H), 9.13 (s, 1H), 8.43 (s, 2H), 8.76 (d, J = 9.2 Hz, 1H), 8.44 (d, J = 8.4 Hz, 1H), 8.40 (d, J = 8.8 Hz, 1H), 7.71 (d, J = 8.0 Hz, 1H), 7.61 (t, J = 7.8 Hz, 1H), 4.29 (m, 2H), 4.05 (m, 4H), 3.29 (s, 1H), 2.82 (s, 2H), 2.19 (m, 2H), 1.67 (m, 2H), 1.88 (t, J = 7.2 Hz, 3H), |
| 158 | A | | 6-(3-chloro-phenyl)quinazolin-4-amine | / | | 1H NMR (400 MHz, DMSO) δ 8.62-8.59 (s, 1H), 8.41-8.38 (s, 1H), 8.17-8.12 (d, J = 8.7 Hz, 1H), 7.94-7.92 (s, 1H), 7.84-7.79 (d, J = 7.7 Hz, 1H), 7.76-7.71 (d, J = 8.7 Hz, 1H), 7.58-7.52 (t, J = 8.0 Hz, 1H), 7.49-7.44 (d, J = 8.0 Hz, 1H). |
| 159 | A | | N-[3-(4-amino-quinazolin-6-yl)phenyl]acetamide | / | | 1H NMR (400 MHz, DMSO) δ 10.07-10.00 (s, 1H), 8.52-8.48 (s, 1H), 8.40-8.37 (s, 1H), 8.00-7.93 (m, 2H), 7.93-7.77 (bs, 2H), 7.77-7.73 (d, J = 8.7 Hz, 1H), 7.63-7.58 (d, J = 7.6 Hz, 1H), 7.52-7.39 (m, 2H), 2.18-1.96 (s, 3H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 160 | A | | tert-butyl N-[4-(4-amino-quinazolin-6-yl)phenyl]carbamate | | / | 1H NMR (400 MHz, DMSO) δ 9.47-9.42 (s, 1H), 8.50-8.48 (s, 1H), 8.38-8.34 (s, 1H), 8.09-8.04 (d, J = 8.7 Hz, 1H), 7.86-7.72 (m, 4H), 7.72-7.67 (d, J = 8.7 Hz, 1H), 7.62-7.57 (d, J = 8.5 Hz, 2H), 1.58-1.40 (s, 9H). |
| 161 | A | | 5-(4-amino-quinazolin-6-yl)pyridine-3-carbonitrile | | / | 1H NMR (400 MHz, DMSO) δ 9.40-9.35 (s, 1H), 9.06-9.03 (s, 1H), 8.79-8.76 (s, 1H), 8.75-8.72 (s, 1H), 8.45-8.42 (s, 1H), 8.30-8.25 (d, J = 8.8 Hz, 1H), 7.99-7.81 (bs, 2H), 7.81-7.77 (d, J = 8.7 Hz, 1H). |
| 162 | A | | 6-(m-tolyl)quinazolin-4-amine | | / | 1H NMR (400 MHz, DMSO) δ 8.56-8.51 (s, 1H), 8.39-8.37 (s, 1H), 8.12-8.06 (d, J = 8.7 Hz, 1H), 7.97-7.75 (s, 2H), 7.75-7.69 (d, J = 8.7 Hz, 1H), 7.68-7.64 (s, 1H), 7.64-7.59 (d, J = 7.7 Hz, 1H), 7.44-7.36 (t, J = 7.6 Hz, 1H), 7.25-7.20 (d, J = 7.5 Hz, 1H), 2.43-2.39 (s, 3H). |
| 163 | A | | 6-(2-fluorophenyl)quinazolin-4-amine | | / | 1H NMR (400 MHz, DMSO) δ 8.45-8.38 (m, 2H), 7.96-7.76 (m, 3H), 7.76-7.72 (d, J = 8.6 Hz, 1H), 7.68-7.61 (t, J = 8.0 Hz, 1H), 7.51-7.43 (m, 1H), 7.40-7.33 (t, J = 8.1 Hz, 2H). |
| 164 | A | | 3-(4-amino-quinazolin-6-yl)benzonitrile | | / | 1H NMR (400 MHz, DMSO) δ 8.68-8.64 (s, 1H), 8.43-8.40 (s, 1H), 8.35-8.31 (s, 1H), 8.22-8.18 (d, J = 8.2 Hz, 2H), 7.97-7.79 (m, 3H), 7.79-7.70 (m, 2H). |
| 165 | A | | 4-(4-amino-quinazolin-6-yl)benzonitrile | | / | 1H NMR (400 MHz, DMSO) δ 8.69-8.67 (s, 1H), 8.43-8.40 (s, 1H), 8.22-8.16 (d, J = 8.7 Hz, 1H), 8.08-8.04 (d, J = 8.3 Hz, 2H), 8.02-7.98 (d, J = 8.3 Hz, 2H), 7.79-7.74 (d, J = 8.7 Hz, 1H). |

-continued

| Ex. No. | General Method | Structure/Name | IUPAC name | Isolated Yield | LCMS $R_T$ (min), M + H+, method | $^1$H NMR (ppm) |
|---|---|---|---|---|---|---|
| 166 | A | | 6-(4-methoxy-phenyl)quinazolin-4-amine | | / | 1H NMR (400 MHz, DMSO) δ 8.52-8.45 (s, 1H), 8.38-8.34 (s, 1H), 8.10-8.03 (d, J = 8.8 Hz, 1H), 7.90-7.73 (d, 3H), 7.73-7.67 (d, J = 8.7 Hz, 1H), 7.13-7.04 (d, J = 8.6 Hz, 2H), 3.86-3.78 (s, 3H). |
| 167 | A | | 6-(3-methoxy-phenyl)quinazolin-4-amine | | / | 1H NMR (400 MHz, DMSO) δ 8.57-8.53 (s, 1H), 8.41-8.38 (s, 1H), 8.14-8.08 (d, J = 8.7 Hz, 1H), 7.99-7.76 (m, 2H), 7.76-7.69 (d, J = 8.7 Hz, 1H), 7.47-7.36 (m, 3H), 7.02-6.95 (d, J = 7.3 Hz, 1H), 3.89-3.85 (s, 3H). |
| 168 | A | | 6-(2-methoxy-phenyl)quinazolin-4-amine | | / | 1H NMR (400 MHz, DMSO) δ 8.40-8.34 (s, 1H), 8.30-8.25 (s, 1H), 7.92-7.85 (d, J = 8.6 Hz, 1H), 7.78-7.68 (m, 2H), 7.69-7.63 (d, J = 8.6 Hz, 1H), 7.42-7.36 (m, 2H), 7.18-7.12 (d, J = 8.6 Hz, 1H), 7.12-7.05 (t, J = 7.4 Hz, 1H), 3.81-3.76 (s, 3H). |
| 169 | A | | 7-(3-chlorophenyl)quinazoline-2,4-diamine | | / | 1H NMR (400 MHz, DMSO) δ 8.08-8.02 (d, J = 8.5 Hz, 1H), 7.78-7.75 (s, 1H), 7.72-7.68 (d, J = 7.6 Hz, 1H), 7.54-7.48 (t, J = 7.8 Hz, 1H), 7.48-7.44 (m, 1H), 7.44-7.41 (d, J = 1.5 Hz, 1H), 7.36-7.31 (dd, J = 8.5, 1.6 Hz, 1H), 7.31-7.23 (bs, 2H), 6.03-5.94 (s, 2H). |
| 170 | A | | 6-(3-chlorophenyl)isoquinolin-1-amine | | / | 1H NMR (400 MHz, DMSO) δ 8.30-8.25 (d, J = 8.7 Hz, 1H), 8.06-8.02 (d, J = 1.6 Hz, 1H), 7.90-7.87 (s, 1H), 7.84-7.77 (m, 3H), 7.58-7.51 (t, J = 7.8 Hz, 1H), 7.51-7.46 (m, 1H), 7.00-6.96 (d, J = 5.8 Hz, 1H), 6.84-6.74 (s, 2H). |
| 171 | A | | 6-(3-chloro-5-fluoro-phenyl)quinazolin-4-amine | | / | 1H NMR (400 MHz, DMSO) δ 8.67-8.63 (d, J = 1.9 Hz, 1H), 8.42-8.39 (s, 1H), 8.22-8.17 (dd, J = 8.7, 1.9 Hz, 1H), 8.06-7.85 (bs, 2H), 7.85-7.82 (s, 1H), 7.77-7.71 (m, 2H), 7.49-7.44 (m, 1H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 172 | A | | 6-(3-chloro-phenyl)pyrido[3,2-d]pyrimidine-2,4-diamine | | / | 1H NMR (400 MHz, DMSO) δ 8.45-8.41 (s, 1H), 8.23-8.15 (m, 2H), 7.79-7.69 (bs, 1H), 7.64-7.59 (d, J = 8.8 Hz, 1H), 7.53-7.42 (m, 2H), 7.44-7.34 (bs, 1H), 6.29-6.21 (bs, 2H). |
| 173 | A, B | | 6-(3-chloro-phenyl)-N-cyclo-propyl-quinazolin-4-amine | | / | 1H NMR (400 MHz, DMSO) δ 8.60-8.49 (m, 2H), 8.44-8.35 (s, 1H), 8.18-8.05 (d, J = 8.7, 1H), 7.93-7.87 (s, 1H), 7.84-7.71 (m, 2H), 7.62-7.51 (t, J = 7.9 Hz, 1H), 7.51-7.43 (d, J = 8.4 Hz, 1H), 3.12-2.98 (m, 1H), 0.90-0.78 (m, 2H), 0.72-0.64 (m, 2H). |
| 174 | A | | 6-(3-fluorophenyl)quinazolin-4-amine | | / | 1H NMR (400 MHz, DMSO) δ 8.63-8.60 (s, 1H), 8.41-8.39 (s, 1H), 8.18-8.13 (dd, J = 8.7, 1.8 Hz, 1H), 7.99-7.77 (m, 2H), 7.77-7.68 (m, 3H), 7.60-7.52 (dd, J = 14.5, 7.6 Hz, 1H), 7.28-7.19 (t, J = 9.0 Hz, 1H). |
| 175 | A | | 3-(4-amino-quinazolin-6-yl)-5-chloro-benzamide | | / | 1H NMR (400 MHz, DMSO) δ 8.67-8.62 (s, 1H), 8.43-8.40 (s, 1H), 8.29-8.26 (s, 1H), 8.24-8.15 (t, J = 7.4 Hz, 2H), 8.10-8.07 (s, 1H), 7.92-7.90 (s, 1H), 7.79-7.74 (d, J = 8.7 Hz, 1H), 7.65-7.57 (s, 1H). |
| 176 | A, B | | 6-(3-chlorophenyl)-N-isobutyl-1-quinazolin-4-amine | | / | 1H NMR (400 MHz, DMSO) δ 8.69-8.59 (s, 1H), 8.52-8.39 (m, 2H), 8.16-8.07 (dd, J = 8.7, 1.7 Hz, 1H), 7.94-7.89 (s, 1H), 7.88-7.80 (d, J = 7.8 Hz, 1H), 7.80-7.69 (d, J = 8.7 Hz, 1H), 7.62-7.52 (t, J = 7.9 Hz, 1H), 7.52-7.43 (d, J = 7.7 Hz, 1H), 3.46-3.37 (t, J = 6.4 Hz, 2H), 2.15-1.99 (m, 1H), 1.05-0.86 (d, J = 6.7 Hz, 6H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 177 | A, B | | 6-(3-chlorophenyl)-N-cyclobutyl-quinazolin-4-amine | | / | 1H NMR (400 MHz, DMSO) δ 8.67-8.58 (s, 1H), 8.48-8.41 (m, 2H), 8.17-8.07 (d, J = 8.7, 1H), 7.95-7.88 (s, 1H), 7.85-7.78 (d, J = 7.8 Hz, 1H), 7.78-7.71 (d, J = 8.7 Hz, 1H), 7.61-7.53 (t, J = 7.9 Hz, 1H), 7.53-7.46 (d, J = 8.4 Hz, 1H), 4.83-4.70 (m, 1H), 2.42-2.30 (m, 2H), 2.26-2.11 (m, 2H), 1.85-1.72 (m, 2H). |
| 178 | A, B | | 6-(3-chlorophenyl)-N-(2,2-difluoro-ethyl)quinazolin-4-amine | | / | 1H NMR (400 MHz, DMSO) δ 8.82-8.74 (t, J = 5.8 Hz, 1H), 8.69-8.64 (s, 1H), 8.58-8.52 (s, 1H), 8.22-8.16 (dd, J = 8.7, 1.7 Hz, 1H), 7.96-7.91 (s, 1H), 7.85-7.77 (m, 2H), 7.62-7.53 (t, J = 7.9 Hz, 1H), 7.53-7.46 (d, J = 8.3 Hz, 1H), 6.48-6.07 (tt, J = 56.1, 4.0 Hz, 1H), 4.09-3.93 (ddd, J = 20.4, 10.3, 5.2 Hz, 2H). |
| 179 | A, B | | 6-(3-chlorophenyl)-N-ethyl-quinazolin-4-amine | | / | 1H NMR (400 MHz, DMSO) δ 8.59-8.57 (d, J = 1.8 Hz, 1H), 8.48-8.46 (s, 1H), 8.45-8.40 (m, 1H), 8.17-8.06 (dd, J = 8.7, 1.9 Hz, 1H), 7.96-7.86 (s, 1H), 7.86-7.78 (d, J = 7.8 Hz, 1H), 7.78-7.70 (d, J = 8.7 Hz, 1H), 7.62-7.52 (t, J = 7.9 Hz, 1H), 7.52-7.44 (d, J = 8.8 Hz, 1H), 3.68-3.53 (m, 2H), 1.32-1.19 (t, J = 7.2 Hz, 3H). |
| 180 | A, B | | 6-(3-chlorophenyl)-N-methyl-quinazolin-4-amine | | / | 1H NMR (400 MHz, DMSO) δ 8.60-8.53 (s, 1H), 8.53-8.43 (m, 2H), 8.16-8.08 (dd, J = 8.7, 1.8 Hz, 1H), 7.99-7.87 (s, 1H), 7.86-7.78 (d, J = 7.8 Hz, 1H), 7.78-7.72 (d, J = 8.6 Hz, 1H), 7.59-7.51 (t, J = 7.9 Hz, 1H), 7.51-7.44 (d, J = 7.7 Hz, 1H), 3.10-3.00 (d, J = 4.5 Hz, 3H). |

-continued

| Ex. No. | General Method | Structure/Name | IUPAC name | Isolated Yield | LCMS $R_T$ (min), M + H+, method | 1H NMR (ppm) |
|---|---|---|---|---|---|---|
| 181 | A | | 6-(3-chlorophenyl) pyrido[3,2-d] pyrimidin-4-amine | | / | 1H NMR (400 MHz, DMSO) δ 8.62-8.58 (s, 1H), 8.50-8.45 (d, J = 8.9 Hz, 1H), 8.44-8.40 (s, 1H), 8.36-8.32 (m, 1H), 8.30-8.23 (bs, 1H), 8.16-8.12 (d, J = 8.8 Hz, 1H), 8.05-7.95 (bs, 1H), 7.57-7.53 (m, 2H). |
| 182 | A | | 6-(5-chloro-2-methyl-phenyl) quinazolin-4-amine | | / | 1H NMR (400 MHz, DMSO) δ 8.42-8.40 (s, 1H), 8.24-8.21 (d, J = 1.5 Hz, 1H), 7.82-7.68 (m, 4H), 7.39-7.37 (s, 2H), 7.37-7.35 (s, 1H), 2.31-2.13 (s, 3H). |
| 183 | A | | 6-(3,5-dichloro-phenyl)quinazolin-4-amine | | / | 1H NMR (400 MHz, DMSO) δ 8.67-8.62 (d, J = 1.8 Hz, 1H), 8.43-8.39 (s, 1H), 8.22-8.16 (dd, J = 8.8, 1.9 Hz, 1H), 8.05-7.78 (m, 4H), 7.76-7.71 (d, J = 8.7 Hz, 1H), 7.66-7.62 (s, 1H). |
| 184 | A | | 6-(3-fluoro-phenyl)pyrido[3,2-d]pyrimidin-4-amine | | / | 1H NMR (400 MHz, DMSO) δ 8.51-8.44 (d, J = 8.9 Hz, 1H), 8.44-8.38 (m, 2H), 8.30-8.18 (m, 2H), 8.17-8.12 (d, J = 8.8 Hz, 1H), 8.05-7.92 (bs, 1H), 7.62-7.53 (m, 1H), 7.36-7.29 (m, 1H). |
| 185 | A | | 3-(4-amino-quinazolin-6-yl)-5-fluoro-benzonitrile | | / | 1H NMR (400 MHz, DMSO) δ 8.72-8.69 (d, J = 1.8 Hz, 1H), 8.44-8.41 (s, 1H), 8.25-8.23 (s, 2H), 8.16-8.10 (m, 1H), 8.00-7.81 (d, J = 8.3 Hz, 3H), 7.78-7.73 (d, J = 8.7 Hz, 1H). |
| 186 | A | | 6-(3,5-difluoro-phenyl)quinazolin-4-amine | | / | 1H NMR (400 MHz, DMSO) δ 8.68-8.63 (d, J = 1.9 Hz, 1H), 8.42-8.39 (s, 1H), 8.23-8.16 (dd, J = 8.7, 2.0 Hz, 1H), 8.07-7.76 (s, 2H), 7.76-7.71 (d, J = 8.7 Hz, 1H), 7.68-7.60 (m, 2H), 7.32-7.20 (m, 1H). |

| Ex. No. | General Method | Structure/Name | IUPAC name | Isolated Yield | LCMS $R_T$ (min), $M + H^+$, method | $^1H$ NMR (ppm) |
|---|---|---|---|---|---|---|
| 187 | A | | 6-(3-amino-5-fluoro-phenyl) quinazolin-4-amine | | / | 1H NMR (400 MHz, DMSO) δ 8.52-8.47 (d, J = 1.4 Hz, 1H), 8.43-8.39 (s, 1H), 8.15-7.81 (m, 3H), 7.74-7.69 (d, J = 8.7 Hz, 1H), 6.83-6.78 (s, 1H), 6.78-6.72 (d, J = 10.3 Hz, 1H), 6.40-6.33 (d, J = 11.4 Hz, 1H), 5.66-5.36 (bs, 2H). |
| 188 | L | | N-[3-(4-amino-quinazolin-6-yl)-5-fluoro-phenyl]-2-tetrahydro-furan-2-yl-acetamide | | / | 1H NMR (400 MHz, DMSO) δ 10.26-10.22 (s, 1H), 8.57-8.54 (d, J = 1.5 Hz, 1H), 8.44-8.37 (s, 1H), 8.03-7.98 (dd, J = 8.7, 1.8 Hz, 1H), 7.98-7.79 (bs, 2H), 7.79-7.73 (d, J = 8.7 Hz, 1H), 7.73-7.70 (s, 1H), 7.66-7.60 (d, J = 11.2 Hz, 1H), 7.39-7.33 (d, J = 10.0 Hz, 1H), 4.25-4.15 (m, 1H), 3.83-3.75 (m, 1H), 3.67-3.57 (m, 1H), 2.63-2.52 (m, 2H), 2.09-1.96 (m, 1H), 1.93-1.77 (m, 2H), 1.63-1.52 (m, 1H). |
| 189 | L | | N-[3-(4-amino-quinazolin-6-yl)-5-fluoro-phenyl] tetrahydro-pyran-4-carboxamide | | / | 1H NMR (400 MHz, DMSO) δ 10.25-10.17 (s, 1H), 8.58-8.53 (d, J = 1.6 Hz, 1H), 8.41-8.39 (s, 1H), 8.03-7.97 (dd, J = 8.7, 1.8 Hz, 1H), 7.96-7.79 (s, 2H), 7.79-7.73 (m, 2H), 7.65-7.58 (d, J = 11.2 Hz, 1H), 7.38-7.32 (d, J = 10.0 Hz, 1H), 3.98-3.87 (m, 2H), 3.45-3.33 (m, 2H), 2.70-2.57 (m, 1H), 1.79-1.65 (m, 4H). |
| 190 | L | | 1-acetyl-N-[3-(4-amino-quinazolin-6-yl)-5-fluoro-phenyl] azetidine-3-carboxamide | | / | 1H NMR (400 MHz, DMSO) δ 10.47-10.32 (s, 1H), 8.61-8.53 (d, J = 1.7 Hz, 1H), 8.44-8.36 (s, 1H), 8.08-7.99 (d, J = 8.7 Hz, 1H), 7.99-7.80 (bs, 2H), 7.79-7.72 (m, 2H), 7.65-7.61 (d, J = 11.0 Hz, 1H), 7.44-7.37 (d, J = 10.0 Hz, 1H), 4.36-4.17 (m, 2H), 4.09-3.91 (m, 2H), 3.62-3.46 (m, 1H), 1.82-1.74 (s, 3H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 191 | L | | N-[3-(4-amino-quinazolin-6-yl)-5-fluoro-phenyl]-2-pyrrolidin-1-yl-acetamide | | / | 1H NMR (400 MHz, DMSO) δ 10.04-9.94 (s, 1H), 8.59-8.52 (d, J = 1.7 Hz, 1H), 8.42-8.36 (s, 1H), 8.09-8.03 (dd, J = 8.7, 1.9 Hz, 1H), 8.00-7.79 (s, 3H), 7.78-7.70 (t, J = 9.2 Hz, 2H), 7.43-7.37 (d, J = 10.0 Hz, 1H), 3.30-3.29 (s, 2H), 2.66-2.57 (m, 2H), 1.83-1.73 (m, 4H). |
| 192 | L | | N-[3-(4-amino-quinazolin-6-yl)-5-fluoro-phenyl]-3-(dimethylamino)propanamide | | / | 1H NMR (400 MHz, DMSO) δ 10.44-10.29 (s, 1H), 8.60-8.51 (d, J = 1.7 Hz, 1H), 8.45-8.37 (s, 1H), 8.06-7.97 (dd, J = 8.7, 1.8 Hz, 1H), 7.97-7.79 (bs, 2H), 7.79-7.71 (d, J = 8.7 Hz, 1H), 7.71-7.67 (s, 1H), 7.67-7.59 (d, J = 11.2 Hz, 1H), 7.42-7.31 (d, J = 10.0 Hz, 1H), 2.63-2.54 (t, J = 6.8 Hz, 2H), 2.21-2.15 (s, 6H). |
| 193 | A | | N-[3-(4-amino-quinazolin-6-yl)-5-fluoro-phenyl]cyclobutane-carboxamide | | / | 1H NMR (400 MHz, DMSO) δ 10.06-10.00 (s, 1H), 8.56-8.53 (d, J = 1.7 Hz, 1H), 8.43-8.38 (s, 1H), 8.03-7.99 (dd, J = 8.7, 1.8 Hz, 1H), 7.96-7.79 (bs, 1H), 7.78-7.71 (d, J = 8.9 Hz, 2H), 7.68-7.61 (d, J = 11.2 Hz, 1H), 7.38-7.29 (d, J = 10.0 Hz, 1H), 3.24-3.17 (m, 1H), 2.35-2.19 (m, 2H), 2.19-2.08 (m, 2H), 2.04-1.89 (m, 1H), 1.89-1.77 (m, 1H). |
| 194 | L | | N-[3-(4-amino-quinazolin-6-yl)-5-fluoro-phenyl]-2-cyclopropyl-acetamide | | / | 1H NMR (400 MHz, DMSO) δ 10.18-10.08 (s, 1H), 8.58-8.51 (d, J = 1.6 Hz, 1H), 8.43-8.38 (s, 1H), 8.05-7.97 (dd, J = 8.7, 1.8 Hz, 1H), 7.89-7.84 (s, 1H), 7.79-7.70 (m, 2H), 7.69-7.58 (d, J = 11.2 Hz, 1H), 7.40-7.30 (d, J = 10.0 Hz, 1H), 2.28-2.22 (d, J = 7.0 Hz, 2H), 1.28-1.01 (m, 1H), 0.55-0.39 (m, 2H), 0.26-0.17 (m, 2H). |

-continued

| Ex. No. | General Method | Structure/Name | IUPAC name | Isolated Yield | LCMS $R_T$ (min), M + H+, method | 1H NMR (ppm) |
|---|---|---|---|---|---|---|
| 195 | L | 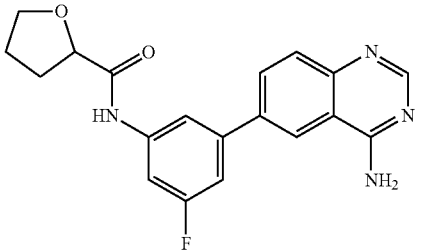 [SMILES: Nc1ncnc2ccc(-c3cc(F)cc(NC(=O)C4CCCO4)c3)cc12] | N-[3-(4-amino-quinazolin-6-yl)-5-fluoro-phenyl] tetrahydrofuran-2-carboxamide | | / | 1H NMR (400 MHz, DMSO) δ 10.01-9.83 (s, 1H), 8.60-8.51 (d, J = 1.6 Hz, 1H), 8.43-8.36 (s, 1H), 8.09-8.01 (dd, J = 8.7, 1.8 Hz, 1H), 8.00-7.78 (m, 3H), 7.79-7.69 (m, 2H), 7.46-7.35 (d, J = 10.0 Hz, 1H), 4.49-4.39 (m, 1H), 4.07-3.96 (m, 1H), 3.96-3.82 (m, 1H), 2.28-2.15 (m, 1H), 2.13-1.96 (m, 1H), 1.96-1.83 (m, 2H). |
| 196 | L | 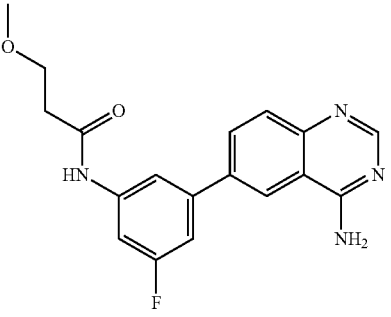 [SMILES: COCCC(=O)Nc1cc(F)cc(-c2ccc3ncnc(N)c3c2)c1] | N-[3-(4-amino-quinazolin-6-yl)-5-fluoro-phenyl]-3-methoxy-propanamide | | / | 1H NMR (400 MHz, DMSO) δ 10.31-10.23 (s, 1H), 8.59-8.52 (d, J = 1.7 Hz, 1H), 8.42-8.39 (s, 1H), 8.04-7.98 (dd, J = 8.7, 1.8 Hz, 1H), 7.94-7.78 (bs, 2H), 7.79-7.74 (d, J = 8.7 Hz, 1H), 7.74-7.70 (s, 1H), 7.66-7.59 (d, J = 11.1 Hz, 1H), 7.40-7.32 (d, J = 10.0 Hz, 1H), 3.72-3.56 (t, J = 6.1 Hz, 2H), 3.26-3.25 (s, 3H), 2.63-2.56 (t, J = 6.1 Hz, 2H). |
| 197 | L | 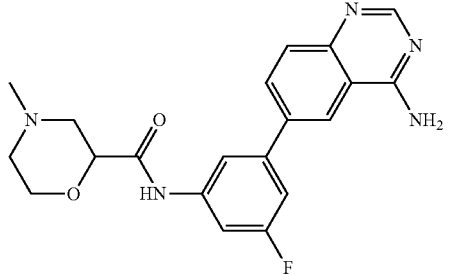 [SMILES: CN1CCOC(C(=O)Nc2cc(F)cc(-c3ccc4ncnc(N)c4c3)c2)C1] | N-[3-(4-amino-quinazolin-6-yl)-5-fluoro-phenyl]-4-methyl-morpholine-2-carboxamide | | / | 1H NMR (400 MHz, DMSO) δ 9.96-9.87 (s, 1H), 8.59-8.54 (d, J = 1.7 Hz, 1H), 8.42-8.39 (s, 1H), 8.08-8.02 (dd, J = 8.7, 1.8 Hz, 1H), 7.96-7.93 (s, 1H), 7.94-7.78 (bs, 2H), 7.78-7.70 (m, 2H), 7.46-7.39 (d, J = 10.0 Hz, 1H), 4.18-4.12 (dd, J = 9.9, 2.7 Hz, 1H), 4.01-3.92 (d, J = 11.3 Hz, 1H), 3.73-3.61 (td, J = 11.0, 2.4 Hz, 1H), 3.00-2.92 (d, J = 11.6 Hz, 1H), 2.71-2.60 (m, 1H), 2.26-2.20 (s, 3H), 2.16-2.02 (m, 2H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 198 | D | 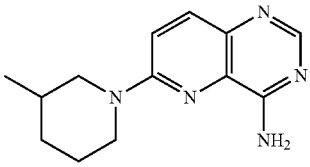 [SMILES: CC1CCCN(c2ccc3ncnc(N)c3n2)C1] | 6-(3-methyl-1-piperidyl)pyrido[3,2-d]pyrimidin-4-amine | | / | 1H NMR (400 MHz, DMSO) δ 8.18-8.11 (s, 1H), 7.77-7.70 (d, J = 9.4 Hz, 1H), 7.49-7.40 (d, J = 9.4 Hz, 1H), 7.40-7.10 (s, 2H), 4.52-4.34 (t, J = 11.1 Hz, 2H), 2.97-2.83 (m, 1H), 2.63-2.54 (m, 1H), 1.87-1.75 (m, 1H), 1.75-1.65 (m, 1H), 1.65-1.54 (m, 1H), 1.54-1.41 (m, 1H), 1.26-1.10 (m, 1H), 0.99-0.90 (d, J = 6.6 Hz, 3H). |
| 199 | D | 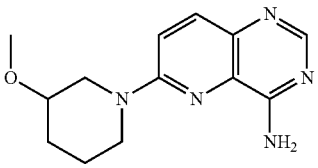 [SMILES: COC1CCCN(c2ccc3ncnc(N)c3n2)C1] | 6-(3-methoxy-1-piperidyl)pyrido[3,2-d]pyrimidin-4-amine | | / | 1H NMR (400 MHz, DMSO) δ 8.21-8.06 (s, 1H), 7.79-7.70 (d, J = 9.3 Hz, 1H), 7.50-7.42 (d, J = 9.4 Hz, 1H), 7.42-7.09 (s, 2H), 4.15-4.06 (dd, J = 13.1, 3.1 Hz, 1H), 3.95-3.80 (m, 1H), 3.50-3.38 (m, 2H), 3.31-3.30 (s, 3H), 1.99-1.90 (m, 1H), 1.81-1.69 (m, 1H), 1.60-1.40 (m, 2H). |
| 200 | D | 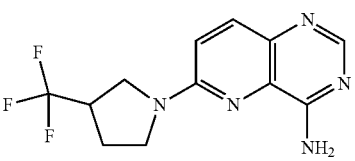 [SMILES: Nc1ncnc2ccc(N3CCC(C(F)(F)F)C3)nc12] | 6-[3-(trifluoromethyl)pyrrolidin-1-yl]pyrido[3,2-d]pyrimidin-4-amine | | / | 1H NMR (400 MHz, DMSO) δ 8.20-8.13 (s, 1H), 7.85-7.76 (d, J = 9.2 Hz, 1H), 7.44-7.19 (m, 2H), 7.19-7.14 (d, J = 9.2 Hz, 1H), 3.94-3.83 (m, 1H), 3.77-3.63 (m, 2H), 3.63-3.52 (m, 1H), 3.50-3.33 (m, 1H), 2.40-2.25 (m, 1H), 2.22-2.09 (m, 1H). |
| 201 | D | 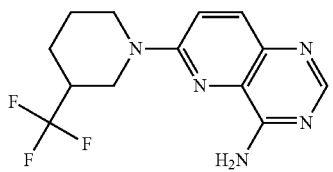 | 6-[3-(trifluoromethyl)-1-piperidyl]pyrido[3,2-d]pyrimidin-4-amine | | / | 1H NMR (400 MHz, DMSO) δ 8.21-8.16 (s, 1H), 7.85-7.77 (d, J = 9.3 Hz, 1H), 7.55-7.47 (d, J = 9.4 Hz, 1H), 7.46-7.07 (m, 2H), 4.74-4.61 (d, J = 13.1 Hz, 1H), 4.49-4.36 (d, J = 13.5 Hz, 1H), 3.08-2.96 (m, 2H), 2.08-1.90 (m, 1H), 1.81-1.72 (m, 1H), 1.70-1.49 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 202 | D | | 6-[3-(methoxy-methyl)-1-piperidyl]pyrido[3,2-d]pyrimidin-4-amine | | / | 1H NMR (400 MHz, DMSO) δ 8.18-8.08 (s, 1H), 7.82-7.70 (d, J = 9.3 Hz, 1H), 7.43-7.36 (d, J = 9.4 Hz, 1H), 7.36-7.02 (m, 2H), 4.42-4.22 (m, 2H), 3.34-3.24 (m, 5H), 3.11-3.00 (m, 1H), 2.94-2.80 (m, 1H), 1.89-1.75 (m, 2H), 1.75-1.63 (m, 1H), 1.56-1.41 (m, 1H), 1.41-1.21 (m, 1H). |
| 203 | D | | [1-(4-amino-pyrido[3,2-d]pyrimidin-6-yl)-3-piperidyl]methanol | | / | 1H NMR (400 MHz, DMSO) δ 8.19-8.09 (s, 1H), 7.81-7.71 (d, J = 9.3 Hz, 1H), 7.46-7.39 (d, J = 9.4 Hz, 1H), 7.39-7.04 (bs, 2H), 4.61-4.47 (s, 1H), 4.47-4.36 (t, J = 10.4 Hz, 2H), 3.39-3.33 (m, 2H), 3.07-2.93 (m, 1H), 2.87-2.69 (dd, J = 13.1, 10.3 Hz, 1H), 1.84-1.57 (m, 3H), 1.56-1.38 (m, 1H), 1.37-1.19 (m, 1H). |
| 204 | A | | 6-(4-pyridyl)quinazolin-4-amine | | / | 1H NMR (400 MHz, DMSO) δ 8.76-8.73 (s, 1H), 8.71-8.68 (d, J = 6.0 Hz, 2H), 8.44-8.41 (s, 1H), 8.26-8.19 (dd, J = 8.7, 1.8 Hz, 1H), 8.06-7.84 (m, 3H), 7.80-7.75 (d, J = 8.7 Hz, 1H). |
| 205 | A | | 6-(2-methyl-4-pyridyl)quinazolin-4-amine | | / | 1H NMR (400 MHz, DMSO) δ 8.74-8.68 (s, 1H), 8.58-8.53 (d, J = 5.3 Hz, 1H), 8.43-8.41 (s, 1H), 8.25-8.17 (dd, J = 8.7, 1.9 Hz, 1H), 8.04-7.80 (s, 2H), 7.80-7.74 (m, 2H), 7.68-7.64 (d, J = 5.2 Hz, 1H), 2.61-2.55 (s, 3H). |
| 206 | L | | N-[3-(4-amino-quinazolin-6-yl)phenyl]-2-cyclopropyl-acetamide | | / | 1H NMR (400 MHz, DMSO) δ 9.96-9.87 (s, 1H), 8.55-8.47 (s, 1H), 8.43-8.36 (s, 1H), 8.03-7.97 (m, 2H), 7.92-7.75 (bs, 2H), 7.79-7.71 (d, J = 8.7 Hz, 1H), 7.70-7.60 (d, J = 7.6 Hz, 1H), 7.50-7.41 (m, 2H), 2.27-2.23 (d, J = 7.0 Hz, 2H), 1.17-1.02 (m, 1H), 0.55-0.44 (m, 2H), 0.29-0.17 (m, 2H). |

-continued

| Ex. No. | General Method | Structure/Name | IUPAC name | Isolated Yield | LCMS $R_T$ (min), M + H[+], method | $^1$H NMR (ppm) |
|---|---|---|---|---|---|---|
| 207 | L | | N-[3-(4-amino-quinazolin-6-yl)phenyl]cyclo-butanecarboxamide | | / | 1H NMR (400 MHz, DMSO) δ 9.85-9.77 (s, 1H), 8.54-8.45 (s, 1H), 8.44-8.32 (s, 1H), 8.03-7.96 (m, 2H), 7.96-7.77 (bs, 2H), 7.79-7.73 (d, J = 8.7 Hz, 1H), 7.69-7.61 (d, J = 7.5 Hz, 1H), 7.50-7.40 (m, 2H), 2.36-2.20 (m, 2H), 2.20-2.05 (m, 2H), 2.05-1.90 (m, 1H), 1.90-1.77 (m, 1H). |
| 208 | L | | N-[3-(4-amino-quinazolin-6-yl)phenyl]propanamide | | / | 1H NMR (400 MHz, DMSO) δ 9.98-9.93 (s, 1H), 8.52-8.48 (d, J = 1.7 Hz, 1H), 8.41-8.36 (s, 1H), 8.02-7.97 (m, 2H), 7.93-7.77 (s, 2H), 7.77-7.72 (d, J = 8.7 Hz, 1H), 7.65-7.59 (d, J = 7.5 Hz, 1H), 7.51-7.39 (m, 3H), 2.40-2.29 (q, J = 7.6 Hz, 3H), 1.14-1.08 (t, J = 7.6 Hz, 4H). |
| 209 | L | | N-[3-(4-amino-quinazolin-6-yl)phenyl]-2,2-difluoro-acetamide | | / | 1H NMR (400 MHz, DMSO) δ 10.88-10.78 (s, 1H), 8.57-8.50 (s, 1H), 8.46-8.35 (s, 1H), 8.08-7.98 (m, 2H), 7.98-7.81 (bs, 1H), 7.81-7.73 (d, J = 8.7 Hz, 1H), 7.73-7.66 (d, J = 8.1 Hz, 1H), 7.66-7.58 (d, J = 7.9 Hz, 1H), 7.58-7.47 (t, J = 7.9 Hz, 1H), 6.60-6.21 (t, J = 53.6 Hz, 1H). |
| 210 | L | | N-[3-(4-amino-quinazolin-6-yl)phenyl]-3,3,3-trifluoro-propanamide | | / | 1H NMR (400 MHz, DMSO) δ 10.50-10.32 (s, 1H), 8.57-8.47 (s, 1H), 8.47-8.33 (s, 1H), 8.04-7.78 (m, 4H), 7.78-7.73 (m, 1H), 7.62-7.45 (m, 3H), 3.63-3.44 (q, J = 11.1 Hz, 2H). |
| 211 | L | | N-[3-(4-amino-quinazolin-6-yl)phenyl]tetrahydro-pyran-4-carboxamide | | / | 1H NMR (400 MHz, DMSO) δ 10.00-9.94 (s, 1H), 8.52-8.47 (s, 1H), 8.43-8.36 (s, 1H), 8.08-8.02 (s, 1H), 8.02-7.96 (m, 1H), 7.96-7.76 (bs, 2H), 7.79-7.72 (d, J = 8.7 Hz, 1H), 7.65-7.58 (d, J = 7.7 Hz, 1H), 7.53-7.39 (m, 2H), 3.99-3.87 (m, 2H), 3.46-3.29 (m, 2H), 2.72-2.56 (m, 1H), 1.81-1.63 (m, 4H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 212 | L | | N-[3-(4-amino-quinazolin-6-yl)phenyl]-4-methyl-morpholine-2-carboxamide | | / | 1H NMR (400 MHz, DMSO) δ 9.72-9.63 (s, 1H), 8.56-8.48 (d, J = 1.5 Hz, 1H), 8.45-8.35 (s, 1H), 8.11-7.98 (m, 2H), 7.98-7.80 (s, 1H), 7.95-7.77 (d, J = 25.5 Hz, 2H), 7.80-7.71 (t, J = 8.1 Hz, 2H), 7.58-7.49 (d, J = 7.8 Hz, 1H), 7.49-7.42 (t, J = 7.9 Hz, 1H), 4.18-4.08 (dd, J = 10.0, 2.7 Hz, 1H), 4.03-3.94 (d, J = 11.3 Hz, 1H), 3.75-3.59 (m, 1H), 3.02-2.92 (d, J = 11.5 Hz, 1H), 2.67-2.58 (d, J = 11.5 Hz, 1H), 2.27-2.17 (s, 3H), 2.17-1.97 (m, 2H). |
| 213 | L | | N-[3-(4-amino-quinazolin-6-yl)phenyl]-2,2-difluoro-cyclopropane-carboxamide | | / | 1H NMR (400 MHz, DMSO) δ 10.56-10.49 (s, 1H), 8.54-8.49 (s, 1H), 8.44-8.35 (s, 1H), 8.05-7.97 (dd, J = 11.0, 1.9 Hz, 2H), 7.95-7.77 (bs, 2H), 7.81-7.72 (d, J = 8.7 Hz, 1H), 7.66-7.57 (d, J = 7.8 Hz, 1H), 7.57-7.44 (m, 2H), 2.92-2.77 (m, 1H), 2.11-1.92 (m, 2H). |
| 214 | L | | N-[3-(4-amino-quinazolin-6-yl)phenyl]tetrahydro-furan-2-carboxamide | | / | 1H NMR (400 MHz, DMSO) δ 9.77-9.63 (s, 1H), 8.55-8.48 (s, 1H), 8.40-8.36 (s, 1H), 8.10-8.05 (s, 1H), 8.05-7.99 (dd, J = 8.7, 1.8 Hz, 1H), 7.95-7.68 (m, 4H), 7.56-7.50 (d, J = 7.8 Hz, 1H), 7.49-7.42 (t, J = 7.9 Hz, 1H), 4.48-4.39 (m, 1H), 4.07-3.98 (m, 1H), 3.93-3.81 (m, 1H), 2.31-2.16 (m, 1H), 2.06-1.96 (m, 1H), 1.96-1.85 (m, 2H). |
| 215 | L | | N-[3-(4-amino-quinazolin-6-yl)phenyl]tetra-hydrofuran-3-carboxamide | | / | 1H NMR (400 MHz, DMSO) δ 10.20-10.08 (s, 1H), 8.57-8.47 (s, 1H), 8.44-8.35 (s, 1H), 8.05-7.96 (m, 2H), 7.96-7.77 (bs, 2H), 7.77-7.71 (d, J = 8.7 Hz, 1H), 7.68-7.59 (d, J = 7.8 Hz, 1H), 7.53-7.39 (m, 2H), 4.02-3.92 (m, 1H), 3.85-3.67 (m, 3H), 3.22-3.12 (m, 1H), 2.19-2.07 (m, 2H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 216 | L | | N-[3-(4-amino-quinazolin-6-yl) phenyl]-2-pyrrolidin-1-yl-acetamide | | / | 1H NMR (400 MHz, DMSO) δ 9.82-9.74 (s, 1H), 8.55-8.48 (s, 1H), 8.43-8.35 (s, 1H), 8.06-7.97 (m, 2H), 7.99-7.76 (bs, 2H), 7.80-7.71 (d, J = 8.7 Hz, 2H), 7.55-7.50 (d, J = 7.8 Hz, 1H), 7.50-7.43 (t, J = 7.8 Hz, 1H), 3.29-3.27 (s, 2H), 2.68-2.54 (m, 4H), 1.89-1.71 (m, 4H). |
| 217 | L | | N-[3-(4-amino-quinazolin-6-yl)phenyl]-2-tetra-hydrofuran-2-yl-acetamide | | / | 1H NMR (400 MHz, DMSO) δ 10.04-10.00 (s, 1H), 8.53-8.50 (s, 1H), 8.40-8.37 (s, 1H), 8.02-7.97 (m, 2H), 7.95-7.76 (bs, 2H), 7.78-7.72 (d, J = 8.7 Hz, 1H), 7.65-7.59 (d, J = 7.7 Hz, 1H), 7.51-7.40 (m, 2H), 4.26-4.15 (m, 1H), 3.84-3.72 (m, 2H), 3.68-3.56 (m, 2H), 2.62-2.45 (m, 1H), 2.10-1.96 (m, 1H), 1.96-1.77 (m, 3H), 1.65-1.48 (m, 1H). |
| 218 | L | | N-[3-(4-amino-quinazolin-6-yl) phenyl]-2,2-dimethyl-propanamide | | / | 1H NMR (400 MHz, DMSO) δ 9.35-9.24 (s, 1H), 8.55-8.48 (s, 1H), 8.42-8.36 (s, 1H), 8.08-7.97 (m, 2H), 7.97-7.77 (bs, 2H), 7.79-7.69 (m, 2H), 7.55-7.37 (m, 2H). 1.29-1.22 (s, 9H). |
| 219 | L | | N-[3-(4-amino-quinazolin-6-yl)phenyl]-3-methoxy-propanamide | | / | 1H NMR (400 MHz, DMSO) δ 10.12-10.01 (s, 1H), 8.54-8.47 (s, 1H), 8.43-8.36 (s, 1H), 8.04-7.95 (m, 2H), 7.95-7.79 (bs, 2H), 7.78-7.72 (d, J = 8.7 Hz, 1H), 7.68-7.60 (d, J = 7.6 Hz, 1H), 7.55-7.38 (m, 2H), 3.69-3.58 (t, J = 6.2 Hz, 2H), 3.27-3.24 (s, 3H), 2.64-2.56 (t, J = 6.2 Hz, 2H). |
| 220 | L | | N-[3-(4-amino-quinazolin-6-yl)phenyl]-2-morpholino-acetamide | | / | 1H NMR (400 MHz, DMSO) δ 9.86-9.77 (s, 1H), 8.56-8.46 (s, 1H), 8.44-8.36 (s, 1H), 8.08-7.97 (m, 2H), 7.97-7.77 (d, J = 30.5 Hz, 2H), 7.77-7.66 (dd, J = 15.3, 8.3 Hz, 2H), 7.55-7.50 (d, J = 7.8 Hz, 1H), 7.50-7.43 (t, J = 7.8 Hz, 1H), 3.72-3.62 (m, 4H), 3.19-3.12 (s, 2H), 2.57-2.52 (m, 4H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 221 | C | | 2-[3-(4-amino-quinazolin-6-yl)phenyl]-N-cyclopentyl-acetamide | | / | 1H NMR (400 MHz, DMSO) δ 8.56-8.52 (s, 1H), 8.42-8.35 (s, 1H), 8.11-8.02 (m, 2H), 7.99-7.78 (bs, 2H), 7.78-7.73 (d, J = 8.7 Hz, 1H), 7.71-7.66 (m, 2H), 7.48-7.40 (t, J = 8.0 Hz, 1H), 7.33-7.24 (d, J = 7.6 Hz, 1H), 4.07-3.92 (m, 1H), 3.51-3.45 (s, 2H), 1.89-1.71 (m, 2H), 1.71-1.58 (m, 2H), 1.58-1.45 (m, 2H), 1.45-1.31 (m, 2H). |
| 222 | L | | N-[3-(4-amino-quinazolin-6-yl)phenyl]-2-pyrrolidin-2-yl-propanamide | | / | 1H NMR (400 MHz, DMSO) δ 9.91-9.69 (s, 1H), 8.56-8.48 (s, 1H), 8.45-8.36 (s, 1H), 8.07-7.99 (m, 2H), 8.02-7.78 (bs, 2H), 7.80-7.71 (m, 2H), 7.55-7.49 (d, J = 7.8 Hz, 1H), 7.49-7.41 (t, J = 7.8 Hz, 1H), 3.21-3.03 (m, 1H), 2.71-2.54 (m, 4H), 1.82-1.65 (m, 4H), 1.44-1.20 (d, J = 6.8 Hz, 3H). |
| 223 | A | | 2-[3-(4-amino-quinazolin-6-yl)phenyl]-N-cyclopentyl-N-methyl-acetamide | | / | 1H NMR (400 MHz, DMSO) δ 8.58-8.50 (s, 1H), 8.43-8.36 (s, 1H), 8.11-8.04 (m, 1H), 8.02-7.76 (bs, 2H), 7.78-7.72 (d, J = 8.7 Hz, 1H), 7.72-7.63 (t, J = 8.5 Hz, 2H), 7.50-7.40 (t, J = 7.8 Hz, 1H), 7.30-7.19 (d, J = 7.6 Hz, 1H), 4.91-4.74 (m, 0.5H), 4.48-4.35 (s, 0.5H), 3.91-3.82 (s, 1H), 3.82-3.75 (s, 1H), 2.93-2.85 (d, J = 3.8 Hz, 1.5H), 2.74-2.68 (s, 1.5H), 1.72-1.57 (d, J = 7.2 Hz, 4H), 1.55-1.45 (s, 4H). |
| 224 | L | | N-[3-(4-amino-quinazolin-6-yl)phenyl]-2-(dimethylamino)acetamide | | / | 1H NMR (400 MHz, DMSO) δ 9.84-9.75 (s, 1H), 8.55-8.49 (s, 1H), 8.42-8.35 (s, 1H), 8.08-8.01 (dd, J = 8.6, 1.9 Hz, 2H), 8.01-7.81 (s, 1H), 7.96-7.77 (s, 2H), 7.78-7.72 (t, J = 7.9 Hz, 2H), 7.55-7.49 (d, J = 7.9 Hz, 1H), 7.49-7.40 (t, J = 7.8 Hz, 1H), 3.14-3.05 (s, 2H), 2.34-2.30 (s, 6H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 225 | A | | N6-[2-(4-fluorophenyl)ethyl]pyrido[3,2-d]pyrimidine-4,6-diamine | | / | 1H NMR (400 MHz, DMSO) δ 8.18-8.09 (s, 1H), 7.69-7.57 (d, J = 9.1 Hz, 1H), 7.38-7.29 (m, 2H), 7.29-7.22 (t, J = 5.4 Hz, 1H), 7.18-7.06 (t, J = 8.8 Hz, 2H), 7.03-6.95 (d, J = 9.1 Hz, 1H), 3.71-3.57 (m, 2H), 2.93-2.83 (t, J = 7.3 Hz, 2H). |
| 226 | D | | 6-(1-piperidyl)pyrido[3,2-d]pyrimidin-4-amine | | / | 1H NMR (400 MHz, DMSO) δ 8.21-8.08 (s, 1H), 7.78-7.69 (d, J = 9.4 Hz, 1H), 7.49-7.41 (d, J = 9.4 Hz, 1H), 7.41-7.12 (bs, 2H), 3.76-3.64 (m, 4H), 1.70-1.48 (m, 6H). |
| 227 | D | | [1-(4-aminopyrido[3,2-d]pyrimidin-6-yl)-4-piperidyl]-pyrrolidin-1-yl-methanone | | / | 1H NMR (400 MHz, DMSO) δ 8.19-8.11 (s, 1H), 7.82-7.73 (d, J = 9.3 Hz, 1H), 7.49-7.44 (d, J = 9.4 Hz, 1H), 7.43-7.13 (s, 2H), 4.67-4.45 (d, J = 13.3 Hz, 2H), 3.61-3.45 (t, J = 6.7 Hz, 2H), 3.30-3.20 (t, J = 6.9 Hz, 2H), 3.04-2.90 (t, J = 11.7 Hz, 2H), 2.81-2.68 (m, 1H), 1.97-1.84 (m, 2H), 1.84-1.68 (m, 4H), 1.68-1.49 (m, 2H). |
| 228 | D | | 6-(3-morpholino-pyrrolidin-1-yl)pyrido[3,2-d]pyrimidin-4-amine | | / | 1H NMR (400 MHz, DMSO) δ 8.58-8.50 (s, 1H), 8.43-8.36 (s, 1H), 8.11-8.04 (m, 1H), 8.02-7.76 (s, 2H), 7.78-7.72 (d, J = 8.7 Hz, 1H), 7.72-7.63 (m, 2H), 7.50-7.40 (t, J = 7.8 Hz, 1H), 7.30-7.19 (d, J = 7.6 Hz, 1H), 4.91-4.74 (m, 1H), 4.48-4.35 (s, 1H), 3.91-3.82 (s, 1H), 3.82-3.75 (s, 1H), 2.93-2.85 (d, J = 3.8 Hz, 2H), 2.74-2.68 (s, 1H), 1.72-1.57 (d, J = 7.2 Hz, 4H), 1.55-1.45 (s, 4H). |
| 229 | D | | 6-[4-(2-methoxyethyl)piperazin-1-yl]pyrido[3,2-d]pyrimidin-4-amine | | / | 1H NMR (400 MHz, DMSO) δ 8.18-8.14 (s, 1H), 7.82-7.75 (d, J = 9.3 Hz, 1H), 7.46-7.42 (d, J = 9.4 Hz, 1H), 7.41-7.18 (s, 2H), 3.71-3.64 (m, 4H), 3.54-3.45 (t, J = 5.7 Hz, 2H), 3.27-3.23 (s, 3H), 2.60-2.49 (m, 6H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 230 | D | | N-[1-(4-amino-pyrido[3,2-d]pyrimidin-6-yl)pyrrolidin-3-yl]-N-methyl-acetamide | | / | 1H NMR (400 MHz, DMSO) δ 8.16-8.14 (s, 1H), 7.82-7.76 (m, 1H), 7.49-7.22 (bs, 1H), 7.22-7.00 (m, 2H), 5.27-5.14 (m, 0.55H), 4.76-4.62 (m, 0.45H), 3.92-3.66 (m, 2H), 3.56-3.39 (m, 2H), 2.94-2.88 (s, 1.70H), 2.81-2.74 (s, 1.35H), 2.26-2.16 (m, 1H), 2.16-2.07 (m, 2.35H), 2.07-2.01 (s, 1.75H). |
| 231 | D | | 1-[4-(4-amino-pyrido[3,2-d]pyrimidin-6-yl)piperazin-1-yl]ethanone | | / | 1H NMR (400 MHz, DMSO) δ 8.22-8.15 (s, 1H), 7.85-7.78 (d, J = 9.3 Hz, 1H), 7.51-7.45 (d, J = 9.3 Hz, 1H), 7.45-7.26 (bs, 2H), 3.82-3.74 (m, 2H), 3.74-3.67 (m, 2H), 3.63-3.49 (m, 4H), 2.09-2.01 (s, 3H). |
| 232 | D | | 1-[4-(4-amino-pyrido[3,2-d]pyrimidin-6-yl)piperazin-1-yl]-2-methyl-propan-1-one | | / | 1H NMR (400 MHz, DMSO) δ 8.19-8.16 (s, 1H), 7.86-7.78 (d, J = 9.3 Hz, 1H), 7.50-7.45 (d, J = 9.3 Hz, 1H), 7.45-7.29 (s, 2H), 3.79-3.67 (d, J = 14.9 Hz, 4H), 3.67-3.55 (s, 4H), 2.97-2.88 (dt, J = 13.5, 6.7 Hz, 1H), 1.08-0.97 (d, J = 6.7 Hz, 6H). |
| 233 | D | | 6-[3-(4-methyl-1H-pyrazol-3-yl)-1-piperidyl]pyrido[3,2-d]pyrimidin-4-amine | | LCMS M/Z (M + H) 310 | 1H NMR (400 MHz, DMSO) δ 12.49-12.14 (m, 1H), 8.22-8.10 (s, 1H), 7.84-7.71 (d, J = 9.3 Hz, 1H), 7.56-7.47 (d, J = 9.4 Hz, 1H), 7.43-7.16 (bs, 2H), 4.75-4.51 (m, 2H), 3.08-2.88 (m, 2H), 2.88-2.68 (s, 1H), 1.97-1.73 (m, 3H), 1.67-1.50 (m, 1H). |
| 234 | D | | tert-butyl 4-(4-amino-pyrido[3,2-d]pyrimidin-6-yl)-2-methyl-piperazine-1-carboxylate | | / | 1H NMR (400 MHz, DMSO) δ 8.21-8.13 (s, 1H), 7.86-7.72 (d, J = 9.3 Hz, 1H), 7.47-7.22 (m, 3H), 4.52-4.40 (d, J = 12.8 Hz, 1H), 4.40-4.28 (d, J = 13.4 Hz, 1H), 4.28-4.12 (d, J = 3.5 Hz, 1H), 3.89-3.74 (d, J = 13.2 Hz, 1H), 3.31-3.22 (m, 1H), 3.20-3.09 (m, 1H), 3.04-2.89 (m, 1H), 1.48-1.39 (s, 9H), 1.14-1.03 (d, J = 6.7 Hz, 3H). |

| Ex. No. | General Method | Structure/Name | IUPAC name | Isolated Yield | LCMS R_T (min), M + H+, method | 1H NMR (ppm) |
|---|---|---|---|---|---|---|
| 235 | D | | 2-[1-(4-amino-pyrido[3,2-d]pyrimidin-6-yl)-4-piperidyl]-N-methyl-acetamide | | / | 1H NMR (400 MHz, DMSO) δ 8.18-8.12 (s, 1H), 7.78-7.67 (m, 2H), 7.48-7.41 (d, J = 9.4 Hz, 1H), 7.41-7.09 (bs, 2H), 4.58-4.44 (d, J = 13.3 Hz, 2H), 2.96-2.84 (t, J = 11.6 Hz, 2H), 2.60-2.54 (d, J = 4.6 Hz, 3H), 2.09-1.87 (m, 3H), 1.78-1.62 (d, J = 11.7 Hz, 2H), 1.22-1.07 (m, 2H). |
| 236 | D | | 6-[4-(1H-pyrazol-5-yl)-1-piperidyl]pyrido[3,2-d]pyrimidin-4-amine | | / | 1H NMR (400 MHz, DMSO) δ 12.70-12.32 (s, 1H), 8.22-8.05 (s, 1H), 7.84-7.71 (d, J = 9.3 Hz, 1H), 7.54-7.42 (d, J = 9.4 Hz, 2H), 7.42-7.11 (bs, 2H), 6.21-5.94 (s, 1H), 4.74-4.49 (d, J = 13.3 Hz, 2H), 3.11-2.99 (t, J = 11.7 Hz, 2H), 2.99-2.84 (t, J = 11.6 Hz, 1H), 2.04-1.91 (d, J = 10.8 Hz, 2H), 1.72-1.48 (m, 2H). |
| 237 | D | | 6-[4-(6-methyl-2-pyridyl)-1-piperidyl]pyrido[3,2-d]pyrimidin-4-amine | | / | 1H NMR (400 MHz, DMSO) δ 8.21-8.10 (s, 1H), 7.82-7.74 (d, J = 9.3 Hz, 1H), 7.64-7.55 (t, J = 7.7 Hz, 1H), 7.55-7.47 (d, J = 9.4 Hz, 1H), 7.46-7.14 (s, 2H), 7.12-7.03 (m, 2H), 4.77-4.65 (d, J = 13.3 Hz, 2H), 3.09-2.88 (m, 3H), 2.46-2.39 (s, 3H), 1.97-1.82 (m, 2H), 1.82-1.65 (m, 2H). |
| 238 | D | | 6-(3-morpholino-1-piperidyl)pyrido[3,2-d]pyrimidin-4-amine | | / | 1H NMR (400 MHz, DMSO) δ 8.22-8.10 (s, 1H), 7.80-7.70 (d, J = 9.3 Hz, 1H), 7.50-7.43 (d, J = 9.4 Hz, 1H), 7.43-7.01 (m, 2H), 4.56-4.46 (d, J = 12.9 Hz, 1H), 4.46-4.35 (d, J = 13.2 Hz, 1H), 3.61-3.53 (t, J = 4.6 Hz, 4H), 2.98-2.86 (dd, J = 12.9, 10.2 Hz, 2H), 2.74-2.62 (m, 2H), 2.55-2.48 (m, 2H), 2.29-2.18 (m, 1H), 2.02-1.89 (m, 1H), 1.83-1.72 (m, 1H), 1.57-1.38 (m, 2H). |

| Ex. No. | General Method | Structure/Name | IUPAC name | Isolated Yield | LCMS $R_T$ (min), $M + H^+$, method | $^1H$ NMR (ppm) |
|---|---|---|---|---|---|---|
| 239 | D | | 6-[3-(5-methyl-2-pyridyl)-1-piperidyl]pyrido[3,2-d]pyrimidin-4-amine | / | | 1H NMR (400 MHz, DMSO) δ 8.43-8.31 (s, 1H), 8.19-8.10 (s, 1H), 7.79-7.73 (d, J = 9.3 Hz, 1H), 7.60-7.53 (dd, J = 8.0, 2.0 Hz, 1H), 7.53-7.44 (d, J = 9.4 Hz, 1H), 7.44-7.10 (m, 3H), 4.73-4.51 (t, J = 13.1 Hz, 2H), 3.25-3.10 (m, 1H), 3.04-2.93 (m, 1H), 2.93-2.80 (m, 1H), 2.31-2.24 (s, 3H), 2.07-1.93 (m, 1H), 1.93-1.74 (m, 2H), 1.74-1.50 (m, 1H). |
| 240 | D | | 6-[3-[(1-methylimidazol-2-yl)methyl]pyrrolidin-1-yl]pyrido[3,2-d]pyrimidin-4-amine | / | | 1H NMR (400 MHz, DMSO) δ 8.17-8.12 (s, 1H), 7.81-7.72 (d, J = 9.2 Hz, 1H), 7.49-7.17 (bs, 1H), 7.10-7.05 (d, J = 9.2 Hz, 1H), 7.05-7.01 (s, 1H), 7.00-6.81 (bs, 1H), 6.79-6.75 (s, 1H), 3.85-3.65 (m, 2H), 3.62-3.56 (s, 3H), 3.56-3.44 (m, 1H), 2.82-2.72 (m, 3H), 2.23-2.09 (m, 1H), 1.89-1.72 (m, 1H). |
| 241 | D | | 6-[3-(5-methyl-1,2,4-oxadiazol-3-yl)-1-piperidyl]pyrido[3,2-d]pyrimidin-4-amine | / | | 1H NMR (400 MHz, DMSO) δ 8.23-8.11 (s, 1H), 7.83-7.74 (d, J = 9.3 Hz, 1H), 7.55-7.46 (d, J = 9.4 Hz, 1H), 7.46-7.17 (bs, 2H), 4.60-4.49 (d, J = 13.4 Hz, 2H), 3.24-3.06 (m, 3H), 2.59-2.54 (s, 3H), 2.08-1.96 (m, 2H), 1.81-1.57 (m, 2H). |
| 242 | D | | 6-[4-(3-methylimidazol-4-yl)-1-piperidyl]pyrido[3,2-d]pyrimidin-4-amine | / | | 1H NMR (400 MHz, DMSO) δ 8.20-8.12 (s, 1H), 7.82-7.73 (d, J = 9.3 Hz, 1H), 7.54-7.45 (m, 2H), 7.45-7.16 (bs, 2H), 6.69-6.56 (s, 1H), 4.75-4.63 (d, J = 13.3 Hz, 2H), 3.66-3.58 (s, 3H), 3.12-2.97 (t, J = 11.8 Hz, 2H), 2.97-2.81 (m, 1H), 2.03-1.88 (d, J = 11.7 Hz, 2H), 1.64-1.42 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 243 | A | | 6-(3-amino-5-fluoro-phenyl)pyrido[3,2-d]pyrimidin-4-amine | | / | 1H NMR (400 MHz, DMSO) δ 8.42-8.39 (s, 1H), 8.26-8.21 (d, J = 8.9 Hz, 1H), 8.14-8.09 (d, J = 8.8 Hz, 1H), 8.02-7.93 (s, 2H), 7.45-7.39 (d, J = 10.5 Hz, 1H), 7.34-7.32 (s, 1H), 6.48-6.42 (dt, J = 11.3, 2.1 Hz, 1H), 5.56-5.45 (s, 2H). |
| 244 | D | | 6-[3-(4-pyridyl-methyl)pyrrolidin-1-yl]pyrido[3,2-d]pyrimidin-4-amine | | / | 1H NMR (400 MHz, DMSO) δ 8.54-8.44 (d, J = 5.8 Hz, 2H), 8.17-8.10 (s, 1H), 7.81-7.70 (d, J = 9.2 Hz, 1H), 7.49-7.47 (m, 1H), 7.34-7.28 (d, J = 5.8 Hz, 2H), 7.12-7.05 (d, J = 8.8 Hz, 1H), 3.88-3.63 (s, 2H), 3.54-3.41 (m, 1H), 3.29-3.16 (m, 1H), 2.88-2.71 (m, 2H), 2.71-2.60 (m, 1H), 2.10-1.96 (m, 1H), 1.82-1.67 (m, 1H). |
| 245 | D | | 6-[3-(3-methyl-imidazol-4-yl)pyrrolidin-1-yl]pyrido[3,2-d]pyrimidin-4-amine | | / | 1H NMR (400 MHz, DMSO) δ 8.18-8.14 (s, 1H), 7.82-7.76 (d, J = 9.2 Hz, 1H), 7.62-7.47 (s, 1H), 7.47-7.20 (m, 1H), 7.18-7.00 (m, 2H), 6.83-6.73 (s, 1H), 4.18-4.03 (m, 1H), 3.86-3.70 (m, 1H), 3.69-3.62 (s, 3H), 3.64-3.49 (m, 2H), 3.49-3.38 (m, 1H), 2.48-2.37 (m, 1H), 2.13-2.02 (m, 1H). |
| 246 | D | | 6-[3-(3-methyl-1,2,4-oxadiazol-5-yl)-1-piperidyl]pyrido[3,2-d]pyrimidin-4-amine | | / | 1H NMR (400 MHz, DMSO) δ 8.21-8.13 (s, 1H), 7.84-7.73 (d, J = 9.3 Hz, 1H), 7.56-7.48 (d, J = 9.4 Hz, 1H), 7.48-7.13 (bs, 2H), 4.78-4.59 (d, J = 13.1 Hz, 1H), 4.34-4.18 (d, J = 13.4 Hz, 1H), 3.55-3.40 (m, 1H), 3.34-3.25 (m, 2H), 2.37-2.28 (s, 3H), 2.19-2.08 (m, 1H), 1.95-1.72 (m, 2H), 1.69-1.55 (m, 1H). |
| 247 | D | | 1-(4-amino-pyrido[3,2-d]pyrimidin-6-yl)-N-methyl-pyrrolidine-3-carboxamide | | / | 1H NMR (400 MHz, DMSO) δ 8.15-8.11 (s, 1H), 8.02-7.92 (d, J = 4.5 Hz, 1H), 7.81-7.73 (d, J = 9.2 Hz, 1H), 7.47-7.21 (bs, 1H), 7.16-6.94 (m, 2H), 3.84-3.76 (m, 1H), 3.76-3.66 (m, 1H), 3.63-3.42 (m, 2H), 3.12-2.98 (m, 1H), 2.64-2.59 (m, 3H), 2.28-2.03 (m, 2H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 248 | D | | 6-[3-(2-pyridyl-methyl)pyrrolidin-1-yl]pyrido[3,2-d]pyrimidin-4-amine | | / | 1H NMR (400 MHz, DMSO) δ 8.56-8.48 (d, J = 4.7 Hz, 1H), 8.20-8.09 (s, 1H), 7.79-7.66 (m, 2H), 7.44-7.27 (m, 2H), 7.27-7.20 (dd, J = 7.1, 5.0 Hz, 1H), 7.08-6.87 (d, J = 9.2 Hz, 2H), 3.80-3.61 (m, 2H), 3.51-3.41 (m, 1H), 3.28-3.20 (m, 1H), 3.01-2.85 (m, 2H), 2.85-2.73 (m, 1H), 2.11-2.00 (m, 1H), 1.83-1.70 (m, 1H). |
| 249 | D | | 6-[3-(3-methyl-1,2,4-oxadiazol-5-yl)pyrrolidin-1-yl]pyrido[3,2-d]pyrimidin-4-amine | | / | 1H NMR (400 MHz, DMSO) δ 8.20-8.10 (s, 1H), 7.85-7.76 (d, J = 9.2 Hz, 1H), 7.55-7.27 (bs, 1H), 7.26-6.99 (m, 2H), 4.11-4.03 (m, 1H), 4.03-3.91 (m, 1H), 3.91-3.80 (m, 1H), 3.80-3.61 (m, 2H), 2.56-2.52 (m, 1H), 2.42-2.27 (s, 4H). |
| 250 | D | | 6-[3-(3-pyridyl-methyl)pyrrolidin-1-yl]pyrido[3,2-d]pyrimidin-4-amine | | / | 1H NMR (400 MHz, DMSO) δ 8.55-8.48 (s, 1H), 8.47-8.40 (d, J = 4.7 Hz, 1H), 8.19-8.12 (s, 1H), 7.79-7.75 (d, J = 9.2 Hz, 1H), 7.75-7.68 (d, J = 7.8 Hz, 1H), 7.49-7.15 (m, 2H), 7.15-6.86 (m, 2H), 3.79-3.57 (m, 2H), 3.52-3.41 (m, 1H), 3.27-3.20 (m, 1H), 2.87-2.71 (m, 2H), 2.71-2.56 (m, 1H), 2.12-1.95 (m, 1H), 1.81-1.67 (m, 1H). |
| 251 | D | | 6-(4-methyl-piperazin-1-yl)pyrido[3,2-d]pyrimidin-4-amine | | / | 1H NMR (400 MHz, DMSO) δ 8.20-8.15 (s, 1H), 7.82-7.76 (d, J = 9.3 Hz, 1H), 7.49-7.42 (d, J = 9.3 Hz, 1H), 7.42-7.22 (s, 2H), 3.74-3.64 (m, 4H), 2.45-2.37 (m, 4H), 2.25-2.21 (s, 3H). |
| 252 | D | | 6-(4-methoxy-1-piperidyl)pyrido[3,2-d]pyrimidin-4-amine | | / | 1H NMR (400 MHz, DMSO) δ 8.19-8.12 (s, 1H), 7.82-7.69 (d, J = 9.3 Hz, 1H), 7.50-7.43 (d, J = 9.4 Hz, 1H), 7.43-7.11 (bs, 2H), 4.19-4.07 (m, 2H), 3.49-3.40 (m, 1H), 3.36-3.32 (m, 2H), 3.30-3.28 (s, 3H), 2.01-1.84 (m, 2H), 1.54-1.34 (m, 2H). |

| Ex. No. | General Method | Structure/Name | IUPAC name | Isolated Yield | LCMS R_T (min), M + H+, method | ¹H NMR (ppm) |
|---|---|---|---|---|---|---|
| 253 | D | | 6-[3-(dimethylamino)pyrrolidin-1-yl]pyrido[3,2-d]pyrimidin-4-amine | | / | 1H NMR (400 MHz, DMSO) δ 8.17-8.09 (s, 1H), 7.81-7.71 (d, J = 9.2 Hz, 1H), 7.52-7.23 (bs, 1H), 7.22-6.97 (m, 2H), 3.96-3.81 (m, 1H), 3.81-3.67 (m, 1H), 3.49-3.36 (m, 1H), 3.27-3.18 (m, 1H), 2.84-2.73 (m, 1H), 2.26-2.13 (m, 7H), 1.91-1.76 (m, 1H). |
| 254 | D | | ethyl 4-[(4-aminopyrido[3,2-d]pyrimidin-6-yl)amino]piperidine-1-carboxylate | | / | 1H NMR (400 MHz, DMSO) δ 8.15-8.11 (s, 1H), 7.67-7.60 (d, J = 9.1 Hz, 1H), 7.18-7.10 (d, J = 7.6 Hz, 1H), 7.00-6.95 (d, J = 9.1 Hz, 1H), 4.32-4.18 (m, 1H), 4.10-4.01 (q, J = 7.1 Hz, 2H), 3.97-3.87 (d, J = 13.3 Hz, 2H), 3.15-2.97 (m, 2H), 2.02-1.92 (m, 2H), 1.39-1.23 (m, 2H), 1.23-1.15 (t, J = 7.1 Hz, 3H). |
| 255 | D | | 6-(3,4,6,7,8,8a-hexahydro-1H-pyrrolo[1,2-a]pyrazin-2-yl)pyrido[3,2-d]pyrimidin-4-amine | | / | 1H NMR (400 MHz, DMSO) δ 8.19-8.12 (s, 1H), 7.81-7.74 (d, J = 9.3 Hz, 1H), 7.50-7.43 (d, J = 9.4 Hz, 1H), 7.43-7.22 (bs, 2H), 4.75-4.63 (d, J = 12.0 Hz, 1H), 4.58-4.46 (d, J = 12.8 Hz, 1H), 3.12-2.99 (m, 2H), 2.99-2.88 (m, 1H), 2.65-2.54 (dd, J = 12.3, 10.3 Hz, 1H), 2.22-2.10 (m, 1H), 2.10-2.01 (m, 1H), 2.01-1.81 (m, 2H), 1.81-1.62 (m, 2H), 1.49-1.32 (m, 1H). |
| 256 | D | | N6-cyclopentyl-pyrido[3,2-d]pyrimidin-4,6-diamine | | / | 1H NMR (400 MHz, DMSO) δ 8.13-8.09 (s, 1H), 7.64-7.56 (d, J = 9.1 Hz, 1H), 7.21-7.15 (d, J = 6.8 Hz, 1H), 7.01-6.94 (d, J = 9.1 Hz, 1H), 4.45-4.31 (h, J = 6.8 Hz, 1H), 2.12-1.95 (m, 2H), 1.75-1.51 (m, 4H), 1.51-1.36 (m, 2H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 257 | D | | 4-(4-amino-pyrido[3,2-d]pyrimidin-6-yl)-N-cyclopentyl-morpholine-2-carboxamide | | / | 1H NMR (400 MHz, DMSO) δ 8.23-8.15 (s, 1H), 7.87-7.78 (d, J = 9.3 Hz, 1H), 7.76-7.71 (d, J = 7.7 Hz, 1H), 7.54-7.17 (d, J = 9.4 Hz, 3H), 4.43-4.30 (m, 2H), 4.16-3.92 (m, 3H), 3.72-3.58 (m, 1H), 3.17-2.98 (m, 2H), 1.87-1.71 (m, 2H), 1.71-1.57 (m, 2H), 1.57-1.40 (m, 4H). |
| 258 | D | | 6-[3-(6-methyl-2-pyridyl)-1-piperidyl]pyrido[3,2-d]pyrimidin-4-amine | | / | 1H NMR (400 MHz, DMSO) δ 8.20-8.12 (s, 1H), 7.80-7.72 (d, J = 9.3 Hz, 1H), 7.66-7.59 (t, J = 7.7 Hz, 1H), 7.53-7.47 (d, J = 9.4 Hz, 1H), 7.42-7.18 (bs, 2H), 7.19-7.14 (d, J = 7.7 Hz, 1H), 7.13-7.08 (d, J = 7.6 Hz, 1H), 4.68-4.56 (d, J = 13.1 Hz, 2H), 3.26-3.16 (dd, J = 13.0, 11.2 Hz, 1H), 3.09-2.95 (m, 1H), 2.95-2.81 (m, 1H), 2.47-2.45 (s, 3H), 2.07-1.73 (m, 3H), 1.73-1.50 (m, 1H). |
| 259 | D | | tert-butyl 4-(4-aminopyrido[3,2-d]pyrimidin-6-yl)piperazine-1-carboxylate | | / | 1H NMR (400 MHz, DMSO) δ 8.21-8.13 (s, 1H), 7.86-7.76 (d, J = 9.3 Hz, 1H), 7.49-7.27 (d, J = 9.3 Hz, 3H), 3.78-3.63 (m, 4H), 3.54-3.39 (m, 4H), 1.48-1.36 (s, 9H). |
| 260 | D | | 6-[4-(5-methyl-1,2,4-oxadiazol-3-yl)-1-piperidyl]pyrido[3,2-d]pyrimidin-4-amine | | / | 1H NMR (400 MHz, DMSO) δ 8.20-8.12 (s, 1H), 7.83-7.75 (d, J = 9.3 Hz, 1H), 7.53-7.47 (d, J = 9.4 Hz, 1H), 7.47-7.19 (bs, 2H), 4.60-4.49 (d, J = 13.4 Hz, 2H), 3.24-3.05 (m, 3H), 2.59-2.53 (s, 3H), 2.12-1.94 (m, 2H), 1.83-1.55 (m, 2H). |
| 261 | F | | 1-[3-(4-amino-quinazolin-6-yl)phenyl]-3-cyclopentyl-urea | | / | 1H NMR (400 MHz, DMSO) δ 8.51-8.45 (d, J = 1.8 Hz, 1H), 8.45-8.40 (s, 1H), 8.40-8.37 (s, 1H), 8.03-7.95 (dd, J = 8.7, 1.9 Hz, 1H), 7.95-7.76 (s, 2H), 7.76-7.70 (d, J = 8.7 Hz, 1H), 7.43-7.28 (m, 3H), 6.33-6.20 (d, J = 7.2 Hz, 1H), 4.04-3.90 (dd, J = 13.4, 6.7 Hz, 1H), 1.93-1.80 (m, 2H), 1.74-1.46 (m, 4H), 1.46-1.32 (m, 2H). |

| Ex. No. | General Method | Structure/Name | IUPAC name | Isolated Yield | LCMS $R_T$ (min), M + H⁺, method | ¹H NMR (ppm) |
|---|---|---|---|---|---|---|
| 262 | L | | N-[3-(4-amino-quinazolin-6-yl)phenyl]-2-(2-oxopyrrolidin-1-yl)acetamide | | / | 1H NMR (400 MHz, DMSO) δ 10.26-10.17 (s, 1H), 8.56-8.48 (s, 1H), 8.43-8.36 (s, 1H), 8.33-8.25 (s, 1H), 8.07-7.97 (m, 2H), 7.97-7.77 (bs, 2H), 7.81-7.69 (d, J = 8.7 Hz, 1H), 7.63-7.55 (d, J = 7.8 Hz, 1H), 7.55-7.38 (m, 2H), 4.12-4.02 (s, 2H), 3.50-3.43 (m, 5H), 2.36-2.20 (t, J = 8.1 Hz, 2H), 2.08-1.92 (m, 2H). |
| 263 | L | | N-[3-(4-amino-pyrido[3,2-d]pyrimidin-6-yl)-5-fluoro-phenyl]-2-cyclopentyl-acetamide | | / | 1H NMR (400 MHz, DMSO) δ 10.20-10.17 (s, 1H), 8.44-8.42 (s, 1H), 8.30-8.24 (d, J = 8.9 Hz, 1H), 8.21-8.16 (d, J = 8.8 Hz, 1H), 8.15-8.12 (s, 1H), 8.11-8.01 (d, J = 12.1 Hz, 3H), 7.78-7.69 (d, J = 11.1 Hz, 1H), 2.40-2.20 (m, 3H), 1.84-1.72 (m, 2H), 1.68-1.46 (m, 4H), 1.29-1.15 (m, 2H). |
| 264 | A | | 2-[3-(4-amino-quinazolin-6-yl)phenyl]ethanol | | / | 1H NMR (400 MHz, DMSO) δ 8.56-8.50 (d, J = 1.7 Hz, 1H), 8.40-8.36 (s, 1H), 8.13-8.06 (dd, J = 8.7, 1.8 Hz, 1H), 8.05-7.76 (bs, 2H), 7.76-7.69 (d, J = 8.7 Hz, 1H), 7.68-7.64 (m, 2H), 7.46-7.38 (t, J = 7.6 Hz, 1H), 7.29-7.24 (d, J = 7.6 Hz, 1H), 4.75-4.62 (s, 1H), 3.75-3.65 (t, J = 6.8 Hz, 2H), 2.89-2.78 (t, J = 7.1 Hz, 2H). |
| 265 | A | | 3-(4-amino-quinazolin-6-yl)phenol | | / | 1H NMR (400 MHz, DMSO) δ 8.53-8.48 (s, 1H), 8.39-8.37 (s, 1H), 8.05-7.98 (dd, J = 8.7, 1.8 Hz, 1H), 7.98-7.73 (bs, 2H), 7.73-7.69 (d, J = 8.7 Hz, 1H), 7.34-7.27 (t, J = 7.8 Hz, 1H), 7.25-7.21 (d, J = 7.8 Hz, 1H), 7.20-7.17 (s, 1H), 6.84-6.78 (dd, J = 7.8, 1.7 Hz, 1H). |
| 266 | A | | 6-(3-amino-4-fluoro-phenyl)quinazolin-4-amine | | / | 1H NMR (400 MHz, DMSO) δ 8.45-8.40 (d, J = 1.8 Hz, 1H), 8.39-8.34 (s, 1H), 7.97-7.90 (dd, J = 8.7, 1.9 Hz, 1H), 7.91-7.72 (bs, 2H), 7.73-7.67 (d, J = 8.7 Hz, 1H), 7.18-7.08 (m, 2H), 6.97-6.90 (m, 1H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 267 | A | | 6-(3-ethoxy-phenyl)quinazolin-4-amine | / | | 1H NMR (400 MHz, DMSO) δ 8.58-8.52 (d, J = 1.9 Hz, 1H), 8.41-8.35 (s, 1H), 8.15-8.08 (dd, J = 8.7, 2.0 Hz, 1H), 8.05-7.75 (bs, 2H), 7.75-7.70 (d, J = 8.7 Hz, 1H), 7.44-7.35 (m, 3H), 7.00-6.93 (dt, J = 7.4, 2.1 Hz, 1H), 4.21-4.08 (q, J = 7.0 Hz, 2H), 1.44-1.32 (t, J = 7.0 Hz, 3H). |
| 268 | A | | 6-phenyl-quinazolin-4-amine | / | | 1H NMR (400 MHz, DMSO) δ 8.58-8.55 (d, J = 1.9 Hz, 1H), 8.40-8.38 (s, 1H), 8.13-8.08 (dd, J = 8.7, 2.0 Hz, 1H), 7.86-7.82 (d, J = 7.4 Hz, 2H), 7.75-7.71 (d, J = 8.7 Hz, 1H), 7.56-7.49 (t, J = 7.7 Hz, 2H), 7.44-7.38 (t, J = 7.3 Hz, 1H). |
| 269 | A | | 6-(5-amino-2-fluoro-phenyl)quinazolin-4-amine | / | | 1H NMR (400 MHz, DMSO) δ 8.41-8.37 (s, 1H), 8.37-8.32 (s, 1H), 7.91-7.73 (m, 3H), 7.73-7.68 (d, J = 8.6 Hz, 1H), 7.03-6.96 (dd, J = 10.5, 8.8 Hz, 1H), 6.76-6.68 (dd, J = 6.8, 2.8 Hz, 1H), 6.62-6.56 (m, 1H), 5.12-5.03 (s, 2H). |
| 270 | D | | N6-benzylpyrido[3,2-d]pyrimidine-4,6-diamine | / | | 1H NMR (400 MHz, DMSO) δ 8.16-8.10 (s, 1H), 7.72-7.63 (m, 2H), 7.45-7.38 (d, J = 7.4 Hz, 2H), 7.36-7.29 (t, J = 7.5 Hz, 2H), 7.27-7.19 (t, J = 7.3 Hz, 1H), 7.08-7.04 (d, J = 9.1 Hz, 1H), 4.73-4.63 (d, J = 5.8 Hz, 2H). |
| 271 | D | | 6-[3-(4-methyl-1H-pyrazol-3-yl)-1-piperidyl]pyrido[3,2-d]pyrimidin-4-amine | / | | 1H NMR (400 MHz, DMSO) δ 12.55-12.07 (m, 1H), 8.24-8.10 (s, 1H), 7.83-7.71 (d, J = 9.3 Hz, 1H), 7.60-7.01 (m, 4H), 4.75-4.47 (dd, J = 27.8, 12.0 Hz, 2H), 3.11-2.90 (m, 2H), 2.90-2.73 (s, 1H), 2.04-2.01 (s, 3H), 2.01-1.75 (m, 3H), 1.69-1.49 (m, 1H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 272 | D | | 6-[3-(4-methyl-1H-pyrazol-3-yl)-1-piperidyl]pyrido[3,2-d]pyrimidin-4-amine | / | | 1H NMR (400 MHz, DMSO) δ 12.51-12.05 (s, 1H), 8.20-8.11 (s, 1H), 7.81-7.71 (d, J = 9.3 Hz, 1H), 7.55-6.98 (m, 4H), 4.70-4.49 (m, 2H), 3.10-2.89 (m, 2H), 2.89-2.73 (s, 1H), 2.06-2.00 (s, 3H), 2.00-1.73 (m, 3H), 1.69-1.47 (m, 1H). |
| 273 | D | | 6-[3-(4,6-dimethyl-pyrimidin-2-yl)-1-piperidyl]pyrido[3,2-d]pyrimidin-4-amine | / | | 1H NMR (400 MHz, DMSO) δ 8.17-8.13 (s, 1H), 7.80-7.73 (d, J = 9.3 Hz, 1H), 7.53-7.46 (d, J = 9.4 Hz, 1H), 7.46-7.14 (m, 2H), 7.13-7.08 (s, 1H), 4.70-4.60 (d, J = 12.2 Hz, 1H), 4.60-4.50 (d, J = 13.3 Hz, 1H), 3.41-3.29 (m, 1H), 3.16-3.03 (m, 1H), 3.02-2.89 (m, 1H), 2.43-2.37 (s, 6H), 2.11-2.01 (m, 1H), 1.99-1.83 (m, 1H), 1.83-1.75 (m, 1H), 1.69-1.49 (m, 1H). |
| 274 | D | | 6-[1-(4-amino-pyrido[3,2-d]pyrimidin-6-yl)-3-piperidyl]-N,N-dimethyl-pyridine-2-carboxamide | / | | 1H NMR (400 MHz, DMSO) δ 8.17-8.14 (s, 1H), 7.92-7.83 (t, J = 7.8 Hz, 1H), 7.81-7.73 (d, J = 9.3 Hz, 1H), 7.53-7.48 (d, J = 9.4 Hz, 1H), 7.48-7.44 (d, J = 7.8 Hz, 1H), 7.4 -7.40 (d, J = 7.6 Hz, 1H), 7.39-7.11 (m, 2H), 4.74-4.65 (d, J = 12.0 Hz, 1H), 4.65-4.55 (d, J = 13.0 Hz, 1H), 3.28-3.18 (m, 1H), 3.09-2.91 (m, 8H), 2.10-1.97 (m, 1H), 1.97-1.75 (m, 2H), 1.70-1.54 (m, 1H). |
| 275 | D | | 6-[3-[(5-methyl-2-pyridyl)methyl]pyrrolidin-1-yl]pyrido[3,2-d]pyrimidin-4-amine | / | | 1H NMR (400 MHz, DMSO) δ 8.39- 8.30 (s, 1H), 8.16-8.10 (s, 1H), 7.79-7.71 (d, J = 9.2 Hz, 1H), 7.58-7.50 (dd, J = 7.9, 2.0 Hz, 1H), 7.46-7.24 (bs, 1H), 7.26-7.19 (d, J = 7.9 Hz, 1H), 7.10-7.03 (d, J = 9.2 Hz, 1H), 7.02-6.77 (bs, 1H), 3.78-3.64 (m, 2H), 3.55-3.42 (m, 1H), 3.27-3.20 (m, 1H), 2.95-2.70 (m, 3H), 2.10-1.97 (m, 1H), 1.82-1.67 (m, 1H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 276 | D | | 6-[3-(pyrimidin-2-ylmethyl)pyrrolidin-1-yl]pyrido[3,2-d]pyrimidin-4-amine | | / | 1H NMR (400 MHz, DMSO) δ 8.80-8.72 (d, J = 4.9 Hz, 2H), 8.18-8.11 (s, 1H), 7.80-7.71 (d, J = 9.2 Hz, 1H), 7.41-7.35 (t, J = 4.9 Hz, 1H), 7.09-7.03 (d, J = 9.2 Hz, 1H), 3.85-3.65 (m, 2H), 3.55-3.44 (m, 1H), 3.30-3.23 (m, 1H), 3.15-3.00 (m, 2H), 2.94-2.84 (m, 1H), 2.18-2.08 (m, 1H), 1.84-1.72 (m, 1H). |
| 277 | D | | 6-[3-[6-(dimethylamino)-2-pyridyl]-1-piperidyl]pyrido[3,2-d]pyrimidin-4-amine | | / | 1H NMR (400 MHz, DMSO) δ 8.18-8.13 (s, 1H), 7.80-7.73 (d, J = 9.3 Hz, 1H), 7.52-7.41 (m, 2H), 6.57-6.51 (d, J = 7.2 Hz, 1H), 6.51-6.46 (d, J = 8.4 Hz, 1H), 4.68-4.55 (m, 2H), 3.24-3.13 (m, 1H), 3.04-2.99 (m, 7H), 2.82-2.63 (m, 1H), 2.04-1.94 (m, 1H), 1.93-1.76 (m, 2H), 1.66-1.55 (m, 1H). |
| 278 | D | | 6-[3-(pyrimidin-2-ylmethyl)-1-piperidyl]pyrido[3,2-d]pyrimidin-4-amine | | / | 1H NMR (400 MHz, DMSO) δ 8.78-8.73 (d, J = 4.9 Hz, 2H), 8.21-8.12 (s, 1H), 7.79-7.71 (d, J = 9.3 Hz, 1H), 7.52-7.32 (m, 3H), 7.17-6.86 (bs, 1H), 4.45-4.32 (m, 2H), 3.12-2.93 (m, 2H), 2.93-2.74 (m, 2H), 2.27-2.13 (m, 1H), 1.81-1.64 (m, 2H), 1.51-1.26 (m, 2H). |
| 279 | D | | 6-[3-(4-methylsulfonyl-1H-pyrazol-5-yl)-1-piperidyl]pyrido[3,2-d]pyrimidin-4-amine | | / | 1H NMR (400 MHz, DMSO) δ 13.65-13.44 (s, 1H), 8.19-8.14 (s, 1H), 7.83-7.74 (d, J = 9.3 Hz, 1H), 7.54-7.46 (d, J = 9.4 Hz, 1H), 7.44-7.11 (bs, 2H), 4.88-4.75 (d, J = 12.0 Hz, 1H), 4.68-4.54 (d, J = 13.5 Hz, 1H), 3.22-3.18 (s, 3H), 3.13-2.86 (m, 3H), 2.10-2.01 (m, 1H), 2.01-1.89 (m, 1H), 1.89-1.78 (m, 1H), 1.70-1.53 (m, 1H). |

-continued

| Ex. No. | General Method | Structure/Name | IUPAC name | Isolated Yield | LCMS R_T (min), M + H+, method | 1H NMR (ppm) |
|---|---|---|---|---|---|---|
| 280 | D | | 6-[3-[6-(dimethyl-amino)pyrazin-2-yl]-1-piperidyl]pyrido[3,2-d]pyrimidin-4-amine | | / | 1H NMR (400 MHz, DMSO) δ 8.18-8.14 (s, 1H), 8.01-7.97 (s, 1H), 7.82-7.78 (s, 1H), 7.78-7.74 (d, J = 9.3 Hz, 1H), 7.54-7.47 (d, J = 9.4 Hz, 1H), 4.69-4.60 (d, J = 11.9 Hz, 1H), 4.60-4.52 (m, 1H), 3.26-3.17 (m, 1H), 3.11-2.97 (s, 7H), 2.86-2.74 (m, 1H), 2.05-1.96 (m, 1H), 1.96-1.77 (m, 2H), 1.71-1.53 (m, 1H). |
| 281 | D | | 6-[3-[[6-(methyl-amino)pyrimidin-4-yl]methyl]pyrrolidin-1-yl]pyrido[3,5-d]pyrimidin-4-amine | | / | 1H NMR (400 MHz, DMSO) δ 8.39- 8.32 (s, 1H), 8.16-8.10 (t, J = 4.4 Hz, 1H), 7.78-7.73 (d, J = 9.2 Hz, 1H), 7.23-7.15 (s, 1H), 7.10-7.03 (d, J = 9.2 Hz, 1H), 6.36-6.31 (s, 1H), 3.77-3.65 (m, 2H), 3.53-3.43 (m, 1H), 3.26-3.17 (m, 1H), 2.82-2.77 (d, J = 4.3 Hz, 3H), 2.77-2.58 (m, 3H), 2.14-2.03 (m, 1H), 1.78- 1.67 (m, 1H). |
| 282 | D | | 6-[3-(2-methyl-pyrimidin-4-yl)pyrrolidin-1-yl]pyrido[3,2-d]pyrimidin-4-amine | | / | 1H NMR (400 MHz, DMSO) δ 8.66-8.61 (d, J = 5.2 Hz, 1H), 8.18-8.11 (s, 1H), 7.83-7.75 (d, J = 9.2 Hz, 1H), 7.38-7.32 (d, J = 5.2 Hz, 1H), 7.17-7.12 (d, J = 9.2 Hz, 1H), 4.14-4.02 (s, 1H), 3.87-3.76 (m, 1H), 3.76-3.53 (m, 3H), 2.63-2.58 (s, 3H), 2.47-2.37 (m, 1H), 2.37-2.21 (m, 1H). |
| 283 | D | | 6-[3-[6-(dimethyl-amino)-2-methyl-pyrimidin-4-yl]pyrrolidin-1-yl]pyrido[3,2-d]pyrimidin-4-amine | | / | 1H NMR (400 MHz, DMSO) δ 8.18-8.11 (s, 1H), 7.83-7.74 (d, J = 9.2 Hz, 1H), 7.47-7.19 (s, 1H), 7.17-7.10 (d, J = 9.2 Hz, 1H), 7.11-6.96 (m, 1H), 6.49-6.44 (s, 1H), 4.05-3.94 (s, 1H), 3.86-3.78 (s, 1H), 3.69-3.62 (m, 1H), 3.62-3.51 (m, 1H), 3.51-3.41 (m, 1H), 3.06-3.02 (s, 6H), 2.37-2.35 (s, 3H), 2.34-2.23 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 284 | D | | 6-[3-[[6-(dimethyl-amino)pyrimidin-4-yl]methyl]-1-piperidyl]pyrido[3,2-d]pyrimidin-4-amine | | / | 1H NMR (400 MHz, DMSO) δ 8.47-8.39 (s, 1H), 8.18-8.12 (s, 1H), 7.80-7.71 (d, J = 9.3 Hz, 1H), 7.50-7.28 (m, 2H), 7.17-6.97 (bs, 1H), 6.53-6.49 (s, 1H), 4.41-4.29 (t, J = 11.9 Hz, 2H), 3.16-2.99 (m, 7H), 2.89-2.78 (dd, J = 13.0, 10.2 Hz, 1H), 2.73-2.58 (m, 1H), 2.47-2.40 (m, 1H), 2.13-1.98 (m, 1H), 1.79-1.65 (m, 2H), 1.49-1.35 (m, 1H), 1.35-1.21 (m, 1H). |
| 285 | D | | 6-[3-(1H-pyrazol-3-yl)pyrrolidin-1-yl]pyrido[3,2-d]pyrimidin-4-amine | | / | 1H NMR (400 MHz, DMSO) δ 12.85-12.41 (d, J = 81.7 Hz, 1H), 8.19-8.08 (s, 1H), 7.84-7.72 (d, J = 9.1 Hz, 1H), 7.69-6.87 (m, 4H), 6.29-6.10 (s, 1H), 4.16-3.92 (m, 1H), 3.84-3.69 (m, 1H), 3.69-3.51 (m, 3H), 2.43-2.27 (m, 1H), 2.27-2.06 (m, 1H). |
| 286 | D | | 6-[3-[[6-(dimethyl-amino)pyrimidin-4-yl]methyl]pyrrolidin-1-yl]pyrido[3,2-d]pyrimidin-4-amine | | / | 1H NMR (400 MHz, DMSO) δ 8.43-8.40 (s, 1H), 8.17-8.13 (s, 1H), 7.81-7.72 (d, J = 9.2 Hz, 1H), 7.45-7.19 (bs, 1H), 7.09-7.03 (d, J = 9.2 Hz, 1H), 7.03-6.82 (m, 1H), 6.59-6.56 (s, 1H), 3.78-3.63 (m, 2H), 3.55-3.42 (m, 1H), 3.28-3.20 (m, 1H), 2.84-2.62 (m, 3H), 2.15-2.01 (m, 1H), 1.82-1.66 (m, 1H). |
| 287 | D | | 6-[3-[2-(dimethyl-amino)pyrimidin-4-yl]-1-piperidyl]pyrido[3,2-d]pyrimidin-4-amine | | / | 1H NMR (400 MHz, DMSO) δ 8.28-8.23 (d, J = 5.0 Hz, 1H), 8.18-8.15 (s, 1H), 7.80-7.74 (d, J = 9.3 Hz, 1H), 7.54-7.47 (d, J = 9.4 Hz, 1H), 7.47-7.04 (bs, 2H), 6.64-6.57 (d, J = 5.0 Hz, 1H), 4.69-4.59 (d, J =11.7 Hz, 1H), 4.59-4.48 (d, J = 13.3 Hz, 1H), 3.28-3.16 (dd, J= 13.0, 10.8 Hz, 1H), 3.16-3.10 (s, 6H), 3.10-2.98 (t, J = 11.3 Hz, 1H), 2.79-2.64 (m, 1H), 2.04-1.94 (m, 1H), 1.90-1.75 (m, 2H), 1.67-1.49 (m, 1H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 288 | D | | 6-[1-(4-amino-pyrido[3,2-d]pyrimidin-6-yl)-3-piperidyl]pyridine-2-carboxamide | / | | 1H NMR (400 MHz, DMSO) δ 8.19-8.10 (s, 2H), 7.98-7.86 (m, 2H), 7.80-7.73 (d, J = 9.3 Hz, 1H), 7.67-7.61 (s, 1H), 7.60-7.52 (m, 2H), 7.37-7.16 (s, 2H), 4.74-4.58 (m, 2H), 3.47-3.34 (m, 1H), 3.11-2.93 (m, 2H), 2.09-1.89 (m, 2H), 1.87-1.78 (m, 1H), 1.73-1.55 (m, 1H). |
| 289 | D | | 6-[3-[3-(dimethyl-amino)pyrazin-2-yl]-1-piperidyl]pyrido[3,2-d]pyrimidin-4-amine | / | | 1H NMR (400 MHz, DMSO) δ 8.18-8.12 (m, 2H), 8.11-8.07 (d, J = 2.5 Hz, 1H), 7.81-7.75 (d, J = 9.3 Hz, 1H), 7.54-7.47 (d, J = 9.4 Hz, 1H), 7.41-7.08 (d, J = 44.8 Hz, 2H), 4.94-4.82 (d, J = 9.4 Hz, 1H), 4.62-4.54 (d, J = 13.2 Hz, 1H), 3.22-3.09 (m, 2H), 3.09-2.97 (m, 1H), 1.98-1.74 (m, 3H), 1.66-1.50 (m, 1H). |
| 290 | D | | 6-[3-(2-methyl-pyrimidin-4-yl)-1-piperidyl]pyrido[3,2-d]pyrimidin-4-amine | / | | 1H NMR (400 MHz, DMSO) δ 8.63-8.58 (d, J = 5.2 Hz, 1H), 8.18-8.14 (s, 1H), 7.82-7.73 (d, J = 9.3 Hz, 1H), 7.54-7.48 (d, J = 9.4 Hz, 1H), 7.34-7.30 (d, J = 5.2 Hz, 1H), 4.74-4.63 (d, J = 13.1 Hz, 1H), 4.57-4.49 (d, J = 13.2 Hz, 1H), 3.30-3.19 (m, 1H), 3.10-3.01 (m, 1H), 2.94-2.82 (m, 1H), 2.63-2.58 (s, 3H), 2.06-1.94 (m, 1H), 1.91-1.75 (m, 2H), 1.68-1.54 (m, 1H). |
| 291 | D | | 6-(3-pyrimidin-4-yl-1-piperidyl)pyrido[3,2-d]pyrimidin-4-amine | / | | 1H NMR (400 MHz, DMSO) δ 9.18-9.09 (s, 1H), 8.76-8.70 (d, J = 5.2 Hz, 1H), 8.18-8.15 (s, 1H), 7.81-7.74 (d, J = 9.3 Hz, 1H), 7.58-7.48 (m, 2H), 7.48-7.16 (s, 2H), 4.76-4.68 (d, J = 12.8 Hz, 1H), 4.59-4.51 (d, J = 13.3 Hz, 1H), 3.29-3.21 (m, 1H), 3.10-2.99 (m, 1H), 2.99-2.88 (m, 1H), 2.07-1.98 (m, 1H), 1.94-1.77 (m, 2H), 1.70-1.57 (m, 1H). |

| Ex. No. | General Method | Structure/Name | IUPAC name | Isolated Yield | LCMS $R_T$ (min), M + H⁺, method | ¹H NMR (ppm) |
|---|---|---|---|---|---|---|
| 292 | D | | 6-[3-[5-(trifluoromethyl)-1H-pyrazol-3-yl]-1-piperidyl]pyrido[3,2-d]pyrimidin-4-amine | / | | 1H NMR (400 MHz, DMSO) δ 13.58-13.45 (s, 1H), 8.20-8.11 (s, 1H), 7.85-7.72 (d, J = 9.3 Hz, 1H), 7.60-7.50 (d, J = 9.4 Hz, 1H), 7.50-7.24 (s, 2H), 6.70-6.59 (s, 1H), 4.86-4.77 (d, J = 11.7 Hz, 1H), 4.50-4.42 (d, J = 13.3 Hz, 1H), 3.09-2.90 (m, 3H), 2.19-2.10 (m, 1H), 1.85-1.66 (m, 2H), 1.66-1.50 (m, 1H). |
| 293 | D | | 6-(3-pyrazin-2-yl-1-piperidyl)pyrido[3,2-d]pyrimidin-4-amine | / | | 1H NMR (400 MHz, DMSO) δ 8.74-8.65 (d, J = 1.2 Hz, 1H), 8.64-8.56 (m, 1H), 8.55-8.49 (d, J = 2.5 Hz, 1H), 8.23-8.12 (s, 1H), 7.81-7.74 (d, J = 9.3 Hz, 1H), 7.57-7.49 (d, J = 9.4 Hz, 1H), 7.43-7.19 (s, 2H), 4.82-4.70 (d, J = 13.2 Hz, 1H), 4.65-4.52 (d, J = 13.1 Hz, 1H), 3.28-3.18 (m, 1H), 3.10-2.95 (m, 2H), 2.09-1.98 (d, J = 12.6 Hz, 1H), 1.98-1.77 (m, 2H), 1.74-1.55 (m, 1H). |
| 294 | D | | 6-[3-(pyrazin-2-ylmethyl)-1-piperidyl]pyrido[3,2-d]pyrimidin-4-amine | / | | 1H NMR (400 MHz, DMSO) δ 8.66-8.54 (d, J = 3.7 Hz, 2H), 8.54-8.46 (s, 1H), 8.21-8.11 (d, J = 3.9 Hz, 1H), 7.81-7.70 (dd, J = 9.2, 3.9 Hz, 1H), 7.45-7.37 (dd, J = 9.2, 3.9 Hz, 1H), 4.50-4.27 (dd, J = 30.6, 12.7 Hz, 2H), 3.13-2.99 (s, 1H), 2.99-2.80 (m, 2H), 2.80-2.65 (m, 1H), 2.17-1.97 (s, 1H), 1.76-1.64 (s, 2H), 1.51-1.22 (m, 2H). |
| 295 | D | | 6-[3-[5-(dimethylamino)-2-pyridyl]-1-piperidyl]pyrido[3,2-d]pyrimidin-4-amine | / | | 1H NMR (400 MHz, DMSO) δ 8.17-8.13 (s, 1H), 8.12-8.05 (d, J = 3.0 Hz, 1H), 7.80-7.72 (d, J = 9.3 Hz, 1H), 7.53-7.44 (d, J = 9.4 Hz, 1H), 7.20-7.13 (d, J = 8.6 Hz, 1H), 7.13-7.07 (m, 1H), 4.70-4.61 (d, J = 13.0 Hz, 1H), 4.61-4.50 (d, J = 11.9 Hz, 1H), 3.20-3.07 (dd, J = 24.1, 11.2 Hz, 1H), 3.01-2.92 (m, 1H), 2.84-2.74 (m, 1H), 2.03-1.91 (m, 1H), 1.91-1.74 (m, 2H), 1.70-1.53 (m, 1H). |

-continued

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 296 | D | | 6-[3-(4-methyl-pyrimidin-2-yl)-1-piperidyl]pyrido[3,2-d]pyrimidin-4-amine | / | | 1H NMR (400 MHz, DMSO) δ 8.65-8.57 (d, J = 5.1 Hz, 1H), 8.19-8.14 (s, 1H), 7.82-7.74 (d, J = 9.3 Hz, 1H), 7.53-7.46 (d, J = 9.4 Hz, 1H), 7.27-7.21 (d, J = 5.1 Hz, 1H), 4.73-4.63 (d, J = 12.7 Hz, 1H), 4.63-4.53 (d, J = 13.3 Hz, 1H), 3.14-2.94 (m, 2H), 2.48-2.44 (s, 3H), 2.14-2.04 (m, 1H), 1.97-1.76 (m, 2H), 1.70-1.53 (m, 1H). |
| 297 | D | | 6-[3-(2-pyridyl)-1-piperidyl]pyrido[3,2-d]pyrimidin-4-amine | / | | 1H NMR (400 MHz, DMSO) δ 8.59-8.50 (d, J = 4.2 Hz, 1H), 8.18-8.14 (s, 1H), 7.81-7.71 (m, 2H), 7.54-7.48 (d, J = 9.4 Hz, 1H), 7.42-7.36 (m, 1H), 7.28-7.22 (m, 1H), 4.69-4.60 (d, J = 13.0 Hz, 2H), 3.27-3.17 (m, 1H), 3.05-2.83 (m, 2H), 2.07-1.97 (m, 1H), 1.97-1.76 (m, 2H), 1.70-1.55 (m, 1H). |
| 298 | D | | 6-[3-(4-methyl-1,2,4-triazol-3-yl)-1-piperidyl]pyrido[3,2-d]pyrimidin-4-amine | / | | 1H NMR (400 MHz, DMSO) δ 8.41-8.34 (s, 1H), 8.19-8.15 (s, 1H), 7.82-7.74 (d, J = 9.3 Hz, 1H), 7.57-7.48 (d, J = 9.4 Hz, 1H), 7.45-7.20 (bs, 2H), 4.89-4.80 (d, J = 13.1 Hz, 1H), 4.60-4.49 (d, J = 13.4 Hz, 1H), 3.70-3.62 (s, 3H), 3.13-3.03 (m, 2H), 3.03-2.91 (m, 1H), 2.08-1.78 (m, 3H), 1.68-1.53 (qm, 1H). |
| 299 | D | | 6-[3-[5-(methoxymethyl)-1,2,4-oxadiazol-3-yl]-1-piperidyl]pyrido[3,2-d]pyrimidin-4-amine | / | | 1H NMR (400 MHz, DMSO) δ 8.18-8.14 (s, 1H), 7.82-7.76 (d, J = 9.3 Hz, 1H), 7.53-7.48 (d, J = 9.4 Hz, 1H), 7.47-7.13 (d, J = 72.0 Hz, 2H), 4.76-4.72 (s, 2H), 4.68-4.61 (d, J = 13.3 Hz, 1H), 4.41-4.31 (d, J = 13.3 Hz, 1H), 3.43-3.34 (d, J = 3.9 Hz, 4H), 3.28-3.19 (m, 1H), 3.16-3.04 (m, 1H), 2.15-2.04 (m, 1H), 1.92-1.75 (m, 2H), 1.70-1.57 (m, 1H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 300 | D | | 6-[1-(4-amino-pyrido[3,2-d]pyrimidin-6-yl)-3-piperidyl]-N-methyl-pyridine-2-carboxamide | | / | 1H NMR (400 MHz, DMSO) δ 8.72-8.60 (d, J = 4.8 Hz, 1H), 8.19-8.10 (s, 1H), 7.97-7.83 (dd, J = 15.6, 7.1 Hz, 2H), 7.80-7.72 (d, J = 9.3 Hz, 1H), 7.59-7.52 (dd, J = 11.5, 8.4 Hz, 2H), 7.45-7.12 (s, 2H), 4.74-4.55 (m, 2H), 3.48-3.39 (m, 1H), 3.11-2.94 (m, 2H), 2.88-2.82 (m, 3H), 2.10-1.87 (m, 2H), 1.87-1.78 (m, 1H), 1.71-1.58 (m, 1H). |
| 301 | D | | 6-[3-(5-methyl-sulfonylpyrimidin-4-yl)-1-piperidyl]pyrido[3,2-d]pyrimidin-4-amine | | / | 1H NMR (400 MHz, DMSO) δ 9.50-9.44 (s, 1H), 9.18-9.14 (s, 1H), 8.18-8.14 (s, 1H), 7.82-7.74 (d, J = 9.3 Hz, 1H), 7.56-7.48 (d, J = 9.4 Hz, 1H), 7.42-7.17 (s, 2H), 5.08-4.97 (d, J = 12.7 Hz, 1H), 4.63-4.51 (d, J = 13.3 Hz, 1H), 3.65-3.53 (m, 1H), 3.42-3.36 (s, 3H), 3.36-3.24 (s, 1H), 3.18-3.07 (t, J = 12.1 Hz, 1H), 2.05-1.93 (m, 2H), 1.88-1.74 (d, J = 13.4 Hz, 1H), 1.64-1.47 (m, 1H). |
| 302 | D | | 6-[3-(4-pyridyl)pyrrolidin-1-yl]pyrido[3,2-d]pyrimidin-4-amine | | / | 1H NMR (400 MHz, DMSO) δ 8.55-8.50 (d, J = 6.0 Hz, 2H), 8.19-8.13 (s, 1H), 7.83-7.77 (d, J = 9.2 Hz, 1H), 7.43-7.38 (d, J = 6.0 Hz, 2H), 7.19-7.12 (d, J = 9.2 Hz, 1H), 4.20-4.09 (s, 1H), 3.86-3.76 (d, J = 8.0 Hz, 1H), 3.65-3.49 (m, 3H), 2.46-2.42 (m, 1H), 2.25-2.07 (m, 1H). |
| 303 | K | | 4-amino-6-(3-fluorophenyl)-N-methyl-N-(1-methylpyrrolidin-3-yl)quinazoline-8-carboxamide | | / | 1H NMR (400 MHz, DMSO) δ 8.68-8.61 (s, 1H), 8.42-8.35 (m, 1H), 8.04-7.99 (m, 1H), 7.78-7.70 (m, 2H), 7.60-7.52 (m, 1H), 7.30-7.20 (m, 1H), 5.32-5.25 (s, 0.35H), 3.95-3.86 (m, 0.65H), 3.03-3.00 (s, 1.8H), 2.92-2.70 (m, 1H), 2.68-2.65 (s, 1.2H), 2.65-2.53 (m, 1H), 2.28-2.24 (m, 1.2H), 2.23-2.16 (m, 1H), 2.15-2.09 (m, 1.8H), 2.10-1.90 (m, 1H), 1.90-1.67 (m, 2H). |

| Ex. No. | General Method | Structure/Name | IUPAC name | Isolated Yield | LCMS R_T (min), M + H+, method | 1H NMR (ppm) |
|---|---|---|---|---|---|---|
| 304 | K | | 4-amino-6-(3-fluorophenyl)-N-(2-methoxyethyl)-N-methyl-quinazoline-8-carboxamide | | / | 1H NMR (400 MHz, DMSO) δ 8.68-8.61 (m, 1H), 8.43-8.36 (m, 1H), 8.05-7.99 (m, 1H), 7.78-7.68 (m, 2H), 7.61-7.52 (m, 1H), 7.30-7.20 (m, 1H), 3.89-3.77 (m, 0.5H), 3.66-3.59 (m, 1H), 3.59-3.47 (m, 0.5H), 3.47-3.37 (m, 0.5H), 3.35-3.33 (s, 1.4H), 3.29-3.12 (m, 1.5H), 3.11-3.10 (s, 1.7H), 3.09-3.08 (s, 1.6H), 2.76-2.74 (s, 1.3H). |
| 305 | K | | 4-amino-6-(3-fluorophenyl)-N-(2-pyrrolidin-1-ylethyl)quinazoline-8-carboxamide | | / | 1H NMR (400 MHz, DMSO) δ 11.27-11.19 (t, J = 5.3 Hz, 1H), 8.90-8.84 (d, J = 2.1 Hz, 1H), 8.83-8.75 (d, J = 2.1 Hz, 1H), 8.52-8.46 (s, 1H), 8.44-8.04 (m, 2H), 7.78-7.65 (m, 2H), 7.64-7.54 (m, 1H), 7.32-7.22 (m, 1H), 3.63-3.49 (m, 2H), 2.73-2.61 (t, J = 6.6 Hz, 2H), 2.57-2.52 (m, 4H), 1.75-1.69 (m, 4H). |
| 306 | A | | 6-(2-ethyl-4-pyridyl)pyrido[3,2-d]pyrimidin-4-amine | | / | 1H NMR (400 MHz, DMSO) δ 8.66-8.60 (d, J = 5.2 Hz, 1H), 8.57-8.51 (d, J = 8.8 Hz, 1H), 8.47-8.42 (s, 1H), 8.35-8.23 (d, J = 14.0 Hz, 2H), 8.23-8.14 (d, J = 8.6 Hz, 2H), 8.14-8.03 (s, 1H), 2.95-2.80 (q, J = 7.6 Hz, 2H), 1.37-1.28 (t, J = 7.6 Hz, 3H). |
| 307 | A | | 6-(2-methyl-4-pyridyl)pyrido[3,2-d]pyrimidin-4-amine | | / | 1H NMR (400 MHz, DMSO) δ 8.62-8.59 (d, J = 5.2 Hz, 1H), 8.54-8.51 (d, J = 8.8 Hz, 1H), 8.45-8.44 (s, 1H), 8.34-8.32 (s, 1H), 8.30-8.24 (s, 1H), 8.21-8.16 (m, 2H), 8.12-8.06 (s, 1H), 2.64-2.58 (s, 3H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 308 | K | | [4-amino-6-(3-fluorophenyl)quinazolin-8-yl]-[3-(dimethylamino)pyrrolidin-1-yl]methanone | | / | 1H NMR (400 MHz, DMSO) δ 8.68-8.63 (m, 1H), 8.44-8.39 (d, J = 3.1 Hz, 1H), 8.10-8.04 (s, 1H), 7.81-7.70 (m, 2H), 7.61-7.51 (dd, J = 14.5, 7.9 Hz, 1H), 7.30-7.18 (dd, J = 11.6, 5.4 Hz, 1H), 3.91-3.81 (m, 0.5H), 3.81-3.69 (m, 0.5H), 3.54-3.40 (m, 0.5H), 3.25-3.07 (m, 2H), 2.82-2.62 (m, 1.5H), 2.20-2.19 (s, 3H), 2.15-2.05 (m, 0.5H), 2.05-1.99 (s, 3H), 1.99-1.89 (m, 0.5H), 1.81-1.60 (m, 1H). |
| 309 | K | | [4-amino-6-(3-fluorophenyl)quinazolin-8-yl]-[4-(dimethylamino)-1-piperidyl]methanone | | / | 1H NMR (400 MHz, DMSO) δ 8.67-8.62 (s, 1H), 8.45-8.33 (d, J = 7.1 Hz, 1H), 8.23-7.80 (m, 3H), 7.80-7.70 (dd, J = 14.0, 7.7 Hz, 2H), 7.63-7.49 (dd, J = 12.7, 6.8 Hz, 1H), 7.29-7.20 (t, J = 8.5 Hz, 1H), 4.65-4.47 (m, 1H), 3.25-3.15 (m, 1H), 2.97-2.83 (m, 2.5H), 2.36-2.25 (s, 1H), 2.18-2.16 (s, 3H), 2.16-2.15 (s, 3H), 1.90-1.80 (m, 1H), 1.61-1.33 (m, 2.5H), 1.33-1.19 (d, J = 14.0 Hz, 1H). |
| 310 | K | | [4-amino-6-(3-fluorophenyl)quinazolin-8-yl]-(3-hydroxyazetidin-1-yl)methanone | | / | 1H NMR (400 MHz, DMSO) δ 8.70-8.65 (s, 1H), 8.46-8.43 (s, 1H), 8.10-8.07 (s, 1H), 7.77-7.70 (m, 2H), 7.60-7.52 (m, 1H), 7.30-7.21 (m, 1H), 4.54-4.46 (m, 1H), 4.33-4.23 (m, 1H), 3.95-3.86 (m, 1H), 3.86-3.78 (m, 1H), 3.67-3.59 (m, 1H). |
| 311 | K | | 4-amino-6-(3-fluorophenyl)-N-(oxetan-3-yl)quinazoline-8-carboxamide | | / | 1H NMR (400 MHz, DMSO) δ 11.72-11.65 (d, J = 6.3 Hz, 1H), 8.84-8.76 (s, 2H), 8.62-8.55 (s, 1H), 8.48-8.07 (m, 2H), 7.76-7.64 (m, 2H), 7.63-7.54 (m, 1H), 7.33-7.23 (m, 1H), 5.17-5.00 (m, 1H), 4.94-4.84 (t, J = 6.9 Hz, 2H), 4.67-4.55 (t, J = 6.4 Hz, 2H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 312 | K | | [4-amino-6-(3-fluorophenyl)quinazolin-8-yl]-(4-methyl-piperazin-1-yl)methanone | | / | 1H NMR (400 MHz, DMSO) δ 8.68-8.63 (s, 1H), 8.43-8.38 (s, 1H), 8.09-8.04 (s, 1H), 7.80-7.70 (m, 2H), 7.63-7.52 (dd, J = 14.4, 8.1 Hz, 1H), 7.30-7.21 (m, 1H), 3.86-3.77 (m, 1H), 3.67-3.54 (m, 1H), 3.10-2.99 (m, 2H), 2.39-2.26 (m, 2H), 2.23-2.17 (s, 3H), 2.17-2.09 (m, 1H). |
| 313 | D | | 6-[3-[(1-methyl-imidazol-2-yl)methyl]-1-piperidyl]pyrido[3,2-d]pyrimidin-4-amine | | / | 1H NMR (400 MHz, DMSO) δ 8.19-8.09 (s, 1H), 7.80-7.72 (d, J = 9.3 Hz, 1H), 7.54-7.46 (s, 2H), 7.46-7.39 (d, J = 9.4 Hz, 1H), 7.06-7.01 (s, 1H), 6.86-6.83 (s, 1H), 4.68-4.54 (d, J = 11.6 Hz, 1H), 4.37-4.26 (d, J = 13.5 Hz, 1H), 3.58-3.51 (s, 3H), 3.14-3.02 (dd, J = 17.8, 7.0 Hz, 1H), 2.79-2.68 (dd, J = 12.7, 10.4 Hz, 1H), 2.68-2.53 (m, 2H), 2.22-2.08 (m, 1H), 1.87-1.76 (m, 1H), 1.76-1.65 (m, 1H), 1.50-1.28 (m, 2H). |
| 314 | J | | N-[3-(4-amino-pyrido[3,2-d]pyrimidin-6-yl)-5-fluoro-phenyl]-2-pyrrolidin-1-yl-acetamide | | / | 1H NMR (400 MHz, DMSO) δ 9.97-9.91 (s, 1H), 8.44-8.41 (s, 1H), 8.37-8.33 (d, J = 8.9 Hz, 1H), 8.31-8.26 (s, 1H), 8.21-8.07 (m, 3H), 8.07-7.99 (s, 1H), 7.91-7.86 (d, J = 11.1 Hz, 1H), 2.67-2.59 (m, 4H), 1.83-1.76 (m, 4H). |
| 315 | L | | N-[6-(3-amino-5-fluoro-phenyl)pyrido[3,2-d]pyrimidin-4-yl]-2-pyrrolidin-1-yl-acetamide | | / | 1H NMR (400 MHz, DMSO) δ 11.83-11.71 (s, 1H), 9.01-8.93 (s, 1H), 8.48-8.38 (m, 2H), 7.30-7.20 (m, 2H), 6.54-6.49 (d, J = 11.3 Hz, 1H), 5.69-5.60 (s, 2H), 3.51-3.47 (s, 2H), 2.81-2.71 (m, 4H), 1.93-1.83 (m, 4H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 316 | A | | 3-(4-amino-pyrido[3,2-d]pyrimidin-6-yl)phenol | | / | 1H NMR (400 MHz, DMSO) δ 9.73-9.59 (s, 1H), 8.42-8.39 (s, 1H), 8.35-8.27 (d, J = 8.8 Hz, 1H), 8.14-8.08 (d, J = 8.8 Hz, 1H), 8.02-7.88 (s, 2H), 7.83-7.76 (d, J = 7.9 Hz, 1H), 7.76-7.71 (d, J = 1.9 Hz, 1H), 7.36-7.30 (t, J = 7.9 Hz, 1H), 6.96-6.86 (dd, J = 7.9, 2.3 Hz, 1H). |
| 317 | A | | 6-[6-(1-methyl-3-piperidyl)-3-pyridyl]quinazolin-4-amine | | / | 1H NMR (400 MHz, DMSO) δ 8.91-8.85 (s, 1H), 8.62-8.56 (m, 1H), 8.43-8.39 (s, 1H), 8.01-7.95 (d, J = 7.8 Hz, 1H), 7.91-7.86 (d, J = 7.7 Hz, 1H), 7.79-7.73 (d, J = 8.8 Hz, 1H), 7.32-7.27 (d, J = 7.3 Hz, 1H), 3.01-2.91 (d, J = 11.2 Hz, 2H), 2.84-2.67 (m, 1H), 2.30-2.25 (s, 3H), 2.17-2.06 (m, 2H), 1.98-1.84 (m, 4H). |
| 318 | D | | 5-[1-(4-amino-pyrido[3,2-d]pyrimidin-6-yl)-3-piperidyl]-2-methyl-pyrazol-3-ol | | / | 1H NMR (400 MHz, DMSO) δ 8.19-8.11 (s, 1H), 7.82-7.70 (d, J = 9.3 Hz, 1H), 7.52-7.44 (d, J = 9.4 Hz, 1H), 7.44-6.99 (m, 2H), 5.32-5.24 (s, 1H), 4.62-4.51 (d, J = 12.2 Hz, 1H), 4.51-4.38 (d, J = 13.4 Hz, 1H), 3.50-3.40 (s, 3H), 3.12-2.92 (m, 2H), 2.69-2.57 (m, 1H), 2.03-1.94 (d, J = 12.8 Hz, 1H), 1.83-1.49 (m, 3H). |
| 319 | A | | 6-[2-(2-pyrrolidin-1-ylethylamino)-4-pyridyl]quinazolin-4-amine | | / | 1H NMR (400 MHz, DMSO) δ 8.62-8.56 (s, 1H), 8.42-8.38 (s, 1H), 8.32-8.16 (m, 2H), 8.11-8.02 (m, 2H), 7.77-7.72 (d, J = 8.7 Hz, 1H), 6.98-6.92 (d, J = 5.4 Hz, 1H), 6.90-6.84 (s, 1H), 6.53-6.44 (t, J = 5.4 Hz, 1H), 3.49-3.40 (t, J = 6.7 Hz, 2H), 2.73-2.65 (t, J = 6.7 Hz, 2H), 2.64-2.55 (m, 4H), 1.80-1.63 (m, 4H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 320 | A | 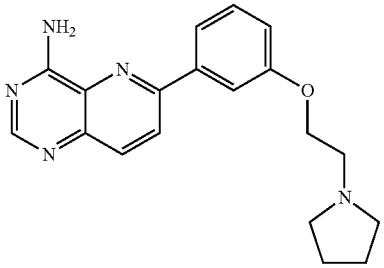 [SMILES: Nc1ncnc2ccc(-c3cccc(OCCN4CCCC4)c3)nc12] | 6-[3-(2-pyrrolidin-1-ylethoxy)phenyl]pyrido[3,2-d]pyrimidin-4-amine | | / | 1H NMR (400 MHz, DMSO) δ 8.48-8.39 (m, 2H), 8.15-8.08 (m, 2H), 8.00-7.89 (m, 3H), 7.47-7.40 (t, J = 7.9 Hz, 1H), 7.12-7.03 (dd, J = 8.1, 2.3 Hz, 1H), 4.27-4.18 (t, J = 5.9 Hz, 2H), 2.90-2.81 (t, J = 5.9 Hz, 2H), 2.59-2.53 (m, 4H), 1.76-1.66 (m, 4H). |
| 321 | D | 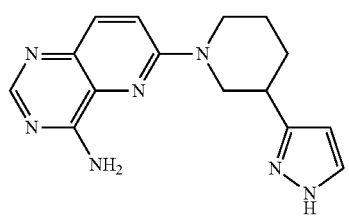 [SMILES: Nc1ncnc2ccc(N3CCCC(c4cc[nH]n4)C3)nc12] | 6-[3-(1H-pyrazol-3-yl)-1-piperidyl]pyrido[3,2-d]pyrimidin-4-amine | | / | 1H NMR (400 MHz, DMSO) δ 8.20-8.13 (s, 1H), 7.81-7.74 (d, J = 9.3 Hz, 1H), 7.54-7.47 (d, J = 9.4 Hz, 2H), 7.47-7.17 (bs, 2H), 6.26-6.14 (s, 1H), 4.73-4.59 (s, 1H), 4.59-4.46 (d, J = 13.4 Hz, 1H), 3.14-2.95 (m, 2H), 2.92-2.77 (m, 1H), 2.18-2.04 (m, 1H), 1.85-1.67 (m, 2H), 1.67-1.52 (m, 1H). |
| 322 | D | 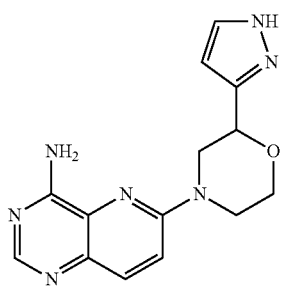 [SMILES: Nc1ncnc2ccc(N3CCOC(c4cc[nH]n4)C3)nc12] | 6-[2-(1H-pyrazol-3-yl)morpholin-4-yl]pyrido[3,2-d]pyrimidin-4-amine | | / | 1H NMR (400 MHz, DMSO) δ 8.22-8.16 (s, 1H), 7.85-7.79 (d, J = 9.3 Hz, 1H), 7.70-7.55 (s, 1H), 7.55-7.48 (d, J = 9.4 Hz, 1H), 7.48-7.30 (s, 2H), 6.36-6.31 (d, J = 2.1 Hz, 1H), 4.67-4.60 (d, J = 10.2 Hz, 1H), 4.60-4.49 (s, 1H), 4.49-4.38 (d, J = 12.6 Hz, 1H), 4.08-3.99 (d, J = 11.6 Hz, 1H), 3.79-3.68 (td, J = 11.5, 2.6 Hz, 1H), 3.22-3.06 (m, 2H). |
| 323 | D | 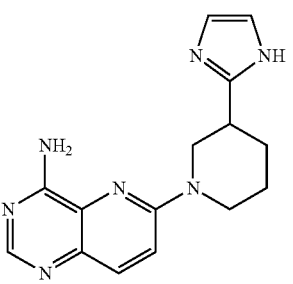 [SMILES: Nc1ncnc2ccc(N3CCCC(c4ncc[nH]4)C3)nc12] | 6-[3-(1H-imidazol-2-yl)-1-piperidyl]pyrido[3,2-d]pyrimidin-4-amine | | / | 1H NMR (400 MHz, DMSO) δ 8.20-8.14 (m, 3H), 7.82-7.77 (m, 1H), 7.54-7.49 (d, J = 9.4 Hz, 1H), 7.38-7.28 (d, J = 8.1 Hz, 2H), 6.96-6.94 (s, 2H), 4.79-4.71 (d, J = 12.7 Hz, 1H), 4.53-4.46 (d, J = 17.4 Hz, 1H), 3.17-3.07 (m, 1H), 3.07-2.96 (m, 1H), 2.96-2.84 (m, 1H), 2.18-2.08 (m, 1H), 1.91-1.77 (m, 2H), 1.66-1.51 (m, 1H). |

| Ex. No. | General Method | Structure/Name | IUPAC name | Isolated Yield | LCMS $R_T$ (min), M + H+, method | 1H NMR (ppm) |
|---|---|---|---|---|---|---|
| 324 | A | 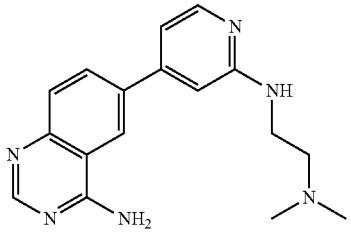 [SMILES: CN(C)CCNc1cc(-c2ccc3ncnc(N)c3c2)ccn1] | N-[4-(4-amino-quinazolin-6-yl)-2-pyridyl]-N',N'-dimethyl-ethane-1,2-diamine | | / | 1H NMR (400 MHz, DMSO) δ 8.60-8.55 (s, 1H), 8.42-8.37 (s, 1H), 8.27-8.23 (s, 1H), 8.11-8.01 (m, 2H), 8.00-7.79 (bs, 2H), 7.77-7.71 (d, J = 8.7 Hz, 1H), 6.98-6.92 (d, J = 5.4 Hz, 1H), 6.92-6.85 (s, 1H), 6.40-6.28 (t, J = 5.4 Hz, 1H), 3.46-3.36 (m, 2H), 2.50-2.42 (m, 2H), 2.22-2.20 (s, 6H). |
| 325 | D | 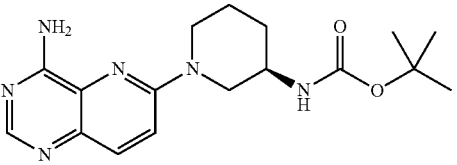 [SMILES: CC(C)(C)OC(=O)N[C@@H]1CCCN(c2ccc3ncnc(N)c3n2)C1] | tert-butyl N-[(3R)-1-(4-amino-pyrido[3,2-d]pyrimidin-6-yl)-3-piperidyl]carbamate | | / | 1H NMR (400 MHz, DMSO) δ 8.19-8.13 (s, 1H), 7.81-7.74 (d, J = 9.3 Hz, 1H), 7.43-7.39 (d, J = 9.1 Hz, 1H), 6.95-6.85 (d, J = 6.6 Hz, 1H), 4.32-4.19 (m, 2H), 3.50-3.38 (m, 1H), 3.19-3.04 (m, 1H), 2.96-2.85 (m, 1H), 1.90-1.80 (m, 1H), 1.80-1.67 (m, 1H), 1.60-1.34 (m, 11H). |
| 326 | D | 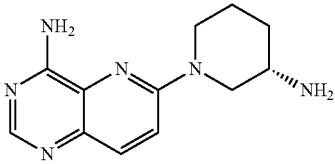 [SMILES: Nc1ncnc2ccc(N3CCC[C@H](N)C3)nc12] | 6-[(3S)-3-amino-1-piperidyl]pyrido[3,2-d]pyrimidin-4-amine | | / | 1H NMR (400 MHz, DMSO) δ 8.17-8.13 (s, 1H), 7.77-7.73 (d, J = 9.3 Hz, 1H), 7.46-7.39 (d, J = 9.4 Hz, 1H), 7.39-7.07 (s, 2H), 4.48-4.26 (m, 2H), 3.03-2.90 (m, 1H), 2.73-2.62 (m, 2H), 1.93-1.82 (m, 1H), 1.82-1.67 (m, 1H), 1.52-1.36 (m, 1H), 1.34-1.16 (m, 1H). |
| 327 | D | 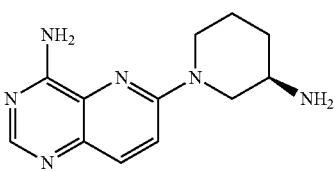 [SMILES: Nc1ncnc2ccc(N3CCC[C@@H](N)C3)nc12] | 6-[(3R)-3-amino-1-piperidyl[3,2-d]pyrimidin-4-amine | | / | 1H NMR (400 MHz, DMSO) δ 8.17-8.13 (s, 1H), 7.77-7.73 (d, J = 9.3 Hz, 1H), 7.46-7.39 (d, J = 9.4 Hz, 1H), 7.39-7.07 (s, 2H), 4.48-4.26 (m, 2H), 3.03-2.90 (m, 1H), 2.73-2.62 (m, 2H), 1.93-1.82 (m, 1H), 1.82-1.67 (m, 1H), 1.52-1.36 (m, 1H), 1.34-1.16 (m, 1H). |

| Ex. No. | General Method | Structure/Name | IUPAC name | Isolated Yield | LCMS $R_T$ (min), $M+H^+$, method | $^1$H NMR (ppm) |
|---|---|---|---|---|---|---|
| 328 | D | | N-[(3S)-1-(4-aminopyrido[3,2-d]pyrimidin-6-yl)-3-piperidyl]-3-pyrrolidin-1-yl-propanamide | | / | 1H NMR (400 MHz, DMSO) δ 8.24-8.19 (d, J = 6.8 Hz, 1H), 8.18-8.14 (s, 1H), 7.81-7.72 (d, J = 9.3 Hz, 1H), 7.43-7.38 (d, J = 9.4 Hz, 1H), 4.06-3.96 (d, J = 12.7 Hz, 1H), 3.96-3.85 (M, 1H), 3.84-3.77 (m, 1H), 3.61-3.49 (m, 1H), 3.37-3.31 (m, 1H), 2.62-2.54 (m, 1H), 2.39-2.28 (m, 4H), 2.27-2.17 (t, J = 6.7 Hz, 2H), 1.90-1.80 (m, 1H), 1.80-1.70 (m, 1H), 1.70-1.62 (m, 1H), 1.62-1.45 (m, 6H). |
| 329 | D | | N-[(3S)-1-(4-aminopyrido[3,2-d]pyrimidin-6-yl)-3-piperidyl]-2-(4-methylpiperazin-1-yl)acetamide | | / | 1H NMR (400 MHz, DMSO) δ 8.19-8.13 (s, 1H), 7.82-7.74 (d, J = 9.3 Hz, 1H), 7.64-7.57 (d, J = 7.4 Hz, 1H), 7.48-7.42 (d, J = 9.4 Hz, 1H), 7.41-7.21 (s, 2H), 3.93-3.81 (dd, J = 14.6, 8.2 Hz, 2H), 3.81-3.64 (dd, J = 13.0, 6.8 Hz, 3H), 2.85-2.81 (s, 2H), 2.35-2.23 (s, 4H), 2.12-1.94 (s, 6H), 1.88-1.78 (m, 1H), 1.78-1.59 (m, 2H), 1.59-1.48 (s, 1H). |
| 330 | D | | N-[(3R)-1-(4-aminopyrido[3,2-d]pyrimidin-6-yl)-3-piperidyl]-3-methoxy-propanamide | | / | 1H NMR (400 MHz, DMSO) δ 8.19-8.14 (s, 1H), 7.91-7.83 (d, J = 7.0 Hz, 1H), 7.82-7.73 (d, J = 9.3 Hz, 1H), 7.44-7.38 (d, J = 9.3 Hz, 1H), 7.38-7.18 (m, 2H), 4.25-4.17 (d, J = 12.7 Hz, 1H), 4.17-4.08 (d, J = 13.8 Hz, 1H), 3.85-3.72 (m, 1H), 3.58-3.48 (m, 2H), 3.23-3.18 (s, 3H), 3.10-2.99 (m, 1H), 2.37-2.28 (m, 2H), 1.90-1.81 (m, 1H), 1.81-1.70 (m, J = 8.7 Hz, 1H), 1.63-1.40 (m, 2H). |

| Ex. No. | General Method | Structure/Name | IUPAC name | Isolated Yield | LCMS $R_T$ (min), M + H+, method | $^1$H NMR (ppm) |
|---|---|---|---|---|---|---|
| 331 | D | | N-[(3R)-1-(4-aminopyrido[3,2-d]pyrimidin-6-yl)-3-piperidyl]-3-pyrrolidin-1-yl-propanamide | / | | 1H NMR (400 MHz, DMSO) δ 8.24-8.19 (d, J = 6.8 Hz, 1H), 8.18-8.14 (s, 1H), 7.81-7.72 (d, J = 9.3 Hz, 1H), 7.43-7.38 (d, J = 9.4 Hz, 1H), 4.06-3.96 (d, J = 12.7 Hz, 1H), 3.96-3.85 (M, 1H), 3.84-3.77 (m, 1H), 3.61-3.49 (m, 1H), 3.37-3.31 (m, 1H), 2.62-2.54 (m, 1H), 2.39-2.28 (m, 4H), 2.27-2.17 (t, J = 6.7 Hz, 2H), 1.90-1.80 (m, 1H), 1.80-1.70 (m, 1H), 1.70-1.62 (m, 1H), 1.62-1.45 (m, 6H). |
| 332 | D | | N-[(3R)-1-(4-aminopyrido[3,2-d]pyrimidin-6-yl)-3-piperidyl]-2-(4-methylpiperazin-1-yl)acetamide | / | | 1H NMR (400 MHz, DMSO) δ 8.19-8.13 (s, 1H), 7.82-7.74 (d, J = 9.3 Hz, 1H), 7.64-7.57 (d, J = 7.4 Hz, 1H), 7.48-7.42 (d, J = 9.4 Hz, 1H), 7.41-7.21 (s, 2H), 3.93-3.81 (dd, J = 14.6, 8.2 Hz, 2H), 3.81-3.64 (dd, J = 13.0, 6.8 Hz, 3H), 2.85-2.81 (s, 2H), 2.35-2.23 (s, 4H), 2.12-1.94 (s, 6H), 1.88-1.78 (m, 1H), 1.78-1.59 (m, 2H), 1.59-1.48 (s, 1H). |
| 333 | D | | N6-[(2-fluorophenyl)methyl]pyrido[3,2-d]pyrimidine-4,6-diamine | / | | 1H NMR (400 MHz, DMSO) δ 8.15-8.13 (s, 1H), 7.72-7.62 (m, 2H), 7.55-7.48 (td, J = 7.7, 1.7 Hz, 1H), 7.35-7.25 (m, 1H), 7.22-7.11 (m, 2H), 7.11-7.06 (d, J = 9.1 Hz, 1H), 4.73-4.66 (d, J = 5.8 Hz, 2H). |
| 334 | D | | N6-(1-phenylethyl)pyrido[3,2-d]pyrimidine-4,6-diamine | / | | 1H NMR (400 MHz, DMSO) δ 8.12-8.08 (s, 1H), 7.71-7.60 (dm, 2H), 7.53-7.44 (d, J = 7.3 Hz, 2H), 7.35-7.25 (t, J = 7.6 Hz, 2H), 7.24-7.15 (t, J = 7.3 Hz, 1H), 7.08-7.01 (d, J = 9.1 Hz, 1H), 5.41-5.30 (p, J = 7.0 Hz, 1H), 1.51-1.42 (d, J = 6.9 Hz, 3H). |
| 335 | A | | 6-[2-(trifluoromethyl)-4-pyridyl]pyrido[3,2-d]pyrimidin-4-amine | / | | 1H NMR (400 MHz, DMSO) δ 8.95-8.92 (m, 2H), 8.74-8.67 (m, 2H), 8.57-8.49 (bs, 1H), 8.47-8.45 (s, 1H), 8.26-8.21 (d, J = 8.8 Hz, 1H), 8.18-8.09 (bs, 1H). |

-continued

| Ex. No. | General Method | Structure/Name | IUPAC name | Isolated Yield | LCMS $R_T$ (min), M + H+, method | $^1$H NMR (ppm) |
|---|---|---|---|---|---|---|
| 336 | G | | 6-(2-methyl-phenoxy)pyrido[3,2-d]pyrimidin-4-amine | | / | 1H NMR (400 MHz, DMSO) δ 8.40-8.33 (s, 1H), 8.17-8.11 (d, J = 9.0 Hz, 1H), 7.44-7.35 (dd, J = 13.1, 8.3 Hz, 2H), 7.32-7.26 (m, 1H), 7.26-7.17 (m, 2H), 2.17-2.13 (s, 3H). |
| 337 | G | | 6-(3-methyl-phenoxy)pyrido[3,2-d]pyrimidin-4-amine | | / | 1H NMR (400 MHz, DMSO) δ 8.41-8.36 (s, 1H), 8.17-8.11 (d, J = 9.0 Hz, 1H), 7.83-7.63 (bs, 1H), 7.45-7.39 (d, J = 9.0 Hz, 1H), 7.39-7.32 (t, J = 8.0 Hz, 1H), 7.11-7.03 (m, 3H), 6.96-6.75 (bs, 1H), 2.36-2.33 (s, 3H). |
| 338 | G | | 6-(4-pyridyloxy)pyrido[3,2-d]pyrimidin-4-amine | | / | 1H NMR (400 MHz, DMSO) δ 8.95-8.88 (m, 2H), 8.45-8.41 (s, 1H), 8.30-8.27 (s, 2H), 8.27-8.19 (bs, 1H), 8.06-7.97 (bs, 1H), 6.34-6.27 (m, 2H). |
| 339 | G | | 6-(4-methyl-phenoxy)pyrido[3,2-d]pyrimidin-4-amine | | / | 1H NMR (400 MHz, DMSO) δ 8.40-8.36 (s, 1H), 8.16-8.09 (d, J = 9.0 Hz, 1H), 7.45-7.39 (d, J = 9.0 Hz, 1H), 7.30-7.24 (d, J = 8.4 Hz, 2H), 7.20-7.14 (dd, J = 6.6, 4.5 Hz, 2H), 2.38-2.32 (s, 3H). |
| 340 | G | | 6-(3-fluoro-phenoxy)pyrido[3,2-d]pyrimidin-4-amine | | / | 1H NMR (400 MHz, DMSO) δ 8.40-8.38 (s, 1H), 8.21-8.14 (d, J = 9.0 Hz, 1H), 7.54-7.47 (m, 2H), 7.26-7.19 (m, 1H), 7.18-7.07 (m, 2H). |
| 341 | G | | 2-(4-amino-pyrido[3,2-d]pyrimidin-6-yl)oxy-benzonitrile | | / | 1H NMR (400 MHz, DMSO) δ 8.41-8.40 (s, 1H), 8.25-8.21 (d, J = 9.0 Hz, 1H), 7.98-7.95 (dd, J = 7.8, 1.6 Hz, 1H), 7.84-7.77 (m, 1H), 7.68-7.65 (d, J = 9.0 Hz, 1H), 7.56-7.52 (d, J = 8.3 Hz, 1H), 7.50-7.44 (t, J = 7.6 Hz, 1H). |
| 342 | G | | 6-[(6-methyl-3-pyridyl)oxy]pyrido[3,2-d]pyrimidin-4-amine | | / | 1H NMR (400 MHz, DMSO) δ 8.46-8.42 (d, J = 2.8 Hz, 1H), 8.40-8.36 (s, 1H), 8.20-8.13 (d, J = 9.0 Hz, 1H), 7.72-7.67 (dd, J = 8.4, 2.8 Hz, 1H), 7.58-7.52 (d, J = 9.0 Hz, 1H), 7.39-7.34 (d, J = 8.5 Hz, 1H), 2.52-2.51 (s, 3H). |

| Ex. No. | General Method | Structure/Name | IUPAC name | Isolated Yield | LCMS $R_T$ (min), M + H+, method | ¹H NMR (ppm) |
|---|---|---|---|---|---|---|
| 343 | G | | 6-[(2-methyl-3-pyridyl)oxy]pyrido[3,2-d]pyrimidin-4-amine | | / | 1H NMR (400 MHz, DMSO) δ 8.39-8.36 (d, J = 4.4 Hz, 2H), 8.21-8.15 (d, J = 9.0 Hz, 1H), 7.73-7.69 (m, 1H), 7.59-7.55 (d, J = 9.0 Hz, 1H), 7.39-7.31 (dd, J = 8.1, 4.7 Hz, 1H), 2.37-2.35 (s, 3H). |
| 344 | G | | 6-phenoxypyrido[3,2-d]pyrimidin-4-amine | | / | 1H NMR (400 MHz, DMSO) δ 8.40-8.36 (s, 1H), 8.18-8.12 (d, J = 9.0 Hz, 1H), 7.53-7.43 (m, 3H), 7.33-7.23 (m, 3H). |
| 345 | G | | 6-(3-pyridyloxy)pyrido[3,2-d]pyrimidin-4-amine | | / | 1H NMR (400 MHz, DMSO) δ 8.60-8.57 (d, J = 2.8 Hz, 1H), 8.50-8.48 (dd, J = 4.7, 1.3 Hz, 1H), 8.40-8.38 (s, 1H), 8.20-8.17 (d, J = 9.0 Hz, 1H), 7.86-7.81 (m, 1H), 7.60-7.57 (m, 1H), 7.54-7.49 (m, 1H). |
| 346 | G | | 4-(4-amino-pyrido[3,2-d]pyrimidin-6-yl)oxybenzamide | | / | 1H NMR (400 MHz, DMSO) δ 8.40-8.38 (s, 1H), 8.19-8.15 (d, J = 9.0 Hz, 1H), 8.00-7.94 (m, 3H), 7.54-7.50 (d, J = 9.0 Hz, 1H), 7.37-7.31 (m, 3H). |
| 347 | G | | 4-(4-amino-pyrido[3,2-d]pyrimidin-6-yl)oxybenzonitrile | | / | 1H NMR (400 MHz, DMSO) δ 8.40-8.39 (s, 1H), 8.22-8.18 (d, J = 9.0 Hz, 1H), 7.95-7.91 (m, 2H), 7.60-7.57 (d, J = 9.0 Hz, 1H), 7.52-7.47 (m, 2H). |
| 348 | G | | 3-(4-amino-pyrido[3,2-d]pyrimidin-6-yl)oxy-benzonitrile | | / | 1H NMR (400 MHz, DMSO) δ 8.39-8.38 (s, 1H), 8.20-8.17 (d, J = 9.0 Hz, 1H), 7.87-7.84 (m, 1H), 7.77-7.70 (m, 1H), 7.69-7.64 (m, 2H), 7.59-7.54 (d, J = 9.0 Hz, 1H). |
| 349 | G | | 6-(2-chloro-phenoxy)pyrido[3,2-d]pyrimidin-4-amine | | / | 1H NMR (400 MHz, DMSO) δ 8.41-8.37 (s, 1H), 8.22-8.16 (d, J = 9.0 Hz, 1H), 7.67-7.62 (d, J = 8.3 Hz, 1H), 7.56-7.51 (d, J = 9.0 Hz, 1H), 7.48-7.44 (m, 2H), 7.39-7.32 (m, 1H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 350 | G | | 6-(4-methoxy-phenoxy)pyrido[3,2-d]pyrimidin-4-amine | | / | 1H NMR (400 MHz, DMSO) δ 8.39-8.35 (s, 1H), 8.15-8.09 (d, J = 9.0 Hz, 1H), 7.43-7.39 (d, J = 9.0 Hz, 1H), 7.26-7.19 (m, 2H), 7.05-6.98 (m, 2H), 3.82-3.77 (s, 3H). |
| 351 | G | | 6-(4-chloro-phenoxy)pyrido[3,2-d]pyrimidin-4-amine | | / | 1H NMR (400 MHz, DMSO) δ 8.39-8.37 (s, 1H), 8.18-8.13 (d, J = 9.0 Hz, 1H), 7.54-7.49 (m, 3H), 7.37-7.31 (m, 2H). |
| 352 | G | | 6-(3-chloro-phenoxy)pyrido[3,2-d]pyrimidin-4-amine | | / | 1H NMR (400 MHz, DMSO) δ 8.40-8.38 (s, 1H), 8.19-8.14 (d, J = 9.0 Hz, 1H), 7.54-7.46 (m, 2H), 7.43-7.40 (t, J = 2.1 Hz, 1H), 7.37-7.31 (dd, J = 7.7, 1.8 Hz, 1H), 7.31-7.25 (dd, J = 8.2, 2.2 Hz, 1H). |
| 353 | G | | 6-(2,4-difluoro-phenoxy)pyrido[3,2-d]pyrimidin-4-amine | | / | 1H NMR (400 MHz, DMSO) δ 8.39-8.37 (s, 1H), 8.20-8.16 (d, J = 9.0 Hz, 1H), 7.62-7.58 (d, J = 9.0 Hz, 1H), 7.56-7.43 (m, 2H), 7.21-7.14 (m, 1H). |
| 354 | G | | 6-(3,4-difluoro-phenoxy)pyrido[3,2-d]pyrimidin-4-amine | | / | 1H NMR (400 MHz, DMSO) δ 8.39-8.37 (s, 1H), 8.18-8.14 (d, J = 9.0 Hz, 1H), 7.75-7.64 (bs, 1H), 7.55-7.46 (m, 3H), 7.19-7.12 (m, 1H), 6.98-6.86 (bs, 1H). |
| 355 | D | | N6-[(2-chloro-phenyl)methyl]pyrido[3,2-d]pyrimidine-4,6-diamine | | / | 1H NMR (400 MHz, DMSO) δ 8.15-8.12 (s, 1H), 7.76-7.70 (t, J = 5.8 Hz, 1H), 7.70-7.66 (d, J = 9.1 Hz, 1H), 7.55-7.49 (m, 1H), 7.48-7.42 (m, 1H), 7.32-7.25 (m, 2H), 7.14-7.09 (d, J = 9.1 Hz, 1H), 4.78-4.70 (d, J = 5.8 Hz, 2H). |
| 356 | G | | 6-(2-fluoro-phenoxy)pyrido[3,2-d]pyrimidin-4-amine | | / | 1H NMR (400 MHz, DMSO) δ 8.40-8.38 (s, 1H), 8.21-8.17 (d, J = 9.0 Hz, 1H), 7.60-7.55 (d, J = 9.0 Hz, 1H), 7.50-7.39 (m, 2H), 7.39-7.27 (m, 2H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 357 | D | | N6-[(3-chlorophenyl)methyl]pyrido[3,2-d]pyrimidine-4,6-diamine | | / | 1H NMR (400 MHz, DMSO) δ 8.15-8.11 (s, 1H), 7.78-7.72 (t, J = 6.0 Hz, 1H), 7.70-7.65 (d, J = 9.1 Hz, 1H), 7.51-7.48 (s, 1H), 7.42-7.38 (d, J = 7.6 Hz, 1H), 7.38-7.32 (t, J = 7.6 Hz, 1H), 7.32-7.26 (d, J = 7.7 Hz, 1H), 7.09-7.02 (d, J = 9.1 Hz, 1H), 4.73-4.66 (d, J = 6.0 Hz, 2H). |
| 358 | D | | N6-[(4-chlorophenyl)methyl]pyrido[3,2-d]pyrimidine-4,6-diamine | | / | 1H NMR (400 MHz, DMSO) δ 8.15-8.09 (s, 1H), 7.77-7.70 (t, J = 5.9 Hz, 1H), 7.69-7.64 (d, J = 9.1 Hz, 1H), 7.48-7.42 (d, J = 8.4 Hz, 2H), 7.42-7.34 (d, J = 8.4 Hz, 2H), 7.09-7.02 (d, J = 9.1 Hz, 1H), 4.70-4.63 (d, J = 5.9 Hz, 2H). |
| 359 | D | | N6-(o-tolylmethyl)pyrido[3,2-d]pyrimidine-4,6-diamine | | / | 1H NMR (400 MHz, DMSO) δ 8.16-8.11 (s, 1H), 7.69-7.62 (d, J = 9.1 Hz, 1H), 7.53-7.46 (t, J = 5.5 Hz, 1H), 7.40-7.33 (m, 1H), 7.22-7.11 (m, 3H), 7.11-7.07 (d, J = 9.1 Hz, 1H), 4.70-4.62 (d, J = 5.5 Hz, 2H), 2.37-2.33 (s, 3H). |
| 360 | D | | N6-[1-(6-methyl-2-pyridyl)ethyl]pyrido[3,2-d]pyrimidine-4,6-diamine | | / | 1H NMR (400 MHz, DMSO) δ 8.13-8.08 (s, 1H), 7.69-7.66 (d, J = 7.3 Hz, 1H), 7.66-7.61 (d, J = 9.1 Hz, 1H), 7.61-7.55 (t, J = 7.7 Hz, 1H), 7.31-7.24 (d, J = 7.7 Hz, 1H), 7.15-7.09 (d, J = 9.1 Hz, 1H), 7.09-7.04 (d, J = 7.6 Hz, 1H), 5.37-5.22 (p, J = 7.0 Hz, 1H), 2.49-2.46 (s, 3H). |
| 361 | D | | N6-[(3-pyrrolidin-1-ylphenyl)methyl]pyrido[3,2-d]pyrimidine-4,6-diamine | | / | 1H NMR (400 MHz, DMSO) δ 8.16-8.10 (s, 1H), 7.66-7.62 (d, J = 9.1 Hz, 1H), 7.62-7.57 (t, J = 5.6 Hz, 1H), 7.15-7.03 (m, 3H), 6.68-6.61 (m, 2H), 6.46-6.39 (d, J = 8.9 Hz, 1H), 4.60-4.53 (d, J = 5.7 Hz, 2H), 3.23-3.17 (m, 4H), 1.96-1.91 (m, 4H). |

| Ex. No. | General Method | Structure/Name | IUPAC name | Isolated Yield | LCMS R$_T$ (min), M + H$^+$, method | $^1$H NMR (ppm) |
|---|---|---|---|---|---|---|
| 362 | D | | N6-(pyrazin-2-ylmethyl)pyrido[3,2-d]pyrimidine-4,6-diamine | / | | 1H NMR (400 MHz, DMSO) δ 8.80-8.77 (s, 1H), 8.61-8.56 (m, 1H), 8.53-8.49 (d, J = 2.6 Hz, 1H), 8.16-8.11 (s, 1H), 7.96-7.89 (t, J = 5.9 Hz, 1H), 7.72-7.63 (d, J = 9.1 Hz, 1H), 7.16-7.09 (d, J = 9.1 Hz, 1H). |
| 363 | F | | 6-[3-(difluoromethoxy)phenyl]pyrido[3,2-d]pyrimidin-4-amine | / | | 1H NMR (400 MHz, DMSO) δ 8.50-8.46 (d, J = 8.9 Hz, 1H), 8.43-8.42 (s, 1H), 8.31-8.28 (s, 1H), 8.28-8.24 (d, J = 7.9 Hz, 1H), 8.23-8.17 (s, 1H), 8.17-8.13 (d, J = 8.8 Hz, 1H), 8.05-7.98 (s, 1H), 7.62-7.58 (d, J = 7.6 Hz, 1H), 7.58-7.23 (m, 2H). |
| 364 | A | | 6-(3-(6-methylpyridin-2-yloxy)phenyl)pyrido[3,2-d]pyrimidin-4-amine | 5% | 1.188 min, 329.9, 0-60AB | 1H NMR (400 MHz, MeOD-d$_4$) δ 8.75 (s, , 1H), 8.70 (d, J = 8.8 Hz, 1H), 8.54 (s, 1H), 8.44 (d, J = 8.8 Hz, 1H), 8.28 (m, 2H), 7.81-7.77 (t, J = 8.8 Hz, 1H), 7.55 (m, 1H), 7.47 (d, J = 7.6 Hz, 1H), 7.03 (d, J = 8.4 Hz, 1H), 2.76 (s, 3H). |
| 365 | F | | 6-(3-isopropoxyphenyl)pyrido[3,2-d]pyrimidin-4-amine | 27% | 1.117 min, 281.2, 0-60AB | $^1$H NMR (400 MHz, DMSO-d6) δ 9.95 (s, 1H), 9.91 (s, 1H), 8.84 (s, 1H), 8.68 (d, J = 9.2 Hz, 1H), 8.37 (d, J = 8.8 Hz, 1H), 8.05 (s, 1H), 7.96 (m, 1H), 7.48-7.44 (t, J = 8.0 Hz, 1H), 7.11 (m, 1H), 4.84 (m, 1H), 1.31 (m, 6H). |
| 366 | A | | 6-(1H-indazol-4-yl)pyrido[3,2-d]pyrimidin-4-amine | 3% | 1.107 min, 363.3, 0-60AB | 1H NMR (400 MHz, MeOD-d$_4$) δ 8.87 (s, 1H), 8.77 (s, 1H), 8.69 (d, J = 8.8 Hz, 1H), 8.33 (d, J = 8.8 Hz, 1H), 7.97 (d, J = 7.2 Hz, 1H), 7.81 (m, 1H), 7.70 (m, 1H). |
| 367 | F | | 6-(3-methoxyphenyl)pyrido[3,2-d]pyrimidin-4-amine | 17% | 1.013 min, 253.3, 0-60AB | 1H NMR (400 MHz, DMSO-d6) δ 9.98 (s, 1H), 9.92 (s, 1H), 8.85 (s, 1H), 8.64 (d, J = 8.8 Hz, 1H), 8.39 (d, J = 8.8 Hz, 1H), 8.03 (m, 1H), 7.98 (m, 1H), 7.50-7.46 (t, J = 8.0 Hz, 1H), 7.20 (m, 1H), 3.89 (s, 1H). |

-continued

| Ex. No. | General Method | Structure/Name | IUPAC name | Isolated Yield | LCMS $R_T$ (min), M + H[+], method | $^1$H NMR (ppm) |
|---|---|---|---|---|---|---|
| 368 | A | 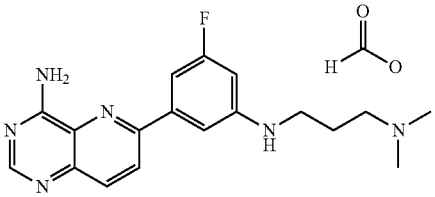 [SMILES: CN(C)CCCNc1cc(F)cc(-c2ccc3ncnc(N)c3n2)c1 ; O=CO] | N1-(3-(4-amino-pyrido[3,2-d]pyrimidin-6-yl)-5-fluorophenyl)-N3,N3-dimethyl-propane-1,3-diamine formate | 13% | 0.917 min, 340.9, 0-60AB | $^1$H-NMR (Methanol-d4, 400 MHz): δ 8.45 (s, 2H), 8.29 (d, J = 8.8 Hz, 1H), 8.11 (d, J = 8.8 Hz, 1H), 7.31-7.28 (m, 2H), 6.52-6.48 (m, 1H), 3.37-3.26 (m, 4H), 2.85 (s, 6H), 2.13-2.06 (m, 2H). |

MAP4K4 Inhibition Assay Protocol

The kinase activity of purified human MAP4K4 kinase domain was measured by monitoring the phosphorylation of a peptide substrate derived from moesin protein (Leu-Gly-Arg-Asp-Lys-Tyr-Lys-Thr-Leu-Arg-Gln-Ile-Arg-Gln) fluorescently labeled on the N-terminus with 5-carboxyfluorescein using the Caliper LabChip technology (Caliper Life Sciences, Hopkinton, Mass.). To determine inhibition constants (IC50), compounds were serially diluted in DMSO and added to 10 uL kinase reactions containing 1 nM purified MAP4K4 enzyme, 1 uM peptide substrate, 10 uM ATP, 10 mM MgCl$_2$, 1 mM EGTA, 50 mM Hepes pH 7.2, 1 mM DTT, 0.01% Triton X-100, and 2% DMSO. Reactions were incubated at room temperature in Perkin Elmer Proxiplates for 45 minutes and stopped by the addition of 10 uL of an EDTA-containing solution (50 mM Hepes pH 7.2, 40 mM EDTA, 0.02% Triton X-100). The fraction of phosphorylated peptide was determined as a fraction of total peptide substrate using the Caliper Lab Chip 3000 according to the manufacturer's instructions. IC$_{50}$ values were determined using the four-parameter non-linear fit model.

The compounds of the present invention were tested for their capacity to inhibit a MAP4K4 activity and activation as described herein.

| Compound | MAP4K4 IC$_{50}$ (μM) |
|---|---|
| 6-(3-chlorophenyl)quinazolin-4-amine | 0.0927 |
| N-[3-(4-aminoquinazolin-6-yl)phenyl]acetamide | 0.783 |
| tert-butyl N-[4-(4-aminoquinazolin-6-yl)phenyl]carbamate | 0.503 |
| 5-(4-aminoquinazolin-6-yl)pyridine-3-carbonitrile | 6.2 |
| 6-(m-tolyl)quinazolin-4-amine | 0.415 |
| 6-(2-fluorophenyl)quinazolin-4-amine | 0.341 |
| 3-(4-aminoquinazolin-6-yl)benzonitrile | 0.258 |
| 4-(4-aminoquinazolin-6-yl)benzonitrile | 2.6 |
| 6-(4-methoxyphenyl)quinazolin-4-amine | 1.2 |
| 6-(3-methoxyphenyl)quinazolin-4-amine | 0.591 |
| 6-(2-methoxyphenyl)quinazolin-4-amine | 0.751 |
| 6-(3-chlorophenyl)-N-(4-pyridyl)quinazolin-4-amine | 0.579 |
| 7-(3-chlorophenyl)quinazoline-2,4-diamine | 10. |
| 6-(3-chlorophenyl)isoquinolin-1-amine | 3.3 |
| 6-(3-chloro-5-fluoro-phenyl)quinazolin-4-amine | 0.226 |
| 6-(3-chlorophenyl)pyrido[3,2-d]pyrimidine-2,4-diamine | 0.783 |
| 6-(3-chlorophenyl)-N-cyclopropyl-quinazolin-4-amine | 0.646 |
| 6-(3-fluorophenyl)quinazolin-4-amine | 0.0459 |
| 3-(4-aminoquinazolin-6-yl)-5-chloro-benzamide | 1.3 |
| 6-(3-chlorophenyl)-N-isobutyl-quinazolin-4-amine | 0.604 |
| 6-(3-chlorophenyl)-N-cyclobutyl-quinazolin-4-amine | 0.67 |
| 6-(3-chlorophenyl)-N-(2,2-difluoroethyl)quinazolin-4-amine | 0.404 |
| 6-(3-chlorophenyl)-N-ethyl-quinazolin-4-amine | 0.337 |
| 6-(3-chlorophenyl)-N-methyl-quinazolin-4-amine | 0.348 |
| 6-(3-chlorophenyl)pyrido[3,2-d]pyrimidin-4-amine | 0.0197 |
| 6-(5-chloro-2-methyl-phenyl)quinazolin-4-amine | 0.0905 |
| 6-(3,5-dichlorophenyl)quinazolin-4-amine | 0.497 |
| 6-(3-fluorophenyl)pyrido[3,2-d]pyrimidin-4-amine | 0.0118 |
| 3-(4-aminoquinazolin-6-yl)-5-fluoro-benzonitrile | 0.413 |
| 6-(3,5-difluorophenyl)quinazolin-4-amine | 0.19 |
| 6-(3-amino-5-fluoro-phenyl)quinazolin-4-amine | 0.084 |
| N-[3-(4-aminoquinazolin-6-yl)-5-fluoro-phenyl]acetamide | 0.665 |
| 4-amino-6-(3-fluorophenyl)quinazoline-8-carbonitrile | 1.0 |
| N-[3-(4-aminoquinazolin-6-yl)-5-fluoro-phenyl]-2-tetrahydrofuran-2-yl-acetamide | 0.844 |
| N-[3-(4-aminoquinazolin-6-yl)-5-fluoro-phenyl]tetrahydropyran-4-carboxamide | 0.42 |
| 1-acetyl-N-[3-(4-aminoquinazolin-6-yl)-5-fluoro-phenyl]azetidine-3-carboxamide | 0.172 |
| N-[3-(4-aminoquinazolin-6-yl)-5-fluoro-phenyl]-2-pyrrolidin-1-yl-acetamide | 0.0586 |
| N-[3-(4-aminoquinazolin-6-yl)-5-fluoro-phenyl]-3-(dimethylamino)propanamide | 0.0884 |
| N-[3-(4-aminoquinazolin-6-yl)-5-fluoro-phenyl]-2-morpholino-acetamide | 0.273 |
| N-[3-(4-aminoquinazolin-6-yl)-5-fluoro-phenyl]cyclobutanecarboxamide | 0.424 |
| N-[3-(4-aminoquinazolin-6-yl)-5-fluoro-phenyl]-2-cyclopropyl-acetamide | 0.54 |
| N-[3-(4-aminoquinazolin-6-yl)-5-fluoro-phenyl]tetrahydrofuran-2-carboxamide | 1.5 |

-continued

| Compound | MAP4K4 IC$_{50}$ (μM) |
|---|---|
| N-[3-(4-aminoquinazolin-6-yl)-5-fluoro-phenyl]-3-methoxy-propanamide | 0.432 |
| N-[3-(4-aminoquinazolin-6-yl)-5-fluoro-phenyl]-4-methyl-morpholine-2-carboxamide | 0.264 |
| 6-(3-methyl-1-piperidyl)pyrido[3,2-d]pyrimidin-4-amine | 0.825 |
| 6-(3-methoxy-1-piperidyl)pyrido[3,2-d]pyrimidin-4-amine | 1.3 |
| 6-[3-(trifluoromethyl)pyrrolidin-1-yl]pyrido[3,2-d]pyrimidin-4-amine | 1.8 |
| 6-[3-(trifluoromethyl)-1-piperidyl]pyrido[3,2-d]pyrimidin-4-amine | 3.9 |
| 6-[3-(methoxymethyl)-1-piperidyl]pyrido[3,2-d]pyrimidin-4-amine | 1.6 |
| [1-(4-aminopyrido[3,2-d]pyrimidin-6-yl)-3-piperidyl]methanol | 1.9 |
| 6-(4-pyridyl)quinazolin-4-amine | 0.19 |
| 6-(2-methyl-4-pyridyl)quinazolin-4-amine | 0.148 |
| N-[3-(4-aminoquinazolin-6-yl)phenyl]-2-cyclopropyl-acetamide | 0.653 |
| N-[3-(4-aminoquinazolin-6-yl)phenyl]cyclobutanecarboxamide | 0.676 |
| N-[3-(4-aminoquinazolin-6-yl)phenyl]propanamide | 0.982 |
| N-[3-(4-aminoquinazolin-6-yl)phenyl]-2,2-difluoro-acetamide | 0.433 |
| N-[3-(4-aminoquinazolin-6-yl)phenyl]-3,3,3-trifluoro-propanamide | 0.468 |
| N-[3-(4-aminoquinazolin-6-yl)phenyl]tetrahydropyran-4-carboxamide | 1.7 |
| N-[3-(4-aminoquinazolin-6-yl)phenyl]-4-methyl-morpholine-2-carboxamide | 0.777 |
| N-[3-(4-aminoquinazolin-6-yl)phenyl]-2,2-difluoro-cyclopropanecarboxamide | 0.981 |
| N-[3-(4-aminoquinazolin-6-yl)phenyl]tetrahydrofuran-2-carboxamide | 1.1 |
| N-[3-(4-aminoquinazolin-6-yl)phenyl]tetrahydrofuran-3-carboxamide | 0.438 |
| N-[3-(4-aminoquinazolin-6-yl)phenyl]-2-pyrrolidin-1-yl-acetamide | 0.216 |
| N-[3-(4-aminoquinazolin-6-yl)phenyl]-2-tetrahydrofuran-2-yl-acetamide | 1.7 |
| N-[3-(4-aminoquinazolin-6-yl)phenyl]-2,2-dimethyl-propanamide | 2.6 |
| N-[3-(4-aminoquinazolin-6-yl)phenyl]-3-methoxy-propanamide | 1.3 |
| N-[3-(4-aminoquinazolin-6-yl)phenyl]-2-morpholino-acetamide | 1.4 |
| 2-[3-(4-aminoquinazolin-6-yl)phenyl]-N-cyclopentyl-acetamide | 1.3 |
| N-[3-(4-aminoquinazolin-6-yl)phenyl]-2-pyrrolidin-1-yl-propanamide | 0.899 |
| 2-[3-(4-aminoquinazolin-6-yl)phenyl]-N-cyclopentyl-N-methyl-acetamide | 1.6 |
| N-[3-(4-aminoquinazolin-6-yl)phenyl]-2-(dimethylamino)acetamide | 0.263 |
| N6-[2-(4-fluorophenyl)ethyl]pyrido[3,2-d]pyrimidine-4,6-diamine | 0.0701 |
| 6-(1-piperidyl)pyrido[3,2-d]pyrimidin-4-amine | 0.445 |
| [1-(4-aminopyrido[3,2-d]pyrimidin-6-yl)-4-piperidyl]-pyrrolidin-1-yl-methanone | 10.0 |
| 6-(3-morpholinopyrrolidin-1-yl)pyrido[3,2-d]pyrimidin-4-amine | 10.0 |
| 6-[4-(2-methoxyethyl)piperazin-1-yl]pyrido[3,2-d]pyrimidin-4-amine | 10.0 |
| N-[1-(4-aminopyrido[3,2-d]pyrimidin-6-yl)pyrrolidin-3-yl]-N-methyl-acetamide | 4.0 |
| 1-[4-(4-aminopyrido[3,2-d]pyrimidin-6-yl)piperazin-1-yl]ethanone | 8.1 |
| 1-[4-(4-aminopyrido[3,2-d]pyrimidin-6-yl)piperazin-1-yl]-2-methyl-propan-1-one | 10. |
| 6-[3-(4-methyl-1H-pyrazol-3-yl)-1-piperidyl]pyrido[3,2-d]pyrimidin-4-amine | 0.0121 |
| tert-butyl 4-(4-aminopyrido[3,2-d]pyrimidin-6-yl)-2-methyl-piperazine-1-carboxylate | 5.3 |
| 2-[1-(4-aminopyrido[3,2-d]pyrimidin-6-yl)-4-piperidyl]-N-methyl-acetamide | 10.0 |
| 6-[4-(1H-pyrazol-5-yl)-1-piperidyl]pyrido[3,2-d]pyrimidin-4-amine | 4.1 |
| 6-[4-(6-methyl-2-pyridyl)-1-piperidyl]pyrido[3,2-d]pyrimidin-4-amine | 8.5 |
| 6-(3-morpholino-1-piperidyl)pyrido[3,2-d]pyrimidin-4-amine | 10.0 |
| 6-[3-(5-methyl-2-pyridyl)-1-piperidyl]pyrido[3,2-d]pyrimidin-4-amine | 1.5 |
| 6-[3-[(1-methylimidazol-2-yl)methyl]pyrrolidin-1-yl]pyrido[3,2-d]pyrimidin-4-amine | 0.945 |
| 6-[3-(5-methyl-1,2,4-oxadiazol-3-yl)-1-piperidyl]pyrido[3,2-d]pyrimidin-4-amine | 10.0 |
| 6-[4-(3-methylimidazol-4-yl)-1-piperidyl]pyrido[3,2-d]pyrimidin-4-amine | 10.0 |
| 6-(3-amino-5-fluoro-phenyl)pyrido[3,2-d]pyrimidin-4-amine | 0.0169 |
| 6-[3-(4-pyridylmethyl)pyrrolidin-1-yl]pyrido[3,2-d]pyrimidin-4-amine | 1.8 |
| 6-[3-(3-methylimidazol-4-yl)pyrrolidin-1-yl]pyrido[3,2-d]pyrimidin-4-amine | 3.1 |
| 6-[3-(3-methyl-1,2,4-oxadiazol-5-yl)-1-piperidyl]pyrido[3,2-d]pyrimidin-4-amine | 8.4 |
| 1-(4-aminopyrido[3,2-d]pyrimidin-6-yl)-N-methyl-pyrrolidine-3-carboxamide | 4.0 |
| 6-[3-(2-pyridylmethyl)pyrrolidin-1-yl]pyrido[3,2-d]pyrimidin-4-amine | 0.0656 |
| 6-[3-(3-methyl-1,2,4-oxadiazol-5-yl)pyrrolidin-1-yl]pyrido[3,2-d]pyrimidin-4-amine | 4.6 |
| 6-[3-(3-pyridylmethyl)pyrrolidin-1-yl]pyrido[3,2-d]pyrimidin-4-amine | 0.934 |
| 6-(4-methylpiperazin-1-yl)pyrido[3,2-d]pyrimidin-4-amine | 10. |
| 6-(4-methoxy-1-piperidyl)pyrido[3,2-d]pyrimidin-4-amine | 7.9 |
| 6-[3-(dimethylamino)pyrrolidin-1-yl]pyrido[3,2-d]pyrimidin-4-amine | 10.0 |
| ethyl 4-[(4-aminopyrido[3,2-d]pyrimidin-6-yl)amino]piperidine-1-carboxylate | 10.0 |
| 6-(3,4,6,7,8,8a-hexahydro-1H-pyrrolo[1,2-a]pyrazin-2-yl)pyrido[3,2-d]pyrimidin-4-amine | 10.0 |
| N6-cyclopentylpyrido[3,2-d]pyrimidine-4,6-diamine | 1.2 |
| 4-(4-aminopyrido[3,2-d]pyrimidin-6-yl)-N-cyclopentyl-morpholine-2-carboxamide | 10.0 |
| 6-[3-(6-methyl-2-pyridyl)-1-piperidyl]pyrido[3,2-d]pyrimidin-4-amine | 0.145 |
| tert-butyl 4-(4-aminopyrido[3,2-d]pyrimidin-6-yl)piperazine-1-carboxylate | 10.0 |
| 6-[4-(5-methyl-1,2,4-oxadiazol-3-yl)-1-piperidyl]pyrido[3,2-d]pyrimidin-4-amine | 10.0 |
| 1-[3-(4-aminoquinazolin-6-yl)phenyl]-3-cyclopentyl-urea | 0.136 |
| N-[3-(4-aminoquinazolin-6-yl)phenyl]-2-(2-oxopyrrolidin-1-yl)acetamide | 0.328 |
| N-[3-(4-aminopyrido[3,2-d]pyrimidin-6-yl)-5-fluoro-phenyl]-2-cyclopentyl-acetamide | 0.107 |
| 2-[3-(4-aminoquinazolin-6-yl)phenyl]ethanol | 0.38 |
| 3-(4-aminoquinazolin-6-yl)phenol | 0.0147 |
| 6-(3-amino-4-fluoro-phenyl)quinazolin-4-amine | 0.228 |
| 6-(3-ethoxyphenyl)quinazolin-4-amine | 0.157 |
| 6-phenylquinazolin-4-amine | 0.0812 |
| 6-(5-amino-2-fluoro-phenyl)quinazolin-4-amine | 0.174 |
| N6-benzylpyrido[3,2-d]pyrimidine-4,6-diamine | 0.161 |

| Compound | MAP4K4 IC$_{50}$ (µM) |
|---|---|
| 6-[3-(4-methyl-1H-pyrazol-3-yl)-1-piperidyl]pyrido[3,2-d]pyrimidin-4-amine | 1.0 |
| 6-[3-(4-methyl-1H-pyrazol-3-yl)-1-piperidyl]pyrido[3,2-d]pyrimidin-4-amine | 0.0062 |
| 6-[3-(4,6-dimethylpyrimidin-2-yl)-1-piperidyl]pyrido[3,2-d]pyrimidin-4-amine | 10.0 |
| 6-[1-(4-aminopyrido[3,2-d]pyrimidin-6-yl)-3-piperidyl]-N,N-dimethyl-pyridine-2-carboxamide | 5.4 |
| 6-[3-[(5-methyl-2-pyridyl)methyl]pyrrolidin-1-yl]pyrido[3,2-d]pyrimidin-4-amine | 1.3 |
| 6-[3-(pyrimidin-2-ylmethyl)pyrrolidin-1-yl]pyrido[3,2-d]pyrimidin-4-amine | 0.46 |
| 6-[3-[6-(dimethylamino)-2-pyridyl]-1-piperidyl]pyrido[3,2-d]pyrimidin-4-amine | 0.29 |
| 6-[3-(pyrimidin-2-ylmethyl)-1-piperidyl]pyrido[3,2-d]pyrimidin-4-amine | 2.9 |
| 6-[3-(4-methylsulfonyl-1H-pyrazol-5-yl)-1-piperidyl]pyrido[3,2-d]pyrimidin-4-amine | 9.6 |
| 6-[3-[6-(methylamino)pyrazin-2-yl]-1-piperidyl]pyrido[3,2-d]pyrimidin-4-amine | 4.6 |
| 6-[3-[[6-(methylamino)pyrimidin-4-yl]methyl]pyrrolidin-1-yl]pyrido[3,2-d]pyrimidin-4-amine | 3.5 |
| 6-[3-(2-methylpyrimidin-4-yl)pyrrolidin-1-yl]pyrido[3,2-d]pyrimidin-4-amine | 10.0 |
| 6-[3-[6-(dimethylamino)-2-methyl-pyrimidin-4-yl]pyrrolidin-1-yl]pyrido[3,2-d]pyrimidin-4-amine | 10.0 |
| 6-[3-[[6-(dimethylamino)pyrimidin-4-yl]methyl]-1-piperidyl]pyrido[3,2-d]pyrimidin-4-amine | 10.0 |
| 6-[3-(1H-pyrazol-3-yl)pyrrolidin-1-yl]pyrido[3,2-d]pyrimidin-4-amine | 1.3 |
| 6-[3-[[6-(dimethylamino)pyrimidin-4-yl]methyl]pyrrolidin-1-yl]pyrido[3,2-d]pyrimidin-4-amine | 6.2 |
| 6-[3-[2-(dimethylamino)pyrimidin-4-yl]-1-piperidyl]pyrido[3,2-d]pyrimidin-4-amine | 0.93 |
| 6-[1-(4-aminopyrido[3,2-d]pyrimidin-6-yl)-3-piperidyl]pyridine-2-carboxamide | 0.803 |
| 6-[3-[3-(dimethylamino)pyrazin-2-yl]-1-piperidyl]pyrido[3,2-d]pyrimidin-4-amine | 4.6 |
| 6-[3-(2-methylpyrimidin-4-yl)-1-piperidyl]pyrido[3,2-d]pyrimidin-4-amine | 1.9 |
| 6-(3-pyrimidin-4-yl-1-piperidyl)pyrido[3,2-d]pyrimidin-4-amine | 0.59 |
| 6-[3-[5-(trifluoromethyl)-1H-pyrazol-3-yl]-1-piperidyl]pyrido[3,2-d]pyrimidin-4-amine | 2.2 |
| 6-(3-pyrazin-2-yl-1-piperidyl)pyrido[3,2-d]pyrimidin-4-amine | 0.872 |
| 6-[3-(pyrazin-2-ylmethyl)-1-piperidyl]pyrido[3,2-d]pyrimidin-4-amine | 4.9 |
| 6-[3-[5-(dimethylamino)-2-pyridyl]-1-piperidyl]pyrido[3,2-d]pyrimidin-4-amine | 10. |
| 6-[3-(4-methylpyrimidin-2-yl)-1-piperidyl]pyrido[3,2-d]pyrimidin-4-amine | 4.2 |
| 6-[3-(2-pyridyl)-1-piperidyl]pyrido[3,2-d]pyrimidin-4-amine | 0.0764 |
| 6-[3-(4-methyl-1,2,4-triazol-3-yl)-1-piperidyl]pyrido[3,2-d]pyrimidin-4-amine | 3.2 |
| 6-[3-[5-(methoxymethyl)-1,2,4-oxadiazol-3-yl]-1-piperidyl]pyrido[3,2-d]pyrimidin-4-amine | 5.5 |
| 6-[1-(4-aminopyrido[3,2-d]pyrimidin-6-yl)-3-piperidyl]-N-methyl-pyridine-2-carboxamide | 3.8 |
| 6-[3-(5-methylsulfonylpyrimidin-4-yl)-1-piperidyl]pyrido[3,2-d]pyrimidin-4-amine | 10.0 |
| 6-[3-(4-pyridyl)pyrrolidin-1-yl]pyrido[3,2-d]pyrimidin-4-amine | 4.0 |
| 4-amino-6-(3-fluorophenyl)-N-methyl-N-(1-methylpyrrolidin-3-yl)quinazoline-8-carboxamide | 6.5 |
| 4-amino-6-(3-fluorophenyl)-N-(2-methoxyethyl)-N-methyl-quinazoline-8-carboxamide | 10.0 |
| 4-amino-6-(3-fluorophenyl)-N-(2-pyrrolidin-1-ylethyl)quinazoline-8-carboxamide | 8.8 |
| N-(2-acetamidoethyl)-4-amino-6-(3-fluorophenyl)quinazoline-8-carboxamide | 6.3 |
| 6-(2-fluoro-4-pyridyl)pyrido[3,2-d]pyrimidin-4-amine | 0.0115 |
| 6-(2-ethyl-4-pyridyl)pyrido[3,2-d]pyrimidin-4-amine | 0.204 |
| 6-(2-methyl-4-pyridyl)pyrido[3,2-d]pyrimidin-4-amine | 0.0505 |
| [4-amino-6-(3-fluorophenyl)quinazolin-8-yl]-[3-(dimethylamino)pyrrolidin-1-yl]methanone | 5.4 |
| 4-amino-6-(3-fluorophenyl)quinazolin-8-yl]-[4-(dimethylamino)-1-piperidyl]methanone | 3.6 |
| [4-amino-6-(3-fluorophenyl)quinazolin-8-yl]-(3-hydroxyazetidin-1-yl)methanone | 4.1 |
| 4-amino-6-(3-fluorophenyl)-N-(oxetan-3-yl)quinazoline-8-carboxamide | 0.776 |
| [4-amino-6-(3-fluorophenyl)quinazolin-8-yl]-(4-methylpiperazin-1-yl)methanone | 1.6 |
| 6-[3-[(1-methylimidazol-2-yl)methyl]-1-piperidyl]pyrido[3,2-d]pyrimidin-4-amine | 9.3 |
| N-[3-(4-aminopyrido[3,2-d]pyrimidin-6-yl)-5-fluoro-phenyl]-2-pyrrolidin-1-yl-acetamide | 0.00725 |
| N-[6-(3-amino-5-fluoro-phenyl)pyrido[3,2-d]pyrimidin-4-yl]-2-pyrrolidin-1-yl-acetamide | 0.232 |
| 3-(4-aminopyrido[3,2-d]pyrimidin-6-yl)phenol | 0.011 |
| 6-[6-(1-methyl-3-piperidyl)-3-pyridyl]quinazolin-4-amine | 4.4 |
| 5-[1-(4-aminopyrido[3,2-d]pyrimidin-6-yl)-3-piperidyl]-2-methyl-pyrazol-3-ol | 10.0 |
| 6-[2-(2-pyrrolidin-1-ylethylamino)-4-pyridyl]quinazolin-4-amine | 3.3 |
| 6-[3-(2-pyrrolidin-1-ylethoxy)phenyl]pyrido[3,2-d]pyrimidin-4-amine | 0.226 |
| 6-[3-(1H-pyrazol-3-yl)-1-piperidyl]pyrido[3,2-d]pyrimidin-4-amine | 0.515 |
| 6-[2-(1H-pyrazol-3-yl)morpholin-4-yl]pyrido[3,2-d]pyrimidin-4-amine | 3.0 |
| 6-[3-(1,4-dimethylpyrazol-3-yl)-1-piperidyl]pyrido[3,2-d]pyrimidin-4-amine | 5.0 |
| 6-[3-(2,4-dimethylpyrazol-3-yl)-1-piperidyl]pyrido[3,2-d]pyrimidin-4-amine | 0.0939 |
| 6-[3-(1,4-dimethylpyrazol-3-yl)-1-piperidyl]pyrido[3,2-d]pyrimidin-4-amine | 0.0321 |
| 6-[3-(2,4-dimethylpyrazol-3-yl)-1-piperidyl]pyrido[3,2-d]pyrimidin-4-amine | 1.8 |
| 6-[3-(1H-imidazol-2-yl)-1-piperidyl]pyrido[3,2-d]pyrimidin-4-amine | 8.2 |
| N-[4-(4-aminoquinazolin-6-yl)-2-pyridyl]-N',N'-dimethyl-ethane-1,2-diamine | 1.2 |
| 1-[4-[[3-(4-aminopyrido[3,2-d]pyrimidin-6-yl)-5-fluoro-phenyl]methyl]-1,4-diazepan-1-yl]ethanone | 0.476 |
| 1-[4-[[3-(4-aminopyrido[3,2-d]pyrimidin-6-yl)-5-fluoro-phenyl]methyl]piperazin-1-yl]ethanone | 0.553 |
| 1-[[3-(4-aminopyrido[3,2-d]pyrimidin-6-yl)-5-fluoro-phenyl]methyl]piperidin-4-ol | 0.634 |
| [1-[[3-(4-aminopyrido[3,2-d]pyrimidin-6-yl)-5-fluoro-phenyl]methyl]-4-piperidyl]methanol | 1.3 |
| 2-[4-[[3-(4-aminopyrido[3,2-d]pyrimidin-6-yl)-5-fluoro-phenyl]methyl]piperazin-1-yl]ethanol | 0.347 |

| Compound | MAP4K4 IC$_{50}$ (µM) |
|---|---|
| 6-[3-fluoro-5-[[4-(2-methoxyethyl)piperazin-1-yl]methyl]phenyl]pyrido[3,2-d]pyrimidin-4-amine | 0.416 |
| 4-[[3-(4-aminopyrido[3,2-d]pyrimidin-6-yl)-5-fluoro-phenyl]methyl]-N,N-dimethyl-piperazine-1-carboxamide | 0.527 |
| 1-[[3-(4-aminopyrido[3,2-d]pyrimidin-6-yl)-5-fluoro-phenyl]methyl]piperidine-4-carboxamide | 0.908 |
| 6-[3-[(3,3-difluoroazetidin-1-yl)methyl]-5-fluoro-phenyl]pyrido[3,2-d]pyrimidin-4-amine | 0.212 |
| 4-[[3-(4-aminopyrido[3,2-d]pyrimidin-6-yl)-5-fluoro-phenyl]methyl]-N,N-dimethyl-piperazine-1-sulfonamide | 0.507 |
| 6-[3-fluoro-5-(1,4-oxazepan-4-ylmethyl)phenyl]pyrido[3,2-d]pyrimidin-4-amine | 0.645 |
| 2-[4-[[3-(4-aminopyrido[3,2-d]pyrimidin-6-yl)-5-fluoro-phenyl]methyl]piperazin-1-yl]-N,N-dimethyl-acetamide | 0.585 |
| 1-[4-[[3-(4-aminopyrido[3,2-d]pyrimidin-6-yl)-5-fluoro-phenyl]methyl]piperazin-1-yl]-2-methyl-propan-1-one | 0.513 |
| 6-[3-fluoro-5-[(4-methylsulfonylpiperazin-1-yl)methyl]phenyl]pyrido[3,2-d]pyrimidin-4-amine | 0.49 |
| 6-[3-[[(1,1-dioxothiolan-3-yl)-methyl-amino]methyl]-5-fluoro-phenyl]pyrido[3,2-d]pyrimidin-4-amine | 0.325 |
| 2-[[3-(4-aminopyrido[3,2-d]pyrimidin-6-yl)-5-fluoro-phenyl]methyl-methyl-amino]-1-morpholino-ethanone | 0.705 |
| N-[1-[[3-(4-aminopyrido[3,2-d]pyrimidin-6-yl)-5-fluoro-phenyl]methyl]pyrrolidin-3-yl]-N-methyl-acetamide | 0.999 |
| [1-[[3-(4-aminopyrido[3,2-d]pyrimidin-6-yl)-5-fluoro-phenyl]methyl]azetidin-3-yl]-(4-methylpiperazin-1-yl)methanone | 0.264 |
| 6-[3-[[4-(dimethylamino)-1-piperidyl]methyl]-5-fluoro-phenyl]pyrido[3,2-d]pyrimidin-4-amine | 0.43 |
| 6-[3-fluoro-5-[(4-methoxy-1-piperidyl)methyl]phenyl]pyrido[3,2-d]pyrimidin-4-amine | 1.1 |
| 6-[3-fluoro-5-(pyrrolidin-1-ylmethyl)phenyl]pyrido[3,2-d]pyrimidin-4-amine | 0.554 |
| 6-[3-fluoro-5-[(2-methylpyrrolidin-1-yl)methyl]phenyl]pyrido[3,2-d]pyrimidin-4-amine | 2.3 |
| 6-[3-fluoro-5-[[methyl-(1-methylpyrrolidin-3-yl)amino]methyl]phenyl]pyrido[3,2-d]pyrimidin-4-amine | 0.271 |
| 2-[[3-(4-aminopyrido[3,2-d]pyrimidin-6-yl)-5-fluoro-phenyl]methyl-methyl-amino]-N,N-dimethyl-acetamide | 1.5 |
| 6-[3-fluoro-5-[[2-methoxyethyl(methyl)amino]methyl]phenyl]pyrido[3,2-d]pyrimidin-4-amine | 0.521 |
| 4-[[3-(4-aminopyrido[3,2-d]pyrimidin-6-yl)-5-fluoro-phenyl]methyl]-N,1-dimethyl-piperazine-2-carboxamide | 0.975 |
| 1-[3-(4-aminopyrido[3,2-d]pyrimidin-6-yl)-5-fluoro-phenyl]methyl]azetidine-3-carboxamide | 0.186 |
| 1-[[3-(4-aminopyrido[3,2-d]pyrimidin-6-yl)-5-fluoro-phenyl]methyl]-N-methyl-pyrrolidine-3-carboxamide | 0.731 |
| 1-[[3-(4-aminopyrido[3,2-d]pyrimidin-6-yl)-5-fluoro-phenyl]methyl]-N,N-dimethyl-azetidine-3-carboxamide | 0.461 |
| 4-[[3-(4-aminopyrido[3,2-d]pyrimidin-6-yl)-5-fluoro-phenyl]methyl]-1-methyl-piperazine-2-carboxamide | 0.36 |
| 1-[[3-(4-aminopyrido[3,2-d]pyrimidin-6-yl)-5-fluoro-phenyl]methyl]-N-methyl-azetidine-3-carboxamide | 0.226 |
| 2-[1-[[3-(4-aminopyrido[3,2-d]pyrimidin-6-yl)-5-fluoro-phenyl]methyl]-4-piperidyl]-N,N-dimethyl-acetamide | 0.508 |
| 4-[[3-(4-aminopyrido[3,2-d]pyrimidin-6-yl)-5-fluoro-phenyl]methyl]-N-methyl-morpholine-2-carboxamide | 0.952 |
| [1-[[3-(4-aminopyrido[3,2-d]pyrimidin-6-yl)-5-fluoro-phenyl]methyl]-3-piperidyl]methanol | 0.947 |
| 6-[3-fluoro-5-[(4-methylpiperazin-1-yl)methyl]phenyl]pyrido[3,2-d]pyrimidin-4-amine | 0.374 |
| 1-[[3-(4-aminopyrido[3,2-d]pyrimidin-6-yl)-5-fluoro-phenyl]methyl]piperidin-3-ol | 0.711 |
| (3R)-1-[[3-(4-aminopyrido[3,2-d]pyrimidin-6-yl)-5-fluoro-phenyl]methyl]piperidin-3-ol | 0.571 |
| 6-[3-fluoro-5-[[methyl-(1-methyl-4-piperidyl)amino]methyl]phenyl]pyrido[3,2-d]pyrimidin-4-amine | 0.449 |
| 6-[3-[[(3S)-3-(dimethylamino)pyrrolidin-1-yl]methyl]-5-fluoro-phenyl]pyrido[3,2-d]pyrimidin-4-amine | 0.598 |
| 6-[3-[[3-(dimethylamino)pyrrolidin-1-yl]methyl]-5-fluoro-phenyl]pyrido[3,2-d]pyrimidin-4-amine | 0.547 |
| 6-[3-fluoro-5-[(3-morpholinopyrrolidin-1-yl)methyl]phenyl]pyrido[3,2-d]pyrimidin-4-amine | 1.6 |
| tert-butyl N-[(3R)-1-(4-aminopyrido[3,2-d]pyrimidin-6-yl)-3-piperidyl]carbamate | 10. |
| tert-butyl N-[(3S)-1-(4-aminopyrido[3,2-d]pyrimidin-6-yl)-3-piperidyl]carbamate | 5.6 |
| 6-[(3S)-3-amino-1-piperidyl]pyrido[3,2-d]pyrimidin-4-amine | 10.0 |
| 6-[(3R)-3-amino-1-piperidyl]pyrido[3,2-d]pyrimidin-4-amine | 10.0 |
| N-[(3S)-1-(4-aminopyrido[3,2-d]pyrimidin-6-yl)-3-piperidyl]-3-methoxy-propanamide | 9.3 |
| N-[(3S)-1-(4-aminopyrido[3,2-d]pyrimidin-6-yl)-3-piperidyl]-3-pyrrolidin-1-yl-propanamide | 1.9 |
| N-[(3S)-1-(4-aminopyrido[3,2-d]pyrimidin-6-yl)-3-piperidyl]-2-(4-methylpiperazin-1-yl)acetamide | 10.0 |
| N-[(3R)-1-(4-aminopyrido[3,2-d]pyrimidin-6-yl)-3-piperidyl]-3-methoxy-propanamide | 10.0 |
| N-[(3R)-1-(4-aminopyrido[3,2-d]pyrimidin-6-yl)-3-piperidyl]-3-pyrrolidin-1-yl-propanamide | 10.0 |
| N-[(3R)-1-(4-aminopyrido[3,2-d]pyrimidin-6-yl)-3-piperidyl]-2-(4-methylpiperazin-1-yl)acetamide | 10.0 |

| Compound | MAP4K4 IC$_{50}$ (μM) |
|---|---|
| 4-(4-aminopyrido[3,2-d]pyrimidin-6-yl)-1H-pyridin-2-one | 3.1 |
| N6-[(2-fluorophenyl)methyl]pyrido[3,2-d]pyrimidine-4,6-diamine | 0.253 |
| N6-(1-phenylethyl)pyrido[3,2-d]pyrimidine-4,6-diamine | 2.7 |
| 6-[2-(trifluoromethyl)-4-pyridyl]pyrido[3,2-d]pyrimidin-4-amine | 2.2 |
| 6-(2-methylphenoxy)pyrido[3,2-d]pyrimidin-4-amine | 2.2 |
| 6-(3-methylphenoxy)pyrido[3,2-d]pyrimidin-4-amine | 0.818 |
| 6-(4-pyridyloxy)pyrido[3,2-d]pyrimidin-4-amine | 2.9 |
| 6-(4-methylphenoxy)pyrido[3,2-d]pyrimidin-4-amine | 0.746 |
| 6-(3-fluorophenoxy)pyrido[3,2-d]pyrimidin-4-amine | 1.3 |
| 2-(4-aminopyrido[3,2-d]pyrimidin-6-yl)oxybenzonitrile | 3.1 |
| 6-[(6-methyl-3-pyridyl)oxy]pyrido[3,2-d]pyrimidin-4-amine | 1.0 |
| 6-[(2-methyl-3-pyridyl)oxy]pyrido[3,2-d]pyrimidin-4-amine | 5.2 |
| 6-phenoxypyrido[3,2-d]pyrimidin-4-amine | 1.6 |
| 6-(3-pyridyloxy)pyrido[3,2-d]pyrimidin-4-amine | 1.2 |
| 4-(4-aminopyrido[3,2-d]pyrimidin-6-yl)oxybenzamide | 5.0 |
| 4-(4-aminopyrido[3,2-d]pyrimidin-6-yl)oxybenzonitrile | 3.6 |
| 3-(4-aminopyrido[3,2-d]pyrimidin-6-yl)oxybenzonitrile | 0.625 |
| 6-(2-chlorophenoxy)pyrido[3,2-d]pyrimidin-4-amine | 1.4 |
| 6-(4-methoxyphenoxy)pyrido[3,2-d]pyrimidin-4-amine | 1.4 |
| 6-(3-chlorophenoxy)pyrido[3,2-d]pyrimidin-4-amine | 0.145 |
| 6-(2,4-difluorophenoxy)pyrido[3,2-d]pyrimidin-4-amine | 0.634 |
| 6-(3,4-difluorophenoxy)pyrido[3,2-d]pyrimidin-4-amine | 0.623 |
| N6-[(2-chlorophenyl)methyl]pyrido[3,2-d]pyrimidine-4,6-diamine | 0.528 |
| 6-(2-fluorophenoxy)pyrido[3,2-d]pyrimidin-4-amine | 1.3 |
| N6-[(3-chlorophenyl)methyl]pyrido[3,2-d]pyrimidine-4,6-diamine | 0.0856 |
| N6-[(4-chlorophenyl)methyl]pyrido[3,2-d]pyrimidine-4,6-diamine | 1.6 |
| N6-(o-tolylmethyl)pyrido[3,2-d]pyrimidine-4,6-diamine | 0.556 |
| N6-[1-(6-methyl-2-pyridyl)ethyl]pyrido[3,2-d]pyrimidine-4,6-diamine | 9.4 |
| N6-[(3-pyrrolidin-1-ylphenyl)methyl]pyrido[3,2-d]pyrimidine-4,6-diamine | 2.2 |
| N6-(pyrazin-2-ylmethyl)pyrido[3,2-d]pyrimidine-4,6-diamine | 4.8 |
| 3-(4-aminopyrido[3,2-d]pyrimidin-6-yl)-5-fluoro-N-(2-hydroxy-1,1-dimethyl-ethyl)benzamide | 2.0 |
| 3-(4-aminopyrido[3,2-d]pyrimidin-6-yl)-5-fluoro-N-methyl-benzamide | 0.382 |
| 3-(4-aminopyrido[3,2-d]pyrimidin-6-yl)-5-fluoro-N-(2-hydroxyethyl)benzamide | 0.783 |
| 3-(4-aminopyrido[3,2-d]pyrimidin-6-yl)-5-fluoro-N-(3-hydroxycyclobutyl)benzamide | 1.5 |
| 3-(4-aminopyrido[3,2-d]pyrimidin-6-yl)-N-(3-hydroxycyclobutyl)benzamide | 2.3 |
| 3-(4-aminopyrido[3,2-d]pyrimidin-6-yl)-N-(2-hydroxyethyl)benzamide | 1.1 |
| 3-(4-aminopyrido[3,2-d]pyrimidin-6-yl)-N-(2-hydroxy-1-methyl-ethyl)benzamide | 2.3 |
| 3-(4-aminopyrido[3,2-d]pyrimidin-6-yl)-5-fluoro-N-(2-hydroxy-1-methyl-ethyl)benzamide | 1.1 |
| 3-(4-aminopyrido[3,2-d]pyrimidin-6-yl)-N-(2-hydroxy-1,1-dimethyl-ethyl)benzamide | 2.6 |
| 3-(4-aminopyrido[3,2-d]pyrimidin-6-yl)-N-cyclobutyl-benzamide | 1.1 |
| 3-(4-aminopyrido[3,2-d]pyrimidin-6-yl)-5-fluoro-N-[(1-methyl-4-piperidyl)methyl]benzamide | 6.0 |
| 3-(4-aminopyrido[3,2-d]pyrimidin-6-yl)-5-fluoro-N-(2-morpholinoethyl)benzamide | 0.855 |
| 6-[3-fluoro-5-(2-pyrrolidin-1-ylethylamino)phenyl]pyrido[3,2-d]pyrimidin-4-amine | 0.0888 |
| 3-(4-aminopyrido[3,2-d]pyrimidin-6-yl)-N-methyl-benzamide | 0.847 |
| 3-(4-aminopyrido[3,2-d]pyrimidin-6-yl)-N-(2-morpholinoethyl)benzamide | 0.895 |
| 3-(4-aminopyrido[3,2-d]pyrimidin-6-yl)-5-fluoro-N-(2-pyrrolidin-1-ylethyl)benzamide | 0.256 |
| 3-(4-aminopyrido[3,2-d]pyrimidin-6-yl)-N-(2-pyrrolidin-1-ylethyl)benzamide | 0.403 |
| 3-(4-aminopyrido[3,2-d]pyrimidin-6-yl)-N-[2-(dimethylamino)ethyl]-5-fluoro-benzamide | 0.215 |
| 3-(4-aminopyrido[3,2-d]pyrimidin-6-yl)-N-[2-(dimethylamino)ethyl]benzamide | 0.453 |
| 3-(4-aminopyrido[3,2-d]pyrimidin-6-yl)-N-[(1-methyl-4-piperidyl)methyl]benzamide | 5.6 |
| N-[3-(4-aminopyrido[3,2-d]pyrimidin-6-yl)-5-fluoro-phenyl]-2-(1-piperidyl)ethanesulfonamide | 0.484 |
| N-[3-(4-aminopyrido[3,2-d]pyrimidin-6-yl)-5-fluoro-phenyl]-2-(4-methylpiperazin-1-yl)ethanesulfonamide | 0.138 |
| N-[3-(4-aminopyrido[3,2-d]pyrimidin-6-yl)-5-fluoro-phenyl]-2-morpholino-ethanesulfonamide | 0.32 |
| 6-[3-fluoro-5-[[3-(pyrrolidin-1-ylmethyl)oxetan-3-yl]amino]phenyl]pyrido[3,2-d]pyrimidin-4-amine | 3.1 |
| 6-(3-fluorophenyl)-N-isopropyl-pyrido[3,2-d]pyrimidin-4-amine | 0.705 |
| 6-(3-fluorophenyl)-N-methyl-pyrido[3,2-d]pyrimidin-4-amine | 0.597 |
| N-cyclobutyl-6-(3-fluorophenyl)pyrido[3,2-d]pyrimidin-4-amine | 0.673 |
| N-(cyclopropylmethyl)-6-(3-fluorophenyl)pyrido[3,2-d]pyrimidin-4-amine | 0.432 |
| N-ethyl-6-(3-fluorophenyl)pyrido[3,2-d]pyrimidin-4-amine | 0.267 |
| 6-(3-fluorophenyl)-N-isobutyl-pyrido[3,2-d]pyrimidin-4-amine | 0.49 |
| N-[3-(4-aminopyrido[3,2-d]pyrimidin-6-yl)-5-fluoro-phenyl]-N',N'-dimethyl-propane-1,3-diamine | 0.0955 |
| 6-[3-(difluoromethoxy)phenyl]pyrido[3,2-d]pyrimidin-4-amine | 0.0718 |
| N-[3-(4-aminopyrido[3,2-d]pyrimidin-6-yl)-5-fluoro-phenyl]pyrrolidine-1-sulfonamide | 0.623 |
| 6-[3-[(cyclopropylamino)methyl]-5-fluoro-phenyl]pyrido[3,2-d]pyrimidin-4-amine | 0.11 |
| 2-[[3-(4-aminopyrido[3,2-d]pyrimidin-6-yl)-5-fluoro-phenyl]methylamino]ethanol | 0.131 |
| 6-[3-fluoro-5-[(isobutylamino)methyl]phenyl]pyrido[3,2-d]pyrimidin-4-amine | 0.724 |
| 4-[[3-(4-aminopyrido[3,2-d]pyrimidin-6-yl)-5-fluoro-phenyl]methylamino]cyclohexanol | 1.6 |
| 6-[3-(2-pyridyloxy)phenyl]pyrido[3,2-d]pyrimidin-4-amine | 0.0257 |
| 6-[3-[2-(pyrrolidin-1-ylmethyl)cyclopropyl]phenyl]pyrido[3,2-d]pyrimidin-4-amine | 0.977 |
| 6-[3-[(cyclopropylmethylamino)methyl]-5-fluoro-phenyl]pyrido[3,2-d]pyrimidin-4-amine | 0.193 |

-continued

| Compound | MAP4K4 IC$_{50}$ (µM) |
|---|---|
| 6-[3-[(cyclobutylamino)methyl]-5-fluoro-phenyl]pyrido[3,2-d]pyrimidin-4-amine | 0.14 |
| 6-[3-fluoro-5-[(oxetan-3-ylamino)methyl]phenyl]pyrido[3,2-d]pyrimidin-4-amine | 0.249 |
| 2-[[3-(4-aminopyrido[3,2-d]pyrimidin-6-yl)-5-fluoro-phenyl]methylamino]propan-1-ol | 0.267 |
| 6-[3-[(cyclopentylamino)methyl]-5-fluoro-phenyl]pyrido[3,2-d]pyrimidin-4-amine | 0.258 |
| 6-[3-fluoro-5-[(isopropylamino)methyl]phenyl]pyrido[3,2-d]pyrimidin-4-amine | 0.29 |
| 6-[3-fluoro-5-[(tetrahydropyran-4-ylamino)methyl]phenyl]pyrido[3,2-d]pyrimidin-4-amine | 0.288 |
| 6-[3-fluoro-5-[(tetrahydrofuran-3-ylmethylamino)methyl]phenyl]pyrido[3,2-d]pyrimidin-4-amine | 0.288 |
| 6-[3-fluoro-5-[[(1-methyl-4-piperidyl)amino]methyl]phenyl]pyrido[3,2-d]pyrimidin-4-amine | 0.55 |
| [1-[[3-(4-aminopyrido[3,2-d]pyrimidin-6-yl)-5-fluoro-phenyl]methylamino]cyclopropyl]methanol | 0.206 |
| ethyl 4-[[3-(4-aminopyrido[3,2-d]pyrimidin-6-yl)-5-fluoro-phenyl]methylamino]piperidine-1-carboxylate | 0.71 |
| 2-[[3-(4-aminopyrido[3,2-d]pyrimidin-6-yl)phenyl]methylamino]ethanol | 0.451 |
| 6-[3-[(cyclopropylmethylamino)methyl]phenyl]pyrido[3,2-d]pyrimidin-4-amine | 0.707 |
| 6-[3-[(cyclobutylamino)methyl]phenyl]pyrido[3,2-d]pyrimidin-4-amine | 0.578 |
| 6-[3-[(isobutylamino)methyl]phenyl]pyrido[3,2-d]pyrimidin-4-amine | 1.6 |
| [1-[[3-(4-aminopyrido[3,2-d]pyrimidin-6-yl)phenyl]methylamino]cyclopropyl]methanol | 0.655 |
| N-[[3-(4-aminopyrido[3,2-d]pyrimidin-6-yl)-5-fluoro-phenyl]methyl]-N',N'-dimethyl-ethane-1,2-diamine | 0.0955 |
| 2-[[3-(4-aminopyrido[3,2-d]pyrimidin-6-yl)-5-fluoro-phenyl]methylamino]-N,N-dimethyl-acetamide | 0.335 |
| 6-[3-fluoro-5-[(2-pyrrolidin-1-ylethylamino)methyl]phenyl]pyrido[3,2-d]pyrimidin-4-amine | 0.0669 |
| 6-[3-fluoro-5-[(tetrahydropyran-4-ylmethylamino)methyl]phenyl]pyrido[3,2-d]pyrimidin-4-amine | 0.785 |
| 6-[3-fluoro-5-[[(1-methyl-2-piperidyl)methylamino]methyl]phenyl]pyrido[3,2-d]pyrimidin-4-amine | 0.311 |
| 6-[3-fluoro-5-[[(1-methyl-4-piperidyl)methylamino]methyl]phenyl]pyrido[3,2-d]pyrimidin-4-amine | 0.664 |
| 6-[3-fluoro-5-[(2-morpholinoethylamino)methyl]phenyl]pyrido[3,2-d]pyrimidin-4-amine | 0.481 |
| 1-[4-[[3-(4-aminopyrido[3,2-d]pyrimidin-6-yl)-5-fluoro-phenyl]methylamino]-1-piperidyl]ethanone | 0.70 |
| 6-[3-fluoro-5-[[(1-methylazetidin-3-yl)amino]methyl]phenyl]pyrido[3,2-d]pyrimidin-4-amine | 0.124 |
| 6-[3-[(cyclopropylamino)methyl]phenyl]pyrido[3,2-d]pyrimidin-4-amine | 0.225 |
| 2-[[3-(4-aminopyrido[3,2-d]pyrimidin-6-yl)phenyl]methylamino]propan-1-ol | 0.538 |
| 6-[3-[(cyclopentylamino)methyl]phenyl]pyrido[3,2-d]pyrimidin-4-amine | 0.646 |
| N-[[3-(4-aminopyrido[3,2-d]pyrimidin-6-yl)phenyl]methyl]-N',N'-dimethyl-ethane-1,2-diamine | 0.197 |
| 6-[3-[(isopropylamino)methyl]phenyl]pyrido[3,2-d]pyrimidin-4-amine | 0.786 |
| 6-[3-[(tetrahydropyran-4-ylamino)methyl]phenyl]pyrido[3,2-d]pyrimidin-4-amine | 0.648 |
| 6-[3-[(tetrahydrofuran-3-ylmethylamino)methyl]phenyl]pyrido[3,2-d]pyrimidin-4-amine | 0.701 |
| 2-[[3-(4-aminopyrido[3,2-d]pyrimidin-6-yl)phenyl]methylamino]-N,N-dimethyl-acetamide | 0.979 |
| 6-[3-[(2-pyrrolidin-1-ylethylamino)methyl]phenyl]pyrido[3,2-d]pyrimidin-4-amine | 0.177 |
| 6-[3-[[(1-methyl-4-piperidyl)amino]methyl]phenyl]pyrido[3,2-d]pyrimidin-4-amine | 1.8 |
| 6-[3-[(tetrahydropyran-4-ylmethylamino)methyl]phenyl]pyrido[3,2-d]pyrimidin-4-amine | 3.8 |
| 6-[3-[[(1-methyl-2-piperidyl)methylamino]methyl]phenyl]pyrido[3,2-d]pyrimidin-4-amine | 0.613 |
| 6-[3-[[(1-methyl-4-piperidyl)methylamino]methyl]phenyl]pyrido[3,2-d]pyrimidin-4-amine | 2.7 |
| 6-[3-[(2-morpholinoethylamino)methyl]phenyl]pyrido[3,2-d]pyrimidin-4-amine | 1.6 |
| 6-[3-[[(1-methylazetidin-3-yl)amino]methyl]phenyl]pyrido[3,2-d]pyrimidin-4-amine | 0.44 |
| ethyl 4-[[3-(4-aminopyrido[3,2-d]pyrimidin-6-yl)phenyl]methylamino]piperidine-1-carboxylate | 1.5 |
| 6-[3-[(oxetan-3-ylamino)methyl]phenyl]pyrido[3,2-d]pyrimidin-4-amine | 0.377 |
| 6-[3-[[(1,1-dimethyl-2-morpholino-ethyl)amino]methyl]-5-fluoro-phenyl]pyrido[3,2-d]pyrimidin-4-amine | 4.1 |
| 6-[3-fluoro-5-(4-methyl-1H-pyrazol-3-yl)phenyl]pyrido[3,2-d]pyrimidin-4-amine | 0.0101 |
| 6-[3-(4-methyl-1H-pyrazol-3-yl)phenyl]pyrido[3,2-d]pyrimidin-4-amine | 0.00311 |
| 6-[3-[[(1,1-dimethyl-2-morpholino-ethyl)amino]methyl]phenyl]pyrido[3,2-d]pyrimidin-4-amine | 9.3 |
| 6-(3-methoxyphenyl)pyrido[3,2-d]pyrimidin-4-amine | 0.0997 |
| 6-(3-isopropoxyphenyl)pyrido[3,2-d]pyrimidin-4-amine | 0.179 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method for the inhibition of angiogenesis which method comprises administering to a patient a therapeutically effective amount of a compound of claim formula (I)

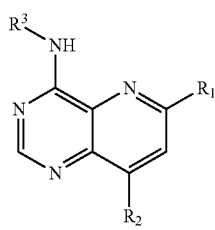

(I)

and stereoisomers, geometric isomers, tautomers, or pharmaceutically acceptable salts thereof, wherein:

$R^1$ is —NR—$C_1$-$C_{12}$-hydroxyalkyl, —NR—($C_1$-$C_{12}$-alkylenyl)$_n$-$C_3$-$C_6$-cycloalkyl, —NR—($C_1$-$C_{12}$-alkylenyl)$_n$-heterocyclyl, —NR—($C_1$-$C_{12}$-alkylenyl)$_n$-$C_6$-$C_{20}$-aryl, —NR—($C_1$-$C_{12}$-alkylenyl)$_n$-heteroaryl, —NR—($C_1$-$C_{12}$-alkylenyl)$_n$-$C_6$-$C_{20}$-aryloxy, $C_6$-$C_{20}$-aryl, pyridine, N-linked piperidine, N-linked pyrrolidine, N-linked piperazine, N-linked morpholine, 1H-pyrazol-4-yl, $C_6$-$C_{20}$-aryloxy or heteroaryloxy, each of which can be unsubstituted or substituted by one or more substituent(s) selected from the group consisting of:

CN;
oxo;
OH;
$NH_2$;
halo;
$C_1$-$C_{12}$-alkyl;
($C_1$-$C_{12}$-alkylenyl)$_n$-$C_1$-$C_{12}$-alkoxy, unsubstituted or substituted by one or more substituent(s) selected from the group consisting of $C_3$-$C_6$-cycloalkyl, heterocyclyl, aryl and heteroaryl;
$C_1$-$C_{12}$-hydroxyalkyl;
$C_1$-$C_{12}$-haloalkyl;
$C_1$-$C_{12}$-haloalkoxy;
($C_1$-$C_{12}$-alkylenyl)$_n$-C(O)O—$C_1$-$C_{12}$-alkyl;
—C(O)—$C_1$-$C_{12}$-alkyl;
O—R', wherein R' is $C_3$-$C_6$-cycloalkyl, heterocycloalkyl, aryl or heteroaryl, each of which are unsubstituted or substituted by one or more $R^g$;
—($C_1$-$C_{12}$-alkylenyl)$_n$-cycloalkyl or ($C_1$-$C_{12}$-alkylenyl)$_n$-heterocyclyl unsubstituted or substituted by one or more substituent(s) selected from the group consisting of:
halo, oxo, OH, $NH_2$, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —NH($C_1$-$C_{12}$-alkyl), —N($C_1$-$C_{12}$-alkyl)$_2$, —N($C_1$-$C_{12}$-alkyl)-C(O)—$C_1$-$C_{12}$-alkyl, —C(O)—$C_1$-$C_{12}$-alkyl, —C(O)O—$C_1$-$C_{12}$-alkyl, ($C_1$-$C_{12}$-alkylenyl)$_n$-C(O)—$NH_2$, ($C_1$-$C_{12}$-alkylenyl)$_n$-C(O)—NH($C_1$-$C_{12}$-alkyl), —C(O)—NH($C_1$-$C_{12}$-hydroxyalkyl), ($C_1$-$C_{12}$-alkylenyl)$_n$-C(O)—N($C_1$-$C_{12}$-alkyl)$_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl)$_2$, —C(O)OH, —C(O)-heterocyclyl, ($C_1$-$C_{12}$-alkylenyl)$_n$-heterocyclyl and ($C_1$-$C_{12}$-alkylenyl)$_n$-heteroaryl, which heterocyclyl and heteroaryl group(s) can be unsubstituted or substituted by one or more substituent(s) selected from the group consisting of:
OH, $NH_2$, halo, $C_1$-$C_{12}$-alkyl, $C_1$-$C_{12}$-alkoxy, $C_1$-$C_{12}$-haloalkyl and $C_1$-$C_{12}$-hydroxyalkyl;

($C_1$-$C_{12}$-alkylenyl)$_n$-aryl or ($C_1$-$C_{12}$-alkylenyl)$_n$-heteroaryl, wherein the aryl or heteroaryl is unsubstituted or substituted by one or more substituent(s) selected from the group consisting of:
halo, OH, $NH_2$, $C_1$-$C_{12}$-alkyl, $C_1$-$C_{12}$-hydroxyalkyl, $C_1$-$C_{12}$-haloalkyl, ($C_1$-$C_{12}$-alkylenyl)$_n$-$C_1$-$C_{12}$-alkoxy, —NH($C_1$-$C_{12}$-alkyl), —N($C_1$-$C_{12}$-alkyl)$_2$, —N($C_1$-$C_{12}$-alkyl)C(O)—$C_1$-$C_{12}$-alkyl, —C(O)—$C_1$-$C_{12}$-alkyl, —C(O)—$NH_2$, —C(O)—NH($C_1$-$C_{12}$-alkyl), —C(O)—NH($C_1$-$C_{12}$-hydroxyalkyl), —C(O)—N($C_1$-$C_{12}$-alkyl)$_2$, —C(O)—NH($C_1$-$C_{12}$-haloalkyl), —C(O)—NH-heterocyclyl, —S(O)$_2$—$C_1$-$C_{12}$-alkyl, —S(O)$_2$—N($C_1$-$C_{12}$-alkyl)$_2$, $C_1$-$C_{12}$-alkylenyl-C(O)N($C_1$-$C_{12}$-alkyl)$_2$, —C(O)OH, —C(O)-heterocyclyl and heterocyclyl, which heterocyclyl group(s) can be unsubstituted or substituted by one or more substituent(s) selected from the group consisting of:
OH, $NH_2$, halo, $C_1$-$C_{12}$-alkyl, $C_1$-$C_{12}$-alkoxy, $C_1$-$C_{12}$-haloalkyl, and $C_1$-$C_{12}$-hydroxyalkyl;

($C_1$-$C_{12}$-alkylenyl)$_n$-NR$^a$R$^b$, wherein R$^a$ and R$^b$ are independently selected from:
H,
$C_1$-$C_{12}$-alkyl,
$C_1$-$C_{12}$-hydroxyalkyl,
$C_1$-$C_{12}$-haloalkyl,
($C_1$-$C_{12}$-alkylenyl)$_n$-$C_1$-$C_{12}$-alkoxy,
—S(O)$_2$—($C_1$-$C_{12}$-alkylenyl)$_n$-heterocyclyl unsubstituted or substituted by one or more $R^g$,
($C_1$-$C_{12}$-alkylenyl)$_n$-$C_6$-$C_{20}$-aryl, which aryl is unsubstituted or substituted by one or more $R^g$,
($C_1$-$C_{12}$-alkylenyl)$_n$-$C_3$-$C_6$-cycloalkyl unsubstituted or substituted by one or more $R^g$,
($C_1$-$C_{12}$-alkylenyl)$_n$-heterocyclyl unsubstituted or substituted by one or more oxo, —C(O)—$C_1$-$C_{12}$-alkyl, —C(O)O—$C_1$-$C_{12}$-alkyl or $R^g$,
$C_1$-$C_{12}$-alkylenyl-C(O)-heteroaryl unsubstituted or substituted by one or more $R^g$,
$C_1$-$C_{12}$-alkylenyl-$NH_2$,
$C_1$-$C_{12}$-alkylenyl-NH($C_1$-$C_{12}$-alkyl),
$C_1$-$C_{12}$-alkylenyl-N($C_1$-$C_{12}$-alkyl)$_2$,
$C_1$-$C_{12}$-alkylenyl-C(O)$NH_2$,
$C_1$-$C_{12}$-alkylenyl-C(O)NH($C_1$-$C_{12}$-alkyl), or,
$C_1$-$C_{12}$-alkylenyl-C(O)N($C_1$-$C_{12}$-alkyl)$_2$, ($C_1$-$C_{12}$-alkylenyl)$_n$-C(O)NR$^c$R$^d$, wherein R$^c$ and R$^d$ are independently selected from:
H,
$C_1$-$C_{12}$-alkyl,
$C_1$-$C_{12}$-hydroxyalkyl,
$C_1$-$C_{12}$-haloalkyl,
($C_1$-$C_{12}$-alkylenyl)$_n$-$C_1$-$C_{12}$-alkoxy,
$C_1$-$C_{12}$-alkylenyl-NH($C_1$-$C_{12}$-alkyl),
$C_1$-$C_{12}$-alkylenyl-N($C_1$-$C_{12}$-alkyl)$_2$,
($C_1$-$C_{12}$-alkylenyl)$_n$-heterocyclyl, unsubstituted or substituted by one or more substituent(s) selected from the group consisting of oxo, —C(O)—$C_1$-$C_{12}$-alkyl and $R^g$,
($C_1$-$C_{12}$-alkylenyl)$_n$-$C_3$-$C_6$-cycloalkyl unsubstituted or substituted by one or more $R^g$,
($C_1$-$C_{12}$-alkylenyl)$_n$-$C_6$-$C_{20}$-aryl unsubstituted or substituted by one or more $R^g$,
—NH—$C_3$-$C_6$-cycloalkyl; or
or R$^c$ and R$^d$ together with the nitrogen atom to which they are attached, form a 5 or 6 membered heterocyclyl which can or cannot comprise 1 or 2 additional heteroatom selected from N, O or S; and, ($C_1$-$C_{12}$-alkylenyl)$_n$-NR$^e$C(O)R$^f$, wherein R$^e$ is H or $C_1$-$C_{12}$-alkyl, R$^f$ is halo, CN, OH, $C_1$-$C_{12}$-alkyl, $C_1$-$C_{12}$-haloalkyl, ($C_1$-$C_{12}$-alkylenyl)$_n$-$C_1$-$C_{12}$-alkoxy, $C_1$-$C_{12}$-hydroxyalkyl, $C_1$-$C_{12}$-cyanoalkyl, ($C_1$-$C_{12}$-alkylenyl)$_n$-NH$_2$, ($C_1$-$C_{12}$-alkylenyl)$_n$-NH($C_1$-$C_{12}$-alkyl), ($C_1$-$C_{12}$-alkylenyl)$_n$-N($C_1$-$C_{12}$-alkyl)$_2$, ($C_1$-$C_{12}$-alkylenyl)$_n$-$C_3$-$C_6$-cycloalkyl, ($C_1$-$C_{12}$-alkylenyl)$_n$-heterocyclyl, or ($C_1$-$C_{12}$-alkylenyl)$_n$-NH—$C_3$-$C_6$-cycloalkyl, wherein said cycloalkyl, heterocyclyl or heteroaryl are unsubstituted or substituted by oxo, —C(O)—$C_1$-$C_{12}$-alkyl or one or more R$^g$;

R$^2$ is H, CN, —C(O)—NH($C_1$-$C_{12}$-alkyl)-NH—C(O)—$C_1$-$C_{12}$-alkyl, —C(O)—N($C_1$-$C_{12}$-alkyl)($C_1$-$C_{12}$-alkoxy), —C(O)—N($C_1$-$C_{12}$-alkyl)($C_1$-$C_{12}$-alkylalkoxy), —C(O)—NH(heterocyclyl), —C(O)—NH($C_1$-$C_{12}$-alkyl-heterocyclyl), —C(O)—N($C_1$-$C_{12}$-alkyl)(heterocyclyl), or —C(O)-heterocyclyl, which heterocyclyl groups are unsubstituted or substituted by one or more R$^g$, —N($C_1$-$C_{12}$-alkyl)-C(O)—$C_1$-$C_{12}$-alkyl, or —N($C_1$-$C_{12}$-alkyl)$_2$;

R$^3$ is H, i-butyl, $C_1$-$C_{12}$-haloalkyl, cyclobutyl, —C(O)—$C_1$-$C_{12}$-alkyl-$C_3$-$C_6$-cycloalkyl, —C(O)—$C_1$-$C_{12}$-alkyl-heterocyclyl —C(O)—$C_1$-$C_{12}$-alkyl-$C_6$-$C_{20}$-aryl, —C(O)—$C_1$-$C_{12}$-alkyl-heteroaryl or pyridinyl;

R is H or $C_1$-$C_{12}$-alkyl;

R$^g$ is H, OH, halo, NH$_2$, $C_1$-$C_{12}$-alkyl, ($C_1$-$C_{12}$-alkylenyl)$_n$-$C_1$-$C_{12}$-alkoxy, $C_1$-$C_{12}$-haloalkyl, $C_1$-$C_{12}$-haloalkoxy, $C_1$-$C_{12}$-hydroxyalkyl, or $C_1$-$C_{12}$-cyanoalkyl;

n is 0 or 1;

wherein in the preceeding heteroaryl groups are 5 or 6 membered heteroaryls comprising 1, 2 or 3 heteroatom(s) selected from N, O or S and heterocyclyl groups are 5 to 10 membered heterocyclyls comprising 1, 2 or 3 heteroatom(s) selected from N, O or S;

with the proviso that the compound of Formula I is not:

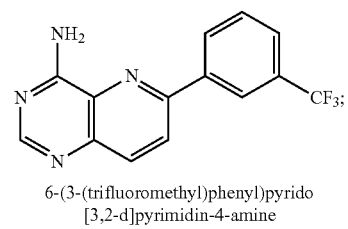

6-(3-(trifluoromethyl)phenyl)pyrido[3,2-d]pyrimidin-4-amine

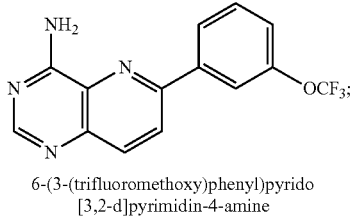

6-(3-(trifluoromethoxy)phenyl)pyrido[3,2-d]pyrimidin-4-amine

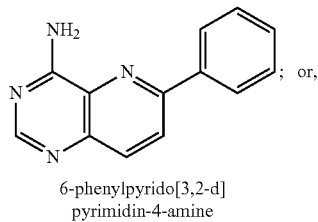

6-phenylpyrido[3,2-d]pyrimidin-4-amine

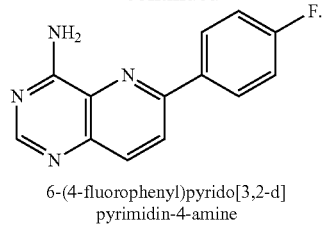

6-(4-fluorophenyl)pyrido[3,2-d]pyrimidin-4-amine

2. The method of claim 1 wherein the compound of formula I is selected from the group consisting of:

6-(2-fluoro-4-pyridyl)pyrido[3,2-d]pyrimidin-4-amine;
4-(4-aminopyrido[3,2-d]pyrimidin-6-yl)pyridin-2(1H)-one;
3-(4-aminopyrido[3,2-d]pyrimidin-6-yl)-5-fluorobenzoic acid;
3-(4-aminopyrido[3,2-d]pyrimidin-6-yl)-5-fluoro-N-(1-hydroxy-2-methylpropan-2-yl)benzamide;
3-(4-aminopyrido[3,2-d]pyrimidin-6-yl)-5-fluoro-N-methylbenzamide;
3-(4-aminopyrido[3,2-d]pyrimidin-6-yl)-N-cyclobutyl-5-fluorobenzamide;
3-(4-aminopyrido[3,2-d]pyrimidin-6-yl)-5-fluoro-N-(2-hydroxyethyl)benzamide;
3-(4-aminopyrido[3,2-d]pyrimidin-6-yl)-5-fluoro-N-(3-hydroxycyclobutyl)benzamide;
3-(4-aminopyrido[3,2-d]pyrimidin-6-yl)-5-fluoro-N-(1-hydroxypropan-2-yl)benzamide;
3-(4-aminopyrido[3,2-d]pyrimidin-6-yl)-5-fluoro-N-((1-methylpiperidin-4-yl)methyl)benzamide;
3-(4-aminopyrido[3,2-d]pyrimidin-6-yl)-5-fluoro-N-(2-morpholinoethyl)benzamide;
3-(4-aminopyrido[3,2-d]pyrimidin-6-yl)-N-(2-(dimethylamino)ethyl)-5-fluorobenzamide;
3-(4-aminopyrido[3,2-d]pyrimidin-6-yl)-5-fluoro-N-(2-(pyrrolidin-1-yl)ethyl)benzamide;
3-(4-aminopyrido[3,2-d]pyrimidin-6-yl)benzoic acid;
3-(4-aminopyrido[3,2-d]pyrimidin-6-yl)-N-(3-hydroxycyclobutyl)benzamide;
3-(4-aminopyrido[3,2-d]pyrimidin-6-yl)-N-(2-hydroxyethyl)benzamide;
3-(4-aminopyrido[3,2-d]pyrimidin-6-yl)-N-(1-hydroxypropan-2-yl)benzamide;
3-(4-aminopyrido[3,2-d]pyrimidin-6-yl)-N-(1-hydroxy-2-methylpropan-2-yl)benzamide;
3-(4-aminopyrido[3,2-d]pyrimidin-6-yl)-N-cyclobutylbenzamide;
3-(4-aminopyrido[3,2-d]pyrimidin-6-yl)-N-methylbenzamide;
3-(4-aminopyrido[3,2-d]pyrimidin-6-yl)-N-(2-morpholinoethyl)benzamide;
3-(4-aminopyrido[3,2-d]pyrimidin-6-yl)-N-((1-methylpiperidin-4-yl)methyl)benzamide;
3-(4-aminopyrido[3,2-d]pyrimidin-6-yl)-N-(2-(dimethylamino)ethyl)benzamide;
3-(4-aminopyrido[3,2-d]pyrimidin-6-yl)-N-(2-(pyrrolidin-1-yl)ethyl)benzamide;
6-(3-fluorophenyl)-N-isopropylpyrido[3,2-d]pyrimidin-4-amine;
6-(3-fluorophenyl)-N-methylpyrido[3,2-d]pyrimidin-4-amine;
N-(cyclobutyl)-6-(3-fluorophenyl)pyrido[3,2-d]pyrimidin-4-amine;

N-(cyclopropylmethyl)-6-(3-fluorophenyl)pyrido[3,2-d]pyrimidin-4-amine;
6-(3-fluorophenyl)-N-ethylpyrido[3,2-d]pyrimidin-4-amine;
Ethyl 4-(3-(4-aminopyrido[3,2-d]pyrimidin-6-yl)-5-fluorobenzylamino)piperidine-1-carboxylate;
6-(3-fluoro-5-(2-(pyrrolidin-1-yl)ethylamino)phenyl)pyrido[3,2-d]pyrimidin-4-amine;
6-(3-Fluoro-5-(3-(pyrrolidin-1-ylmethyl)oxetan-3-ylamino)phenyl)pyrido[3,2-d]pyrimidin-4-amine;
N-(3-(4-aminopyrido[3,2-d]pyrimidin-6-yl)-5-fluorophenyl)pyrrolidine-1-sulfonamide;
2-Morpholin-4-yl-ethanesulfonic acid[3-(4-amino-pyrido[3,2-d]pyrimidin-6-yl)-5-fluoro-phenyl]-amide;
N-(3-(4-aminopyrido[3,2-d]pyrimidin-6-yl)-5-fluorophenyl)-2-(piperidin-1-yl)ethanesulfonamide;
N-(3-(4-aminopyrido[3,2-d]pyrimidin-6-yl)-5-fluorophenyl)-2-(4-methylpiperazin-1-yl)ethanesulfonamide;
6-[3-(2-Pyrrolidin-1-ylmethyl-cyclopropyl)-phenyl]-pyrido[3,2-d]pyrimidin-4-ylamine;
6-(3-(Pyridin-2-yloxy)phenyl)pyrido[3,2-d]pyrimidin-4-amine;
6-(3-Fluoro-5-(4-methyl-1H-pyrazol-3-yl)phenyl)pyrido[3,2-d]pyrimidin-4-amine;
6-(3-(4-methyl-1H-pyrazol-3-yl)phenyl)pyrido[3,2-d]pyrimidin-4-amine;
6-(3-(Cyclopentyloxy)phenyl)pyrido[3,2-d]pyrimidin-4-amine;
6-(3-(1H-imidazol-2-yl)piperidin-1-yl)pyrido[3,2-d]pyrimidin-4-amine;
tert-butyl N-[(3S)-1-(4-aminopyrido[3,2-d]pyrimidin-6-yl)-3-piperidyl]carbamate;
(S)-6-(3-aminopiperidin-1-yl)pyrido[3,2-d]pyrimidin-4-amine;
N-[(3S)-1-(4-aminopyrido[3,2-d]pyrimidin-6-yl)-3-piperidyl]-3-methoxy-propanamide;
N-(6-(3-amino-5-fluorophenyl)pyrido[3,2-d]pyrimidin-4-yl)-2-(pyrrolidin-1-yl)acetamide;
N-(3-(4-aminopyrido[3,2-d]pyrimidin-6-yl)-5-fluorophenyl)-2-(pyrrolidin-1-yl)acetamide;
N6-(2-methylbenzyl)pyrido[3,2-d]pyrimidine-4,6-diamine;
6-(o-tolyloxy)pyrido[3,2-d]pyrimidin-4-amine;
6-(3-(2-(pyrrolidin-1-yl)ethoxyl)phenyl)pyrido[3,2-d]pyrimidin-4-amine;
6-(3-fluorophenyl)-N-isobutylpyrido[3,2-d]pyrimidin-4-amine;
1-[4-(4-aminopyrido[3,2-d]pyrimidin-6-yl)piperazin-1-yl]ethanone;
6-[3-(4-methyl-1H-pyrazol-3-yl)-1-piperidyl]pyrido[3,2-d]pyrimidin-4-amine;
6-(3-(1,4-dimethyl-1H-pyrazol-3-yl)piperidin-1-yl)pyrido[3,2-d]pyrimidin-4-amine;
6-(3-(1,4-dimethyl-1H-pyrazol-5-yl)piperidin-1-yl)pyrido[3,2-d]pyrimidin-4-amine;
1-(4-(3-(4-aminopyrido[3,2-d]pyrimidin-6-yl)-5-fluorobenzyl)-1,4-diazepan-1-yl)ethanone;
1-(4-(3-(4-aminopyrido[3,2-d]pyrimidin-6-yl)-5-fluorobenzyl)piperazin-1-yl)ethanone;
1-(3-(4-aminopyrido[3,2-d]pyrimidin-6-yl)-5-fluorobenzyl)piperidin-4-ol;
6-(3-fluoro-5-((methyl(1-methylpiperidin-4-yl)amino)methyl)phenyl)pyrido[3,2-d]pyrimidin-4-amine;
(1-(3-(4-aminopyrido[3,2-d]pyrimidin-6-yl)-5-fluorobenzyl)piperidin-4-yl)methanol;
2-(4-(3-(4-aminopyrido[3,2-d]pyrimidin-6-yl)-5-fluorobenzyl)piperazin-1-yl)ethanol;
6-(3-fluoro-5-((4-(2-methoxyethyl)piperazin-1-yl)methyl)phenyl)pyrido[3,2-d]pyrimidin-4-amine;
(S)-6-(3-((3-(dimethylamino)pyrrolidin-1-yl)methyl)-5-fluorophenyl)pyrido[3,2-d]pyrimidin-4-amine;
4-(3-(4-aminopyrido[3,2-d]pyrimidin-6-yl)-5-fluorobenzyl)-N,N-dimethylpiperazine-1-carboxamide;
1-(3-(4-aminopyrido[3,2-d]pyrimidin-6-yl)-5-fluorobenzyl)piperidine-4-carboxamide;
6-(3-((3,3-difluoroazetidin-1-yl)methyl)-5-fluorophenyl)pyrido[3,2-d]pyrimidin-4-amine;
4-(3-(4-aminopyrido[3,2-d]pyrimidin-6-yl)-5-fluorobenzyl)-N,N-dimethylpiperazine-1-sulfonamide;
6-(3-((1,4-oxazepan-4-yl)methyl)-5-fluorophenyl)pyrido[3,2-d]pyrimidin-4-amine;
2-(4-(3-(4-aminopyrido[3,2-d]pyrimidin-6-yl)-5-fluorobenzyl)piperazin-1-yl)-N,N-dimethylacetamide;
1-(4-(3-(4-aminopyrido[3,2-d]pyrimidin-6-yl)-5-fluorobenzyl)piperazin-1-yl)-2-methylpropan-1-one;
6-(3-fluoro-5-((4-(methylsulfonyl)piperazin-1-yl)methyl)phenyl)pyrido[3,2-d]pyrimidin-4-amine;
6-(3-fluoro-5-((methyl(1,1-dioxo-tetrahydrothiophen-3-yl)amino)methyl)phenyl)pyrido[3,2-d]pyrimidin-4-amine;
2-((3-(4-aminopyrido[3,2-d]pyrimidin-6-yl)-5-fluorobenzyl)(methyl)amino)-1-morpholinoethanone;
N-(1-(3-(4-aminopyrido[3,2-d]pyrimidin-6-yl)-5-fluorobenzyl)pyrrolidin-3-yl)-N-methylacetamide;
(1-(3-(4-aminopyrido[3,2-d]pyrimidin-6-yl)-5-fluorobenzyl)azetidin-3-yl)(4-methylpiperazin-1-yl)methanone;
6-(3-((4-(dimethylamino)piperidin-1-yl)methyl)-5-fluorophenyl)pyrido[3,2-d]pyrimidin-4-amine;
6-(3-fluoro-5-((4-methoxypiperidin-1-yl)methyl)phenyl)pyrido[3,2-d]pyrimidin-4-amine;
6-(3-fluoro-5-(pyrrolidin-1-ylmethyl)phenyl)pyrido[3,2-d]pyrimidin-4-amine;
6-(3-fluoro-5-((2-methylpyrrolidin-1-yl)methyl)phenyl)pyrido[3,2-d]pyrimidin-4-amine;
6-(3-fluoro-5-((methyl(1-methylpyrrolidin-3-yl)amino)methyl)phenyl)pyrido[3,2-d]pyrimidin-4-amine;
2-((3-(4-aminopyrido[3,2-d]pyrimidin-6-yl)-5-fluorobenzyl)(methyl)amino)-N,N-dimethylacetamide;
6-(3-fluoro-5-(((2-methoxyethyl)(methyl)amino)methyl)phenyl)pyrido[3,2-d]pyrimidin-4-amine;
4-(3-(4-aminopyrido[3,2-d]pyrimidin-6-yl)-5-fluorobenzyl)-N,1-dimethylpiperazine-2-carboxamide;
1-(3-(4-aminopyrido[3,2-d]pyrimidin-6-yl)-5-fluorobenzyl)azetidine-3-carboxamide;
1-(3-(4-aminopyrido[3,2-d]pyrimidin-6-yl)-5-fluorobenzyl)-N-methylpyrrolidine-3-carboxamide;
1-(3-(4-aminopyrido[3,2-d]pyrimidin-6-yl)-5-fluorobenzyl)-N,N-dimethylazetidine-3-carboxamide;
4-(3-(4-aminopyrido[3,2-d]pyrimidin-6-yl)-5-fluorobenzyl)-1-methylpiperazine-2-carboxamide;
1-(3-(4-aminopyrido[3,2-d]pyrimidin-6-yl)-5-fluorobenzyl)-N-methylazetidine-3-carboxamide;
2-(1-(3-(4-aminopyrido[3,2-d]pyrimidin-6-yl)-5-fluorobenzyl)piperidin-4-yl)-N,N-dimethylacetamide;
4-(3-(4-aminopyrido[3,2-d]pyrimidin-6-yl)-5-fluorobenzyl)-N-methylmorpholine-2-carboxamide;
6-(3-((3-(dimethylamino)pyrrolidin-1-yl)methyl)-5-fluorophenyl)pyrido[3,2-d]pyrimidin-4-amine;
(1-(3-(4-aminopyrido[3,2-d]pyrimidin-6-yl)-5-fluorobenzyl)piperidin-3-yl)methanol;
6-(3-fluoro-5-((3-morpholinopyrrolidin-1-yl)methyl)phenyl)pyrido[3,2-d]pyrimidin-4-amine;
6-(3-fluoro-5-((4-methylpiperazin-1-yl)methyl)phenyl)pyrido[3,2-d]pyrimidin-4-amine;

1-(3-(4-aminopyrido[3,2-d]pyrimidin-6-yl)-5-fluorobenzyl)piperidin-3-ol;
(R)-1-(3-(4-aminopyrido[3,2-d]pyrimidin-6-yl)-5-fluorobenzyl)piperidin-3-ol;
6-(3-((cyclopropylamino)methyl)-5-fluorophenyl)pyrido[3,2-d]pyrimidin-4-amine;
2-(3-(4-aminopyrido[3,2-d]pyrimidin-6-yl)-5-fluorobenzylamino)ethanol;
6-(3-((cyclopropylmethylamino)methyl)-5-fluorophenyl)pyrido[3,2-d]pyrimidin-4-amine hydrochloride;
6-(3-((cyclobutylamino)methyl)-5-fluorophenyl)pyrido[3,2-d]pyrimidin-4-amine hydrochloride;
6-(3-fluoro-5-((oxetan-3-ylamino)methyl)phenyl)pyrido[3,2-d]pyrimidin-4-amine hydrochloride;
6-(3-fluoro-5-((isobutylamino)methyl)phenyl)pyrido[3,2-d]pyrimidin-4-amine;
2-(3-(4-aminopyrido[3,2-d]pyrimidin-6-yl)-5-fluorobenzylamino)propan-1-ol hydrochloride;
6-(3-((cyclopentylamino)methyl)-5-fluorophenyl)pyrido[3,2-d]pyrimidin-4-amine hydrochloride;
N1-(3-(4-aminopyrido[3,2-d]pyrimidin-6-yl)-5-fluorobenzyl)-N2,N2-dimethylethane-1,2-diamine hydrochloride;
6-(3-fluoro-5-((isopropylamino)methyl)phenyl)pyrido[3,2-d]pyrimidin-4-amine hydrochloride;
6-(3-fluoro-5-((tetrahydro-2H-pyran-4-ylamino)methyl)phenyl)pyrido[3,2-d]pyrimidin-4-amine hydrochloride;
6-(3-fluoro-5-(((tetrahydrofuran-3-yl)methylamino)methyl)phenyl)pyrido[3,2-d]pyrimidin-4-amine;
2-(3-(4-aminopyrido[3,2-d]pyrimidin-6-yl)-5-fluorobenzylamino)-N,N-dimethylacetamide hydrochloride;
6-(3-fluoro-5-((4-methylcyclohexylamino)methyl)phenyl)pyrido[3,2-d]pyrimidin-4-amine hydrochloride;
6-(3-fluoro-5-((2-(pyrrolidin-1-yl)ethylamino)methyl)phenyl)pyrido[3,2-d]pyrimidin-4-amine hydrochloride;
6-(3-fluoro-5-((1-methylpiperidin-4-ylamino)methyl)phenyl)pyrido[3,2-d]pyrimidin-4-amine hydrochloride;
6-(3-((cyclopropylamino)methyl)phenyl)pyrido[3,2-d]pyrimidin-4-amine hydrochloride;
2-(3-(4-aminopyrido[3,2-d]pyrimidin-6-yl)benzylamino)ethanol hydrochloride;
6-(3-((cyclopropylmethylamino)methyl)phenyl)pyrido[3,2-d]pyrimidin-4-amine hydrochloride;
6-(3-((cyclobutylamino)methyl)phenyl)pyrido[3,2-d]pyrimidin-4-amine;
6-(3-((oxetan-3-ylamino)methyl)phenyl)pyrido[3,2-d]pyrimidin-4-amine;
6-(3-((isobutylamino)methyl)phenyl)pyrido[3,2-d]pyrimidin-4-amine hydrochloride;
2-(3-(4-aminopyrido[3,2-d]pyrimidin-6-yl)benzylamino)propan-1-ol hydrochloride;
N1-(3-(4-aminopyrido[3,2-d]pyrimidin-6-yl)benzyl)-N2,N2-dimethylethane-1,2-diamine hydrochloride;
6-(3-((isopropylamino)methyl)phenyl)pyrido[3,2-d]pyrimidin-4-amine hydrochloride;
6-(3-((tetrahydro-2H-pyran-4-ylamino)methyl)phenyl)pyrido[3,2-d]pyrimidin-4-amine hydrochloride;
6-(3-(((tetrahydrofuran-3-yl)methylamino)methyl)phenyl)pyrido[3,2-d]pyrimidin-4-amine hydrochloride;
6-(3-fluoro-5-(((tetrahydro-2H-pyran-4-yl)methylamino)methyl)phenyl)pyrido[3,2-d]pyrimidin-4-amine hydrochloride;
4-(3-(4-aminopyrido[3,2-d]pyrimidin-6-yl)-5-fluorobenzylamino)cyclohexanol;
(1-(3-(4-aminopyrido[3,2-d]pyrimidin-6-yl)-5-fluorobenzylamino)cyclopropyl)methanol hydrochloride;
6-(3-fluoro-5-(((1-methylpiperidin-2-yl)methylamino)methyl)phenyl)pyrido[3,2-d]pyrimidin-4-amine hydrochloride;
6-(3-fluoro-5-(((1-methylpiperidin-4-yl)methylamino)methyl)phenyl)pyrido[3,2-d]pyrimidin-4-amine hydrochloride;
6-(3-fluoro-5-((2-morpholinoethylamino)methyl)phenyl)pyrido[3,2-d]pyrimidin-4-amine hydrochloride;
1-(4-(3-(4-aminopyrido[3,2-d]pyrimidin-6-yl)-5-fluorobenzylamino)piperidin-1-yl)ethanone hydrochloride;
6-(3-fluoro-5-((2-methyl-1-morpholinopropan-2-ylamino)methyl)phenyl)pyrido[3,2-d]pyrimidin-4-amine hydrochloride;
6-(3-fluoro-5-((1-methylazetidin-3-ylamino)methyl)phenyl)pyrido[3,2-d]pyrimidin-4-amine hydrochloride;
ethyl 4-(3-(4-aminopyrido[3,2-d]pyrimidin-6-yl)-5-fluorobenzylamino)piperidine-1-carboxylate hydrochloride;
2-(3-(4-aminopyrido[3,2-d]pyrimidin-6-yl)benzylamino)propan-1-ol hydrochloride;
6-(3-((cyclopentylamino)methyl)phenyl)pyrido[3,2-d]pyrimidin-4-amine hydrochloride;
2-(3-(4-aminopyrido[3,2-d]pyrimidin-6-yl)benzylamino)-N,N-dimethylacetamide hydrochloride;
6-(3-((4-methylcyclohexylamino)methyl)phenyl)pyrido[3,2-d]pyrimidin-4-amine hydrochloride;
6-(3-((2-(pyrrolidin-1-yl)ethylamino)methyl)phenyl)pyrido[3,2-d]pyrimidin-4-amine hydrochloride;
6-(3-((1-methylpiperidin-4-ylamino)methyl)phenyl)pyrido[3,2-d]pyrimidin-4-amine hydrochloride;
6-(3-(((tetrahydro-2H-pyran-4-yl)methylamino)methyl)phenyl)pyrido[3,2-d]pyrimidin-4-amine hydrochloride;
N1-(3-(4-aminopyrido[3,2-d]pyrimidin-6-yl)benzyl)cyclohexane-1,4-diamine hydrochloride;
(1-(3-(4-aminopyrido[3,2-d]pyrimidin-6-yl)benzylamino)cyclopropyl)methanol hydrochloride;
6-(3-(((1-methylpiperidin-2-yl)methylamino)methyl)phenyl)pyrido[3,2-d]pyrimidin-4-amine hydrochloride;
6-(3-(((1-methylpiperidin-4-yl)methylamino)methyl)phenyl)pyrido[3,2-d]pyrimidin-4-amine hydrochloride;
6-(3-((2-morpholinoethylamino)methyl)phenyl)pyrido[3,2-d]pyrimidin-4-amine hydrochloride;
1-(4-(3-(4-aminopyrido[3,2-d]pyrimidin-6-yl)benzylamino)piperidin-1-yl)ethanone hydrochloride;
6-(3-((2-methyl-1-morpholinopropan-2-ylamino)methyl)phenyl)pyrido[3,2-d]pyrimidin-4-amine hydrochloride;
6-(3-((1-methylazetidin-3-ylamino)methyl)phenyl)pyrido[3,2-d]pyrimidin-4-amine hydrochloride;
Ethyl 4-(3-(4-aminopyrido[3,2-d]pyrimidin-6-yl)benzylamino)piperidine-1-carboxylate hydrochloride;
6-(3-chlorophenyl)pyrido[3,2-d]pyrimidine-2,4-diamine;
6-(3-fluorophenyl)pyrido[3,2-d]pyrimidin-4-amine;
6-(3-methyl-1-piperidyl)pyrido[3,2-d]pyrimidin-4-amine;
6-(3-methoxy-1-piperidyl)pyrido[3,2-d]pyrimidin-4-amine;
6-[3-(trifluoromethyl)pyrrolidin-1-yl]pyrido[3,2-d]pyrimidin-4-amine;
6-[3-(trifluoromethyl)-1-piperidyl]pyrido[3,2-d]pyrimidin-4-amine;
6-[3-(methoxymethyl)-1-piperidyl]pyrido[3,2-d]pyrimidin-4-amine;

[1-(4-aminopyrido[3,2-d]pyrimidin-6-yl)-3-piperidyl]
   methanol;
N6-[2-(4-fluorophenyl)ethyl]pyrido[3,2-d]pyrimidine-4,
   6-diamine
6-(1-piperidyl)pyrido[3,2-d]pyrimidin-4-amine;
[1-(4-aminopyrido[3,2-d]pyrimidin-6-yl)-4-piperidyl]-
   pyrrolidin-1-yl-methanone;
6-(3-morpholinopyrrolidin-1-yl)pyrido[3,2-d]pyrimidin-
   4-amine;
6-[4-(2-methoxyethyl)piperazin-1-yl]pyrido[3,2-d]py-
   rimidin-4-amine;
N-[1-(4-aminopyrido[3,2-d]pyrimidin-6-yl)pyrrolidin-3-
   yl]-N-methyl-acetamide;
1-[4-(4-aminopyrido[3,2-d]pyrimidin-6-yl)piperazin-1-
   yl]ethanone;
1-[4-(4-aminopyrido[3,2-d]pyrimidin-6-yl)piperazin-1-
   yl]-2-methyl-propan-1-one;
6-[3-(4-methyl-1H-pyrazol-3-yl)-1-piperidyl]pyrido[3,2-
   d]pyrimidin-4-amine;
tert-butyl 4-(4-aminopyrido[3,2-d]pyrimidin-6-yl)-2-
   methyl-piperazine-1-carboxylate;
2[1-(4-aminopyrido[3,2-d]pyrimidin-6-yl)-4-piperidyl]-
   N-methyl-acetamide;
6-[4-(1H-pyrazol-5-yl)-1-piperidyl]pyrido[3,2-d]pyrimi-
   din-4-amine;
6-[4-(6-methyl-2-pyridyl)-1-piperidyl]pyrido[3,2-d]py-
   rimidin-4-amine;
6-(3-morpholino-1-piperidyl)pyrido[3,2-d]pyrimidin-4-
   amine;
6-[3-(5-methyl-2-pyridyl)-1-piperidyl]pyrido[3,2-d]py-
   rimidin-4-amine;
6-[3-[(1-methylimidazol-2-yl)methyl]pyrrolidin-1-yl]
   pyrido[3,2-d]pyrimidin-4-amine;
6-[3-(5-methyl-1,2,4-oxadiazol-3-yl)-1-piperidyl]pyrido
   [3,2-d]pyrimidin-4-amine;
6-[4-(3-methylimidazol-4-yl)-1-piperidyl]pyrido[3,2-d]
   pyrimidin-4-amine;
6-(3-amino-5-fluoro-phenyl)pyrido[3,2-d]pyrimidin-4-
   amine;
6-[3-(4-pyridylmethyl)pyrrolidin-1-yl]pyrido[3,2-d]py-
   rimidin-4-amine;
6-[3-(3-methylimidazol-4-yl)pyrrolidin-1-yl]pyrido[3,2-
   d]pyrimidin-4-amine;
6-[3-(3-methyl-1,2,4-oxadiazol-5-yl)-1-piperidyl]pyrido
   [3,2-d]pyrimidin-4-amine;
1-(4-aminopyrido[3,2-d]pyrimidin-6-yl)-N-methyl-pyr-
   rolidine-3-carboxamide;
6-[3-(2-pyridylmethyl)pyrrolidin-1-yl]pyrido[3,2-d]py-
   rimidin-4-amine;
6-[3-(3-methyl-1,2,4-oxadiazol-5-yl)pyrrolidin-1-yl]
   pyrido[3,2-d]pyrimidin-4-amine;
6-[3-(3-pyridylmethyl)pyrrolidin-1-yl]pyrido[3,2-d]py-
   rimidin-4-amine;
6-(4-methylpiperazin-1-yl)pyrido[3,2-d]pyrimidin-4-
   amine;
6-(4-methoxy-1-piperidyl)pyrido[3,2-d]pyrimidin-4-
   amine;
6-[3-(dimethylamino)pyrrolidin-1-yl]pyrido[3,2-d]py-
   rimidin-4-amine;
ethyl 4-[(4-aminopyrido[3,2-d]pyrimidin-6-yl)amino]pi-
   peridine-1-carboxylate;
6-(3,4,6,7,8,8a-hexahydro-1H-pyrrolo[1,2-a]pyrazin-2-
   yl)pyrido[3,2-d]pyrimidin-4-amine;
N6-cyclopentylpyrido[3,2-d]pyrimidine-4,6-diamine;
4-(4-aminopyrido[3,2-d]pyrimidin-6-yl)-N-cyclopentyl-
   morpholine-2-carboxamide;
6-[3-(6-methyl-2-pyridyl)-1-piperidyl]pyrido[3,2-d]py-
   rimidin-4-amine;
tert-butyl 4-(4-aminopyrido[3,2-d]pyrimidin-6-yl)pipera-
   zine-1-carboxylate;
6-[4-(5-methyl-1,2,4-oxadiazol-3-yl)-1-piperidyl]pyrido
   [3,2-d]pyrimidin-4-amine;
N-[3-(4-aminopyrido[3,2-d]pyrimidin-6-yl)-5-fluoro-
   phenyl]-2-cyclopentyl-acetamide;
N6-benzylpyrido[3,2-d]pyrimidine-4,6-diamine;
6-[3-(4-methyl-1H-pyrazol-3-yl)-1-piperidyl]pyrido[3,2-
   d]pyrimidin-4-amine;
6-[3-(4,6-dimethylpyrimidin-2-yl)-1-piperidyl]pyrido[3,
   2-d]pyrimidin-4-amine;
6-[1-(4-aminopyrido[3,2-d]pyrimidin-6-yl)-3-piperidyl]-
   N,N-dimethyl-pyridine-2-carboxamide;
6-[3-[(5-methyl-2-pyridyl)methyl]pyrrolidin-1-yl]pyrido
   [3,2-d]pyrimidin-4-amine;
6-[3-(pyrimidin-2-ylmethyl)pyrrolidin-1-yl]pyrido[3,2-d]
   pyrimidin-4-amine;
6-[3-[6-(dimethylamino)-2-pyridyl]-1-piperidyl]pyrido
   [3,2-d]pyrimidin-4-amine;
6-[3-(pyrimidin-2-ylmethyl)-1-piperidyl]pyrido[3,2-d]
   pyrimidin-4-amine;
6-[3-(4-methylsulfonyl-1H-pyrazol-5-yl)-1-piperidyl]
   pyrido[3,2-d]pyrimidin-4-amine;
6-[3-[6-(dimethylamino)pyrazin-2-yl]-1-piperidyl]pyrido
   [3,2-d]pyrimidin-4-amine;
6-[3-[[6-(methylamino)pyrimidin-4-yl]methyl]pyrroli-
   din-1-yl]pyrido[3,2-d]pyrimidin-4-amine;
6-[3-(2-methylpyrimidin-4-yl)pyrrolidin-1-yl]pyrido[3,2-
   d]pyrimidin-4-amine;
6-[3-[6-(dimethylamino)-2-methyl-pyrimidin-4-yl]pyrro-
   lidin-1-yl]pyrido[3,2-d]pyrimidin-4-amine;
6-[3-[[6-(dimethylamino)pyrimidin-4-yl]methyl]-1-pip-
   eridyl]pyrido[3,2-d]pyrimidin-4-amine;
6-[3-(1H-pyrazol-3-yl)pyrrolidin-1-yl]pyrido[3,2-d]py-
   rimidin-4-amine;
6-[3-[[6-(dimethylamino)pyrimidin-4-yl]methyl]pyrroli-
   din-1-yl]pyrido[3,2-d]pyrimidin-4-amine;
6-[3-[2-(dimethylamino)pyrimidin-4-yl]-1-piperidyl]
   pyrido[3,2-d]pyrimidin-4-amine;
6-[1-(4-aminopyrido[3,2-d]pyrimidin-6-yl)-3-piperidyl]
   pyridine-2-carboxamide;
6-[3-(dimethylamino)pyrazin-2-yl]-1-piperidyl]pyrido
   [3,2-d]pyrimidin-4-amine;
6-[3-(2-methylpyrimidin-4-yl)-1-piperidyl]pyrido[3,2-d]
   pyrimidin-4-amine; 6-(3-pyrimidin-4-yl-1-piperidyl)
   pyrido[3,2-d]pyrimidin-4-amine;
6-[3-[5-(trifluoromethyl)-1H-pyrazol-3-yl]-1-piperidyl]
   pyrido[3,2-d]pyrimidin-4-amine;
6-(3-pyrazin-2-yl-1-piperidyl)pyrido[3,2-d]pyrimidin-4-
   amine;
6-[3-(pyrazin-2-ylmethyl)-1-piperidyl]pyrido[3,2-d]py-
   rimidin-4-amine;
6-[3-[5-(dimethylamino)-2-pyridyl]-1-piperidyl]pyrido
   [3,2-d]pyrimidin-4-;amine;
6-[3-(4-methylpyrimidin-2-yl)-1-piperidyl]pyrido[3,2-d]
   pyrimidin-4-amine;
6-[3-(2-pyridyl)-1-piperidyl]pyrido[3,2-d]pyrimidin-4-
   amine;
6-[3-(4-methyl-1,2,4-triazol-3-yl)-1-piperidyl]pyrido[3,
   2-d]pyrimidin-4-amine;
6-[3-[5-(methoxymethyl)-1,2,4-oxadiazol-3-yl]-1-piper-
   idyl]pyrido[3,2-d]pyrimidin-4-amine;
6-[1-(4-aminopyrido[3,2-d]pyrimidin-6-yl)-3-piperidyl]-
   N-methyl-pyridine-2-carboxamide;

6-[3-(5-methylsulfonylpyrimidin-4-yl)-1-piperidyl]pyrido[3,2-d]pyrimidin-4-amine;
6-[3-(4-pyridyl)pyrrolidin-1-yl]pyrido[3,2-d]pyrimidin-4-amine;
6-(2-ethyl-4-pyridyl)pyrido[3,2-d]pyrimidin-4-amine;
6-(2-methyl-4-pyridyl)pyrido[3,2-d]pyrimidin-4-amine;
6-[3-[(1-methylimidazol-2-yl)methyl]-1-piperidyl]pyrido[3,2-d]pyrimidin-4-amine;
N-[3-(4-aminopyrido[3,2-d]pyrimidin-6-yl)-5-fluoro-phenyl]-2-pyrrolidin-1-yl-acetamide;
N-[6-(3-amino-5-fluoro-phenyl)pyrido[3,2-d]pyrimidin-4-yl]-2-pyrrolidin-1-yl-acetamide;
3-(4-aminopyrido[3,2-d]pyrimidin-6-yl)phenol;
5-[1-(4-aminopyrido[3,2-d]pyrimidin-6-yl)-3-piperidyl]-2-methyl-pyrazol-3-ol
6-[3-(2-pyrrolidin-1-ylethoxy)phenyl]pyrido[3,2-d]pyrimidin-4-amine
6-[3-(1H-pyrazol-3-yl)-1-piperidyl]pyrido[3,2-d]pyrimidin-4-amine
6-[2-(1H-pyrazol-3-yl)morpholin-4-yl]pyrido[3,2-d]pyrimidin-4-amine
6-[3-(1H-imidazol-2-yl)-1-piperidyl]pyrido[3,2-d]pyrimidin-4-amine
[(3R)-1-(4-aminopyrido[3,2-d]pyrimidin-6-yl)-3-piperidyl]carbamate;
6-[(3S)-3-amino-1-piperidyl]pyrido[3,2-d]pyrimidin-4-amine;
6-[(3R)-3-amino-1-piperidyl]pyrido[3,2-d]pyrimidin-4-amine;
N-[(3S)-1-(4-aminopyrido[3,2-d]pyrimidin-6-yl)-3-piperidyl]-3-pyrrolidin-1-yl-propanamide;
N-[(3S)-1-(4-aminopyrido[3,2-d]pyrimidin-6-yl)-3-piperidyl]-2-(4-methylpiperazin-1-yl)acetamide;
N-[(3R)-1-(4-aminopyrido[3,2-d]pyrimidin-6-yl)-3-piperidyl]-3-methoxy-propanamide;
N-[(3R)-1-(4-aminopyrido[3,2-d]pyrimidin-6-yl)-3-piperidyl]-3-pyrrolidin-1-yl-propanamide;
N-[(3R)-1-(4-aminopyrido[3,2-d]pyrimidin-6-yl)-3-piperidyl]-2-(4-methylpiperazin-1-yl)acetamide;
N6[(2-fluorophenyl)methyl]pyrido[3,2-d]pyrimidine-4,6-diamine;
N6-(1-phenylethyl)pyrido[3,2-d]pyrimidine-4,6-diamine;
6-[2-(trifluoromethyl)-4-pyridyl]pyrido[3,2-d]pyrimidin-4-amine;
6-(2-methylphenoxy)pyrido[3,2-d]pyrimidin-4-amine;
6-(3-methylphenoxy)pyrido[3,2-d]pyrimidin-4-amine;
6-(4-pyridyloxy)pyrido[3,2-d]pyrimidin-4-amine;
6-(4-methylphenoxy)pyrido[3,2-d]pyrimidin-4-amine;
6-(3-fluorophenoxy)pyrido[3,2-d]pyrimidin-4-amine;
2-(4-aminopyrido[3,2-d]pyrimidin-6-yl)oxybenzonitrile;
6[(6-methyl-3-pyridyl)oxy]pyrido[3,2-d]pyrimidin-4-amine;
6[(2-methyl-3-pyridyl)oxy]pyrido[3,2-d]pyrimidin-4-amine;
6-phenoxypyrido[3,2-d]pyrimidin-4-amine;
6-(3-pyridyloxy)pyrido[3,2-d]pyrimidin-4-amine;
4-(4-aminopyrido[3,2-d]pyrimidin-6-yl)oxybenzamide;
4-(4-aminopyrido[3,2-d]pyrimidin-6-yl)oxybenzonitrile;
3-(4-aminopyrido[3,2-d]pyrimidin-6-yl)oxybenzonitrile;
6-(2-chlorophenoxy)pyrido[3,2-d]pyrimidin-4-amine;
6-(4-methoxyphenoxy)pyrido[3,2-d]pyrimidin-4-amine;
6-(4-chlorophenoxy)pyrido[3,2-d]pyrimidin-4-amine;
6-(3-chlorophenoxy)pyrido[3,2-d]pyrimidin-4-amine;
6-(2,4-difluorophenoxy)pyrido[3,2-d]pyrimidin-4-amine;
6-(3,4-difluorophenoxy)pyrido[3,2-d]pyrimidin-4-amine;
N6-[(2-chlorophenyl)methyl]pyrido[3,2-d]pyrimidine-4,6-diamine;
6-(2-fluorophenoxy)pyrido[3,2-d]pyrimidin-4-amine;
N6-[(3-chlorophenyl)methyl]pyrido[3,2-d]pyrimidine-4,6-diamine;
N6-[(4-chlorophenyl)methyl]pyrido[3,2-d]pyrimidine-4,6-diamine;
N6-(o-tolylmethyl)pyrido[3,2-d]pyrimidine-4,6-diamine;
N6-[1-(6-methyl-2-pyridyl)ethyl]pyrido[3,2-d]pyrimidine-4,6-diamine;
N6-[(3-pyrrolidin-1-ylphenyl)methyl]pyrido[3,2-d]pyrimidine-4,6-diamine;
N6-(pyrazin-2-ylmethyl)pyrido[3,2-d]pyrimidine-4,6-diamine;
6-[3-(difluoromethoxy)phenyl]pyrido[3,2-d]pyrimidin-4-amine;
6-(3-(6-methylpyridin-2-yloxy)phenyl]pyrido[3,2-d]pyrimidin-4-amine;
6-(3-isopropoxyphenyl)pyrido[3,2-d]pyrimidin-4-amine;
6-(1H-indazol-4-yl)pyrido[3,2-d]pyrimidin-4-amine;
6-(3-methoxyphenyl)pyrido[3,2-d]pyrimidin-4-amine; and
N1-(3-(4-aminopyrido[3,2-d]pyrimidin-6-yl)-5-fluorophenyl)-N3,N3-dimethylpropane-1,3-diamine formate;
or,
a free base, pharmaceutically acceptable salt or a stereoisomer thereof.

* * * * *